US011248259B2

(12) United States Patent
Levin et al.

(10) Patent No.: US 11,248,259 B2
(45) Date of Patent: Feb. 15, 2022

(54) METHOD OF IDENTIFYING A SUBJECT HAVING A BACTERIAL INFECTION

(71) Applicant: Imperial College of Science, Technology and Medicine, London (GB)

(72) Inventors: Michael Levin, London (GB); Myrsini Kaforou, London (GB); Jethro A. Herberg, London (GB); Victoria J. Wright, London (GB); Lachlan J. M. Coin, London (GB)

(73) Assignee: Imperial College of Science, Technology and Medicine, London (GB)

( * ) Notice: Subject to any disclaimer, the term of this patent is extended or adjusted under 35 U.S.C. 154(b) by 0 days.

(21) Appl. No.: 16/317,518

(22) PCT Filed: Jul. 12, 2017

(86) PCT No.: PCT/EP2017/067637

§ 371 (c)(1),
(2) Date: Jan. 11, 2019

(87) PCT Pub. No.: WO2018/011316

PCT Pub. Date: Jan. 18, 2018

(65) Prior Publication Data

US 2019/0226009 A1 Jul. 25, 2019

(30) Foreign Application Priority Data

Jul. 12, 2016 (GB) ..................................... 1612123

(51) Int. Cl.

| | |
|---|---|
| ***C12Q 1/68*** | (2018.01) |
| ***C12P 19/34*** | (2006.01) |
| ***C12Q 1/686*** | (2018.01) |
| ***C12Q 1/6883*** | (2018.01) |
| ***C12Q 1/6806*** | (2018.01) |
| ***C12Q 1/6851*** | (2018.01) |
| *C12Q 1/689* | (2018.01) |

(52) U.S. Cl.

CPC ........... *C12Q 1/686* (2013.01); *C12Q 1/6806* (2013.01); *C12Q 1/6851* (2013.01); *C12Q 1/6883* (2013.01); *C12Q 1/689* (2013.01); *C12Q 2600/112* (2013.01); *C12Q 2600/158* (2013.01); *C12Q 2600/16* (2013.01); *Y02A 50/30* (2018.01)

(58) Field of Classification Search

CPC . C12Q 1/00; C12Q 1/689; C12Q 1/70; C12Q 2600/158

See application file for complete search history.

(56) References Cited

FOREIGN PATENT DOCUMENTS

| | | | |
|---|---|---|---|
| WO | 2013114123 | A1 | 8/2013 |
| WO | 2014019977 | A1 | 2/2014 |
| WO | 2014067943 | A1 | 5/2014 |

OTHER PUBLICATIONS

Nhan-Chang CL, Romero R, Tarca AL, et al. Characterization of the transcriptome of chorioamniotic membranes at the site of rupture in spontaneous labor at term. Am J Obstet Gynecol 2010;202:462.e1-41. (Year: 2010).*

Illumina—Data Sheet: RNA Analysis "HumanHT-12 v3 Expression BeadChip" Pub. No. 470-2008-005 (2010) (Year: 2010).*

Kim, S.-H. et al. "Outcome of Vancomycin Treatment in Patients with Methicillin-Susceptible *Staphylococcus aureus* Bacteremia", Antimicrobial Agents And Chemotherapy, Jan. 2008, p. 192-197 (Year: 2008).*

Brealey, J.C. et al. "Viral bacterial co-infection of the respiratory tract during early childhood", FEMS Microbiology Letters, 362. (Year: 2015).*

Carey, A.J. et al. "The epidemiology of methicillin-susceptible and methicillin-resistant *Staphylococcus aureus* in a neonatal intensive care unit, 2000-2007" Journal of Perinatology (2010) 30, 135-139 (Year: 2010).*

Ardura, M.I. et al "Enhanced Monocyte Response and Decreased Central Memory T Cells in Children with Invasive *Staphylococcus aureus* Infections" PLoS ONE, May 2009, vol. 4, Issue 5. (Year: 2009).*

Series GSE16129, entry made public on May 20, 2009, from Gene Expression Omnibus Accession Display. pp. 1-5 printed from www.ncbi.nlm.nih.gov/geo. (Year: 2009).*

Hoshikawa, Y. et al. Physiol Genomics 12: 209-219, (Year: 2003).*

Cobb, J. P. et al. Crit Care Med 2002 vol. 30, No. 12 (Year: 2002).*

Cheung, V.G. et al. Nature Genetics, vol. 33, (Mar. 2003).*

Anonymous, "Human-6 v2 and HumanRef-8 v2 Expression BeadChips," Illumina® Gene Expression Profiling Product Information Sheet, Illumina, Inc., San Diego, CA, 4 pages (Dec. 23, 2006, retrieved from the internet Jul. 9, 2013).

Anonymous, "Whole-Genome Expression Analysis Using the Sentrix® Human-6 and HumanRef-8 Expression BeadChips," Illumina® Gene Expression Profiling Product Information Sheet, Illumina, Inc., San Diego, CA, 4 pages (Jan. 1, 2005, retrieved from the internet Sep. 25, 2012).

Herberg et al., "Diagnostic Test Accuracy of a 2-Transcript Host RNA Signature for Discriminating Bacterial vs Viral Infection in Febrile Children," JAMA, vol. 316, No. 8, pp. 835-845 (Aug. 23/30, 2016).

International Search Report, International Application No. PCT/EP2017/067637 (published as WO 2018/011316), 4 pages (dated Nov. 15, 2017).

(Continued)

*Primary Examiner* — Stephen T Kapushoc

(74) *Attorney, Agent, or Firm* — Prismatic Law Group, PLLC

(57) ABSTRACT

A method of identifying a subject having a bacterial infection, which includes discriminating said subject from a subject having a viral infection or an inflammatory disease. Also provided is a gene signature employed in the method and to a bespoke gene chip for use in the method. Further provided are probes and/or primers specific to genes in a signature of the present disclosure.

12 Claims, 24 Drawing Sheets

Specification includes a Sequence Listing.

(56) References Cited

OTHER PUBLICATIONS

Kaforou et al., Diagnosis of Bacterial Infection Using a 2-Transcript Host RNA Signature in Febrile Infants 60 Days or Younger, JAMA, vol. 317, No. 15, p. 1577-1578 (Apr. 18, 2017).
Mahajan et al., "RNA Transcriptional Biosignature Analysis for Identifying Febrile Infants With Serious Bacterial Infections in the Emergency Department: A Feasibility Study," Pediatric Emergency Care, vol. 31, No. 1, pp. 1-5 (Jan. 1, 2015).
Zaas et al., "A Host-Based RT-PCR Gene Expression Signature to Identify Acute Respiratory Viral Infection," Science Translational Medice, 5(203), 203ra126 (Sep. 18, 2013).

* cited by examiner

| | Definite Viral | Probable Viral | Unknown Bacterial or Viral | Probable Bacterial | Definite Bacterial |
|---|---|---|---|---|---|
| $n_{total}$ | 39 | 10 | 77 | 49 | 28 |
| $n_{antibiotics}$ | 33 | 7 | 73 | 49 | 28 |
| $n_{bacterial\ DRS}$ | 1 | 2 | 29 | 32 | 27 |

Test Set

A

| | Clinical coding DB | Clinical coding DV |
|---|---|---|
| DRS predicted bacterial | 9 | 0 |
| DRS predicted viral | 1 | 19 |

B

| | Clinical coding DB | Clinical coding DV |
|---|---|---|
| DRS predicted bacterial | 23 | 1 |
| DRS predicted viral | 0 | 27 |

SEQUENCE LISTING

<160> NUMBER OF SEQ ID NOS: 40

<210> SEQ ID NO 1
<211> LENGTH: 63234
<212> TYPE: DNA
<213> ORGANISM: Artificial Sequence
<220> FEATURE:
<223> OTHER INFORMATION: GENOMIC SEQUENCE FOR IFI44L

<400> SEQUENCE: 1

```
gctgccagct gagttttttt gctgctttga gtctcagttt tctttctttc ctagagtctc     60

tgaagccaca gatctcttaa gaactttctg tctccaaacc gtggctgctc gataaatcag    120

acagaacagt taatcctcaa tttaagcctg atctaacccc tagaaacaga tatagaacaa    180

tggaagtgac aacaagattg acatggaatg atgaaaatca tctgcgcaag ctgcttggaa    240

atgtttcttt gagtcttctc tataagtcta gtgttcatgg aggtagcatt gaagatatgg    300

ttgaaagatg cagccgtcag ggatgtacta taacaatggc ttacattgat tacaatatga    360

ttgtagcctt tatgcttgga aattatatta atttacatga aagttctaca gagccaaatg    420

attccctatg gttttcactt caaaagaaaa atgacaccac tgaaatagaa actttactct    480

taaatacagc accaaaaatt attgatgagc aactggtgtg tcgtttatcg aaaacggata    540

ttttcattat atgtcgagat aataaaattt atctagataa aatgataaca agaaacttga    600

aactaaggtt ttatggccac cgtcagtatt tggaatgtga agtttttcga gttgaaggaa    660

ttaaggataa cctagacgac ataaagagga taattaaagc cagagagcac agaaataggc    720

ttctagcaga catcagagac tataggccct atgcagactt ggtttcagaa attcgtattc    780

ttttggtggg tccagttggg tctggaaagt ccagtttttt caattcagtc aagtctattt    840

ttcatggcca tgtgactggc caagccgtag tggggtctga tatcaccagc ataaccgagc    900

ggtataggat atattctgtt aaagatggaa aaaatggaaa atctctgcca tttatgttgt    960

gtgacactat ggggctagat ggggcagaag gagcaggact gtgcatggat gacattcccc   1020

acatcttaaa aggttgtatg ccagacagat atcagtttaa ttcccgtaaa ccaattacac   1080

ctgagcattc tacttttatc acctctccat ctctgaagga caggattcac tgtgtggctt   1140

atgtcttaga catcaactct attgacaatc tctactctaa aatgttggca aaagtgaagc   1200

aagttcacaa agaagtatta aactgtggta tagcatatgt ggccttgctt actaaagtgg   1260
```

-continued

```
atgattgcag tgaggttctt caagacaact ttttaaacat gagtagatct atgacttctc   1320
aaagccgggt catgaatgtc cataaaatgc taggcattcc tatttccaat attttgatgg   1380
ttggaaatta tgcttcagat ttggaactgg accccatgaa ggatattctc atcctctctg   1440
cactgaggca gatgctgcgg gctgcagatg attttttaga agatttgcct cttgaggaaa   1500
ctggtgcaat tgagagagcg ttacagccct gcatttgaga taagttgcct tgattctgac   1560
atttggccca gcctgtactg gtgtgccgca atgagagtca atctctattg acagcctgct   1620
tcagattttg cttttgttcg ttttgccttc tgtccttgga acagtcatat ctcaagttca   1680
aaggccaaaa cctgagaagc ggtgggctaa gataggtcct actgcaaacc acccctccat   1740
atttccgtac catttacaat tcagtttctg tgacatcttt ttaaaccact ggaggaaaaa   1800
tgagatattc tctaatttat tcttctataa cactctatat agagctatgt gagtactaat   1860
cacattgaat aatagttata aaattattgt atagacatct gcttcttaaa cagattgtga   1920
gttctttgag aaacagcgtg gattttactt atctgtgtat tcacagagct tagcacagtg   1980
cctggtaatg agcaagcata cttgccatta cttttccttc ccactctctc caacatcaca   2040
ttcactttaa atttttctgt atatagaaag gaaaactagc ctgggcaaca tgatgaaacc   2100
ccatctccac tgcaaaaaaa aaaaaaaaaa ataagaaaga acaaaacaaa ccccacaaaa   2160
attagctggg tatgatggca cgtgcctgta gtcccagtta ctcaggatga ttgattgagc   2220
cttggaggtg gaggctacag tgagctgaga ttgtgccact gtactctagc cagggagaaa   2280
gagtgagatc ctggctcaaa aaaaccaaat aaaacaaaac aaacaaacga aaaacagaaa   2340
ggaagactga aagagaatga aaagctgggg agaggaaata aaaataaaga aggaagagtg   2400
tttcatttat atctgaatga aaatatgaat gactctaagt aattgaatta attaaaatga   2460
gccaactttt ttttaacaat ttacatttta tttctatggg aaaaaataaa tattcctctt   2520
ctaacaaacc catgcttgat tttcattaat tgaattccaa atcatcctag ccatgtgtcc   2580
ttccatttag gttactgggg caaatcagta agaaagttct tatatttatg ctccaaataa   2640
ttctgaagtc ctcttactag ctgtgaaagc tagtactatt aagaaagaaa acaaaattcc   2700
caaaagatag ctttcacttt tttttttcct taaagacttc ctaattctct tctccaaatt   2760
cttagtcttc ttcaaaataa tatgctttgg ttcaatagtt atccacattc tgacagtcta   2820
atttagtttt aatcagaatt atactcatct tttgggtagt catagatatt aagaaagcaa   2880
gagtttctta tgtccagtta tggaatattt cctaaagcaa ggctgcaggt gaagttgtgc   2940
tcaagtgaat gttcaggaga cacaattcag tggaagaaat taagtcttta aaaaagacct   3000
aggaatagga gaaccatgga aattgaggag gtaggcctac aagtagatat tgggaacaaa   3060
attagagagg caaccagaaa aagttatttt aggctcacca gagttgttct tattgcacag   3120
taacacacca atataccaaa acagcaggta ttgcagtaga gaaagagttt aataattgaa   3180
tggcagaaaa atgaggaagg ttgaggaaac ctcaaatcta cctccctgct gagtctaagt   3240
ttaggatttt taagagaaag gcaggtaagg tgctgaaggt ctggagctgc tgatttgttg   3300
gggtataggg aatgaaatga aacatacaga gatgaaaact ggaagttttt ttttgtttgt   3360
tttgtttttt ttttgttgtt gttttttttt tttttgttt ttttgctgag tcaattcctt   3420
ggagggggtc ttcagactga ctggtgtcag cagacccatg ggattccaag atctggaaaa   3480
ctttttagat agaaacttga tgtttcttaa cgttacatat attatcttat agaaataact   3540
aagggaagtt agtgccttgt gaccacatct atgtgacttt taggcagtaa gaaactataa   3600
ggaaaggagc taacagtcat gctgtaagta gctacaggga attggcttaa agggcaagtt   3660
```

-continued

```
ggttagtact tagctgtgtt tttattcaaa gtctacattt tatgtagtgg ttaatgtttg   3720
ctgttcatta ggatggtttc acagttacca tacaaatgta gaagcaacag gtccaaaaag   3780
tagggcatga ttttctccat gtaatccagg gagaaaacaa gccatgacca ttgttggttg   3840
ggagactgaa ggtgattgaa ggttcaccat catcctcacc aacttttggg ccataattca   3900
cccaaccctt tggtggagcc tgaaaaaaat ctgggcagaa tgtaggactt ctttattttg   3960
tttaaagggg taacacagag tgcccttatg aaggagttgg agatcctgca aggaagagaa   4020
ggagtgaagg agagatcaag agagagaaac aatgaggaac atttcatttg acccaacatc   4080
ctttaggagc ataaatgttg acactaagtt atccctttttg tgctaaaatg gacagtattg   4140
gcaaaatgat accacaactt cttattctct ggctctatat tgctttggaa acacttaaac   4200
atcaaatgga gttaaataca tatttgaaat ttaggttagg aaatattggt gaggaggcct   4260
caaaaagggg gaaacatctt ttgtctggga ggatattttc cattttgtgg atttccctga   4320
tctttttcta ccaccctgag ggtggtgggg aattatcatt ttgctacatt ttagaggtca   4380
tccaggattt ttgaaacttt acattcttta cggttaagca agatgtacag ctcagtcaaa   4440
gacactaaat tcttcttaga aaaatagtgc taaggagtat agcagatgac ctatatgtgt   4500
gttggctggg agaatatcat cttaaagtga gagtgatgtt gtggagacag ttgaaatgtc   4560
aatgctagag cctctgtggt gtgaatgggc acgttaggtt gttgcattag aaagtgactg   4620
tttctgacag aaatttgtag ctttgtgcaa actcacccac catctacctc aataaaatat   4680
agagaaaaga aaaatagagc agtttgagtt ctatgaggta tgcaggccca gagagacata   4740
agtatgttcc tttagtcttg cttcctgtgt gccacactgc ccctccacaa ccatagctgg   4800
gggcaattgt ttaaagtcat tttgttcccg actagctgcc ttgcacatta tcttcatttt   4860
cctggaattt gatacagaga gcaatttata gccaattgat agcttatgct gtttcaatgt   4920
aaattcgtgg taaataactt aggaactgcc tcttcttttt ctttgaaaac ctacttataa   4980
ctgttgctaa taagaatgtg tattgttcag gacaacttgt ctccatacag ttgggttgta   5040
accctcatgc ttggcccaaa taaactctct acttatatca gtttttccta cacttcttcc   5100
ttttaggtca acaataccaa gaggggttac tgtgctgggt aatgtgtaaa cttgtgtctt   5160
gtttagaaag ataaatttaa agactatcac attgcttttt cataaaacaa gacaggtcta   5220
caattaattt attttgacgc aaattgatag gggggccaag taagccccat atgcttaatg   5280
atcagctgat gaataatcat ctcctagcaa cataactcaa tctaatgcta aggtacccac   5340
aagatggcaa ggctgatcaa agtcgtcatg gaatcctgca accaaaagcc atgggaattt   5400
ggaagccctc aaatcccatt cctaatctga tgagtctatg gaccaatttg tggaggacag   5460
tagattaaat agatctgatt tttgccatca atgtaaggag gataaaaact tgcataccaa   5520
ttgtacaccc ttgcaaaatc tttctctgat gttggagaaa atgggccagt gagatcatgg   5580
atatagaagt acagtcaatg ttcagctgta ccctcccaca atcccacttc cttcctcaac   5640
acaattcaaa caaatagact cagactgttt caggctccag gacaggaagt gcagtgtagg   5700
caaaattgca aaaattgagg gcacaggggt ggaggtgggg gggttgaata acaagctgtg   5760
ctaaataatt acgtgtaaat atattttttc atttttaaaa attgatttct tttgcacatt   5820
ccatgacaat atatgtcaca tttttaaaat aaatgcaaag aagcatacat ccaaatggaa   5880
gtgacaacaa gattgacatg gaatgatgaa aatcatctgc gcaagctgct tggaaatgtt   5940
tctttgagtc ttctctataa gtctagtgtt catggaggta gcattgaaga tatggttgaa   6000
```

-continued agatgcagcc gtcagggatg tactataaca atggcttaca ttgattacaa tatgattgta 6060
gcctttatgc ttggaaatta tattaattta catgaaagtt ctacagagcc aaatgattcc 6120
ctatggtttt cacttcaaaa gaaaaatgac accactgaaa tagaaacttt actcttaaat 6180
acagcaccaa aaattattga tgagcaactg gtgtgtcgtt tatcgaaaac ggatattttc 6240
attatatgtc gagataataa aatttatcta gataaaatga taacaagaaa cttgaaacta 6300
aggttttatg gccaccgtca gtatttggaa tgtgaagttt ttcgagttga aggaattaag 6360
gataacctag acgacataaa gaggataatt aaagccagag agcacagaaa taggcttcta 6420
gcagacatca gagactatag gccctatgca gacttggttt cagaaattcg tattcttttg 6480
gtgggtccag ttgggtctgg aaagtccagt tttttcaatt cagtcaagtc tatttttcat 6540
ggccatgtga ctggccaagc cgtagtgggg tctgatatca ccagcataac cgagcggtat 6600
aggatatatt ctgttaaaga tggaaaaaat ggaaaatctc tgccatttat gttgtgtgac 6660
actatggggc tagatggggc agaaggagca ggactgtgca tggatgacat tccccacatc 6720
ttaaaaggtt gtatgccaga cagatatcag tttaattccc gtaaaccaat tacacctgag 6780
cattctactt ttatcacctc tccatctctg aaggacagga ttcactgtgt ggcttatgtc 6840
ttagacatca actctattga caatctctac tctaaaatgt tggcaaaagt gaagcaagtt 6900
cacaaagaag tattaaactg tggtatagca tatgtggcct tgcttactaa agtggatgat 6960
tgcagtgagg ttcttcaaga caacttttta aacatgagta gatctatgac ttctcaaagc 7020
cgggtcatga atgtccataa aatgctaggc attcctattt ccaatatttt gatggttgga 7080
aattatgctt cagatttgga actggacccc atgaaggata ttctcatcct ctctgcactg 7140
aggcagatgc tgcgggctgc agatgatttt ttagaagatt tgcctcttga ggaaactggt 7200
gcaattgaga gagcgttaca gccctgcatt tgagctgcca gctgagtttt tttgctgctt 7260
tgagtctcag ttttctttct ttcctagagt ctctgaagcc acagatctct taagaacttt 7320
ctgtctccaa accgtggctg ctcgataaat cagacagaac agttaatcct caatttaagc 7380
ctgatctaac ccctagaaac agatatagaa caatggaagt gacaacaaga ttgacatgga 7440
atgatgaaaa tcatctgcgc aagctgcttg gaaatgtttc tttgagtctt ctctataagt 7500
ctagtgttca tggaggtagc attgaagata tggttgaaag atgcagccgt cagggatgta 7560
ctataacaat ggcttacatt gattacaata tgattgtagc ctttatgctt ggaaattata 7620
ttaatttaca tgaaagttct acagagccaa atgattccct atggttttca cttcaaaaga 7680
aaaatgacac cactgaaata gaaactttac tcttaaatac agcaccaaaa attattgatg 7740
agcaactggt gtgtcgttta tcgaaaacgg atattttcat tatatgtcga gataataaaa 7800
tttatctaga taaaatgata acaagaaact tgaaactaag gttttatggc caccgtcagt 7860
atttggaatg tgaagttttt cgagttgaag gaattaagga taacctagac gacataaaga 7920
ggataattaa agccagagag cacagaaata ggcttctagc agacatcaga gactataggc 7980
cctatgcaga cttggtttca gaaattcgta ttcttttggt gggtccagtt gggtctggaa 8040
agtccagttt tttcaattca gtcaagtcta tttttcatgg ccatgtgact ggccaagccg 8100
tagtggggtc tgatatcacc agcataaccg agcggtatag gatatattct gttaaagatg 8160
gaaaaaatgg aaaatctctg ccatttatgt tgtgtgacac tatggggcta gatggggcag 8220
aaggagcagg actgtgcatg gatgacattc cccacatctt aaaaggttgt atgccagaca 8280
gatatcagtt taattcccgt aaaccaatta cacctgagca ttctactttt atcacctctc 8340
catctctgaa ggacaggatt cactgtgtgg cttatgtctt agacatcaac tctattgaca 8400

-continued

```
atctctactc taaaatgttg gcaaaagtga agcaagttca caaagaagta ttaaactgtg   8460
gtatagcata tgtggccttg cttactaaag tggatgattg cagtgaggtt cttcaagaca   8520
actttttaaa catgagtaga tctatgactt ctcaaagccg ggtcatgaat gtccataaaa   8580
tgctaggcat tcctatttcc aatattttga tggttggaaa ttatgcttca gatttggaac   8640
tggaccccat gaaggatatt ctcatcctct ctgcactgag gcagatgctg cgggctgcag   8700
atgatttttt agaagatttg cctcttgagg aaactggtgc aattgagaga gcgttacagc   8760
cctgcatttg agataagttg ccttgattct gacatttggc ccagcctgta ctggtgtgcc   8820
gcaatgagag tcaatctcta ttgacagcct gcttcagatt ttgcttttgt tcgttttgcc   8880
ttctgtcctt ggaacagtca tatctcaagt tcaaaggcca aaacctgaga agcggtgggc   8940
taagataggt cctactgcaa accacccctc catatttccg taccatttac aattcagttt   9000
ctgtgacatc tttttaaacc actggaggaa aaatgagata ttctctaatt tattcttcta   9060
taacactcta tatagagcta tgtgagtact aatcacattg aataatagtt ataaaattat   9120
tgtatagaca tctgcttctt aaacagattg tgagttcttt gagaaacagc gtggatttta   9180
cttatctgtg tattcacaga gcttagcaca gtgcctggta atgagcaagc atacttgcca   9240
ttacttttcc ttcccactct ctccaacatc acattcactt taaatttttc tgtatataga   9300
aaggaaaact agcctgggca acatgatgaa accccatctc cactgcaaaa aaaaaaaaaa   9360
aaaataagaa agaacaaaac aaaccccaca aaaattagct gggtatgatg gcacgtgcct   9420
gtagtcccag ttactcagga tgattgattg agccttggag gtggaggcta cagtgagctg   9480
agattgtgcc actgtactct agccagggag aaagagtgag atcctggctc aaaaaaacca   9540
aataaaacaa aacaaacaaa cgaaaaacag aaaggaagac tgaaagagaa tgaaaagctg   9600
gggagaggaa ataaaaataa agaaggaaga gtgtttcatt tatatctgaa tgaaaatatg   9660
aatgactcta agtaattgaa ttaattaaaa tgagccaact ttttttaac aatttacatt    9720
ttatttctat gggaaaaaat aaatattcct cttctaacaa acccatgctt gattttcatt   9780
aattgaattc caaatcatcc tagccatgtg tccttccatt taggttactg gggcaaatca   9840
gtaagaaagt tcttatattt atgctccaaa taattctgaa gtcctcttac tagctgtgaa   9900
agctagtact attaagaaag aaaacaaaat tcccaaaaga tagctttcac tttttttttt   9960
ccttaaagac ttcctaattc tcttctccaa attcttagtc ttcttcaaaa taatatgctt  10020
tggttcaata gttatccaca ttctgacagt ctaatttagt tttaatcaga attatactca  10080
tcttttgggt agtcatagat attaagaaag caagagtttc ttatgtccag ttatggaata  10140
tttcctaaag caaggctgca ggtgaagttg tgctcaagtg aatgttcagg agacacaatt  10200
cagtggaaga aattaagtct ttaaaaaaga cctaggaata ggagaaccat ggaaattgag  10260
gaggtaggcc tacaagtaga tattgggaac aaaattagag aggcaaccag aaaaagttat  10320
tttaggctca ccagagttgt tcttattgca cagtaacaca ccaatatacc aaaacagcag  10380
gtattgcagt agagaaagag tttaataatt gaatggcaga aaaatgagga aggttgagga  10440
aacctcaaat ctacctccct gctgagtcta agtttaggat ttttaagaga aaggcaggta  10500
aggtgctgaa ggtctggagc tgctgatttg ttggggtata gggaatgaaa tgaaacatac  10560
agagatgaaa actggaagtt ttttttgtt tgttttgttt tttttttgtt gttgtttttt  10620
tttttttttg ttttttgct gagtcaattc cttggagggg gtcttcagac tgactggtgt   10680
cagcagaccc atgggattcc aagatctgga aaacttttta gatagaaact tgatgtttct  10740
```

-continued

```
taacgttaca tatattatct tatagaaata actaagggaa gttagtgcct tgtgaccaca  10800
tctatgtgac ttttaggcag taagaaacta taaggaaagg agctaacagt catgctgtaa  10860
gtagctacag ggaattggct taaagggcaa gttggttagt acttagctgt gtttttattc  10920
aaagtctaca ttttatgtag tggttaatgt ttgctgttca ttaggatggt ttcacagtta  10980
ccatacaaat gtagaagcaa caggtccaaa aagtagggca tgattttctc catgtaatcc  11040
agggagaaaa caagccatga ccattgttgg ttgggagact gaaggtgatt gaaggttcac  11100
catcatcctc accaactttt gggccataat tcacccaacc ctttggtgga gcctgaaaaa  11160
aatctgggca gaatgtagga cttctttatt ttgtttaaag ggtaacaca gagtgccctt  11220
atgaaggagt tggagatcct gcaaggaaga gaaggagtga aggagagatc aagagagaga  11280
aacaatgagg aacatttcat ttgacccaac atcctttagg agcataaatg ttgacactaa  11340
gttatccctt ttgtgctaaa atggacagta ttggcaaaat gataccacaa cttcttattc  11400
tctggctcta tattgctttg gaaacactta aacatcaaat ggagttaaat acatatttga  11460
aatttaggtt aggaaatatt ggtgaggagg cctcaaaaag gggggaaacat cttttgtctg  11520
ggaggatatt ttccattttg tggatttccc tgatcttttt ctaccaccct gaggggtggt  11580
gggaattatc attttgctac attttagagg tcatccagga tttttgaaac tttacattct  11640
ttacggttaa gcaagatgta cagctcagtc aaagacacta aattcttctt agaaaaatag  11700
tgctaaggag tatagcagat gacctatatg tgtgttggct gggagaatat catcttaaag  11760
tgagagtgat gttgtggaga cagttgaaat gtcaatgcta gagcctctgt ggtgtgaatg  11820
ggcacgttag gttgttgcat tagaaagtga ctgtttctga cagaaatttg tagctttgtg  11880
caaactcacc caccatctac ctcaataaaa tatagagaaa agaaaaatag agcagtttga  11940
gttctatgag gtatgcaggc ccagagagac ataagtatgt tcctttagtc ttgcttcctg  12000
tgtgccacac tgcccctcca caaccatagc tgggggcaat tgtttaaagt cattttgttc  12060
ccgactagct gccttgcaca ttatcttcat tttcctggaa tttgatacag agagcaattt  12120
atagccaatt gatagcttat gctgtttcaa tgtaaattcg tggtaaataa cttaggaact  12180
gcctcttctt tttctttgaa aacctactta taactgttgc taataagaat gtgtattgtt  12240
caggacaact tgtctccata cagttgggtt gtaaccctca tgcttggccc aaataaactc  12300
tctacttata tcagtttttc ctacacttct tccttttagg tcaacaatac caagaggggt  12360
tactgtgctg ggtaatgtgt aaacttgtgt cttgtttaga aagataaatt taaagactat  12420
cacattgctt tttcataaaa caagacaggt ctacaattaa tttattttga cgcaaattga  12480
taggggggcc aagtaagccc catatgctta atgatcagct gatgaataat catctcctag  12540
caacataact caatctaatg ctaaggtacc cacaagatgg caaggctgat caaagtcgtc  12600
atggaatcct gcaaccaaaa gccatgggaa tttggaagcc ctcaaatccc attcctaatc  12660
tgatgagtct atggaccaat ttgtggagga cagtagatta aatagatctg atttttgcca  12720
tcaatgtaag gaggataaaa acttgcatac caattgtaca cccttgcaaa atctttctct  12780
gatgttggag aaaatgggcc agtgagatca tggatataga agtacagtca atgttcagct  12840
gtaccctccc acaatcccac ttccttcctc aacacaattc aaacaaatag actcagactg  12900
tttcaggctc caggacagga agtgcagtgt aggcaaaatt gcaaaaaattg agggcacagg  12960
ggtggaggtg ggggggttga ataacaagct gtgctaaata attacgtgta aatatatttt  13020
ttcattttta aaaattgatt tcttttgcac attccatgac aatatatgtc acatttttaa  13080
aataaatgca aagaagcata catccaagta agcgactttt taattgaaac atagtatttg  13140
```

-continued tacgtattta tggggttatg tgtgatattt tgatacaagc atacaatgta atgaccaaat 13200
caggatcatt gggaaatcca tcacctcaac catttatcat ttctttgtat ttggaacatt 13260
ccaaatttc tcttctagct atttcaaaat agacaataaa ttattgttaa ctatagttaa 13320
actgttgtgc tatgaacaca agaacttatt ccttctatgt agctgtattt ttgtaaccat 13380
taaccaacct cttttcatca tctccttcct ctgactttcc caacctctgg taaccaccat 13440
gctactctct gcctccatga aatcaacttt tattttaagc ttccacgtgt gagtgagaac 13500
atcacaggta agtgacttct tgccatccaa ttttgctagc tgtgtgtgaa gaaaaaagct 13560
tgctttcttt ttttctaaaa aggagtttca gagtggaatt gctgctaata ctttgctctt 13620
tcatttgtct tttattttaa tgaaaatttc acacacagat aactagagag tataaatgaa 13680
ccatactgta atctgatata gttttatcca attttaaaaa tgatttgctt tttaaattag 13740
aatagttttc ttttacttaa atacaaaagc attacaaata aagttgaaga aatctatgac 13800
tctctactat atattgtttt cttatgagat ggagtctcac tctattgccc aggctggaga 13860
gcagtgtctc gatgtcggct cactgcaacc tcagcctcct gggttcaagg gattcttgtg 13920
cctcagcctc ccaagtacct gggattacag gcgtgcacca gcatgcctgg ctaatttttg 13980
tatttttagt agagacgagg tttcaccatg ttggccaggc tggtcttgaa ctcctgaccg 14040
caagtgatct gccagcctca gcctcccaaa gtgctgggat tacaggtgtg agccaccaca 14100
cctagcctct cctatattct ttacctttct ttttatttcc agaaggcaac attatctaga 14160
ctttggtata aattattgtc ataattgttt ttatggtttt ctgtatgtgt gtatatattt 14220
atctaaatat gatctctagt ataatttgtt aaaattactt ctgtttttat ataccagcaa 14280
aaatggtttt acacaataac ttaaaaaatt aatatactta tattaatttt atttttattg 14340
atacataata cattacatat ttatggggta caggtgatat ttggtgatgc acttagaatg 14400
tgtaatgatc aagtcagggt atttgtggtt tccatcgctt tgagtattta ttatttccat 14460
gtgctgggaa caacccaagt cttctagcta ctttgaaata gacaatacat tgcttttggc 14520
catagtcact ctactttgtt gttgactaat agaacttcta ccttctattt aactgtatat 14580
ttgtactcat taacctacat ctcttcatct ctccctccta gacacccacc caccccttcct 14640
agcctccagt atttatcatt atactatcca catttataag atcaacattt ttagctgatc 14700
taaaatgatg agtgagaacg tgtgatattt cctgtgccta ggttatttca cttaatattc 14760
tccagttccg tccatgttgc tgcaaatgac atgattttac tgtttttata gctaaatagt 14820
attccattgt gtaatatacc acattttctt tatccatcca cttatggaca gttaggttga 14880
ttccatatct tttctattgt taatagaaat tcacaataga aaggttgctg tgataaacct 14940
gagagacacc agaaggaatt ttaacatatt gaccatacta aacaatattt aacatattga 15000
ttgtattcag ctatctttta caatgtggtg tacagactct aaaatagctc ctaattgtcc 15060
ctgtcctatt tttttttaa tactcatgtc cgtgtataat ccccccttgt ctgtggatgg 15120
aaactgtgac ttaacggtaa caaatagaat ttggcaaatg tgatatgtta agattataat 15180
gtctgctatg ctaggagatt ctctcccttg ctggtttcaa tgaagtaagt ggtcatgttg 15240
gggaggccca tttggcaaag aactaagggt gacttcaggc caatgactaa ctgagaactg 15300
aggataacct ctgatcatta gctagcaaga aatggagttc tcatatctac aaccataagg 15360
aactgaattc tgctaacaac cataggagct tggaagcatg tccttctccc gttaaacatt 15420
cagaagagtc tgcagctgtg gctcgcactt tgataactgc ctcatgaaaa attctgaagc 15480

-continued

```
agagaaccaa actggatttc tgacccagag aaactgtgag actataaatg tgtgttgttt  15540
taagtctcta aacgtatgag aaattgctat gcagcaatag ataaatagca cactaaatta  15600
gttaatacta ttactttatc ggtagatgct ttaaggtttt ccacatataa gataatatca  15660
tctgtgagca gagatgatta tacttccttt ataattcagg taccttttcc tttttcactt  15720
tctttttat tttggcctac ttgttctggc taggacattc agtattatgt tgaatagaag  15780
tggtaaaagt ggataatctt gtcttgtact ttatcttaga ggaaaagctg tcagtttttc  15840
actgctgaat atgatgttaa ctatgaactt tttatacatg tatttactat gttgaggtaa  15900
tttccttcta ctcctggttt aagtgttttt tgttttttt ttttttttt ttttttttt  15960
ttaaatcatg gaaggacttg ggttttatca aatgtctttt ctgtatctat tgagatgacc  16020
aatttgtatt agtcagcgtt cttcagagaa actgaaccaa cataaaaaaa ataaaattaa  16080
aaaaaaacta aggaaatttg ttatgggagg tggctcatgt ggtgttggag ggcgagaagt  16140
ctcactatct gccacctgcc agatgtaaag ccaggaaagc tggtggtgta attcagtctg  16200
aatccaaatg cctgagaact ggtggagcca gtggtggaac tcccagtctg aaatcaaagt  16260
cctgggaact gtgggaactg agagagctgg aggtgtaagt cccagaatcc gaatgtttga  16320
gaaccaggag ctcagatatc tgagagcaga agaagatgga tactccagct caagaataga  16380
gaatttgctc ttcctctgcc tttttgctct atttgggccc tcaatggatt ggatgatgtc  16440
agctcatgtt ggatcttttt tatgcagttt actaattcaa atgctaatct aaaatgtgtt  16500
tgtatattca tttgcctcaa catttctttt cttttctttt tttcctttct tttcttttt  16560
tgagatggag tgtctctctg tcacccaggc tggagtgcag tggtgcaatc tctgcctccc  16620
aggttcaagc gattctccta cttcagcctt ctgagtagct gggactacag gtgcacacca  16680
ccacacccaa tttttgtatt tttgtatttt tgttagagac ggggcttttc cgtattggcc  16740
aggctggtct cagactcatg acctcaagtg ttccgccgaa ctcggcctcc caaagtactg  16800
ggtttacagg tgtgagtcac cacgcctggc ctcaagatat ttttaaaatt cccttttgat  16860
ttcattttga tccactgctt attccagagg gtgtagttta attctcacat ccttgttaat  16920
tttctagatt ttctgatatt gatttctagt ttcattacat ggttatgagg aaagacttga  16980
tatggtttca atcttcttag atttgttaag acttgttttt tgacctaaca tgtaatctat  17040
cctggagaac gctcctataa tacacttgag aagaatgtgt attttgttgt tgctgggtgg  17100
aatgccctgt atatgcctat taggtccatt gggactatag tgttcaagtt ttctgttttc  17160
ctattgatct tctgtttgga tattttataa tggataaagt attgaaagtg ggctatcaaa  17220
atctccttct cttattgtgt tgctgtttct cccttcaatt ctttcagtgt ttgcttcatt  17280
tatttaggtg ctctgatgtt ggatgaacat atatttataa cggttatatt tttctggaga  17340
attgaccctt ttcttattat atgatgtcct tcatagcctg ttatgacagg ttttgattta  17400
atgtctattt tgtgtgggat aaggacacac accccttgcg ggttatcttg cggttcttgc  17460
agttaccatt tgcaaaggta cccttattat cacttgattt tcatcctatg tgtgttctta  17520
agtctaagtg agttcttggg gacagcatgc tgttgtattt tgtcatgaca tgctttgact  17580
cagtattatc cttctttctt tccttccttt tttttttttg gtttgctaat attttgctga  17640
ggatcattcc atctatattt ataaaagaga ttggcctgta atttttcttg cttataacgc  17700
cattaacagg ttttggtatc taagttattc tctggaagaa catgtgtaag attgtgtatt  17760
atttattctt caaaatttgg tagaattcag cagctagact ctgatccttg agttttcttg  17820
gggaagtctt aaattaatta tgaatttagt ttttaaaaat agctatgaga tagtcaaatt  17880
```

-continued ttgtatttac ttttatgtca gctttggtaa gttgtatttt tctagaaatt tgtccactta 17940
ttctcaaatt taattttaca aagttgttta tcttcagacc attttatcgt ttatcattta 18000
ttgcatctgg actgatgttt tctcttacgt tttgatttt aggacattct ttccctttt 18060 tccctttatc agtgtcagca gtgttttaca aattttgtta atccttttga aaactgggtt 18120
ttggttttgt taatcttctc tattgtatac ttgatttgtc cattaatatt tctgtccatt 18180
atttcttgct tttattttta ttgttgattt ctttctactt actttgagtt taattggtat 18240
tttttctgac tttttgaagt gaaagtctat ataattaatt ttcagccttt ctccatttct 18300
aatacatatg tttaaactta tatgattttt gtaacatttt atcttcattg tataagtttt 18360
aacaagtatc ttttgtcatt taattaaatt tcattatgat ttcttatgtg aataatggat 18420
tatttcaaat tatatttttt attttccaat gtatgagggg atctactagt tatcttcttg 18480
ttaaaaaaat tctggcatat actgtctgtt caatattata gtactttgaa aatttttgag 18540
acttgcttgc tttttaaggt ttgtagaata tctcttctat attctttttc ttttattctt 18600
gttttctggt tcatatatct taactaattt tactgtatcc tttaatccct tttgcccttt 18660
tctcttttta ttcttttttt gtctcaatac ttcagttggt aaatttttctt ctaattcttt 18720 atgcctacct tgcagttaaa tgtattcatt taattattaa tttcagatat atatttttac 18780
atagcaaatc tctttttgac ttcttattgt attcatttta ctgtaaatca ttcaatctta 18840
ccttttagct gtttgaacat attaaacata gtaatttaaa aatctctatg ggtaactcca 18900
gtataagtat gtgtttgttt ctagtgtgtg ctttttcctc ttggttttct atcatgttgt 18960
ttcatttacc tccaaacatg aatgtgttta tgatgaatga gagtcactga atatttaaaa 19020
aatcatagag atattttgaa gctggaagaa tgttcttttc atccagacaa gatttatttt 19080
gtttctgcta tgcagctatg gacactagca attctcattt accttaattc aatcaaggac 19140
tgagaatact gaagtatgaa attaactctg tctgcttcca gttcatactt cttccctgta 19200
cctcttttct taaatttttt ttaaaatttt atttcaacag catttggagt ataagtggtt 19260
tttttttacg tggatgaatt atatagtggt gaattctgag attttagtgc atccatcact 19320
caagtagtgt acattgtatc taatatgtag ttttttttaa tccctagctc ctcttccatc 19380
ctctcccttc tgagtctcta aagtccatca tatcagtctg tatgcctttg tgtactcata 19440
gcttagctcc cacttataag tgagagcata tggtttttgg ttttctctgt agctctttag 19500
aatcccaaac tgtagcctaa gggaaaggtt tccaaggtgc tctccttatt gcactccaaa 19560
gtatgatttt tatctcccta actctatgaa tctagcaaac actttgctta acttttcagc 19620
atctcaagtg ccttttctga atttgacaga tacacgtcag aaatgtgctc ccaaatgcct 19680
agcttatctc tctttattaa cttctccaaa tctttgccaa tagctatatg tcttaactgc 19740
cttgtttgct ctttagagct ttgtaacaca tgcattttta tagtttattc tgcttttcaa 19800 gttttttca ttgaaataat tcttgtaatg accaatagtc tagtatgctg ctgtaagact 19860
tctatagctg ttaactcctt tcatatttca atttctttat gtgctgtttt ttgcaagaat 19920
tcctaggctc cattttctaa ttcatacgtt ggcaaatgat gaatgtgata tgacaatgat 19980
gacctctgtt ccagccatat actttttaa agaaaatttt attggaacac agtcatgctc 20040
tcttgtttac atattatcta tgacttcttt tgtattacag tggcaaagtt gagtaattgt 20100
ggaagagacc atatggccta caaaggctaa aatatttact atcttgttca ttaagaaaaa 20160
atttgctgac tcttattgag atttattttt cctttattca actttctgaa gtttgtcaat 20220

-continued

```
tgatttaaaa attttaatga cttttccttt ctaaattata tatttttata tctaacatta  20280
ttgtgccatt tctatatttt tgctatattt tttgccttaa ccaaacaatg tgttttaatt  20340
gagtcagtga ataaagaact cactgaaagt agaagtggaa acctaagcta taagctacta  20400
tattatataa gcttctcaac ctataattgt ttttccatta ggtttgtaaa attagataat  20460
cctacatctc acattatgat tctaatcctt gtgttcggta ggtaataatt gatctacaag  20520
agcaaggaaa gtgaaaggaa cagttagatt catgccatac tctttgataa attctgaaat  20580
gaaacgtggg gaacataagg attatgaggt ttttatccag aacgtatagg ctgctttgag  20640
caaagcaagt tgagaaatat atgtgcagag atagagatga caaaggagat ggggatgtgg  20700
agagagagag atcttatcat cagagctgct ctgttttgac atatgaccca aagatcagac  20760
ccttatatga cccttagaac ttctaggtgt aattatgtga gagcttccag agcaagttaa  20820
tgtgcagaga ggataatttt tcctcctctt cctctcatgt tgccaactct gactcctaac  20880
tgagcagctc agccctgggt tatgcaagaa aactccatgt cttatttcaa aagtagactt  20940
ggccacattt aaccaaacaa gttttaaaaa tgtattatgc tatgtttatt tcctataggt  21000
aagttggatt cttgggctat ctattaatca ttttatttag accaattgta taaagaatgc  21060
tgacaaatat gtggtaaaga taaaaatcat gccactggaa tgattaaaaa agagttataa  21120
tgttattgac ataaaataac aaaagcacta ctaactatga aactttaaat atccacctga  21180
tgacattgac caatttgact tcatttccac tttagaccaa aattttccag gtagggtctg  21240
gataaccatt ttaggtaatt tctctgaatc ctttccttga gaaacagctt ttgagaatcc  21300
tcagtaaatg tcaaaaacaa actttctttt taaatttata gatagctaca ttgcatatat  21360
tttatttga tttctcctta atgtactttt agtgaaaata ataatttatg ttcaatgtca  21420
ctgatatttc ttattacatt catgtgatct aagactaata gttgaaaaat ggtttggttg  21480
caggttaata tttaacttta gtcagatata aaataatgca ttttctttaa gcacaaaatg  21540
tataacttta gatatttcaa atcatattat agaagatctc attatcaaaa taataattaa  21600
gtattgaaaa aatacccttc tcagggaaga gaaagaagct ctaggtgact tgagatgttc  21660
tttatggtat tctttattgg ctgttctgat gctgtattta accactatat tttaacaggt  21720
aagttatttc cctgaggatt ttattttata gattacaatt attatattgc ttatgtcttt  21780
gcctttttct cttagggcaa tcctaatata caattaaatg ctaaatcaaa tggaaaatag  21840
gagtaaaatt ttgatcagaa ccacctccat tgtgctatat tatacagaga agctttcaaa  21900
ttttatggat ggaagaagca gttatataaa gaatactttt tagtatttgt ataaaaaaca  21960
acaaaaaatt aaaaacccta tgaaaatctt tgaccattat atatgatgtt cattttactc  22020
atgtactaca tgattttacc tggtttaaaa tgtttttctt tttttgtaat aaaataatga  22080
gaattatgta aggtaatttt ttttaattac gagaccattc tctaagacat ggtcatgaaa  22140
agcaaaatag caattcactt tggtgggtca actttgaagg agaacttgaa gtgtaaatct  22200
tacaaaaact atcttattta caaaaagata tacataagga aataaaatagt aatatagatt  22260
tcttaattgt tgctctaaag aactacaaat tatgatgcag cacttgtcta gaaaattctt  22320
tcttgtttat gcttttcaat gttatcatgc acatgcaatc aaacaaaaaa taataaaggg  22380
aaagaataga aaattttaga atcaggcttt tttaatgatt accacaaatt aatattgtca  22440
cttgttaggg aatatgctgt gtattatcaa tgcaaaattt agcataagac agcataataa  22500
gacagtaatg gttcatttta gcttttgtgt cacattcaat aactggaaga attttctagg  22560
actttcaaga atcacatctt atttgttgat gttggccaga tactgtgctc ttgagtggct  22620
```

ttattttaat atattagtgt agtctcagaa gccgtggcaa ggtacggcag cacaaattaa 22680
attaattagg cattgattga aatgtttctg tttgctaaat atttattcag acatagagac 22740
ctaaatacaa ataatgcttg gtcccattac ccagatatct cagagaccaa tgcagataat 22800
aaatctgtat cattcattgt gatatatgct ataatagaga tactactcag gacaaaattt 22860
ctctttcttc cttttaagtt ttaaattcca aaggtcttat tttaagagaa gatgtagata 22920
ctgaactcca atgaaatgca aatgttattt aaattgaaga aatatagggc agacttttat 22980
gagggaaatt gaatatttta ttgcttaaaa gactctttcc tttgaataat tgaagttgta 23040
aagaaagcaa attaatgggt aaggaaacta ggaagatgca tattggtgtt cctgaaattt 23100
tacaatgtac tttaactcta gtgcttagta taatttcttt catgttgagg cactggtaag 23160
tcctattctc ctagataaaa atcttcagtg ggattacgcc tctgcgtttc atggcccaat 23220
gagagctttt gattttatta cagattacaa taagtcatag actgttctct cccttctggt 23280
ttgagtgata ctacaccctt gccagcacca cagatggaaa aattgtaatt aaagtgtctc 23340
tgagaaatcc ttttctttgc aatcttccca aatcgtccat atttttttgt gtatgttgaa 23400
tgtatatctg accatcaaat aaaatacttt cagaattgtt ctagaaaata tccttgcaat 23460
aagattgaat gtgtttatct aggaaagaaa gttctgttgt gcttctcaaa gtgaaatttg 23520
tggacccctt gggttcccgg agacatttta agggtatctc tgtgttcaaa actattttta 23580
gaattattct aagttttttt tgtcttttct agtgtattga cacttgaatt aattacacaa 23640
catagtttta cctgttggca cattagtatg aatcaaacgg tggcaccaaa cactactagt 23700
agtcactgta tttctcccaa ttactgcact tacaggaaaa aaaatgccag ttttactcct 23760
tgatgaatag taacagttat tggttttatt taaactccac tttggaatac acatcatttt 23820
gatattcagt gtgataaaat gggaagtgct cataaagtac ttctaatgca tattgaaaat 23880
tggcagttgt ctttagaaaa agcactggag cagctgagtt gttaactgaa ctttttttaa 23940
atgtgacatc atttttactg gacagcacag acttactcat tcatacttgg atatttggca 24000
ggtatcttaa tgcaaatgct caagtgaccc tactaataaa gaacaaaaac aaaaactgac 24060
agtgtttgtt gccaataaca aaatttgagc ttttgagaaa aatcaaactt tgagaaacct 24120
gtattcacta ttctgagcct gacagctttt caacacttaa agacttatcc aatgaaatta 24180
atggtggtat taacaaatgt gatgttttaa tattgcatga tgaaatgtgt caacattagg 24240
aagatctgga taacccagtg gacgaatgtt ttaagatgat caataaatta ggttaaaaaa 24300
tcatgcatga gtaaaggata tattcaaagt ataagacaaa ccaatggatt taatgtggca 24360
gcatataaaa atgtcgcaga ttccacattg caactaacct ttaagaagtt attacttgtt 24420
gagctttgct atattacatt gaggaatatt cacaattacc tgaaagctat acagtgaaat 24480
attacctcct tttcatatta tacatacatg tgagaggcca tattttcttc acatacttca 24540
attgaaacaa catatcaaga gattgaattg gagccacata tgagattaca gttatattct 24600
ttaatccaga cattaaagag aattttacta ataaaccaat gatttctgtt ttctgtaaat 24660
ttttaaaaaa atgcttttta agtaaaaaat gttatttgat gaacatgtga caggtttata 24720
attgaatttt taatgattaa aacaacactt aagagcagga ggggcagagc aagatggtca 24780
cataggtctc tccagcaatc attcctccac tgaaacatca atttgaataa ttattagcac 24840
acaaaatatc acctcagtaa accaggtgaa agattactgt acctagttct agcacaataa 24900
taacaaaaga tacattgaag agggtaggaa agatagtttt acgttatctg catcaccccc 24960
ctcaacccca gggagcatag tgtggagaga actgtcatct gctttgggga aaagagggaa 25020
gtgagcacag gactttgcct ggactccaat atcaggccta ctgcagtaaa atccagcact 25080
ggatagaacc tcatggcccc agactttagg ctgttatttg acggctgagc ctctagcccc 25140
atgctggtgc caagtgagac catgtggccc taggcttcaa gcttgcatgg tggactcagt 25200
ccctggacca caccatggat gggttattag tggcccaacc tctgaacagc acttagtgac 25260
acggatgccg cagtggccct gagctttacg catgcctcag tgctgcacca gtcacagtgg 25320
tcccaggctt tgggactatg caaggcagcc tgcccagaat tttggatag gctgattgtt 25380
gaaggacttt tccagacaaa ggcaatctgc aaagattgga ataagtacct acttccagag 25440
atgtttatac attgacacat tgtcacaaga gtcaaaagca atcagggtaa catgacgtca 25500
gtaaagagag aaaataacgt gccagtggcc aatcctaaag aaatggagat gtatgaacca 25560
cccgaagaat tcaaaataat tattttaagg aagcacagca aacttcaaga aaatacagag 25620
aaacaattta acaaaatgag aaaaatgatg agtgatcaga ataagaaatt taatagaaag 25680
gttgtaataa ttataaaaaa gaaacaaatt tcagagatga aaaatacaat gggtgaaatg 25740
agaaatgaaa tagagagcat caacagcaga attgatcaag tagaagagtc tgtgaactta 25800
aaggtaggtt atttgaaaat atagatagag aataaaaaaa cagaatgaag aggaaggaag 25860
aaagcttatg ggatttatgg gacatcatca aaaggacaaa tattcaagtt acaaggggga 25920
aaggagacaa gaaattaaaa gtaatagaaa tcttaagtaa ataaatagta gcaaaaaact 25980
tttaaaacct ggaggatgat gtaaatatcc aggtaaaact gagagaaaag tccccagtca 26040
gatttaatcc aaagaagatt aacccaagat atattaaaat caaactgtaa aatatcaaag 26100
acaaagagag gattctgaaa actggaagat aaaaaagcaa ataacatatt agaaagtttt 26160
aatatgacta gcagcagact tagcagaaac tctgcaggcc aagagagtag gatgaaatat 26220
tcaaagtgct aaaagaaaaa acaaagaaac aaacaaaccc atccaattga gaatattata 26280
cccagtaaag ctgtgcttca gaaataaagg agggataaag attttcctgg atgaacaaaa 26340
gctgagggag ttcattacaa ttatacctgt cttacaagaa tgttaaagcg agtttttcaa 26400
gctgaaagaa aaggatgcta ataagtaata taaaaatatc tgaaagtata aaactcactg 26460
gtaaaactac agtaaaattc agaatactca tactataatg atggtgatgt ttaaaagaca 26520
aaactgctaa aataataata gctataagat tttgttaaag gacatgcaat atggaaagat 26580
gtaaattgtg gtatcaaagg tgcaaactgt ggggaggagt ggagtaaaaa tgtggagtgt 26640
tttttttttc tctgtaagtg gagctgttat taacttaaaa taaccagtta caaatatgtt 26700
tattttttgt aagcatcatg gttaagcaca aaacaaatac tgatagtaga tacacaaaat 26760
ataaaaagca tggagtcaaa acataccatt atatatatat atatgtgtgt gtgtgtgtgt 26820
gtgtatgtgt atatatatat atatatacac acacgtttta catgataaat tacatagaaa 26880
tttctttttt aattaaaaag gaatatttac attttttca gttgtaattt ccactatttt 26940
aaatatccat agatataacc cacataaaca acagatcttt gggattctca ataactttta 27000
agagtctaaa ggggtcctga gaccaaactg tttgaggacc atggtgttca aatattaacc 27060
aatctctttt cttcttattg tcatgtcttg aatgctgggt gatgaatgaa cctttacact 27120
taatgtattt ttttaacagg taagatttct tcaatatcca aaacatttca aatcattttc 27180
ttcagtattt ttcattgaat ttttaaccac ataaggcaat ttcaactccc ataatgtggt 27240
ttcaacatca atcaacacta ttctactttg aatgaataag aattcatatg aaaaagtaga 27300
gtgactattg ttcttttctg taacattgag aaataaagcc aaaaggcagg attctactca 27360

-continued

```
tttgcattct agtaaaagat caaggagata gtgtgttttt atcactcttt acaataatgt  27420
aaactaatga tagtcactta atcccttgca ctttttgggt tacatagaca aaatattgga  27480
acaagtaact attttgtgtt gaaatgtcat tttatactgt aaatgcttag atttcaccac  27540
taaataccta gattcaaaat ttggctttgc tactaacaga tgtttacccg taagttgcac  27600
acttctctct ctcggtcttt tttttttttt tttcaggtgt gaaatattgc tattaatagt  27660
gtctatctca tagggtggct aagatgatta aatgagatga tatagtttaa gttctcaaaa  27720
aagccaacaa tgattgttac ctttctttta ggtgttgggt atcagcctca atttctaaag  27780
aagaatctct tttgcctccc aattgtgctg aattggaaac cttacctatg tatttattta  27840
ttcattcaaa aaccatctat tataaaccat atttgtgcca aactctaagc cagttactga  27900
aaacacataa gtcaataaca gcacaatcct tatcctccag gagttcataa tccagtcagg  27960
gaaaaggaga cacacagata aagagaggag ggatagagcg aagacattgg agaaatcagg  28020
agcataccaa caccctaatt tttcacagca gggagccagt caattcagtc caacactgaa  28080
atacatagct taataactac atgtttccaa accattgttt cataatctat ttccttaatc  28140
ttagaaagat tactgtcttg tggtaagaag acattaactt caaatttggt atttctttta  28200
tttcacttta gtttattttt cttctataaa atcaaaataa attacagtct tttaatttaa  28260
atagcatttt caacatattt ttctttcttt tattctctct atccagttca tttaagcatg  28320
caaaatgctt agggaggagt cttaaattgt atttaacaaa cgttaatggt gtttatttct  28380
ggatactagg atttgaaatt agcttttcaa aaatattatt taaactttcc tgcaatactt  28440
acaatggata attatcattt ttaccaaagc aataaagtgt ttttttttcct ataagagaga  28500
tataatggca ttatgctcac agtggaaagg aagtaaagag gaggtgctac tgtttgggga  28560
aagagtagct gaggagaaag agggagatca gtagttacag tattagaagc attaattgtg  28620
tctttaaggg ttaaacagag gctctctgat ttctgaatgt taccttatgt ttttataaca  28680
ggtgagtctc actgaactta taaaaaaatt tactttgaaa taattataga tttgtaggaa  28740
gttgcaaaga gagtacagag atttcccatg taccttcat cctatttccc tggagtggtg  28800
gccatcggag ggagagatca ttcacaggca tgactgaaga aagaccccaa atcctaatgt  28860
tcagtcttta aagaatagac tggccaacca tttttttttc gtgtgtgatt ttcctgaggc  28920
tttagatagg gctaaaacct atgtgggtag acagggaaga tcgaaaccag aaaattgatt  28980
attgttaaca atgtgtgttt atagttctat gtcattttat cacatgtgta agtttatgta  29040
cccatcactg caaccaaata ttacatcact ttgtagattt ccctcatggc acccactatt  29100
cctccaccat ccttaactct tggcaaccac taatattttc ttcatttcca taattttgtc  29160
atttcgtgaa tgttatacaa atggaatcat acagtatgtc acctttttgag actggctttt  29220
ttgactcaac ctaatatcct ttgacatcca tccaagatgt atgtatgtat ttattgttca  29280
tttaaaaaat tgtatagtat tccatggtat agatatacca cagtttaacc atgctctatc  29340
aaaaaatatt ccagtttttta gctattgcaa acaaaactcc tatcaagttt tgtgtggata  29400
taagttttta ttcctctggg gtacatctcc agaaatgtaa tgctggatca taaagtaact  29460
gtatgtttag ctttgaaaga gatcaccaaa ctatactcca gagggactgt accattttac  29520
aatcccacca gcaatacatg agagatctat tttttctgca ttcttgctag tatttggtat  29580
cgttgctatt aaaaattcct taactcttct aatagatgta tgctgatatt tcatcagggt  29640
cttaatttgc attgcttaat gactaatgac attgaacatc ttctcatgtg cttatttgcc  29700
```

-continued

```
ttctgtatag cttgtttagt gaaatgcctc ttcacgtctt ttgattattt tctgattgga  29760
tgatttgtgt tttttagaag ttgaatgtta aaagatctat aaatcctaaa tatgagtcaa  29820
ttgtcagata cattgtttgc ggatagtttc tcccagtctg tagttgtctt actattatga  29880
tgatttccat ccctgccatc tctcatctct ccttttggaa ctctgggaca tgaattctag  29940
atattttgtt atagtctcac aatttattta tttatttttt atatctattt gctctttatt  30000
tttcagagtg ggtaatttct attgttatat ctttgaattc acttgttcat cactttgccc  30060
tctccattct gcttttgagc atagctattg tttttcctat cttgggtatt atggtttttt  30120
agctctaaaa tttcaagttg attctttttc aggtcttcta tttctttgct gagacatccc  30180
acttccttca tttgtttcaa gaatgttcct acttggttct taagcatttt tatgatggtt  30240
gctttagaat ccttgccaaa taattctaac atctttgtca tctaattagg gtcatgatct  30300
tctgattagc ttttctcatt caagttgaga atttcctggg ttttgatgtg acaaatgatt  30360
tttaattgca tcttcgatat tttaggtact ttattttatg actctggatc ttacatcttg  30420
tgttttagca aacatattct gatactggta agatggaaag tacaggtttc ccataaggcc  30480
ttgtttgaca cccttggaga aagggcactt tcttactgtg ccccatatag gataccctga  30540
catcacaggg gctagaagcc tccttgcatc gaaggttaat gaaggctaaa gttccagctt  30600
ctcacttgtt ctcctctgac acttccagag agggaaaaga gcacctcatt gctgctgatt  30660
cggtggaagt ctaggatccc caagtagcct cccttgacac catcaagagg gaccttgtta  30720
gtatagtgca ggtataaatg tcctggctcc ctacattttt ttcttctctt atactacctt  30780
ggctaagggt gaaagttggg aaagggaagg acatatccat ggatagggct aaggtgaatt  30840
ctgtggtgtt tgactggggt agtgtggcta ttttctgaaa gtttctgtc ttgctacact  30900
gtccttttc tcatgctttg actagatgaa actagtcaac agcaaaaaaa attttccttt  30960
ttgctggctc taatttgtat tttccagttg tgagtgtctc caaaagccaa tctgggacat  31020
atgaagtaaa aagaaaacct agagagctca tctctgtatt gtttcttggg tctcaaggtc  31080
tctagccaaa ttgcattatc tgcacttttc aatctttatg tttgatttat gcataatgtc  31140
cagagatttt agctacattt agtgtaaaga agagggaaaa gtgtgtctac tccatttggt  31200
ccagaactgg aagtactctc actgaacttc caaaagattt taatataaag aattgttggg  31260
gcatttatac tccaaagcct cgttgcttac tttatcagta gaaagatcac atatttaggt  31320
tccgaaaagt gctatgccgt ttaatgtata gagcatggtc ttgcttaagt gaacctagtt  31380
tttaaatagt agtaaacttt gacctcgaga aaggtaattt aattgctctg aactttatct  31440
cctgttcttc taaaatgggg ataataagtt ttgcatctga acttaataaa ctgtctaaca  31500
aaagtctgag tagtgaacat tagatataca caatgtaaat atataagctt atataagtac  31560
ttaacagctc taaaattatg gagggtttgg ggtaagacag aaatgctaag ttttaaaatg  31620
acttttcaag gatgtatggc aacacattgt ccttggcgtg ctggatggca atgcttaatg  31680
caacttagtg tgctgactta ggacctctaa aaggacattg tattaatttt gaaacagaag  31740
aattacattg caacagaggt tgaaaaaaat tataggtgtc aactgagaac tgctctctac  31800
cagaacctag gtattaattg gccaactttg ctagttattc ctctgaaacc tgaatgaaga  31860
gaaggtagta aaggaaatca tttagtaatg gaaaaaataa acacaagatt ttagtaggaa  31920
gaaggtacta aaagccctgt taaaagagtc ctgggagctt ccttgactgg catttgaaat  31980
taatcttata ttttcctcat aagcagttgt tagcatagca gaattttgat ttgtttagaa  32040
gtcaaatgtg atttactaat tcaatccctg tggtttgagg gagaaaggag taggtcccta  32100
```

-continued

```
ttagaactgt gaaatcagta cagtttgctc tcataaatgc tcatacacaa ccctcctcac  32160
ttcctctttt tcttgtggtt ctttttagtc cccaaagtcc agcaacccct tttttcccct  32220
tgaccaattt aaaacaaacc atttgaatgg aatcgtagat gattgcaatt tagtgtggat  32280
ttagttgcat tgaaaaatgc tgtcacatgt tggaaaaaaa agatcaaaga tcatttctcc  32340
tctagaaaag cttcaggctc catattgaga tgtattgggg atatttcatt cttcagctct  32400
caaaatcacc ctatagagtt gccttcacac atatttaata acttgttgac acattgctat  32460
ttatgatata aaataactga tttatctatt tgatataggt aaaaaatgct gatcataacc  32520
agatattatt gtaatagtat cacaatcata cgtgtgtgtg tttgtgtgtg tctgtacgtg  32580
tatatgtgct tacagagtgt atttgcaggg aaatgaagaa tgggatcaat tgcttgatta  32640
attcaaattt atatcacact ttaaaactgc aatgatctga attattgtat gttccgaaga  32700
taacttatta agccattgct tttttggttt ctttcttaaa ttgtatttaa aattggtcaa  32760
atttcaaata ttaaatacag gacttacact ttttaaatat actttccaca ggtaatctgg  32820
cccttttctc cccctgtcat agatcactgg tgccttttga aaaatcctaa gttatacatc  32880
agttattaga tgactggggc ccacctgcat gccctagtcc tgaaagctac attaggatat  32940
atgtttcatt tccactcttg tttgtttcat tttcaggata agttgccttg attctgacat  33000
ttggcccagc ctgtactggt gtgccgcaat gagagtcaat ctctattgac agcctgcttc  33060
agattttgct tttgttcgtt ttgccttctg tccttggaac agtcatatct caagttcaaa  33120
ggccaaaacc tgagaagcgg tgggctaaga taggtcctac tgcaaaccac ccctccatat  33180
ttccgtacca tttacaattc agtttctgtg acatcttttt aaaccactgg aggaaaaatg  33240
agatattctc taatttattc ttctataaca ctctatatag agctatgtga gtactaatca  33300
cattgaataa tagttataaa attattgtat agacatctgc ttcttaaaca gattgtgagt  33360
tctttgagaa acagcgtgga ttttacttat ctgtgtattc acagagctta gcacagtgcc  33420
tggtaatgag caagcatact tgccattact tttccttccc actctctcca acatcacatt  33480
cactttaaat ttttctgtat atagaaagga aaactagcct gggcaacatg atgaaacccc  33540
atctccactg caaaaaaaaa aaaaaaaaat aagaaagaac aaaacaaacc ccacaaaaat  33600
tagctgggta tgatggcacg tgcctgtagt cccagttact caggatgatt gattgagcct  33660
tggaggtgga ggctacagtg agctgagatt gtgccactgt actctagcca gggagaaaga  33720
gtgagatcct ggctcaaaaa aaccaaataa aacaaaacaa acaaacgaaa aacagaaagg  33780
aagactgaaa gagaatgaaa agctggggag aggaaataaa aataaagaag gaagagtgtt  33840
tcatttatat ctgaatgaaa atatgaatga ctctaagtaa ttgaattaat taaaatgagc  33900
caactttttt ttaacaattt acattttatt tctatgggaa aaaataaata ttcctcttct  33960
aacaaaccca tgcttgattt tcattaattg aattccaaat catcctagcc atgtgtcctt  34020
ccatttaggt tactggggca aatcagtaag aaagttctta tatttatgct ccaaataatt  34080
ctgaagtcct cttactagct gtgaaagcta gtactattaa gaaagaaaac aaaattccca  34140
aaagatagct ttcacttttt tttttcctta aagacttcct aattctcttc tccaaattct  34200
tagtcttctt caaaataata tgctttggtt caatagttat ccacattctg acagtctaat  34260
ttagttttaa tcagaattat actcatcttt tgggtagtca tagatattaa gaaagcaaga  34320
gtttcttatg tccagttatg gaatatttcc taaagcaagg ctgcaggtga agttgtgctc  34380
aagtgaatgt tcaggagaca caattcagtg gaagaaatta agtctttaaa aaagacctag  34440
```

-continued

```
gaataggaga accatggaaa ttgaggaggt aggcctacaa gtagatattg ggaacaaaat  34500
tagagaggca accagaaaaa gttattttag gctcaccaga gttgttctta ttgcacagta  34560
acacaccaat ataccaaaac agcaggtatt gcagtagaga aagagtttaa taattgaatg  34620
gcagaaaaat gaggaaggtt gaggaaacct caaatctacc tccctgctga gtctaagttt  34680
aggattttta agagaaaggc aggtaaggtg ctgaaggtct ggagctgctg atttgttggg  34740
gtatagggaa tgaaatgaaa catacagaga tgaaaactgg aagttttttt ttgtttgttt  34800
tgtttttttt ttgttgttgt tttttttttt ttttgttttt ttgctgagtc aattccttgg  34860
agggggtctt cagactgact ggtgtcagca gacccatggg attccaagat ctggaaaact  34920
ttttagatag aaacttgatg tttcttaacg ttacatatat tatcttatag aaataactaa  34980
gggaagttag tgccttgtga ccacatctat gtgactttta ggcagtaaga aactataagg  35040
aaaggagcta acagtcatgc tgtaagtagc tacagggaat tggcttaaag ggcaagttgg  35100
ttagtactta gctgtgtttt tattcaaagt ctacatttta tgtagtggtt aatgtttgct  35160
gttcattagg atggtttcac agttaccata caaatgtaga agcaacaggt ccaaaaagta  35220
gggcatgatt ttctccatgt aatccaggga gaaaacaagc catgaccatt gttggttggg  35280
agactgaagg tgattgaagg ttcaccatca tcctcaccaa cttttgggcc ataattcacc  35340
caacccttttg gtggagcctg aaaaaaatct gggcagaatg taggacttct ttattttgtt  35400
taaaggggta acacagagtg cccttatgaa ggagttggag atcctgcaag gaagagaagg  35460
agtgaaggag agatcaagag agagaaacaa tgaggaacat ttcatttgac ccaacatcct  35520
ttaggagcat aaatgttgac actaagttat ccccttttgtg ctaaaatgga cagtattggc  35580
aaaatgatac cacaacttct tattctctgg ctctatattg ctttggaaac acttaaacat  35640
caaatggagt taaatacata tttgaaattt aggttaggaa atattggtga ggaggcctca  35700
aaaaggggga aacatctttt gtctgggagg atattttcca ttttgtggat ttccctgatc  35760
tttttctacc accctgaggg gtggtgggaa ttatcatttt gctacatttt agaggtcatc  35820
caggattttt gaaactttac attctttacg gttaagcaag atgtacagct cagtcaaaga  35880
cactaaattc ttcttagaaa aatagtgcta aggagtatag cagatgacct atatgtgtgt  35940
tggctgggag aatatcatct taaagtgaga gtgatgttgt ggagacagtt gaaatgtcaa  36000
tgctagagcc tctgtggtgt gaatgggcac gttaggttgt tgcattagaa agtgactgtt  36060
tctgacagaa atttgtagct ttgtgcaaac tcacccacca tctacctcaa taaaatatag  36120
agaaaagaaa aatagagcag tttgagttct atgaggtatg caggcccaga gagacataag  36180
tatgttcctt tagtcttgct tcctgtgtgc cacactgccc ctccacaacc atagctgggg  36240
gcaattgttt aaagtcattt tgttcccgac tagctgcctt gcacattatc ttcattttcc  36300
tggaatttga tacagagagc aatttatagc caattgatag cttatgctgt ttcaatgtaa  36360
attcgtggta aataacttag gaactgcctc ttcttttttct ttgaaaacct acttataact  36420
gttgctaata agaatgtgta ttgttcagga caacttgtct ccatacagtt gggttgtaac  36480
cctcatgctt ggcccaaata aactctctac ttatatcagt ttttcctaca cttcttcctt  36540
ttaggtcaac aataccaaga ggggttactg tgctgggtaa tgtgtaaact tgtgtcttgt  36600
ttagaaagat aaatttaaag actatcacat tgctttttca taaaacaaga caggtctaca  36660
attaatttat tttgacgcaa attgataggg gggccaagta agccccatat gcttaatgat  36720
cagctgatga ataatcatct cctagcaaca taactcaatc taatgctaag gtacccacaa  36780
gatggcaagg ctgatcaaag tcgtcatgga atcctgcaac caaaagccat gggaatttgg  36840
```

aagccctcaa atcccattcc taatctgatg agtctatgga ccaatttgtg gaggacagta 36900
gattaaatag atctgatttt tgccatcaat gtaaggagga taaaaacttg cataccaatt 36960
gtacaccctt gcaaaatctt tctctgatgt tggagaaaat gggccagtga gatcatggat 37020
atagaagtac agtcaatgtt cagctgtacc ctcccacaat cccacttcct tcctcaacac 37080
aattcaaaca aatagactca gactgtttca ggctccagga caggaagtgc agtgtaggca 37140
aaattgcaaa aattgagggc acaggggtgg aggtgggggg gttgaataac aagctgtgct 37200
aaataattac gtgtaaatat attttttcat ttttaaaaat tgatttcttt tgcacattcc 37260
atgacaatat atgtcacatt tttaaaataa atgcaaagaa gcatacatcc aagctgccag 37320
ctgagttttt ttgctgcttt gagtctcagt tttctttctt tcctagagtc tctgaagcca 37380
cagatctctt aagaactttc tgtctccaaa ccgtggctgc tcgataaatc agacagaaca 37440
gttaatcctc aatttaagcc tgatctaacc cctagaaaca gatatagaac agctgccagc 37500
tgagtttttt tgctgctttg agtctcagtt ttctttcttt cctagagtct ctgaagccac 37560
agatctctta agaactttct gtctccaaac cgtggctgct cgataaatca gacagaacag 37620
ttaatcctca atttaagcct gatctaaccc ctagaaacag gtaagcgact ttttaattga 37680
aacatagtat ttgtacgtat ttatggggtt atgtgtgata ttttgataca agcatacaat 37740
gtaatgacca aatcaggatc attgggaaat ccatcacctc aaccatttat catttctttg 37800
tatttggaac attccaaatt ttctcttcta gctatttcaa aatagacaat aaattattgt 37860
taactatagt taaactgttg tgctatgaac acaagaactt attccttcta tgtagctgta 37920
tttttgtaac cattaaccaa cctcttttca tcatctcctt cctctgactt tcccaacctc 37980
tggtaaccac catgctactc tctgcctcca tgaaatcaac ttttatttta agcttccacg 38040
tgtgagtgag aacatcacag gtaagtgact tcttgccatc caattttgct agctgtgtgt 38100
gaagaaaaaa gcttgctttc tttttttcta aaaaggagtt tcagagtgga attgctgcta 38160
atactttgct ctttcatttg tcttttattt taatgaaaat ttcacacaca gataactaga 38220
gagtataaat gaaccatact gtaatctgat atagttttat ccaattttaa aaatgatttg 38280
ctttttaaat tagaatagtt ttcttttact taaatacaaa agcattacaa ataaagttga 38340
agaaatctat gactctctac tatatattgt tttcttatga gatggagtct cactctattg 38400
cccaggctgg agagcagtgt ctcgatgtcg gctcactgca acctcagcct cctgggttca 38460
agggattctt gtgcctcagc ctcccaagta cctgggatta caggcgtgca ccagcatgcc 38520
tggctaattt ttgtattttt agtagagacg aggtttcacc atgttggcca ggctggtctt 38580
gaactcctga ccgcaagtga tctgccagcc tcagcctccc aaagtgctgg gattacaggt 38640
gtgagccacc acacctagcc tctcctatat tctttacctt tctttttatt tccagaaggc 38700
aacattatct agactttggt ataaattatt gtcataattg tttttatggt tttctgtatg 38760
tgtgtatata tttatctaaa tatgatctct agtataattt gttaaaatta cttctgtttt 38820
tatataccag caaaaatggt tttacacaat aacttaaaaa attaatatac ttatattaat 38880
tttattttta ttgatacata atacattaca tatttatggg gtacaggtga tatttggtga 38940
tgcacttaga atgtgtaatg atcaagtcag ggtatttgtg gtttccatcg ctttgagtat 39000
ttattatttc catgtgctgg gaacaaccca agtcttctag ctactttgaa atagacaata 39060
cattgctttt ggccatagtc actctacttt gttgttgact aatagaactt ctaccttcta 39120
tttaactgta tatttgtact cattaaccta catctcttca tctctccctc ctagacaccc 39180

-continued

```
acccaccctt cctagcctcc agtatttatc attatactat ccacatttat aagatcaaca  39240
tttttagctg atctaaaatg atgagtgaga acgtgtgata tttcctgtgc ctaggttatt  39300
tcacttaata ttctccagtt ccgtccatgt tgctgcaaat gacatgattt tactgttttt  39360
atagctaaat agtattccat tgtgtaatat accacatttt ctttatccat ccacttatgg  39420
acagttaggt tgattccata tcttttctat tgttaataga aattcacaat agaaaggttg  39480
ctgtgataaa cctgagagac accagaagga attttaacat attgaccata ctaaacaata  39540
tttaacatat tgattgtatt cagctatctt ttacaatgtg gtgtacagac tctaaaatag  39600
ctcctaattg tccctgtcct attttttttt taatactcat gtccgtgtat aatccccccct  39660
tgtctgtgga tggaaactgt gacttaacgg taacaaatag aatttggcaa atgtgatatg  39720
ttaagattat aatgtctgct atgctaggag attctctccc ttgctggttt caatgaagta  39780
agtggtcatg ttggggaggc ccatttggca aagaactaag ggtgacttca ggccaatgac  39840
taactgagaa ctgaggataa cctctgatca ttagctagca agaaatggag ttctcatatc  39900
tacaaccata aggaactgaa ttctgctaac aaccatagga gcttggaagc atgtccttct  39960
cccgttaaac attcagaaga gtctgcagct gtggctcgca ctttgataac tgcctcatga  40020
aaaattctga agcagagaac caaactggat ttctgaccca gagaaactgt gagactataa  40080
atgtgtgttg ttttaagtct ctaaacgtat gagaaattgc tatgcagcaa tagataaata  40140
gcacactaaa ttagttaata ctattacttt atcggtagat gctttaaggt tttccacata  40200
taagataata tcatctgtga gcagagatga ttatacttcc tttataattc aggtaccttt  40260
tcctttttca ctttcttttt tattttggcc tacttgttct ggctaggaca ttcagtatta  40320
tgttgaatag aagtggtaaa agtggataat cttgtcttgt actttatctt agaggaaaag  40380
ctgtcagttt ttcactgctg aatatgatgt taactatgaa ctttttatac atgtatttac  40440
tatgttgagg taatttcctt ctactcctgg tttaagtgtt ttttgttttt tttttttttt  40500
tttttttttt tttttaaatc atggaaggac ttgggtttta tcaaatgtct tttctgtatc  40560
tattgagatg accaatttgt attagtcagc gttcttcaga gaaactgaac caacataaaa  40620
aaaataaaat taaaaaaaaa ctaaggaaat ttgttatggg aggtggctca tgtggtgttg  40680
gagggcgaga agtctcacta tctgccacct gccagatgta aagccaggaa agctggtggt  40740
gtaattcagt ctgaatccaa atgcctgaga actggtggag ccagtggtgg aactcccagt  40800
ctgaaatcaa agtcctggga actgtgggaa ctgagagagc tggaggtgta agtcccagaa  40860
tccgaatgtt tgagaaccag gagctcagat atctgagagc agaagaagat ggatactcca  40920
gctcaagaat agagaatttg ctcttcctct gcctttttgc tctatttggg ccctcaatgg  40980
attggatgat gtcagctcat gttggatctt ttttatgcag tttactaatt caaatgctaa  41040
tctaaaatgt gtttgtatat tcatttgcct caacatttct tttcttttct ttttttcctt  41100
tcttttcttt ttttgagatg gagtgtctct ctgtcaccca ggctggagtg cagtggtgca  41160
atctctgcct cccaggttca agcgattctc ctacttcagc cttctgagta gctgggacta  41220
caggtgcaca ccaccacacc caatttttgt atttttgtat ttttgttaga gacggggctt  41280
ttccgtattg gccaggctgg tctcagactc atgacctcaa gtgttccgcc gaactcggcc  41340
tcccaaagta ctgggtttac aggtgtgagt caccacgcct ggcctcaaga tatttttaaa  41400
attccctttt gatttcattt tgatccactg cttattccag agggtgtagt ttaattctca  41460
catccttgtt aattttctag attttctgat attgatttct agtttcatta catggttatg  41520
aggaaagact tgatatggtt tcaatcttct tagatttgtt aagacttgtt ttttgaccta  41580
```

acatgtaatc tatcctggag aacgctccta taatacactt gagaagaatg tgtattttgt 41640
tgttgctggg tggaatgccc tgtatatgcc tattaggtcc attgggacta tagtgttcaa 41700
gttttctgtt ttcctattga tcttctgttt ggatatttta taatggataa agtattgaaa 41760
gtgggctatc aaaatctcct tctcttattg tgttgctgtt tctcccttca attctttcag 41820
tgtttgcttc atttatttag gtgctctgat gttggatgaa catatattta taacggttat 41880
atttttctgg agaattgacc cttttcttat tatatgatgt ccttcatagc ctgttatgac 41940
aggttttgat ttaatgtcta ttttgtgtgg gataaggaca cacacccctt gcgggttatc 42000
ttgcggttct tgcagttacc atttgcaaag gtacccttat tatcacttga ttttcatcct 42060
atgtgtgttc ttaagtctaa gtgagttctt ggggacagca tgctgttgta ttttgtcatg 42120
acatgctttg actcagtatt atccttcttt ctttccttcc tttttttttt ttggtttgct 42180
aatattttgc tgaggatcat tccatctata tttataaaag agattggcct gtaatttttc 42240
ttgcttataa cgccattaac aggttttggt atctaagtta ttctctggaa gaacatgtgt 42300
aagattgtgt attatttatt cttcaaaatt tggtagaatt cagcagctag actctgatcc 42360
ttgagttttc ttggggaagt cttaaattaa ttatgaattt agtttttaaa aatagctatg 42420
agatagtcaa attttgtatt tacttttatg tcagctttgg taagttgtat ttttctagaa 42480
atttgtccac ttattctcaa atttaatttt acaaagttgt ttatcttcag accattttat 42540
cgtttatcat ttattgcatc tggactgatg ttttctctta cgtttttgat tttaggacat 42600
tctttccctt ttttcccttt atcagtgtca gcagtgtttt acaaattttg ttaatccttt 42660
tgaaaactgg gttttggttt tgttaatctt ctctattgta tacttgattt gtccattaat 42720
atttctgtcc attatttctt gcttttattt ttattgttga tttctttcta cttactttga 42780
gtttaattgg tattttttct gactttttga agtgaaagtc tatataatta attttcagcc 42840
tttctccatt tctaatacat atgtttaaac ttatatgatt tttgtaacat tttatcttca 42900
ttgtataagt tttaacaagt atcttttgtc atttaattaa atttcattat gatttcttat 42960
gtgaataatg gattatttca aattatattt tttattttcc aatgtatgag gggatctact 43020
agttatcttc ttgttaaaaa aattctggca tatactgtct gttcaatatt atagtacttt 43080
gaaaattttt gagacttgct tgctttttaa ggtttgtaga atatctcttc tatattcttt 43140
ttcttttatt cttgttttct ggttcatata tcttaactaa ttttactgta tcctttaatc 43200
ccttttgccc ttttctcttt ttattctttt tttgtctcaa tacttcagtt ggtaaatttt 43260
cttctaattc tttatgccta ccttgcagtt aaatgtattc atttaattat taatttcaga 43320
tatatatttt tacatagcaa atctcttttt gacttcttat tgtattcatt ttactgtaaa 43380
tcattcaatc ttacctttta gctgtttgaa catattaaac atagtaattt aaaaatctct 43440
atgggtaact ccagtataag tatgtgtttg tttctagtgt gtgctttttc ctcttggttt 43500
tctatcatgt tgtttcattt acctccaaac atgaatgtgt ttatgatgaa tgagagtcac 43560
tgaatattta aaaaatcata gagatatttt gaagctggaa gaatgttctt ttcatccaga 43620
caagatttat tttgtttctg ctatgcagct atggacacta gcaattctca tttaccttaa 43680
ttcaatcaag gactgagaat actgaagtat gaaattaact ctgtctgctt ccagttcata 43740
cttcttccct gtacctcttt tcttaaattt tttttaaaat tttatttcaa cagcatttgg 43800
agtataagtg gttttttttt acgtggatga attatatagt ggtgaattct gagattttag 43860
tgcatccatc actcaagtag tgtacattgt atctaatatg tagttttttt taatccctag 43920
ctcctcttcc atcctctcct ttctgagtct ctaaagtcca tcatatcagt ctgtatgcct 43980
ttgtgtactc atagcttagc tcccacttat aagtgagagc atatggtttt tggttttctc 44040
tgtagctctt tagaatccca aactgtagcc taagggaaag gtttccaagg tgctctcctt 44100
attgcactcc aaagtatgat ttttatctcc ctaactctat gaatctagca aacactttgc 44160
ttaacttttc agcatctcaa gtgccttttc tgaatttgac agatacacgt cagaaatgtg 44220
ctcccaaatg cctagcttat ctctctttat taacttctcc aaatctttgc caatagctat 44280
atgtcttaac tgccttgttt gctctttaga gctttgtaac acatgcattt ttatagttta 44340
ttctgctttt caagtttttt tcattgaaat aattcttgta atgaccaata gtctagtatg 44400
ctgctgtaag acttctatag ctgttaactc ctttcatatt tcaatttctt tatgtgctgt 44460
tttttgcaag aattcctagg ctccattttc taattcatac gttggcaaat gatgaatgtg 44520
atatgacaat gatgacctct gttccagcca tatacttttt taaagaaaat tttattggaa 44580
cacagtcatg ctctcttgtt tacatattat ctatgacttc ttttgtatta cagtggcaaa 44640
gttgagtaat tgtggaagag accatatggc ctacaaaggc taaaatattt actatcttgt 44700
tcattaagaa aaaatttgct gactcttatt gagatttatt tttcctttat tcaactttct 44760
gaagtttgtc aattgattta aaaattttaa tgacttttcc tttctaaatt atatattttt 44820
atatctaaca ttattgtgcc atttctatat ttttgctata ttttttgcct taaccaaaca 44880
atgtgtttta attgagtcag tgaataaaga actcactgaa agtagaagtg gaaacctaag 44940
ctataagcta ctatattata taagcttctc aacctataat tgtttttcca ttagatatag 45000
aacaatggaa gtgacaacaa gattgacatg gaatgatgaa aatcatctgc gcaagctgct 45060
tggaaatgtt tctttgagtc ttctctataa gtctagtgtt catggaggta gcattgaaga 45120
tatggttgaa agatgcagcc gtcagggatg tactataaca atggcttaca ttgattacaa 45180
tatgattgta gcctttatgc ttggaaatta tattaattta catgaaagtt ctacagagcc 45240
aaatgattcc ctatggtttt cacttcaaaa gaaaaatgac accactgaaa tagaaacttt 45300
actcttaaat acagcaccaa aaattattga tgagcaactg gtgtgtcgtt tatcgaaaac 45360
ggatattttc attatatgtc gagataataa aatttatcta gataaaatga taacaagaaa 45420
cttgaaacta aggttttatg gccaccgtca gtatttggaa tgtgaagttt ttcgagttga 45480
aggtttgtaa aattagataa tcctacatct cacattatga ttctaatcct tgtgttcggt 45540
aggtaataat tgatctacaa gagcaaggaa agtgaaagga acagttagat tcatgccata 45600
ctctttgata aattctgaaa tgaaacgtgg ggaacataag gattatgagg tttttatcca 45660
gaacgtatag gctgctttga gcaaagcaag ttgagaaata tatgtgcaga gatagagatg 45720
acaaaggaga tggggatgtg gagagagaga gatcttatca tcagagctgc tctgttttga 45780
catatgaccc aaagatcaga cccttatatg acccttagaa cttctaggtg taattatgtg 45840
agagcttcca gagcaagtta atgtgcagag aggataattt ttcctcctct tcctctcatg 45900
ttgccaactc tgactcctaa ctgagcagct cagccctggg ttatgcaaga aaactccatg 45960
tcttatttca aaagtagact tggccacatt taaccaaaca agttttaaaa atgtattatg 46020
ctatgtttat ttcctatagg aattaaggat aacctagacg acataaagag gataattaaa 46080
gccagagagt aagttggatt cttgggctat ctattaatca ttttatttag accaattgta 46140
taaagaatgc tgacaaatat gtggtaaaga taaaaatcat gccactggaa tgattaaaaa 46200
agagttataa tgttattgac ataaaataac aaaagcacta ctaactatga aactttaaat 46260
atccacctga tgacattgac caatttgact tcatttccac tttagaccaa aattttccag 46320

-continued

```
gtagggtctg gataaccatt ttaggtaatt tctctgaatc ctttccttga gaaacagctt  46380
ttgagaatcc tcagtaaatg tcaaaaacaa actttctttt taaatttata gatagctaca  46440
ttgcatatat tttattttga tttctcctta atgtactttt agtgaaaata ataatttatg  46500
ttcaatgtca ctgatatttc ttattacatt catgtgatct aagactaata gttgaaaaat  46560
ggtttggttg caggttaata tttaacttta gtcagatata aaataatgca ttttctttaa  46620
gcacaaaatg tataacttta gatatttcaa atcatattat agaagatctc attatcaaaa  46680
taataattaa gtattgaaaa aatacccttc tcagggaaga gaaagaagct ctaggtgact  46740
tgagatgttc tttatggtat tctttattgg ctgttctgat gctgtattta accactatat  46800
tttaacaggc acagaaatag gcttctagca gacatcagag actataggcc ctatgcagac  46860
ttggtttcag aaattcgtat tcttttggtg ggtccagttg ggtctggaaa gtccagtttt  46920
ttcaattcag tcaagtctat ttttcatggc catgtgactg gccaagccgt agtggggtct  46980
gatatcacca gcataaccga gcgggtaagt tatttccctg aggattttat tttatagatt  47040
acaattatta tattgcttat gtctttgcct ttttctctta gggcaatcct aatatacaat  47100
taaatgctaa atcaaatgga aaataggagt aaaattttga tcagaaccac ctccattgtg  47160
ctatattata cagagaagct ttcaaatttt atggatggaa gaagcagtta tataaagaat  47220
actttttagt atttgtataa aaaacaacaa aaaattaaaa accctatgaa aatctttgac  47280
cattatatat gatgttcatt ttactcatgt actacatgat tttacctggt ttaaaatgtt  47340
tttctttttt tgtaataaaa taatgagaat tatgtaaggt aatttttttt aattacgaga  47400
ccattctcta agacatggtc atgaaaagca aaatagcaat tcactttggt gggtcaactt  47460
tgaaggagaa cttgaagtgt aaatcttaca aaaactatct tatttacaaa aagatataca  47520
taaggaaata aatagtaata tagatttctt aattgttgct ctaaagaact acaaattatg  47580
atgcagcact tgtctagaaa attctttctt gtttatgctt ttcaatgtta tcatgcacat  47640
gcaatcaaac aaaaaataat aaagggaaag aatagaaaat tttagaatca ggctttttta  47700
atgattacca caaattaata ttgtcacttg ttagggaata tgctgtgtat tatcaatgca  47760
aaatttagca taagacagca taataagaca gtaatggttc attttagctt ttgtgtcaca  47820
ttcaataact ggaagaattt tctaggactt tcaagaatca catcttattt gttgatgttg  47880
gccagatact gtgctcttga gtggctttat tttaatatat tagtgtagtc tcagaagccg  47940
tggcaaggta cggcagcaca aattaaatta attaggcatt gattgaaatg tttctgtttg  48000
ctaaatattt attcagacat agagacctaa atacaaataa tgcttggtcc cattacccag  48060
atatctcaga gaccaatgca gataataaat ctgtatcatt cattgtgata tatgctataa  48120
tagagatact actcaggaca aaatttctct ttcttccttt taagttttaa attccaaagg  48180
tcttatttta agagaagatg tagatactga actccaatga aatgcaaatg ttatttaaat  48240
tgaagaaata tagggcagac ttttatgagg gaaattgaat attttattgc ttaaaagact  48300
ctttcctttg aataattgaa gttgtaaaga aagcaaatta atgggtaagg aaactaggaa  48360
gatgcatatt ggtgttcctg aaattttaca atgtacttta actctagtgc ttagtataat  48420
ttctttcatg ttgaggcact ggtaagtcct attctcctag ataaaaatct tcagtgggat  48480
tacgcctctg cgtttcatgg cccaatgaga gcttttgatt ttattacaga ttacaataag  48540
tcatagactg ttctctccct tctggtttga gtgatactac acccttgcca gcaccacaga  48600
tggaaaaatt gtaattaaag tgtctctgag aaatcctttt ctttgcaatc ttcccaaatc  48660
```

-continued

```
gtccatattt ttttgtgtat gttgaatgta tatctgacca tcaaataaaa tactttcaga  48720
attgttctag aaaatatcct tgcaataaga ttgaatgtgt ttatctagga aagaaagttc  48780
tgttgtgctt ctcaaagtga aatttgtgga ccccttgggt tcccggagac attttaaggg  48840
tatctctgtg ttcaaaacta tttttagaat tattctaagt tttttttgtc ttttctagtg  48900
tattgacact tgaattaatt acacaacata gttttacctg ttggcacatt agtatgaatc  48960
aaacggtggc accaaacact actagtagtc actgtatttc tcccaattac tgcacttaca  49020
ggaaaaaaaa tgccagtttt actccttgat gaatagtaac agttattggt tttatttaaa  49080
ctccactttg gaatacacat cattttgata ttcagtgtga taaaatggga agtgctcata  49140
aagtacttct aatgcatatt gaaaattggc agttgtcttt agaaaaagca ctggagcagc  49200
tgagttgtta actgaacttt ttttaaatgt gacatcattt ttactggaca gcacagactt  49260
actcattcat acttggatat ttggcaggta tcttaatgca aatgctcaag tgaccctact  49320
aataaagaac aaaaacaaaa actgacagtg tttgttgcca ataacaaaat ttgagctttt  49380
gagaaaaatc aaactttgag aaacctgtat tcactattct gagcctgaca gcttttcaac  49440
acttaaagac ttatccaatg aaattaatgg tggtattaac aaatgtgatg ttttaatatt  49500
gcatgatgaa atgtgtcaac attaggaaga tctggataac ccagtggacg aatgttttaa  49560
gatgatcaat aaattaggtt aaaaaatcat gcatgagtaa aggatatatt caaagtataa  49620
gacaaaccaa tggatttaat gtggcagcat ataaaaatgt cgcagattcc acattgcaac  49680
taacctttaa gaagttatta cttgttgagc tttgctatat tacattgagg aatattcaca  49740
attacctgaa agctatacag tgaaatatta cctccttttc atattataca tacatgtgag  49800
aggccatatt ttcttcacat acttcaattg aaacaacata tcaagagatt gaattggagc  49860
cacatatgag attacagtta tattctttaa tccagacatt aaagagaatt ttactaataa  49920
accaatgatt tctgttttct gtaaattttt aaaaaaatgc tttttaagta aaaaatgtta  49980
tttgatgaac atgtgacagg tttataattg aatttttaat gattaaaaca acacttaaga  50040
gcaggagggg cagagcaaga tggtcacata ggtctctcca gcaatcattc ctccactgaa  50100
acatcaattt gaataattat tagcacacaa aatatcacct cagtaaacca ggtgaaagat  50160
tactgtacct agttctagca caataataac aaaagataca ttgaagaggg taggaaagat  50220
agttttacgt tatctgcatc accccccctca accccaggga gcatagtgtg gagagaactg  50280
tcatctgctt tggggaaaag agggaagtga gcacaggact ttgcctggac tccaatatca  50340
ggcctactgc agtaaaatcc agcactggat agaacctcat ggccccagac tttaggctgt  50400
tatttgacgg ctgagcctct agccccatgc tggtgccaag tgagaccatg tggccctagg  50460
cttcaagctt gcatggtgga ctcagtccct ggaccacacc atggatgggt tattagtggc  50520
ccaacctctg aacagcactt agtgacacgg atgccgcagt ggccctgagc tttacgcatg  50580
cctcagtgct gcaccagtca cagtggtccc aggctttggg actatgcaag gcagcctgcc  50640
cagaattttt ggataggctg attgttgaag gacttttcca gacaaaggca atctgcaaag  50700
attggaataa gtacctactt ccagagatgt ttatacattg acacattgtc acaagagtca  50760
aaagcaatca gggtaacatg acgtcagtaa agagagaaaa taacgtgcca gtggccaatc  50820
ctaaagaaat ggagatgtat gaaccacccg aagaattcaa aataattatt ttaaggaagc  50880
acagcaaact tcaagaaaat acagagaaac aatttaacaa aatgagaaaa atgatgagtg  50940
atcagaataa gaaatttaat agaaaggttg taataattat aaaaaagaaa caaatttcag  51000
agatgaaaaa tacaatgggt gaaatgagaa atgaaataga gagcatcaac agcagaattg  51060
```

atcaagtaga agagtctgtg aacttaaagg taggttattt gaaaatatag atagagaata 51120
aaaaaacaga atgaagagga aggaagaaag cttatgggat ttatgggaca tcatcaaaag 51180
gacaaatatt caagttacaa gggggaaagg agacaagaaa ttaaaagtaa tagaaatctt 51240
aagtaaataa atagtagcaa aaaactttta aaacctggag gatgatgtaa atatccaggt 51300
aaaactgaga gaaaagtccc cagtcagatt taatccaaag aagattaacc caagatatat 51360
taaaatcaaa ctgtaaaata tcaaagacaa agagaggatt ctgaaaactg gaagataaaa 51420
aagcaaataa catattagaa agttttaata tgactagcag cagacttagc agaaactctg 51480
caggccaaga gagtaggatg aaatattcaa agtgctaaaa gaaaaaaacaa agaaacaaac 51540 aaacccatcc aattgagaat attataccca gtaaagctgt gcttcagaaa taaaggaggg 51600
ataaagattt tcctggatga acaaaagctg agggagttca ttacaattat acctgtctta 51660
caagaatgtt aaagcgagtt tttcaagctg aaagaaaagg atgctaataa gtaatataaa 51720
aatatctgaa agtataaaac tcactggtaa aactacagta aaattcagaa tactcatact 51780
ataatgatgg tgatgtttaa aagacaaaac tgctaaaata ataatagcta taagattttg 51840
ttaaaggaca tgcaatatgg aaagatgtaa attgtggtat caaaggtgca aactgtgggg 51900
aggagtggag taaaaatgtg gagtgttttt tttttctctg taagtggagc tgttattaac 51960
ttaaaataac cagttacaaa tatgtttatt ttttgtaagc atcatggtta agcacaaaac 52020
aaatactgat agtagataca caaaatataa aaagcatgga gtcaaaacat accattatat 52080
atatatatat gtgtgtgtgt gtgtgtgtgt atgtgtatat atatatatat atacacacac 52140
gttttacatg ataaattaca tagaaatttc ttttttaatt aaaaaggaat atttacattt 52200
ttttcagttg taatttccac tattttaaat atccatagat ataacccaca taaacaacag 52260
atctttggga ttctcaataa cttttaagag tctaaagggg tcctgagacc aaactgtttg 52320
aggaccatgg tgttcaaata ttaaccaatc tcttttcttc ttattgtcat gtcttgaatg 52380
ctgggtgatg aatgaacctt tacacttaat gtattttttt aacagtatag gatatattct 52440
gttaaagatg gaaaaaatgg aaaatctctg ccatttatgt tgtgtgacac tatggggcta 52500
gatggggcag aaggagcagg actgtgcatg gatgacattc cccacatctt aaaaggttgt 52560
atgccagaca gatatcaggt aagatttctt caatatccaa aacatttcaa atcattttct 52620
tcagtatttt tcattgaatt tttaaccaca taaggcaatt tcaactccca taatgtggtt 52680
tcaacatcaa tcaacactat tctactttga atgaataaga attcatatga aaaagtagag 52740
tgactattgt tcttttctgt aacattgaga aataaagcca aaaggcagga ttctactcat 52800
ttgcattcta gtaaaagatc aaggagatag tgtgttttta tcactcttta caataatgta 52860
aactaatgat agtcacttaa tcccttgcac tttttgggtt acatagacaa aatattggaa 52920
caagtaacta ttttgtgttg aaatgtcatt ttatactgta aatgcttaga tttcaccact 52980
aaatacctag attcaaaatt tggctttgct actaacagat gtttacccgt aagttgcaca 53040
cttctctctc tcggtctttt tttttttttt ttcaggtgtg aaatattgct attaatagtg 53100
tctatctcat agggtggcta agatgattaa atgagatgat atagtttaag ttctcaaaaa 53160
agccaacaat gattgttacc tttcttttag gtgttgggta tcagcctcaa tttctaaaga 53220
agaatctctt ttgcctccca attgtgctga attggaaacc ttacctatgt atttatttat 53280
tcattcaaaa accatctatt ataaaccata tttgtgccaa actctaagcc agttactgaa 53340
aacacataag tcaataacag cacaatcctt atcctccagg agttcataat ccagtcaggg 53400

-continued

```
aaaaggagac acacagataa agagaggagg gatagagcga agacattgga gaaatcagga  53460
gcataccaac accctaattt ttcacagcag ggagccagtc aattcagtcc aacactgaaa  53520
tacatagctt aataactaca tgtttccaaa ccattgtttc ataatctatt tccttaatct  53580
tagaaagatt actgtcttgt ggtaagaaga cattaacttc aaatttggta tttcttttat  53640
ttcactttag tttatttttc ttctataaaa tcaaaataaa ttacagtctt ttaatttaaa  53700
tagcattttc aacatatttt tctttctttt attctctcta tccagttcat ttaagcatgc  53760
aaaatgctta gggaggagtc ttaaattgta tttaacaaac gttaatggtg tttatttctg  53820
gatactagga tttgaaatta gcttttcaaa aatattattt aaactttcct gcaatactta  53880
caatggataa ttatcatttt taccaaagca ataaagtgtt ttttttccta taagagagat  53940
ataatggcat tatgctcaca gtggaaagga agtaaagagg aggtgctact gtttggggaa  54000
agagtagctg aggagaaaga gggagatcag tagttacagt attagaagca ttaattgtgt  54060
ctttaagggt taaacagagg ctctctgatt tctgaatgtt accttatgtt tttataacag  54120
tttaattccc gtaaaccaat tacacctgag cattctactt ttatcacctc tccatctctg  54180
aaggacagga ttcactgtgt ggcttatgtc ttagacatca actctattga caatctctac  54240
tctaaaatgt tggcaaaagt gaagcaagtt cacaaagaag tattaaactg tggtgagtct  54300
cactgaactt ataaaaaaat ttactttgaa ataattatag atttgtagga agttgcaaag  54360
agagtacaga gatttcccat gtacctttca tcctatttcc ctggagtggt ggccatcgga  54420
gggagagatc attcacaggc atgactgaag aaagacccca aatcctaatg ttcagtcttt  54480
aaagaataga ctggccaacc attttttttt cgtgtgtgat tttcctgagg ctttagatag  54540
ggctaaaacc tatgtgggta gacagggaag atcgaaacca gaaaattgat tattgttaac  54600
aatgtgtgtt tatagttcta tgtcatttta tcacatgtgt aagtttatgt acccatcact  54660
gcaaccaaat attacatcac tttgtagatt tccctcatgg cacccactat tcctccacca  54720
tccttaactc ttggcaacca ctaatatttt cttcatttcc ataattttgt catttcgtga  54780
atgttataca aatggaatca tacagtatgt caccttttga gactggcttt tttgactcaa  54840
cctaatatcc tttgacatcc atccaagatg tatgtatgta tttattgttc atttaaaaaa  54900
ttgtatagta ttccatggta tagatatacc acagtttaac catgctctat caaaaaaatat  54960
tccagttttt agctattgca aacaaaactc ctatcaagtt ttgtgtggat ataagttttt  55020
attcctctgg ggtacatctc cagaaatgta atgctggatc ataaagtaac tgtatgttta  55080
gctttgaaag agatcaccaa actatactcc agagggactg taccatttta caatcccacc  55140
agcaatacat gagagatcta ttttttctgc attcttgcta gtatttggta tcgttgctat  55200
taaaaattcc ttaactcttc taatagatgt atgctgatat ttcatcaggg tcttaatttg  55260
cattgcttaa tgactaatga cattgaacat cttctcatgt gcttatttgc cttctgtata  55320
gcttgtttag tgaaatgcct cttcacgtct tttgattatt ttctgattgg atgatttgtg  55380
ttttttagaa gttgaatgtt aaaagatcta taaatcctaa atatgagtca attgtcagat  55440
acattgtttg cggatagttt ctcccagtct gtagttgtct tactattatg atgatttcca  55500
tccctgccat ctctcatctc tccttttgga actctgggac atgaattcta gatattttgt  55560
tatagtctca caatttattt atttattttt tatatctatt tgctctttat ttttcagagt  55620
gggtaatttc tattgttata tctttgaatt cacttgttca tcactttgcc ctctccattc  55680
tgcttttgag catagctatt gtttttccta tcttgggtat tatggttttt tagctctaaa  55740
atttcaagtt gattcttttt caggtcttct atttctttgc tgagacatcc cacttccttc  55800
```

atttgtttca agaatgttcc tacttggttc ttaagcattt ttatgatggt tgctttagaa 55860
tccttgccaa ataattctaa catctttgtc atctaattag ggtcatgatc ttctgattag 55920
cttttctcat tcaagttgag aatttcctgg gttttgatgt gacaaatgat ttttaattgc 55980
atcttcgata ttttaggtac tttattttat gactctggat cttacatctt gtgttttagc 56040
aaacatattc tgatactggt aagatggaaa gtacaggttt cccataaggc cttgtttgac 56100
acccttggag aaagggcact ttcttactgt gccccatata ggataccctg acatcacagg 56160
ggctagaagc ctccttgcat cgaaggttaa tgaaggctaa agttccagct tctcacttgt 56220
tctcctctga cacttccaga gagggaaaag agcacctcat tgctgctgat tcggtggaag 56280
tctaggatcc ccaagtagcc tcccttgaca ccatcaagag ggaccttgtt agtatagtgc 56340
aggtataaat gtcctggctc cctacatttt tttcttctct tatactacct tggctaaggg 56400
tgaaagttgg gaaagggaag gacatatcca tggatagggc taaggtgaat tctgtggtgt 56460
ttgactgggg tagtgtggct attttctgaa agttttctgt cttgctacac tgtccttttt 56520
ctcatgcttt gactagatga aactagtcaa cagcaaaaaa aattttcctt tttgctggct 56580
ctaatttgta ttttccagtt gtgagtgtct ccaaaagcca atctgggaca tatgaagtaa 56640
aaagaaaacc tagagagctc atctctgtat tgtttcttgg gtctcaaggt ctctagccaa 56700
attgcattat ctgcactttt caatctttat gtttgattta tgcataatgt ccagagattt 56760
tagctacatt tagtgtaaag aagagggaaa agtgtgtcta ctccatttgg tccagaactg 56820
gaagtactct cactgaactt ccaaaagatt ttaatataaa gaattgttgg ggcatttata 56880
ctccaaagcc tcgttgctta ctttatcagt agaaagatca catatttagg ttccgaaaag 56940
tgctatgccg tttaatgtat agagcatggt cttgcttaag tgaacctagt ttttaaatag 57000
tagtaaactt tgacctcgag aaaggtaatt taattgctct gaactttatc tcctgttctt 57060
ctaaaatggg gataataagt tttgcatctg aacttaataa actgtctaac aaaagtctga 57120
gtagtgaaca ttagatatac acaatgtaaa tatataagct tatataagta cttaacagct 57180
ctaaaattat ggagggtttg gggtaagaca gaaatgctaa gttttaaaat gacttttcaa 57240
ggatgtatgg caacacattg tccttggcgt gctggatggc aatgcttaat gcaacttagt 57300
gtgctgactt aggacctcta aaaggacatt gtattaattt tgaaacagaa gaattacatt 57360
gcaacagagg ttgaaaaaaa ttataggtgt caactgagaa ctgctctcta ccagaaccta 57420
ggtattaatt ggccaacttt gctagttatt cctctgaaac ctgaatgaag agaaggtagt 57480
aaaggaaatc atttagtaat ggaaaaaata aacacaagat tttagtagga agaaggtact 57540
aaaagccctg ttaaaagagt cctgggagct tccttgactg gcatttgaaa ttaatcttat 57600
attttcctca taagcagttg ttagcatagc agaattttga tttgtttaga agtcaaatgt 57660
gatttactaa ttcaatccct gtggtttgag ggagaaagga gtaggtccct attagaactg 57720
tgaaatcagt acagtttgct ctcataaatg ctcatacaca accctcctca cttcctcttt 57780
ttcttgtggt tctttttagt ccccaaagtc cagcaacccc ttttttcccc ttgaccaatt 57840
taaaacaaac catttgaatg gaatcgtaga tgattgcaat ttagtgtgga tttagttgca 57900
ttgaaaaatg ctgtcacatg ttggaaaaaa aagatcaaag atcatttctc ctctagaaaa 57960
gcttcaggct ccatattgag atgtattggg gatatttcat tcttcagctc tcaaaatcac 58020
cctatagagt tgccttcaca catatttaat aacttgttga cacattgcta tttatgatat 58080
aaaataactg atttatctat ttgatatagg tatagcatat gtggccttgc ttactaaagt 58140

-continued ggatgattgc agtgaggttc ttcaagacaa ctttttaaac atgagtagat ctatgacttc 58200
tcaaagccgg gtaaaaaatg ctgatcataa ccagatatta ttgtaatagt atcacaatca 58260
tacgtgtgtg tgtttgtgtg tgtctgtacg tgtatatgtg cttacagagt gtatttgcag 58320
ggaaatgaag aatgggatca attgcttgat taattcaaat ttatatcaca ctttaaaact 58380
gcaatgatct gaattattgt atgttccgaa gataacttat taagccattg ctttttttggt 58440
ttctttctta aattgtattt aaaattggtc aaatttcaaa tattaaatac aggacttaca 58500
ctttttaaat atactttcca caggtcatga atgtccataa aatgctaggc attcctattt 58560
ccaatatttt gatggttgga aattatgctt cagatttgga actggacccc atgaaggata 58620
ttctcatcct ctctgcactg aggcagatgc tgcgggctgc agatgatttt ttagaagatt 58680
tgcctcttga ggaaactggt aatctggccc ttttctcccc ctgtcataga tcactggtgc 58740
cttttgaaaa atcctaagtt atacatcagt tattagatga ctggggccca cctgcatgcc 58800
ctagtcctga aagctacatt aggatatatg tttcatttcc actcttgttt gtttcatttt 58860
caggtgcaat tgagagagcg ttacagccct gcatttgaga taagttgcct tgattctgac 58920
atttggccca gcctgtactg gtgtgccgca atgagagtca atctctattg acagcctgct 58980
tcagattttg cttttgttcg ttttgccttc tgtccttgga acagtcatat ctcaagttca 59040
aaggccaaaa cctgagaagc ggtgggctaa gataggtcct actgcaaacc acccctccat 59100
atttccgtac catttacaat tcagtttctg tgacatcttt ttaaaccact ggaggaaaaa 59160
tgagatattc tctaatttat tcttctataa cactctatat agagctatgt gagtactaat 59220
cacattgaat aatagttata aaattattgt atagacatct gcttcttaaa cagattgtga 59280
gttctttgag aaacagcgtg gattttactt atctgtgtat tcacagagct tagcacagtg 59340
cctggtaatg agcaagcata cttgccatta cttttccttc ccactctctc caacatcaca 59400
ttcactttaa atttttctgt atatagaaag gaaaactagc ctgggcaaca tgatgaaacc 59460
ccatctccac tgcaaaaaaa aaaaaaaaaa ataagaaaga acaaaacaaa ccccacaaaa 59520
attagctggg tatgatggca cgtgcctgta gtcccagtta ctcaggatga ttgattgagc 59580
cttggaggtg gaggctacag tgagctgaga ttgtgccact gtactctagc cagggagaaa 59640
gagtgagatc ctggctcaaa aaaaccaaat aaaacaaaac aaacaaacga aaaacagaaa 59700
ggaagactga aagagaatga aaagctgggg agaggaaata aaaataaaga aggaagagtg 59760
tttcatttat atctgaatga aaatatgaat gactctaagt aattgaatta attaaaatga 59820
gccaactttt ttttaacaat ttacatttta tttctatggg aaaaaataaa tattcctctt 59880
ctaacaaacc catgcttgat tttcattaat tgaattccaa atcatcctag ccatgtgtcc 59940
ttccatttag gttactgggg caaatcagta agaaagttct tatatttatg ctccaaataa 60000
ttctgaagtc ctcttactag ctgtgaaagc tagtactatt aagaaagaaa acaaaattcc 60060
caaaagatag ctttcacttt tttttttcct taaagacttc ctaattctct tctccaaatt 60120
cttagtcttc ttcaaaataa tatgctttgg ttcaatagtt atccacattc tgacagtcta 60180
atttagtttt aatcagaatt atactcatct tttgggtagt catagatatt aagaaagcaa 60240
gagtttctta tgtccagtta tggaatattt cctaaagcaa ggctgcaggt gaagttgtgc 60300
tcaagtgaat gttcaggaga cacaattcag tggaagaaat taagtcttta aaaaagacct 60360
aggaatagga gaaccatgga aattgaggag gtaggcctac aagtagatat tgggaacaaa 60420
attagagagg caaccagaaa aagttatttt aggctcacca gagttgttct tattgcacag 60480
taacacacca atataccaaa acagcaggta ttgcagtaga gaaagagttt aataattgaa 60540
tggcagaaaa atgaggaagg ttgaggaaac ctcaaatcta cctccctgct gagtctaagt 60600
ttaggatttt taagagaaag gcaggtaagg tgctgaaggt ctggagctgc tgatttgttg 60660
gggtataggg aatgaaatga aacatacaga gatgaaaact ggaagttttt ttttgtttgt 60720
tttgtttttt ttttgttgtt gttttttttt tttttgttt ttttgctgag tcaattcctt 60780
ggagggggtc ttcagactga ctggtgtcag cagacccatg ggattccaag atctggaaaa 60840
ctttttagat agaaacttga tgtttcttaa cgttacatat attatcttat agaaataact 60900
aagggaagtt agtgccttgt gaccacatct atgtgacttt taggcagtaa gaaactataa 60960
ggaaaggagc taacagtcat gctgtaagta gctacaggga attggcttaa agggcaagtt 61020
ggttagtact tagctgtgtt tttattcaaa gtctacattt tatgtagtgg ttaatgtttg 61080
ctgttcatta ggatggtttc acagttacca tacaaatgta gaagcaacag gtccaaaaag 61140
tagggcatga ttttctccat gtaatccagg gagaaaacaa gccatgacca ttgttggttg 61200
ggagactgaa ggtgattgaa ggttcaccat catcctcacc aacttttggg ccataattca 61260
cccaaccctt tggtggagcc tgaaaaaaat ctgggcagaa tgtaggactt ctttattttg 61320
tttaaagggg taacacagag tgcccttatg aaggagttgg agatcctgca aggaagagaa 61380
ggagtgaagg agagatcaag agagagaaac aatgaggaac atttcatttg acccaacatc 61440
ctttaggagc ataaatgttg acactaagtt atccctttg tgctaaaatg gacagtattg 61500
gcaaaatgat accacaactt cttattctct ggctctatat tgctttggaa acacttaaac 61560
atcaaatgga gttaaataca tatttgaaat ttaggttagg aaatattggt gaggaggcct 61620
caaaaagggg gaaacatctt ttgtctggga ggatattttc cattttgtgg atttccctga 61680
tctttttcta ccaccctgag ggtggtggg aattatcatt ttgctacatt ttagaggtca 61740
tccaggattt ttgaaacttt acattcttta cggttaagca agatgtacag ctcagtcaaa 61800
gacactaaat tcttcttaga aaaatagtgc taaggagtat agcagatgac ctatatgtgt 61860
gttggctggg agaatatcat cttaaagtga gagtgatgtt gtggagacag ttgaaatgtc 61920
aatgctagag cctctgtggt gtgaatgggc acgttaggtt gttgcattag aaagtgactg 61980
tttctgacag aaatttgtag ctttgtgcaa actcacccac catctacctc aataaaatat 62040
agagaaaaga aaaatagagc agtttgagtt ctatgaggta tgcaggccca gagagacata 62100
agtatgttcc tttagtcttg cttcctgtgt gccacactgc ccctccacaa ccatagctgg 62160
gggcaattgt ttaaagtcat tttgttcccg actagctgcc ttgcacatta tcttcatttt 62220
cctggaattt gatacagaga gcaatttata gccaattgat agcttatgct gtttcaatgt 62280
aaattcgtgg taaataactt aggaactgcc tcttcttttt ctttgaaaac ctacttataa 62340
ctgttgctaa taagaatgtg tattgttcag gacaacttgt ctccatacag ttgggttgta 62400
accctcatgc ttggcccaaa taaactctct acttatatca gtttttccta cacttcttcc 62460
ttttaggtca acaataccaa gaggggttac tgtgctgggt aatgtgtaaa cttgtgtctt 62520
gtttagaaag ataaatttaa agactatcac attgcttttt cataaaacaa gacaggtcta 62580
caattaattt attttgacgc aaattgatag gggggccaag taagccccat atgcttaatg 62640
atcagctgat gaataatcat ctcctagcaa cataactcaa tctaatgcta aggtacccac 62700
aagatggcaa ggctgatcaa agtcgtcatg gaatcctgca accaaaagcc atgggaattt 62760
ggaagccctc aaatcccatt cctaatctga tgagtctatg gaccaatttg tggaggacag 62820
tagattaaat agatctgatt tttgccatca atgtaaggag gataaaaact tgcataccaa 62880

```
ttgtacaccc ttgcaaaatc tttctctgat gttggagaaa atgggccagt gagatcatgg  62940

atatagaagt acagtcaatg ttcagctgta ccctcccaca atcccacttc cttcctcaac  63000

acaattcaaa caaatagact cagactgttt caggctccag gacaggaagt gcagtgtagg  63060

caaaattgca aaaattgagg gcacaggggt ggaggtgggg gggttgaata acaagctgtg  63120

ctaaataatt acgtgtaaat atatttttttc atttttaaaa attgatttct tttgcacatt  63180

ccatgacaat atatgtcaca tttttaaaat aaatgcaaag aagcatacat ccaa        63234
```

<210> SEQ ID NO 2
<211> LENGTH: 22489
<212> TYPE: DNA
<213> ORGANISM: Artificial Sequence
<220> FEATURE:
<223> OTHER INFORMATION: GENOMIC SEQUENCE FOR FAM89A

<400> SEQUENCE: 2

```
cagagatggg ggtgatccgg aagcctgggg tggggggtga gtgggttcgg agctgagggt    60

gagccagtga gctgagggtg gcacagaggg cgtgggggcg gaactggggg tgagccggga   120

agctgggggt tggcacagag gaggtgggga cagagatgcg ggtgagccgg gaagctgggg   180

ttcggggtgg cgcgggtgag agggttcgga gctaggggtg agccgggaag ctgggaggtg   240

gttcagagga ggtggggaca gagatggggg tgaaccggga agctgcgggt cgcgggggggc   300

ttagtaggtt cggagctagg gagtggcaca gaagggttcg tgacggggct ggaggtgagt   360

cggggggtta gagggtagtc acgcggagtt ggagatgaat tagggcgctg gaggggcgcg   420

agggaggagg agacccgggt ggaggcgagc ccggctgctg gacgcggacg ccacccggac   480

ccggggcccg cgcaggggcc tcgaggagag ggggcggggc cggggggggcg tggcgcggga   540

ggggaagtgg gcggggcacc gccgggaagg gggcgggccg ggggaaagcc ttggttcgct   600

gcagcggggc aggcgcgtgg ccgggccgcg gcgcgatgag tggggcccgg gcggcgcccg   660

gggccgcggg caacggcgcg gtccgggggc tgcgggtgga cgggctgccc ccgctgccaa   720

agagcttgag cgggctgctg cactcggcgt cgggcggcgg cgcgtctggg ggctggcggc   780

acctggagcg gctgtacgcg cagaagtcgc gcatccagga cgagctgagc cgcgggggcc   840

cgggcggcgg cggggcccgg gcggcagcgc tgcccgccaa gcctcccaac ctggacgccg   900

ctctggcgct gctccgcaaa gagatggtga gtggggctcc gcgagctggg gctcttcccg   960

gccgggctcg ccgtcccggg aaagttcgcg gggaccgcgc tctgtccgga agtccccgcg  1020

cccacccgcc ctttcgggct cctccgcccc aggcgccggc gccgtcctcc caacgacccc  1080

catttttctc gcgtgctccg tgcccacgat tggaaccccc gcgggagagc cccgcgcgca  1140

gagggcggct ttcttatgcc cggcgccctc agtccggccc cgctggctcg gaaacctggg  1200

cgcccggaag cgctgtgcgg ggttcgtgcc tggcctgggg gcgggggcgg ccttgtcacc  1260

tctccccgag tgaaacagac cttcccggtg ggggaaaggc tttcacagcg gcccaacgga  1320

ttaacgcgat tgcgttttcc taccacgaag aggacaactt ttgtccgccg ccagtgtaga  1380

cagcagattg gaacagcccg gcccccttc cggcgcccca ggccgcgcgt ccgtgatccg   1440

attaccgcgg gatggccccg gcgcacagat ggctgcgaaa gcagacgcgc accccgggcg  1500

agggaggcgg ccgggtccct cagccccgcg aagctgattg cccaaaccct cttgagaaag  1560

gtgggaggtg gctgtcctcc cggtctgggt gctgtccatg tgagttcttc gccttgtgtc  1620

taagctccat accatgggct cagtgtttct ctgtgcttgg gaagtacatt agctgtttgt  1680

ggaccagaac acacatgatt tagggtgacg ctaaaagtag gacaagggca gggatttagg  1740
```

-continued caacagcgag tctttcccca gctttctcgg ccaggcgtag gccaggcaag aagaaatcaa 1800
aaacttttcc tcttttctac catcttactg gcccccatca cctcctccca atcccctcgt 1860
tttaaaagcc tccctttcca ttcacctcgt ccaggttgtc tcctttccct ataggtaaat 1920
tgttaagaaa tctaacatta ggaaagctgc cttttcccaa aactaaattt gccaaaaaat 1980
aaattgttat aggaatcttt taaatatgta tctagtgcat ttaagatatt gtttagaaaa 2040
attcagggta tgcatacttt tttttcagga gcattatctg ttctgaaaac taagacttaa 2100
ttgaattcag aaagcagcct taacactttt aatcaaagag atattgtctt cctactctgt 2160
agctggcatt gaagtgattt ccaattctca ctgaaaagat tttctaagct tcttacagaa 2220
ccacttaaat tccaagccaa ccgtttttaa tttattaaaa aacattcatt gacataagca 2280
tcacacagct ggtgaactgc attttaatta gataaatcta cacgtagtgt gtttacagtc 2340
tgaacttgga catagcagaa ccacgggggt gaagtaggaa gatcatcttt gattatttaa 2400
attccatact tgagcaagag atagaaaaac ctcggggccg ctcctgttgt gaagctgtgg 2460
tttataaaca tgctctggag tcttgctatg gtggcttggg agtcaacgtg ccattcccag 2520
aagtattttt ccaggtccct cctggtgtga ctgaagcaca accacatccg tataattacg 2580
ccttggacca gagctctctg taagcctatt tgaagcacaa gaaaaataaa cagccatctt 2640
tggtctgcct ggtatttagc tgagataaag ataagatatg gctgcaggtt ttgacaagtt 2700
cctttcaaga aatgtcacaa ggcctttaaa gttgcccaga gaatctttcg gctttttaat 2760
tgatttactg acttggggcc atggggtctg agtggacaac tcaagctgag actccctctg 2820
gggaggcctt gcaaaacaag aactgggagt tcattcctga gatatctgca aaatagtttg 2880
tgttgatctg tttaaattga aggcctgacg tcaaatctgt ggcaggggac ataactagat 2940
gtcatggtag aatgtgataa atgccttaaa gaaatttttt tttttaaagc aagcatagaa 3000
agaggggcaa cttctaatag ggacagggag cagggtggtg tggaagacct cagaaggcga 3060
cagaatttcg acaagggaaa gaggcaccag gaaggtagct gcggagctgg aactgggagt 3120
gcgccagttt gaaatgtgag caagaagggc ctgggcaggt ggaccgagtg gactctgaga 3180
agcctgagta gcaaggatgg gcattcagca ggagaatggt attatcccag ttggactttg 3240
aagaaatgaa ttctacagca gggtgcagaa gggagagctg gactttggag gctcaacagg 3300
aagatgagag gtgttcatgg gagaggtgat ggagtcccca gcagggtagg gggcttgcta 3360
atgtgaaaca agactcatgt gggagacact tttctgaagc cgaagctgga ggaattactg 3420
agtcaaggaa gatgatgaaa aggggatcaa agataactta agctttttca tggaaaatgt 3480
agccaagcaa aaaattaaaa attacagtgc cagcacctag aaataatcac ttttagtatt 3540
ttgggatatc ttctgttagg tgcaatgtaa gtgctttcta tatagtatct tatttaatgg 3600
tataaattct ccatgagata gatactcaaa gtctgtttta tattaaagaa ttggatgctg 3660
agagttgaac tcccataagg tcacagaccc taccaggtct ctttggctcc aaagccctat 3720
ttaaccattg cagtctgctg tctgtgcaca tgcatgcact ctcacacaca cacacataca 3780
tatatacaac acattgatca catatatttt ggtttgcttt ttgggctgca cattgcaatt 3840
attttcccag tcaagatata ttataatgac ttcagtgagt gtgtagtata ccactgtatg 3900
gcagttagca aggttttgaa gcttaataat caatcactgg taaagtgggg ttcattatgg 3960
cacttgggga gtcaggagga gtagctgctt tagggaggaa ggtaatttgt catcgcatca 4020
gctgaagagc atgttaaaca tttcagaatg tggagctgga agctggaaga gaggttttgg 4080

-continued

```
tctggagata gccagtagaa gagatggttg gagctgaggg agtaatacca tctcaatggg   4140
aggagaggcc attcggatgc cgagggtgga ggctgggaga gctggagccc agggctgaga   4200
agggtctgtc tcatgactgc tgatgccctc ctctgcttgg agagttgtgg tttcagctcc   4260
acgtttcaac acttcctgtt ctagtaaccc ctgtgaaatt ctgcactact cgtaagtcct   4320
cgtcccctcc ccagaagggc ccacttggaa agcttcaagg gtcacacaga tagttattgc   4380
tctacagacc aaaaaagtcc ttttgaaaaa gttgatgatg atgattttta catcagagaa   4440
tatctttaga tcacgtttaa gagatgatta ctgggtgtat gttagatagc aagtactgtg   4500
gatggtttaa gggtgaatag gaaatatcta gatgttaagg ggcttatcac acctggtaga   4560
tgtgggcatc tttacagaaa aagaattgct ttagtttaga ctagttttca tttttcatga   4620
ccaaagactc tatattagta atagaaactt agtttgaact agctttttca aaaggacaat   4680
cttatagact ggatgtatac agagacaggc tagaactagg gcttatgggg aatccaggaa   4740
gtccactgag gtattctctt cccctcctcc tctgttttgt tttttccctc cattttggaa   4800
cctggcctct aacagtggcc accctcaatt ttggccttgc tgcttagttg cagtttgcaa   4860
atactgtgga aggatgccaa ttggcctagc ttaggtggcc tggccagcct gggccagcca   4920
acagtgacaa ggacaagatt gtattttaat aagatggtgt gagcatgtgg atggagtcgg   4980
acactgggga ttctctaaag aaaggacagt ttgcaaaaat ggagcaaggg gtaaagtagt   5040
agacatctac tgcagacccc gttctatata aaaatacttt gccctcaagg gtcccacaat   5100
ttgaaagatt ttttatctgc taagctgatg gctagcttgg ctaactagat cttggttggc   5160
ctttaaaata tttgcatgtg gttgaaggat gtccctgact gggtgtcagc tgggacccct   5220
ggcacacacc agtccttgca tagattttta catagactgc ccttcccagc acccgtgcga   5280
ggttagatca tcaaccttac aggtaaccag aagtcacact agagtgtaga gacacaaaga   5340
ccttcagccc tgggggcagg agatctttga ggagcagcat ccctggggat tcttgggttc   5400
agctgctccc acagtcagca gcaaggtcta gtagctttga tttggaatct cttcgcctca   5460
tttttttctt taaactatca gttattttgg tctcccacct gtgcagagtg ggaagtcatc   5520
cacacagaac ttttgaattc ccaaattgca atgttgtgta aagaattgaa cctaaggaaa   5580
aaaaaagttg aatttgtgaa actagtaaca attagccttc ctacatttta gttgaaacaa   5640
ctaaatgcct aatgagcttg tccagtgaac tggattccag ctcattagct ggaatagctg   5700
acaccccagt ggagtacagt ccttatcctt tatgtgaaac cagtgtctta cagaggaagt   5760
tttagtcttt aagaggctgt gattgagtca ggctatgaag tgccatttag aataagggga   5820
ttcgctccta gtgcagcatt cttgattggc gttggtcaga ggagactggg gatgtctagc   5880
ggcctttaat actgtctgtt ttcactagtc tttccactag catagtctag cacagcgatc   5940
cccaaaggat ggaccgccag ctccagaatc tcctaggctg cttgcccaaa tgcagatttt   6000
agggccacat tctgtgcttc tggaatcagt agctgggaga aggaatctgc cttttttttt   6060
tttttttttt ttttgagaca gagtttctat cttgttgccc aggctgcagt gcagtggcgc   6120
gatctcggct cactacaacc tccacctccc gggttcaagt gattctcctg cctcagcctc   6180
ctgagtagct gggattacag gcatgcgcca ccatgcccgg ctctttttgt atttttagta   6240
gagatggggt ttctccatct tggtcaggct ggtctcgaac ttctgacctc agatgatccg   6300
cccgcttcag cctcccagag tgctgggatt acaggcgtga gccactgtgc tcagcaggaa   6360
tctgcatttt taacaagccg tttaagactg gagaagcaca tgaatcaagg atcaaaagct   6420
cgaatttggt gttaataaac tatgtgatac agttctgaca agccacttca ctcttttggg   6480
```

```
ctaaaatctc ttattgggaa aatgagaatt aaatgccata aagggtcctt ttggccatgg   6540
cagtattctt taccccctcat gcctctatgg ttctttctga tgcctacaga agaagttggc   6600
tctgtcataa cttttgggca cacgtgcggg gcctgtcacc aagcatattg cttggggtcc   6660
ccaaggacac ttcacagcta tacctagttg ctgtgaattc cttgaatgca aagaatggga   6720
agcagaaaag gaagaaaggt acaagtttgc tattcttgag ctcagttcat caaaaattag   6780
gctgtctaca ccagttatta agattttcag gccactgcta ccctgtactt gtcccatccc   6840
catcccaatg tccaccctat aaaagcaaaa actgaaaaaa gaatatatat tagtttgtgt   6900
gtatgaaagc atgcccatgt ctttggtgtg gggtgggggga cagtaagggc agtgtgtggg   6960
tcattgcctg gcttcattca cttgatgcta tctccaagtg aggttagagt tcttctcccg   7020
agatttgaag atataaagga ttaaaagtaa aaataccact ttaaactttg ctctattact   7080
gtacctacct gcaaagtact ataaattgat atttttccta actcataaat atcttacaac   7140
ccttctcctt tttttccctt ttgtttaaag gtaagcatct gttcaatgta aatgtaaagg   7200
tgccccaata attggcagtg tgggcacctc ttcatttgca gatagcctca agtgagcaat   7260
agccctggca tttctgtacc ttgcagacag cggtgcctcc cctgctctgg gtcctggtct   7320
caccgacatg gctgtagccc cctgaggcca ggtgggcaag gatgtttagg gagggttcaa   7380
gaagggaacc atgcctggct tgcagttcac tcccaccaag ctgcagatgg aagtttcgca   7440
gtttcgctct gggaatgcct gcaggaactc catggagact ttagacccca ctttgaaaaa   7500
ccaagctttt cataatgctg tggaggaaac cagacagacc acagactcca tgctcaggaa   7560
gcgatccccc gaggctggct gctcagatat ttgcccccgt tgccagtgtc attctccata   7620
tggagccctg gcctcctggc cgccttggcc tttgcccacg tgttcctaat gtttggaagt   7680
gatgattaga caggagtcat aaaggctgct cactacttcc tgtggctcgt tccccacaga   7740
cacttaacac agatggtcac cctctcccag gaactctgga gacagaaaaa cctttagcct   7800
actttagaag tctacagaaa ttcattaaga catgtggcct ttcccgtttt tgtgggcact   7860
ctctgttcac ttccttgatt ggccccgaca gccatgagct ggcctagttt tgcaggtgtg   7920
cgctttctga gtctcaagga ttcgggaggg aggcaccatc tttgaccagt ggagggatct   7980
ggggagaagg gagggcctct gtcctctgcc cagagctccc tagtcagcgg gtaattgttg   8040
gggaacccca ggcctgtccc agccaggaga gcctaggctg aggaagaagg tgactgagat   8100
gcaggtgaaa gcgagtgtat tcttaggtgg gtgatttggt taacctaaat ggattaataa   8160
agtttctcag ctttaatttc taataaggta aatattgaca ggtatagctc acataaacaa   8220
aagctctttg ggactctcaa ttgcaattaa aattggatat aaaatatcca aattaaatgc   8280
tgctaaaaga gaagtggcaa ggtgtttaac attccttata accacggatg tatacattaa   8340
gacaataagg tatcatgttg tacctccaag actgacaaag gtagaaaagc atgatcctgt   8400
cacagtgagg gtttggagaa gtaaaccttc tcatgcattg ctgggggtgg ggggtggggg   8460
ctggcggggg cggggtgggg tggggcggtg taaagtgctg cagggttttt tgagcgcagt   8520
ttggtaatac ctctgaaatt gaatatgtgc ctgtcttttg accttgtaat tgcatttttt   8580
aaaaactctg aaatggcttt ctattaaata gcaaagcaga attgcaatat aattttaaaa   8640
tatgtttaag ttaggtcaca aaagggatgt aaaatgtttg cagtatgact gttaaatctt   8700
catacagcta aagccaatta ttgactcttt cttataccaa tacagacata aaattatttt   8760
gtgatgaaaa gtagtccaaa ttgaatcact ttattggtaa acgtctttct tcccattaca   8820
```

```
ttttcccatt gctttggact tgaggcccgg ggttggggag gattggaaag gcgccttggg   8880
cattcttctc tccttgtcct ccttgtcccc cacaatttca tattcacaag tgtaccttac   8940
agaagcatcc acacaagtgg ataatggcac ttatacatgg atgtgtattg caggattttt   9000
tataatagtg atagaatact gtacaattgt tgaaaagaat atggtaacta tatatgtata   9060
tagaaagatg ttcacagtgt aaagttacaa aacagtactt acctaacttt gtgtatgtgg   9120
taacagtaga gaaaaaacaa tatgagtgtg catagtgctt tgaggaatat atgctaaact   9180
actacaagtg gatatctgaa gaaccacagt ttcaaagtgt ggtctgggga cctctagggg   9240
cccctgagat tctttcagag ggtccataat tatatgatgg tgatattgac aaatgtgact   9300
ttttggttat tatataagaa aatgtaccaa catttggaag atcctgcata atttattgaa   9360
tcaattttcc actttttttca tatgactgtg cttgatatta aaagatccat tcaaagtgca   9420
agactgatgg gttttaatgt aatagagtgt gaacatttca ttggtatagt tccaaattcc   9480
acactaaaca gcagtcaact aaagggcggt agcaaagagg aatatccaca attgtctgaa   9540
aaggctattg aaatactcct tcatttccca gttatacagc tgtatgaggc cagattttct   9600
tcatttactt caaccaaaac agcacgtcac aaaggaccaa atgcagaacc agataagcca   9660
gatatttaaa aagatttatg aaaatgttat ttgtgttagc atgtaatagg tttattatta   9720
ttattattat tattattgag acagagtctc actctgttgc ccaggctgga gtgcaatggc   9780
aagatcttgg ctcactgtgg tctctgcctc ccagggtcag gtgatcctcc cacctcagcc   9840
acccaagtag ctggggccac aggcaaatgc caccacaccc agctgatttt tatatttttt   9900
gtggagatag agttttgcca tgttgtccag gctggtctcg aactctcagg ctcaagtgct   9960
ccacctgtct tgtcctccca cagtgctgga attacaggtg taagtcacct cacctggttg  10020
gtgactttta aattttctca gttttaattt ctagtaatgt aaatattgat aggtataacc  10080
cacataaacc aaagctcttt gggaccttca ataatttttt agagtgtttg gagaccaaaa  10140
catttgaagt ctgctatttt ataacaggga attaaggaga actggtttgt atgattacga  10200
accatttgaa tttataatac aattagagtg tttattttta taatcagaaa aaaaataaaa  10260
gaatgtacaa agacatttct taaagaaaat ggtcaattgc ttttcttcat ctatatccag  10320
gacagaacaa gaggaaatgg gcttagtttg tatgaatgtt agtttaggtt agagataaac  10380
aagaatgtcc ttctgagaat tgttaaattg cagaacagtc tctgtgtcag tgtggatgcc  10440
ctcacttgta agttagcaga aaatccaatt caaacagctt tacctggtag aggagtttcc  10500
tggaaagtat agaggtggga tgtgctttgg gtttaatggg ggttaatctg gggcacagt   10560
catgcaaccc ggtttatctt ctgtctctga atcctgatgg cgctttagag tctagtcctc  10620
agcttggcag gtctaaaata ttaacaggag atgaagctga ccagatgaca cgaatatgtt  10680
tccgcccatg ggaggagaag gctacatagg agaccaggtc atcagaagcc gtttagtgag  10740
cacagagctg gaacccacca gggagctgag agtccttcaa gggtgtttct gtcaagcttg  10800
ggtagctggg ctcatagccc gtctccaact gcatcaacac tgatgaagtc tctcttcggc  10860
tttttctaaa cactatgcag ggcagcatcc ttcagtcaac atatctttta tcagaaatca  10920
ggttataatc gattggatct ctgctttctt caattacagt ccaggcctgt ggatataaac  10980
tagacactgt gattagattt ggggcattta ccaagtcttt aaaataaatt tgtgagccat  11040
ctgtatatac ttactcattc attgtgtttt taaaagataa ctgtgaaagt tttctcattg  11100
ttaatacatt ttcacaatag aaaacttaga aaattcagaa aagccaggaa taaaaatggc  11160
ctgtgatcca agcaggttgc tataccactg ctgagactgg ggcctctctc ttcatcttcc  11220
```

-continued ctgtacaggc agtgcagggt gattgtcaaa gcacccattt cagagtcctg cagatctggt 11280
cacctcccca ctctgccact gactagatgg ccttaggcaa gggcctttgt cattcttttt 11340
tttttctttt tttttgagac agggtcttgc tctgttgccc agattggagt gcagtggtgc 11400
gatcacagcg cactgcagcc tcaacctcct gggctcaagt gaacctccca cctcagcctc 11460
ccaagtagct gggaccacag gcacgtacca ccacacccag ccaattttta aaatattttt 11520
gtagaaatga gggtctcgtc atcttgccca ggctggcctg gaactcctgg gctcaagcag 11580
atcctcctgc ctcagcctcc caaagtgctg ggattacagg cgtgagcctg taatctgcaa 11640
atggcagttt tttaatttct aaaaaaatct taacattttt catgatgttt tggtttaaat 11700
caacacaaat ttcctttttaa aggttcctct catcttttaa gccttgtttc ctagtggtca 11760
tatttctatt gtccttgctt taagttagga agaactctct cccccatgca gcctccagag 11820
atactcagag actttcagtg acttaacacc cagctgggag ccaccgccct gtctggagtg 11880
tatttgtatg tggagcctac tgttttgaaa atcccaagtg aaaggaagca gtttcaaggg 11940
tggtttgggc ttgtttggcc ccattgttgg gaatgctgtg gctctcgggg ccacctgtgt 12000
gtgttgcggg aggggtggag gggagctctg ggcatgggag aagaggagtg aatgatcagg 12060
aaggaagcag gaagcctgag cagagagcgg aaggacctgc gctcgcagtt tacggccatg 12120
gaagctgctg attgttcttg aatttaaagt ggagaataag ggaccacaaa ttgcagggtt 12180
tgagcattcc atgtttttct taaatgagcc tgtctgcatt ttcaaaacgt gtgctttcaa 12240
aagagagctg tattttctga atccagctgt gaatgtggag accagccgtc ctccaagggc 12300
atgcgagaac acaccgttga gatccaggct gcttctgctc ggagagtggc ttgctcggcg 12360
gctccccagc cactcttttt ctggaagggt gagaagttct tgttcatggt gacttaacca 12420
tgtcttgcaa tcaagtcctt ttggatggtt gctctctccc cttcctgcat ccaagaccca 12480
cataccttca gtgtagagag actgaccacc agatctgccc tctaaagagc gctcctggag 12540
gaaacttggt tgggtgtctt tggcccttga tgtgatggga ggcacgcggg gactcagtgg 12600
tctgatgctt cccacaggga caccttgtgt acagggcact cggcggctgc ccgttcagtc 12660
tgcacctctg tgactgcccg agggatgcag ccagagggtc tgtgggtgcc agcaccaccc 12720
cactgccagg ccacttctgc ggctacgtgt tctctgggag ggtgagatct ctgcagccag 12780
gcgttttcac tgattcacca aatatctgcc tgtctgctct gagtttctgg gctgggtgct 12840
gagagatcca aaagggaaat ggtgtttgcc ttcatggagc ttgtcctgtg tcaggagaga 12900
gaagacctgt gtgcacaccg ataatataga gagtagtaaa tgtcctaaga caggtggaga 12960
cgccgagggc aaaggatgaa cactggctga accaatcaca gtctgaagag tggagggaat 13020
caggtacagg gcgggtggtc gaggagcatt cacagatgca gtggggatga gggtgtcatg 13080
ggggacagtc ggggctgtgc aggttgggag tcaagggcgt aagcctgaag aacagtcaga 13140
ccagatggtg gagtgctgcc tacggatctt ccacctccct ctagaaaatg ttaagtgtcg 13200
ctgtttaaac agccacagct gaggaagagg ggcccgggct aggaagtctg gtttactgtg 13260
cagtgactta ccttatgtcc tccgagctga tttagaggat ttctggtaaa tcaggaagtt 13320
tagtctggtg cctgaagaca gtggcattga gaggctggga ggtgtgtagg cgtgtgtgtg 13380
cgtgtgcata tgtatgtgtg tgcgtctaat ccttgttaaa tccgtctgaa cttttgccat 13440
gtgtcgggtt gtgtaatagg tgtgtgcggg gctgcgctgt attcctaggc ggtcaggatt 13500
cctttctagg ccagtgttcc acctgacgac aaggcagctt tgtgagtcat ctgggtgcta 13560

-continued cagtgcagaa gtgtccaggg agagatcctc tttgctttcg actccctgcc gggtgcatca 13620
cctcggtggg cctgggaata ccttggaaat ggcactgtca ggagaaaagc ctggagccac 13680
gtgtctggct ggaatggggt catggggagt cagagccttt gaaacctaga agcgttcagg 13740
ctcctgtgtt tacctgggcc gacctcaaac catcccagga aggagaaaag cagacctgct 13800
ctgataccag ggtgcccact gctacttagg tgtttttcca ttattcattc ctggggtaag 13860
aaatcgagtc ttgggtttac ccaccctact ggtgtcagag ggactcagca ggagagtaga 13920
tctaggattc cagatgatct tcttccatgg tttttgagca catactatgt gaccccgaga 13980
gagtgtggct ttctcgatta aagttattat ttcttttatg aaatcctagc aaagataggg 14040
acgtcagagc tggccgagtc agactcctgg gggcatgttg atggcatcca gatgcaattc 14100
tgcagaggaa tcctggaaaa caggagtaag tctagaggaa aggccacggg tgttagtgga 14160
cgagaggtca taatgaaaat aggggaaggg cctgagatat ttagcttgga gagaagaaca 14220
caggtttggt ttttgtttta gggcatgggg tggtggaaag taaatgacct tcagattaaa 14280
gggtagtagt taggagagag ttaaattaga tctgtttgga tgctcagctg tcacacccag 14340
catcaagggc tctgtggggc ctccaggctg ggaggctttg actttgtata aaataatcgt 14400
attggtttgg agaggagtgc agtggtttgg aaggtcctcc ttttggggtt tgaggtaaga 14460
tatcccaagt cttttcctat ttgagagttt cccttcctca tgaggcagtg tcactggcac 14520
gttgtcaccc tgcctgacta tgctggctgt cttctgagcg aaggtgacca tctggttcct 14580
tctcatgtac cacctcagtg ctggattggg agaggagcgg gaggaacaca gtgggatggg 14640
gcgcttctgt tttcagagcc tggctgtacc tgctgctcct tcctgaggtg agtctgccca 14700
ctagcagagt ggaaaagaaa ccatggaaat actaacaatg agaatagagg ctattgattt 14760
tttttttttt tttttaggag ctgagcaatt tatccacagt ttctcagctg gtgagtggcg 14820
gagccaagat ctgaacccag gcagggaggt aggcaggttc cagagcctgc acttttaatt 14880
ctgtgctctt ctgcttggct ggcctgaaat tccaggctta caggataata aatataagtg 14940
gcccaggaaa atcagaaaga tatttgtgtc aagatcactg gttctttgct ggaactgagc 15000
atcagcatca tctgggtact ttttgtatta tttatttatt ttttcaatag aaaattccta 15060
aactgactga cttttctttc cctccttctc tcccttcctt cctttcttcc ttctttcttt 15120
ccctgtctct ccttttttta atagaaaatt cccaaactat ggataatttt taaaacacaa 15180
atgccagata tgctgtttcc ctccctcttg acagacacac atcctttcga actctaatca 15240
agaaaaagag caagcagtgg tgtctgcctt agggtgtggt ggcctgggca tctcttaagt 15300
tgcccattgc ttgcctattc aaggtatgct tttgagatgc cattgaataa agtttgctcc 15360
tgagtacagt actggaaact gtctgtcttt cgcttgcagt tcatttagga cagagaagca 15420
acagtttata tagggtcaca aagtgtttga gctaaccata gatgagcgag cccaaatccc 15480
ccattttata ggctggcaga gggtcgggac ctcaaccaag ccacagagga cggcaaagct 15540
gggcctggag accacgctcc cgacctgcag ctgaggtctc ttcctaagaa agtttagaaa 15600
ttctggtgtc aagggtagtt gtggtggccg ggcacggtgg ctcacgcctg taatcccagc 15660
actctgggag gccgaggcgg gtggatcaca aggtcagaag atcaagacca tcctggctaa 15720
cacggtgaaa ccccgtctct actaaaaata caaaaaatta gccggacgta gtggcgagcg 15780
cctgtagtcc cagctactcg ggaggctgag gcaggagaat ggggtgaacc caggaggcag 15840
agcttgcagt gagccgagat tacaccacta cactccagcc tgggcaacag agcaagactc 15900
tgtctcaaaa aaaaaaaaaa aaaaaaaaaa aagagtagtt gtggtagcaa cagaacccac 15960

```
ctctctatct ggaagtcttc ttgagtgtct tagcaaaaga tgctctgtag gctgggcaca  16020
gtggctcaca cctgtaatac cagcactttg ggaggccaag gcaaatcact tgagcccagg  16080
agtttgagac cagcctgggc aagatggcaa ggccccatct ctacaaagaa tttctttaaa  16140
aaattagcca ggcatggtgg tatgcacctg tagtcccagc agcatgggag gttgaggcag  16200
gaggatccct tgagcccagg agcttgaggt ggcagtgagc tatgatcata ccaccacact  16260
cctgcctggg tgacaaagca agactccatc tctaaatgtg tgtgtgtgtg tgtgtgtgtg  16320
tgtgtgcatg caatgtaata aaacatagtt ctgattttta tggtctattc aggccatagt  16380
agagagacag ccagtgttca cttggcaatt tagaaaagtt ggagggtatg aagagtaaac  16440
ctggaattta acacccaatc tatttacaag atgatcactt tttaccaggc ctcagcttcc  16500
ttttgtgaaa gccatactat cttatgtgga aaatcttatt gctaggtaaa cgagtcattt  16560
cggtaattat aaaatctgta aatcctctga cactttctgt gtgcttttct acatgcgcgt  16620
acccatgcat cttttttttt ttttggttca aattaatggt tttatttcca tctttaacac  16680
tagcagagga gtccaaagca gactgatatc catggatgta gtttaaatgt aacaaagaaa  16740
gagttgaact atgtacattg aaaaaaggaa agacattttt tcataccaac ctttccctag  16800
tttgcagttt ctgaatagta gaaacaaaac acatttttaa atctttttat caatttaatt  16860
taggacgaag tacacaactt ttataattaa ccactgaagt tgtcttcaag gataaaactt  16920
aaagaaattt taaaatgggt gttaccatat tttattagtg gactgactcc aaggttgcct  16980
tgctccaagt ctgggcattg tgacattccc gtgatgccca gaagaaagtt aatggcaatg  17040
atgtccagtc agggggcaga cacgctacac atcacaatga tgggagctga ggattctgcc  17100
ctcttcaact ccaagtagaa aattattatt ttcattcaaa ctaactggaa gtgagccaaa  17160
cagttaaaaa gtcagaatga agaataaaac aattttcttt tcacatagag gagggacact  17220
ccttcagccc cgtctaaagt gaattctgtg ctgagtccct tctccttcag aagggtaaac  17280
tgaaggtcag ttattgctaa caaagccaga agtggcccct ttcccaccct gaagatgttt  17340
cacacgaaaa ggctgtttgt tttgcttgaa gccctctgag gaaggagggc agcggaagag  17400
gaggcatgcc ggcactgtaa ggcctctctc gttagccacc gccaggccct gtgctgtcag  17460
gggcagcttg ggccactttg ctgcccctga gcgaacctga ggctcccacc tacctgtgga  17520
gtgaaggaga ggttgtcctc tgggccccctg tttcaccagt cataacctat ggagcagtca  17580
aaggcccaaa gcatccaagc ccagtgggct tctgaaataa acggcacggg gttgggaagg  17640
atgagaaagc caagtcaggt gggccaggtt ctccgaacat ggggcaacag tgacctgggc  17700
aaaaggctgg aactgagcgg ctgataaggc cacaattact gccaccacct ctcagtatct  17760
acacgggggg cagatgttag gcagtgggaa ctgaggactg gagggcgtgt ggcaaacacc  17820
ggatggattt tatcagaaaa gagaggacac ccaaacatgt gcctgtccta tttatcttgc  17880
atgtcctgtg ccaggtgaag gacgctggag catgggtaag gttcctgaga acaactggtg  17940
ggcagaaatg ggctgggatg ggcactgctc cacaggcaac attaagcctc tgagggggac  18000
actaatagtg ctacatctgg tgggctgctg aaaagtaggt aacgaatggc ctttattgca  18060
ctttttcatt cttaggaaac gggattgccc tgcagagctt ctcttgattt gcagaaatca  18120
ctgcagatca atgataaggt gcaggcagaa tcacgggtga cctctgactc tcaagggaag  18180
aagtccagtg attggtcttt tcagggcctc aaggggccac tcttgcacct gggatcctcg  18240
agctgggtga accgggtctg gcttggtcaa tgtgtggcag gcagattggt cgaccggcag  18300
```

acacttggga caaaaggtgg tgtgcccggg aaagctgggg caaactttcc aaacggaaaa 18360
tttcttggca aatgtgcagg ttctgcaacc agactggaac cacgattccc agtgtgcctg 18420
actccctttc tctcactcta gaactggacc accccagagg aacagagatg gcctgggagg 18480
gccctgggtc cagcgccata gcatcaaact ggagataaca aaaggaaggg gttggaaaca 18540
aaagagcagt ttacatatca gacgtgggtt tcaaaacagt ctttttgagc tcaggaaaat 18600
ggaggcagat accactggag aacctgattg tccatccgtc tctcctgggc gtctctgaat 18660
acttcatata tgaatggagt ggtactgttt gtggttgatc tttttcctac aagttgggca 18720
agtattagcg ttcttcaggg aatcacggag gcactggcta cagaagacat ggccacattc 18780
tgtggaaacg atgagacgtc tattctgcac gatctctgaa tatctgtcca tgcagatagg 18840
acaaccgaca gtacccgagg gcctgaggcc tatagcgccc tcatccctgg tgtttctgga 18900
agtgtgggta gtcacataca cgtctctgtc cctggacaac aactcatcgt cactgctcac 18960
catgcagctg tcagcatggt cctggggcag cctcctagca ttcctccttg gtcttcttct 19020
tttgtcaaca atcacaacag agtcattgtg agtcagatca accaccacag gctctaaaga 19080
ttcacaagtg aggtcaacaa tttcatctcc agcagtttcc acgagttcta tgggttctgc 19140
ttccaaggaa atctcagggg tggaggttgc ttcccgtgtt cgcttctggg cttgtctaga 19200
atttattgct ccacctcgac gctttcttgt actcattgtg ctctttggtg cctttcgttt 19260
cctaacagaa aaggaagtga tctataccaa ggtttgcagg gaagtcgaat gttctcaacc 19320
tttcgtgccc tctggttaat catctggctt gcaaaagaat ttggatcggg acagatttcc 19380
agtattttaa agtcctggag ctagttaggt ctgcaggcgc tgccaccggc gcactccaga 19440
gaagaagctc cttctccagc cgcccaggag agctgtaccc atgcatcttt agtgctttag 19500
cccgggaggc attagaatcc tgtttattga gtggattgat attgaattgc cctaatagct 19560
ccataagaga aattattgtt ccattttgcc atcaaccaag gcacggagat gaaggtgata 19620
aataccttgc tcaggggcca agaagccgaa ggcaggtccc ctggtgtctt cttgagtttc 19680
ttcccgttgc cattcagagc agggtctgtg gaacagcagc atagcacgga atcaccatag 19740
gggcttggtg gaagcacagc catccagtgg ccccagaccc actgaatcag agtctgcttg 19800
ttgaacaaga tccccgggtg gttctcatgc actttaaagg ttaagaggca ccgatgctgg 19860
tctatgctgc atttccaaga ggcttaactg ttctctcttt ggtattggtg taaacgatgc 19920
atttcctgtt ctgactgtga ccgtgctctt ttctctggga tgggtggtgg gggagggagg 19980
aactggaaga taaacaagta tatgactttt ataaatgttc tgtgttcttt tgctgcttgt 20040
ttttgtgggg ctagttttca ggaggaactg tagagccctt catcttccag ggcttcctca 20100
tattcagtca gttactctgg ggagggatcc cagaaccatc tgggataaga ctgaccctgc 20160
ctggaggaga gggaggcagt gtaacctctg accactgaac tgcacagagg tgggtgctcc 20220
agggggatgt cacgttggcc agctgctgtc actggcaaag ggcattctgt tgcccctggg 20280
agttgagaat gactgcatca gtcagatcct aacgcagtag cagggaaggc caatgtgggt 20340
cttctccgag tctgattggg agaggaagtg acacactcgt ttcttggcgt ccaaagtgaa 20400
agcaggtggg gccactagaa tatgcagtgc tgttgcttca tcaggcacac tcaggagcgc 20460
cagggtaaat tctgcaggct gccctggttg ccccacagat gcgatcctca ctggactcaa 20520
tgagtaacgt ctgaggtatg ggcataacac aattaaggtg ttctcaaaac tggaaatcca 20580
aagcatccga gtgatgctct gaatcatgcg ccgtgtggaa ggaatgtgct ggcaggcgca 20640
gatcgccggc tgagtgttcc actgaaatta aactcaagtg ctgacttctc gttttttacc 20700

```
tccccacccc ttccctcaag gttggtctcc gccagctgga catgtccttg ctctgccaac  20760

tgtacagcct ctacgagtcg attcaggagt acaaggggc atgccaggca gcctccagcc  20820

cagactgcac ttacgctctg gagaacggct tcttcgatga agaggaggaa tatttccagg  20880

agcagaactc cctgcacgac aggagggacc gaggccctcc tcgggacttg tcactgcctg  20940

tctcctccct ctccagcagc gactggattc tggagtccat ctagagggtc ttgggaggga  21000

tgtgactgtt gggaagccct tcctactgga cacgctgtca tcatttgctg cttctcttgc  21060

aagaaagcac ctccgttgtg gacggtcctc gggcacaggg gatgagcgct accagtttca  21120

tttgtaggca gggagttctc cgcggatgca tggtggcagt ctgctttgat ggcagcagtt  21180

tctgcttagg tgacctagag gtcctcagca gtatcctcca cacctattta ttgaggtgca  21240

cctgctgggg attcataatg agaatataac aagaggatct cggtgaaagg ccttagtggg  21300

tgttttgtgt gaggtggctt gtagctagct acttccttac agatggtaga gtattccaat  21360

cctctttgtg ttagggttct tgcttccagt ttgggatgta ttaaaaccac catttcactg  21420

cttcccttcc tcaatatgct ctgcagcttt tcttgctgtt taaacctctc gcctcagctt  21480

tatttatttg taagctgcat tactaactgc ccagtgattc ggtgaaagct ttttactgaa  21540

aaagttaaca tttctagtca tcccaatcaa ctggcttttt tcaaccaaaa ttttatatca  21600

ttctttgtct atcagatacg agaggaagga agataatacg aagacatgtt gaatagtgaa  21660

aaaaaaaaaa agaacacaaa aactggggca agccaatgtg atgtatcact cactgtaaga  21720

tggcaaatgt tttcattttt aagattccga atgtaaacta gtgtgctaga aagcaaacca  21780

cccgccactc aaaccagtaa ttaccttaag ccttaatata tttattaaaa tactttatga  21840

gaacattaca ctttgtaggt taaaaatgag gataaaatgc taaactatct gtgtcatgtg  21900

ttattttatt ctgaatttgg aatcatcaac tttcatgact tgaatgcatt gagtccagtc  21960

aaataatgaa agaaaattag tttgtttttc tgccactaaa tgcatttgaa acaagattga  22020

ctctgttgag cttaaggaat cgttttagca agagtagatc accatttaca gctggttctc  22080

agtgctcttt tttttctttg agacggagtc tagctctgct gcctaggctg gagtgcagtg  22140

gcacgatctt ggctccctgc aacctctgcc tctctgggtt taagcaattc tcccacctca  22200

gccttccgag tagctgggat tacaggcgcc tgccaccacg cccagctgat ttttgtattt  22260

ttaatggaga tggggtttca ctgtgttgtc ctagctggtc ttgaactcct gacctcgtga  22320

tccacccgcc tcggcctccc aaagtgctgg gattacaagt gtgagccacc atgcctggct  22380

gctcttctgt ctttgaatgc tgcagactcc ttcatctttc ttttggtgtg ataattgctc  22440

actagagcgt ccttcaggtt agggagagga aggcacctca atgtcatgc            22489
```

<210> SEQ ID NO 3
<211> LENGTH: 50
<212> TYPE: DNA
<213> ORGANISM: Artificial Sequence
<220> FEATURE:
<223> OTHER INFORMATION: IFI27 probe

<400> SEQUENCE: 3

```
ccaagttcat cctgggctcc attgggtctg ccattgcggc tgtcattgcg           50
```

<210> SEQ ID NO 4
<211> LENGTH: 50
<212> TYPE: DNA
<213> ORGANISM: Artificial Sequence
<220> FEATURE:

-continued

<223> OTHER INFORMATION: IFI44L probe

<400> SEQUENCE: 4
gtgggctaag ataggtccta ctgcaaacca cccctccata tttccgtacc 50

<210> SEQ ID NO 5
<211> LENGTH: 50
<212> TYPE: DNA
<213> ORGANISM: Artificial Sequence
<220> FEATURE:
<223> OTHER INFORMATION: IFIT1 probe

<400> SEQUENCE: 5
tgaatgaagc cctggagtac tatgagcggg ccctgagact ggctgctgac 50

<210> SEQ ID NO 6
<211> LENGTH: 50
<212> TYPE: DNA
<213> ORGANISM: Artificial Sequence
<220> FEATURE:
<223> OTHER INFORMATION: RSAD2 probe

<400> SEQUENCE: 6
cgctggaacc ttgggcaagg aagaatgtga gcaagagtag agagagtgcc 50

<210> SEQ ID NO 7
<211> LENGTH: 50
<212> TYPE: DNA
<213> ORGANISM: Artificial Sequence
<220> FEATURE:
<223> OTHER INFORMATION: IFIT3 probe

<400> SEQUENCE: 7
aaaacaaaat caaccgggac cccagctttt cagaactgca gggaaacagc 50

<210> SEQ ID NO 8
<211> LENGTH: 50
<212> TYPE: DNA
<213> ORGANISM: Artificial Sequence
<220> FEATURE:
<223> OTHER INFORMATION: IFIT3 probe

<400> SEQUENCE: 8
acaaatcagc ctggtcacca gcttttcgga acagcagaga cacagagggc 50

<210> SEQ ID NO 9
<211> LENGTH: 50
<212> TYPE: DNA
<213> ORGANISM: Artificial Sequence
<220> FEATURE:
<223> OTHER INFORMATION: OTOF probe

<400> SEQUENCE: 9
gcccgtcaag tgctgcccct gcctgtgtct gggtttctgt tggctgtttt 50

<210> SEQ ID NO 10
<211> LENGTH: 50
<212> TYPE: DNA
<213> ORGANISM: Artificial Sequence
<220> FEATURE:
<223> OTHER INFORMATION: IFIT2 probe

<400> SEQUENCE: 10
gctgacccag catcagccac actctgggtt ggaaaatgtt tgcctgttgg 50

<210> SEQ ID NO 11
<211> LENGTH: 50
<212> TYPE: DNA
<213> ORGANISM: Artificial Sequence
<220> FEATURE:
<223> OTHER INFORMATION: EPSTI1 probe

<400> SEQUENCE: 11
gggagtcact tgatgctttc aggttaatca gagctatggg tgctacaggc 50

<210> SEQ ID NO 12
<211> LENGTH: 50
<212> TYPE: DNA
<213> ORGANISM: Artificial Sequence
<220> FEATURE:
<223> OTHER INFORMATION: SERPING1 probe

<400> SEQUENCE: 12
tgggaccagc agcacaagtt ccctgtcttc atggggcgag tatatgaccc 50

<210> SEQ ID NO 13
<211> LENGTH: 50
<212> TYPE: DNA
<213> ORGANISM: Artificial Sequence
<220> FEATURE:
<223> OTHER INFORMATION: OAS1 probe

<400> SEQUENCE: 13
agagagactt cctgaagcag cgccccacca agctcaagag cctcatccgc 50

<210> SEQ ID NO 14
<211> LENGTH: 50
<212> TYPE: DNA
<213> ORGANISM: Artificial Sequence
<220> FEATURE:
<223> OTHER INFORMATION: IFI6 probe

<400> SEQUENCE: 14
tgcgccgacg atgcccagaa tccagaactt tgtctatcac tctccccaac 50

<210> SEQ ID NO 15
<211> LENGTH: 50
<212> TYPE: DNA
<213> ORGANISM: Artificial Sequence
<220> FEATURE:
<223> OTHER INFORMATION: HLA-DRB6 probe

<400> SEQUENCE: 15
aaccccacag ccttgatggc agcgcctcgt cttcaacttt tgtgcttcct 50

<210> SEQ ID NO 16
<211> LENGTH: 50
<212> TYPE: DNA
<213> ORGANISM: Artificial Sequence
<220> FEATURE:
<223> OTHER INFORMATION: HBZ probe

<400> SEQUENCE: 16
gtcctggagg ttccccagcc ccacttaccg cgtaatgcgc caataaacca 50

<210> SEQ ID NO 17
<211> LENGTH: 50
<212> TYPE: DNA
<213> ORGANISM: Artificial Sequence
<220> FEATURE:
<223> OTHER INFORMATION: HS.386275 probe

<400> SEQUENCE: 17
tgttcttccc catgtcctgg atgccactgg aagtgcacac tgcttgtatg 50

<210> SEQ ID NO 18
<211> LENGTH: 50
<212> TYPE: DNA
<213> ORGANISM: Artificial Sequence
<220> FEATURE:
<223> OTHER INFORMATION: EIF2AK2 probe

<400> SEQUENCE: 18
cgttctctgc ctcacatagc ttacaagcca gctggagaaa tatggtactc 50

<210> SEQ ID NO 19
<211> LENGTH: 50
<212> TYPE: DNA
<213> ORGANISM: Artificial Sequence
<220> FEATURE:
<223> OTHER INFORMATION: IFIT1L probe

<400> SEQUENCE: 19
aggccttgtg gcaccagaca taagaccccc tgaaagtatc atccctcctg 50

<210> SEQ ID NO 20
<211> LENGTH: 50
<212> TYPE: DNA
<213> ORGANISM: Artificial Sequence
<220> FEATURE:
<223> OTHER INFORMATION: FCER1A probe

<400> SEQUENCE: 20
gaaccaggaa aggcttcaga cttctgaacc cacatcctaa gccaaacccc 50

<210> SEQ ID NO 21
<211> LENGTH: 50
<212> TYPE: DNA
<213> ORGANISM: Artificial Sequence
<220> FEATURE:
<223> OTHER INFORMATION: C21ORF7 probe

<400> SEQUENCE: 21
gtgacctcac agtaaacatc tctgcctttg cctgtgtgtg ttctggggga 50

<210> SEQ ID NO 22
<211> LENGTH: 50
<212> TYPE: DNA
<213> ORGANISM: Artificial Sequence
<220> FEATURE:
<223> OTHER INFORMATION: GYPE probe

<400> SEQUENCE: 22
aggatgtggc ctgcatgctg cctgatcttg cctagaacca gctgcacctg 50

<210> SEQ ID NO 23
<211> LENGTH: 50
<212> TYPE: DNA
<213> ORGANISM: Artificial Sequence
<220> FEATURE:
<223> OTHER INFORMATION: GYPB probe

<400> SEQUENCE: 23
tggagaaacg ggacaacttg tccatcgttt cactgtacca gctcctgtag 50

<210> SEQ ID NO 24
<211> LENGTH: 50

<212> TYPE: DNA
<213> ORGANISM: Artificial Sequence
<220> FEATURE:
<223> OTHER INFORMATION: HBM probe

<400> SEQUENCE: 24
tcgtgctgcg cgtggaccca gccaactttc cgctgctaat ccagtgtttc 50

<210> SEQ ID NO 25
<211> LENGTH: 50
<212> TYPE: DNA
<213> ORGANISM: Artificial Sequence
<220> FEATURE:
<223> OTHER INFORMATION: EIF1AY probe

<400> SEQUENCE: 25
ctgaggatgg ttctacagtt gggattttgg ccatcatcaa ccaagaagag 50

<210> SEQ ID NO 26
<211> LENGTH: 50
<212> TYPE: DNA
<213> ORGANISM: Artificial Sequence
<220> FEATURE:
<223> OTHER INFORMATION: LOC649143 probe

<400> SEQUENCE: 26
ggttggtgag agcttcacag tgcagaggcg agtccatcct gaggtgactg 50

<210> SEQ ID NO 27
<211> LENGTH: 50
<212> TYPE: DNA
<213> ORGANISM: Artificial Sequence
<220> FEATURE:
<223> OTHER INFORMATION: HBD probe

<400> SEQUENCE: 27
ggctaatgcc ctggctcaca agtaccattg agatcctgga ctgtttcctg 50

<210> SEQ ID NO 28
<211> LENGTH: 50
<212> TYPE: DNA
<213> ORGANISM: Artificial Sequence
<220> FEATURE:
<223> OTHER INFORMATION: FBXO7 probe

<400> SEQUENCE: 28
aggcgacggg aagcgcgggt ggtcggctgg ggtccggctc ctggagaaca 50

<210> SEQ ID NO 29
<211> LENGTH: 50
<212> TYPE: DNA
<213> ORGANISM: Artificial Sequence
<220> FEATURE:
<223> OTHER INFORMATION: KCNMA1 probe

<400> SEQUENCE: 29
ggttctgcat gacctagcca ctgctggggg ttttcttcta taacgttgtc 50

<210> SEQ ID NO 30
<211> LENGTH: 50
<212> TYPE: DNA
<213> ORGANISM: Artificial Sequence
<220> FEATURE:
<223> OTHER INFORMATION: MERTK probe

<400> SEQUENCE: 30
cttccttacc aagtgaactc catggcccca aagcaccaga tgaatgttgt 50

<210> SEQ ID NO 31
<211> LENGTH: 50
<212> TYPE: DNA
<213> ORGANISM: Artificial Sequence
<220> FEATURE:
<223> OTHER INFORMATION: EBI3 probe

<400> SEQUENCE: 31
gagctgccgg gcaacctcag atgaccgact tttccctttg agcctcagtt 50

<210> SEQ ID NO 32
<211> LENGTH: 50
<212> TYPE: DNA
<213> ORGANISM: Artificial Sequence
<220> FEATURE:
<223> OTHER INFORMATION: FAM89A probe

<400> SEQUENCE: 32
caggggatga gcgctaccag tttcatttgt aggcagggag ttctccgcgg 50

<210> SEQ ID NO 33
<211> LENGTH: 50
<212> TYPE: DNA
<213> ORGANISM: Artificial Sequence
<220> FEATURE:
<223> OTHER INFORMATION: UPB1 probe

<400> SEQUENCE: 33
gaaattctgc ctgaggacag cagcccagtg cttggcgaga gttcctgaca 50

<210> SEQ ID NO 34
<211> LENGTH: 50
<212> TYPE: DNA
<213> ORGANISM: Artificial Sequence
<220> FEATURE:
<223> OTHER INFORMATION: FAM89A probe

<400> SEQUENCE: 34
gatctcggtg aaaggcctta gtgggtgttt tgtgtgaggt ggcttgtagc 50

<210> SEQ ID NO 35
<211> LENGTH: 50
<212> TYPE: DNA
<213> ORGANISM: Artificial Sequence
<220> FEATURE:
<223> OTHER INFORMATION: EMR1 probe

<400> SEQUENCE: 35
tctcagctta acatggaaat gaggatccca ccagccccag aaccctctgg 50

<210> SEQ ID NO 36
<211> LENGTH: 50
<212> TYPE: DNA
<213> ORGANISM: Artificial Sequence
<220> FEATURE:
<223> OTHER INFORMATION: PTPN20 probe

<400> SEQUENCE: 36
gcatcctgag gtggccaagg gcagtggtgc tccagatgtt tctgtttctg 50

<210> SEQ ID NO 37
<211> LENGTH: 50
<212> TYPE: DNA
<213> ORGANISM: Artificial Sequence -continued

```
<220> FEATURE:
<223> OTHER INFORMATION: TMEM119 probe

<400> SEQUENCE: 37

gtctggcagc ctgtgtccac aatattcgtc agtcctcgac agggagcctg              50


<210> SEQ ID NO 38
<211> LENGTH: 50
<212> TYPE: DNA
<213> ORGANISM: Artificial Sequence
<220> FEATURE:
<223> OTHER INFORMATION: SLPI probe

<400> SEQUENCE: 38

ggatcctgtt gacaccccaa acccaacaag gaggaagcct gggaagtgcc              50


<210> SEQ ID NO 39
<211> LENGTH: 50
<212> TYPE: DNA
<213> ORGANISM: Artificial Sequence
<220> FEATURE:
<223> OTHER INFORMATION: S100P probe

<400> SEQUENCE: 39

aatgatgccc tggagatgtc acagattcct ggcagagcca tggtcccagg              50


<210> SEQ ID NO 40
<211> LENGTH: 50
<212> TYPE: DNA
<213> ORGANISM: Artificial Sequence
<220> FEATURE:
<223> OTHER INFORMATION: PI3 probe

<400> SEQUENCE: 40

ctgactgccc aggaatcaag aagtgctgtg aaggctcttg cgggatggcc              50
```

METHOD OF IDENTIFYING A SUBJECT HAVING A BACTERIAL INFECTION

CROSS-REFERENCE TO RELATED APPLICATIONS

This application is a 371 national phase of International Patent Application No. PCT/EP2017/067637 filed Jul. 12, 2017, which claims priority to British Patent Application No. 1612123.8 filed Jul. 12, 2016, the content of each of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "ST-IIL1-NP_sequence.txt", which was created on Jan. 10, 2019, which is 119,011 bytes in size, and which is herein incorporated by reference in its entirety.

The present disclosure relates to a method of identifying a subject having a bacterial infection, which includes discriminating said subject from a subject having a viral infection or an inflammatory disease. The disclosure also relates to a gene signature employed in the said method and to a bespoke gene chip for use in the method. The disclosure further extends to probes and/or primers specific to genes in a signature of the present disclosure. The disclosure further relates to use of known gene chips in the methods of the disclosure and kits comprising the elements required for performing the method. The disclosure also relates to use of the method to provide a composite expression score which can be used in the discrimination of a bacterial infection from a viral infection or inflammatory disease, particularly suitable for use in a low resource setting.

BACKGROUND

Every year, about 2.8 million children die in the first month of life, with 98% of these deaths occurring in developing countries. Neonatal infections, including sepsis and meningitis, are estimated to cause over 420 000 deaths each year, with 136 000 attributed to pneumonia. The current WHO recommendation for management of infections in neonates (0-28 days old) and young infants (0-59 days old) is referral for hospital treatment with at least a seven-day course of a combination of two injectable antibiotics—benzylpenicillin or ampicillin plus gentamicin. However, existing evidence demonstrates that in resource-limited settings many young infants with signs of severe infection do not receive the recommended inpatient treatment. The vast majority of febrile children in the developed world have self-resolving viral infection, but a small proportion of them have life-threatening bacterial infections. Although microbiological culture of bacteria from normally sterile sites remains the "gold standard" for confirming bacterial infection, these bacterial culture tests have disadvantages. For instance, culture results may take several days, and are frequently falsely negative when the infection resides in inaccessible sites (such as the lung or abdominal cavity) or when antibiotics have been previously administered [1-3].

Current practice (for instance, UK NICE guidelines (https://www.nice.org.uk/guidance/cg160)) is to admit ill-appearing febrile children to hospital and to administer parenteral antibiotics while awaiting results from bacterial cultures [4-6]. However, as only a minority of febrile children are ultimately proven to have bacterial infection, many patients with febrile illness undergo unnecessary invasive investigation and antibiotic treatment when in fact they have self-resolving viral illness which does not require intervention. This therefore results in a major unnecessary burden on healthcare resources and inappropriate antibiotic prescription [7]. The latter is particularly problematic in the light of increasing antibiotic resistance found in bacteria. Hence, there is a need to avoid unnecessary administration of antibiotics.

Numerous attempts have been made to improve the identification of bacterial infection, such as serious bacterial infection (SBI), but the distinction between bacterial and viral infection remains problematic [44]. Clinical criteria, including symptoms, vital signs [45, 46], and blood markers such as white cell count, differential, C-reactive protein (CRP), or procalcitonin, do not reliably distinguish bacterial from viral infections [42, 46]. For example a study of 15,750 hospital attendances reported that only 7% had confirmed serious bacterial infection, and a further 7% had clinically diagnosed serious bacterial infection. However, of the remaining 13,500 children, 20% were still treated with antibiotics. Conversely, 1% of those not suspected of having bacterial infection were re-admitted with serious bacterial infection, indicating that clinical diagnosis is very unreliable.[10] Other studies have documented the high proportion of febrile children undergoing investigation and treatment with antibiotics, despite a low prevalence of confirmed SBI [5, 6].

In an attempt to improve pathogen identification in febrile children, various molecular tests have been proposed [8]. However blood culture tests and the results of pathogen detection by molecular approaches are often discordant [42], resulting in reduced confidence in the reliability of the molecular diagnostics. Rapid molecular viral diagnostic tests have increased the proportion of patients detected with respiratory pathogens [9], in particular viruses. However, the same viruses were also found frequently in nasopharyngeal samples from healthy children [10], limiting the clinical value of respiratory virus detection. Moreover, carrying viruses may predispose children to subsequently develop serious bacterial infection [43]. Thus, the detection of a virus in the nasopharynx of a febrile child does not rule out the possibility of a concurrent serious bacterial infection and is of little help in the decision on whether to administer or withhold antibiotics. Thus there is a need for an improved method for identifying with confidence a subject with a bacterial infection in order to aid in the decision on whether to administer or withhold antibiotics from a subject.

SUMMARY OF THE INVENTION

The present inventors have generated data that suggests that a viable alternative to identifying specific pathogens in febrile children, is to employ the subjects inflammatory response to identify the presence of a bacterial infection. The present inventors' data indicates that induction of altered gene expression in host inflammatory cells is likely to be a marker for specific childhood infections including tuberculosis [11], bacterial [47, 12], including in the presence of viral infections [13-15, 48].

The present disclosure is summarised in the following paragraphs:

1. A method for identifying a subject having a bacterial infection comprising detecting in a subject derived RNA sample the modulation in gene expression levels of a gene signature comprising two or more genes, but no more than 10 genes, selected from the group consisting of: IFI44L, FAM89A, IFI27L, IFTI1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7, KCNMA1, MERTK, EBI3, UPB1, EMR1, PTPN20, TMEM119, SLPI, S100P and PI3.

2. The method according to paragraph 1, wherein the gene signature comprises two or more genes but no more than 10 genes selected from the group consisting of: IFI44L, IFI27, IFIT1, RSAD2, IFIT3, OTOF, IFIT2, ESPTI1, OAS1, IFI6, HS.386275, EIF2AK2, FAM89A, KCNMA1, MERTK, EBI3, UPB1, EMR1, PTPN20, TMEM119, SLPI, S100P and PI3.

3. The method according to paragraph 1 or 2, wherein the gene signature comprises at least one gene selected from the group consisting of:
   a) IFI44L, IFI27, IFIT1, RSAD2, IFIT3, OTOF, IFIT2, EPSTI1, OAS1, IFI6, HS.386275, EIF2AK2; and optionally one or more genes selected from the group consisting of:
   b) FAM89A, KCNMA1, MERTK, EBI3, UPB1, EMR1, PTPN20, TMEM119, SLPI, S100P and PI3.

4. The method according to claim 3, wherein the gene signature comprises at least one gene from each of the following groups:
   a) IFI44L, IFI27, IFIT1, RSAD2, IFIT3, OTOF, IFIT2, EPSTI1, OAS1, IFI6, HS.386275 and EIF2AK2; and
   b) FAM89A, KCNMA1, MERTK, EBI3, UPB1, EMR1, PTPN20, TMEM119, SLPI, S100P and PI3.

5. A method according to any one of the preceding paragraphs, wherein the gene signature is based on two genes of primary importance.

6. A method according to any one of the preceding paragraphs, wherein the gene signature comprises one or more of the following pairs of genes: IFI44L and FAM89A, OAS1 and EMR1, EMR1 and IFI44L, OSA1 and FAM89A, EBI3 and IFI44L, S100P and RSAD2, SLPI and IFI44L, S100P and EPSTI1, S100P and IFI44L, OAS1 and FAM89A, EMR1 and RSAD2, IFIT3 and FAM89A, TMEM119 and IFI44L, IFIT3 and EMR1, IFI6 and FAM89A, EPSTI1 and FAM89A, IFIT3 and FAM89A, UPB1 and IFI44L, S100P and IFIT1, RSAD2 and FAM89A, EMR1 and EPSTI1, S100P and EIF2AK2, IFIT3 and FAM89A, OAS1 and SLPI, IFIT1 and FAM89A, IFIT3 and SLPI, EMR1 and IFIT3, OAS1 and S100P, IFIT1 and SLPI, IFIT1 and EMR1, FAM89A and EPSTI1, SLPI and RSAD2, S100P and IFIT2, IFIT1 and TMEM119, IFIT1 and FAM89A, SLPI and EPSTI1, FAM89A and IFIT3, OAS1 and EBI3, EIF2AK2 and FAM89A, EBI3 and EPSTI1, IFIT3 and S100P, S100P and IFI6, OTOF and S100P, OAS1 and TMEM119, EBI3 and RSAD2, OTOF and EBI3, S100P and IFIT3, OTOF and FAM89A, IFIT2 and FAM89A, IFI27 and FAM89A, OAS1 and UPB1, OTOF and FAM89A, IFIT1 and UPB1, EIF2AK2 and FAM89A, RSAD2 and UPB1, IFIT3 and EBI3, SLPI and IFIT2, SLPI and IFIT3, EMR1 and IFIT2, HS.386275 and EBI3, HS.386275 and UPB1, IFIT3 and UPB1, HS.386275 and UPB1, IFIT3 and UPB1, HS.386275 and SLPI, FAM89A and IFI6, SLPI and IFI27, PTPN20 and IFI44L, OTOF and UPB1, HS.386275 and S100P, S100P and IFI27, EIF2AK2 and UPB1, EBI3 and IFI27, IFI44L and KCNMA1, TMEM119 and EPSTI1, IFIT2 and TMEM119, SLPI and IFI6, IFIT3 and TMEM119, UPB1 and EPSTI1, IFIT1 and EBI3, RSAD2 and PTPN20, EBI3 and IFIT3, IFI44L and MERTK, EBI3 and IFI6, PI3 and IFI27, IFI2 and UPB1, HS.386275 and TMEM119, IFIT2 and EBI3, TMEM119 and IFIT3, IFIT2 and MERTK, EIF2AK2 and EBI3, S100P and SERPING1, RSAD2 and MERTK, IFIT3 and MERTK, UPB1 and IFIT3, SERPING1 and FAM89A, IFIT3 and PTPN20, KCNMA1 and EPSTI1, IFIT3 and KCNMA1, SERPING1 and FAM89A, OAS1 and PTPN20, PTPN20 and EPSTI1, OTOF and KCNMA, and PTPN20 and IFIT3.

7. The method according to any one of the preceding paragraphs, wherein the gene signature comprises at least IFI44L and FAM89A.

8. The method according to any one of the preceding paragraphs, wherein the gene signature comprises at least OAS1 and EMR1.

9. The method according to any one of the preceding paragraphs, wherein the gene signature comprises at least IFI44L and IFI27.

10. The method according to any one of paragraphs 1 to 6, wherein the gene signature consists of IFI44L and FAM89A.

11. The method according to any one of paragraphs 1 to 6, wherein the gene signature consists of OAS1 and EMR1.

12. The method according to any one of paragraphs 1 to 6, wherein the gene signature consists of IFI44L and IFI27.

13. The method according to any one of the preceding paragraphs, wherein the gene expression levels of one or more of the genes selected from the group consisting of FAM89A, KCNMA1, MERTK, EBI3, UPB1, EMR1, PTPN20, TMEM119, SLPI, S100P and PI3 are upregulated in a subject having a bacterial infection.

14. The method according to any one of the preceding paragraphs, wherein the gene expression levels of one or more of the genes selected from the group consisting of IFI44L, IFI27, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD and FBXO7 and are downregulated in a subject having a bacterial infection.

15. A method according to any one of the preceding paragraphs, wherein the gene signature employs no more than a total of 10 genes, for example no more than 5 genes, such as 2, 3, 4, or 5 genes.

16. The method according to any one of the preceding paragraphs, wherein the method incorporates one or more such as 1, 2, 3, 4 or 5 housekeeping genes.

17. The method according to any one of the preceding paragraphs, wherein the method is for discriminating a subject having a bacterial infection from a subject having a viral infection.

18. The method according to any one of the preceding claims, wherein the method is for discriminating a subject having a bacterial infection from a subject having an inflammatory disease.

19. The method according to any one of the preceding paragraphs, wherein the bacterial infection is selected from the group consisting of: *Chlamydia pneumoniae, Chlamydia trachomatis, Chlamydophila psittaci, Mycoplasma pneumonia, Corynebacterium diphtheriae, Clostridium botulinum, Clostridium difficile, Clostridium perfringens, Clostridium tetani, Enterococcus faecalis, Enterococcus faecium, Listeria monocytogenes, Staphylococcus aureus, Staphylococcus epidermidis, Staphylococcus saprophyticus*, Group B *streptococcus, Streptococcus agalactiae, Streptococcus pneumoniae, Streptococcus pyogenes*, or acid fast bacteria such as *Mycobacterium leprae, Mycobaterium tuberculosis,*

*Mycobacterium ulcerans, Mycobacterium avium* intercellularae, *Bordetella pertussis, Borrelia burgdorferi, Brucella abortus, Brucella canis, Brucella melitensis, Brucella suis, Campylobacter jejuni, Escherichia coli, Francisella tularensis, Haemophilus influenzae, Helicobacter pylori, Legionella pneumophila, Leptospira interrogans, Neisseria gonorrhoeae, Neisseria meningitidis, Pseudomonas aeruginosa, Pseudomonas* spp, *Rickettsia rickettsii, Salmonella typhi, Salmonella typhimurium, Shigella sonnei, Treponema pallidum, Vibrio cholerae, Yersinia pestis, Kingella kingae, Stenotrophomonas* and *Klebsiella.*

20. The method according to any one of claims the preceding paragraphs, wherein the bacterial infection is a serious bacterial infection, for example bacterial meningitis, a respiratory infection, a urinary tract infection and/or bacteraemia.
21. The method according to any one of the preceding paragraphs, wherein a subject with bacterial infection can be identified in the presence of viral infection and/or an inflammatory disease.
22. The method according to any one of paragraphs 1 to 20, wherein a subject with bacterial infection can be discriminated from a patient with viral infection and/or inflammatory disease only.
23. The method according to any one of the preceding paragraphs, wherein the viral infection is selected from the group consisting of: Influenza such as Influenza A, including but not limited to: H1N1, H2N2, H3N2, H5N1, H7N7, H1N2, H9N2, H7N2, H7N3, H10N7, Influenza B and Influenza C, Respiratory Syncytial Virus (RSV), rhinovirus, enterovirus, bocavirus, parainfluenza, adenovirus, metapneumovirus, herpes simplex virus, Chickenpox virus, Human papillomavirus, Hepatitis, Epstein-Barr virus, Varicella-zoster virus, Human cytomegalovirus, Human herpesvirus, type 8 BK virus, JC virus, Smallpox, Parvovirus B19, Human astrovirus, Norwalk virus, coxsackievirus, poliovirus, Severe acute respiratory syndrome virus, yellow fever virus, dengue virus. West Nile virus. Rubella virus. Human immunodeficiency virus, Guanarito virus, Junin virus, Lassa virus, Machupo virus, Sabia virus, Crimean-Congo haemorrhagic fever virus, Ebola virus, Marburg virus, Measles virus, Mumps virus, Rabies virus and Rotavirus.
24. The method according to any one of the preceding claims, wherein the inflammatory disease is juvenile idiopathic arthritis (JIA), Henoch-Schönlein purpura (HSP) or systemic lupus erythematosus (SLE).
25. The method according to any one of the preceding paragraphs, wherein the subject is a child.
26. The method according to claim 25, where the child is in the age range 2 to 59 months.
27. The method according to any one of paragraphs 1 to 24, wherein the subject is an infant in the age range 0 to 59 days.
28. The method according to any one of the preceding paragraphs, wherein the subject has a fever.
29. The method according to any one of the preceding paragraphs, wherein a patient derived sample is employed in the method.
30. The method according to any one of the preceding paragraphs wherein the analysis of gene expression modulation employs a microarray.
31. The method according to any one of paragraphs 1 to 29, wherein the analysis gene expression modulation employs PCR, such as RT-PCR.
32. The method according to paragraph 31, wherein the PCR is a multiplex PCR.
33. The method according to claim 31 or 32, wherein the PCR is quantitative.
34. The method according to any one of claims 31 to 33, wherein primers employed in the PCR comprise a label or a combination of labels.
35. The method according to paragraph 34, wherein the label is fluorescent or coloured, for example coloured beads.
36. The method according to any one of paragraphs 31 to 35, wherein the analysis of gene expression modulation employs a dual colour reverse transcriptase multiplex ligation dependent probe amplification.
37. The method according to any one of the preceding paragraphs wherein gene expression modulation is detected by employing fluorescence spectroscopy.
38. The method according to any one of paragraphs 1 to 36, wherein gene expression modulation is detected by employing colorimetric analysis.
39. The method according to any one of paragraphs 1 to 36, wherein gene expression modulation is detected by employing impedance spectroscopy.
40. The method according to any one of the preceding paragraphs, which comprises the further step of prescribing a treatment for the subject based on the results of the analysis of said gene signature.
41. A method of treating a patient by administering an anti-bacterial agent such as an antibiotic, wherein the patient is characterised in that they have been identified as positive for bacterial infection by the method defined in any one of paragraphs 1 to 39.
42. A method of treating a patient by administering an anti-viral agent, such as oseltamivir or peramivir, wherein the patient is characterised in that they have been identified as negative for bacterial infection by the defined in any one of paragraphs 1 to 39.
43. A set of primers for use in multiplex PCR wherein the set of primers includes nucleic acid sequences specific to a polynucleotide gene transcript for at least one gene from the group consisting of:
a) IFI44L, IFI27, IFIT1, RSAD2, IFIT3, OTOF, IFIT2, EPSTI1, OAS1, IFI6, HS.386275 and EIF2AK2; and optionally includes nucleic acid sequences specific to a polynucleotide gene transcript for one or more genes selected from the group consisting of:
b) FAM89A, KCNMA1, MERTK, EBI3, UPB1, EMR1, PTPN20, TMEM119, SLPI, S100P and PI3.
44. The set of primers according to paragraph 43 wherein the set of primers includes nucleic acid sequences specific to a polynucleotide gene transcript for at least one gene from each of the following groups:
a) IFI44L, IFI27, IFIT1, RSAD2, IFIT3, OTOF, IFIT2, EPSTI1, OAS1, IFI6, HS.386275, EIF2AK2; and
b) FAM89A, KCNMA1, MERTK, EBI3, UPB1, EMR1, PTPN20, TMEM119, SLPI, S100P and PI3.
45. The set of primers according to paragraphs 43 or 44, wherein the nucleic acid sequences in the set are for no more than a total of 5 genes, such as 2, 3, 4, or 5 genes.
46. The set of primers according to any one of claims 43 to 45, wherein gene transcript is RNA, for example mRNA
47. The set of primers according to any one of paragraphs 43 to 46 wherein the set of primers includes one or more nucleic acids sequences specific to a gene transcript encoding IFI44L, for example the IFI44L sequence shown in SEQ ID NO: 1
48. The set of primers according to any one of paragraphs 43 to 47, wherein the set of primers includes one or more nucleic acid sequences specific to a gene transcript encoding FAM89A, for example the FAM89A sequence shown in SEQ ID NO: 2.

49. The set of primers according to any one of paragraphs 43 to 48, wherein the primers for each gene are at least a pair of nucleic acid primer sequences.

50. The set of primers according to any one of paragraphs 43 to 48 wherein the primer length is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 bases in length.

51. The set of primers according to any one of paragraphs 43 to 50, wherein at least one primer for each gene comprises a label.

52. The set of priers according to paragraph 51, wherein the labels on the primers are independently selected from selected from a fluorescent label, a coloured label, and antibody, step tag, his tag.

53. The set of primers according to paragraph 51 or 52, where each primer in a given pair of primers is labelled, for example where one label quenches the fluorescence of the other label when said labels are within proximity of each other.

54. The set of primers according to any one of paragraphs 43 to 53, wherein the primers comprise or consist of the sequences given in any one of SEQ ID NOs: 3 to 40.

55. A point of care test for identifying bacterial infection in a subject comprising the set of primers defined in any one of paragraphs 43 to 54.

56. Use of the set of primers defined in any one of paragraphs 43 to 54 in an assay to detect bacterial infection in a sample, for example a blood sample.

Accordingly, the present disclosure also provides a method for discriminating a subject having a bacterial infection from a subject having a viral infection or an inflammatory disease, comprising detecting in a subject derived RNA sample the modulation in gene expression levels of a gene signature comprising 2 or more genes selected from the group consisting of: IFI44L, FAM89A, IFI27L, IFTI1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7, KCNMA1, MERTK, EBI3, UPB1, EMR1, PTPN20, TMEM119, SLPI, S100P and PI3.

In one embodiment, the gene expression levels of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 of the genes listed above are detected.

In one embodiment, the gene expression levels of all 36 genes listed above are detected. Accordingly, in one embodiment there is provided a method for identifying a subject having a bacterial infection comprising detecting in a subject derived RNA sample the modulation in gene expression levels of a gene signature consisting of the following genes: IFI44L, FAM89A, IFI27L, IFTI1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7, KCNMA1, MERTK, EBI3, UPB1, EMR1, PTPN20, TMEM119, SLPI, S100P and PI3.

Advantageously, use of the appropriate gene signature in a method according to the present disclosure allows the robust and accurate identification of the presence of a bacterial infection or the differentiation of a bacterial infection from a viral infection or an inflammatory disease. Importantly, the method allows the accurate discrimination between bacterial and viral infections in patients displaying symptoms of bacterial and/or viral infections. In other words, the method allows the accurate detection of a bacterial infection in the presence or absence of a viral infection, without the need to rely on clinical criteria and/or bacterial culture tests.

What is more the gene signature of the present disclosure is based on as little as two genes. Gene signatures often comprise a large number of genes which only in combination show a pattern or marker of biological significance. It is very surprising that the gene signature of the present disclosure can be based on as little as a two genes and still reliably identify the presence of a bacterial infection.

The identification of bacterial infection can be particularly critical in patients which display clinical symptoms of having a viral infection only but in reality also have an underlying acute bacterial infection, such as a serious bacterial infection.

There is a significant unmet clinical need for proper and reliable identification of bacterial infection, particularly in children and infants. The gene signature of the present disclosure is a huge step forward on the road to treating patients, such as febrile patients because it allows accurate and rapid diagnosis which, in turn, allows patients to be appropriately and timely treated.

Furthermore, the components employed in the method disclosed herein can be provided in a simple format, which are cost efficient, rapid, cost effective, and can be employed in low resource and/or rural settings.

In one embodiment of the disclosure, the gene signature comprises at least one gene from each of the following groups:

a) IFI44L, IFI27, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD and FBXO7; and b) FAM89A, KCNMA1, MERTK, EBI3, UPB1, EMR1, PTPN20, TMEM119, SLPI, S100P and PI3.

In one embodiment, the gene signature comprises at least one gene selected from the group consisting of:

a) IFI44L, IFI27, IFIT1, RSAD2, IFIT3, OTOF, IFIT2, EPSTI1, OAS1, IFI6, HS.386275, EIF2AK2; and optionally one or more genes selected from the group consisting of:

b) FAM89A, KCNMA1, MERTK, EBI3, UPB1, EMR1, PTPN20, TMEM119, SLPI, S100P and PI3.

In one embodiment of the disclosure, the gene signature comprises at least one gene from each of the following groups:

a) IFI44L, IFI27, IFIT1, RSAD2, IFIT3, OTOF, IFIT2, EPSTI1, OAS1, IFI6, HS.386275 and EIF2AK2; and b) FAM89A, KCNMA1, MERTK, EBI3, UPB1, EMR1, PTPN20, TMEM119, SLPI, S100P and PI3.

The present inventors found that the genes in group a) tend to be down-regulated in subjects having a bacterial infection, whilst the genes in group b) tend to be up-regulated in subjects having a bacterial infection. Surprisingly, the present inventors have discovered that having at least one gene from each group in the gene signature provides sufficiently discriminatory power to identify subjects having a bacterial infection including discriminating subjects having a bacterial infection from a viral infection or inflammatory disease. Furthermore, the method is also suitable for identify bacterial infection in the presence of a viral infection or inflammatory disease.

In one embodiment, the gene signature comprises or consists of one or more of the following pairs of genes: IFI44L and FAM89A, OAS1 and EMR1, EMR1 and IFI44L, OSA1 and FAM89A, EBI3 and IFI44L, S100P and RSAD2, SLPI and IFI44L, S100P and EPSTI1, S100P and IFI44L, OAS1 and FAM89A, EMR1 and RSAD2, IFIT3 and FAM89A, TMEM119 and IFI44L, IFIT3 and EMR1, IFI6 and FAM89A, EPSTI1 and FAM89A, IFIT3 and FAM89A, UPB1 and IFI44L, S100P and IFIT1, RSAD2 and FAM89A, EMR1 and EPSTI1, S100P and EIF2AK2, IFIT3 and FAM89A, OAS1 and SLPI, IFIT1 and FAM89A, IFIT3 and SLPI, EMR1 and IFIT3, OAS1 and S100P, IFIT1 and SLPI, IFIT1 and EMR1, FAM89A and EPSTI1, SLPI and RSAD2, S100P and IFIT2, IFIT1 and TMEM119, IFIT1 and FAM89A, SLPI and EPSTI1, FAM89A and IFIT3, OAS1 and EBI3, EIF2AK2 and FAM89A, EBI3 and EPSTI1, IFIT3 and S100P, S100P and IFI6, OTOF and S100P, OAS1 and TMEM119, EBI3 and RSAD2, OTOF and EBI3, S100P and IFIT3, OTOF and FAM89A, IFIT2 and FAM89A, IFI27 and FAM89A, OAS1 and UPB1, OTOF and FAM89A, IFIT1 and UPB1, EIF2AK2 and FAM89A, RSAD2 and UPB1, IFIT3 and EBI3, SLPI and IFIT2, SLPI and IFIT3, EMR1 and IFIT2, HS.386275 and EBI3, HS.386275 and UPB1, IFIT3 and UPB1, HS.386275 and UPB1, IFIT3 and UPB1, HS.386275 and SLPI, FAM89A and IFI6, SLPI and IFI27, PTPN20 and IFI44L, OTOF and UPB1, HS.386275 and S100P, S100P and IFI27, EIF2AK2 and UPB1, EBI3 and IFI27, IFI44L and KCNMA1, TMEM119 and EPSTI1, IFIT2 and TMEM119, SLPI and IFI6, IFIT3 and TMEM119, UPB1 and EPSTI1, IFIT1 and EBI3, RSAD2 and PTPN20, EBI3 and IFIT3, IFI44L and MERTK, EBI3 and IFI6, PI3 and IFI27, IFI2 and UPB1, HS.386275 and TMEM119, IFIT2 and EBI3, TMEM119 and IFIT3, IFIT2 and MERTK, EIF2AK2 and EBI3, S100P and SERPING1, RSAD2 and MERTK, IFIT3 and MERTK, UPB1 and IFIT3, SERPING1 and FAM89A, IFIT3 and PTPN20, KCNMA1 and EPSTI1, IFIT3 and KCNMA1, SERPING1 and FAM89A, OAS1 and PTPN20, PTPN20 and EPSTI1, OTOF and KCNMA, and PTPN20 and IFIT3.

In one embodiment, the gene signature comprises or consists of one or more of the following pairs of genes: IFI44L and IFI27, IFIT1 and IFI27, RSAD2 and IFI27, IFIT2 and IFI27, IFIT3 and IFI27, IFI27 and EPSTI1, S100P and EBI3, and EIFT2AK2 and IFI27.

In one embodiment, the gene expression levels of one or more of the genes selected from the group consisting of FAM89A, KCNMA1, MERTK, EBI3, UPB1, EMR1, PTPN20, TMEM119, SLPI, S100P and PI3 are upregulated in a subject having a bacterial infection.

In one embodiment, the gene expression levels of one or more of the genes selected from the group consisting of IFI44L, IFI27, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD and FBXO7 are downregulated in a subject having a bacterial infection.

In another embodiment of the disclosure, the gene signature comprises at least 95%, such as 100% of the genes IFI44L, FAM89A, IFI27L, IFTI1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7, KCNMA1, MERTK, EBI3, UPB1, EMR1, PTPN20, TMEM119, SLPI, S100P and PI3.

In one embodiment of the disclosure, the gene signature comprises IFI44L and FAM89A. In another embodiment, the gene signature comprises OAS1 and EMR1. In yet another embodiment, the gene signature comprises IFI44L and IFI27.

In addition to any of the pair of genes listed above, the gene signature may further comprise one or more of the following genes: IFI27L, IFTI1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7, KCNMA1, MERTK, EBI3, UPB1, EMR1, PTPN20, TMEM119, SLPI, S100P and PI3.

In another embodiment, the gene signature may further comprise one or more of the following genes: IFI44L, IFI27, IFIT1, RSAD2, IFIT3, OTOF, IFIT2, ESPTI1, OAS1, IFI6, HS.386275, EIF2AK2, FAM89A, KCNMA1, MERTK, EBI3, UPB1, EMR1, PTPN20, TMEM119, SLPI, S100P and PI3.

In one embodiment of the disclosure, the gene signature comprises IFI44L and FAM89A and at least one further gene selected from:

a) IFI27, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD and FBXO7; and at least a further gene selected from:
b) KCNMA1, MERTK, EBI3, UPB1, EMR1, PTPN20, TMEM119, SLPI, S100P and PI3, for example where the gene signature comprises between 2 and 10 genes, such as 3, 4, 5, 6, 7, 8 or 9 genes.

In one embodiment of the disclosure, the gene signature comprises OAS1 and EMR1 and at least one further gene selected from:

a) IFI44L, IFI27, IFIT1, RSAD2, IFIT3, OTOF, IFIT2, EPSTI1, SERPING1, IFI6, HLA-DRB6, HBZ, HS.386275, EIF2AK2, IFIT1L, FCER1A, C21ORF7, GYPE, GYPB, HBM, EIF1AY, LOC649143, HBD and FBXO7; and at least a further gene selected from:
b) FAM89A, KCNMA1, MERTK, EBI3, UPB1, PTPN20, TMEM119, SLPI, S100P and PI3, for example where the gene signature comprises between 2 and 10 genes, such as 3, 4, 5, 6, 7, 8 or 9 genes.

In one embodiment of the disclosure, the gene signature comprises IFI44L and IFI27 and at least one further gene selected from:

a) IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD and FBXO7; and at least a further gene selected from:
b) FAM89A, KCNMA1, MERTK, EMR1, EBI3, UPB1, PTPN20, TMEM119, SLPI, S100P and PI3, for example where the gene signature comprises between 2 and 10 genes, such as 3, 4, 5, 6, 7, 8 or 9 genes.

Advantageously, the present inventors were able to discriminate subjects having a bacterial infection from subjects having a viral infection with a high degree of sensitivity (100%) and specificity (above 85%) using a gene signature which detects the modulation in gene expression levels of the 36 genes listed above.

In one embodiment the gene signature of the present disclosure employs no more than 5 genes.

In one embodiment the gene signature is based on 2 genes of primary importance.

In one embodiment the gene signature consists of only IFI44L and FAM89A.

Surprisingly, the present inventors were able to discriminate subjects having a bacterial infection from subjects having a viral infection with a high sensitivity (above 90%) and specificity (above 96%) using a gene signature having only these 2 genes.

Accordingly, although the 2-gene signature comprising IFI44L and FAM89A can discriminate between bacterial and viral infections with a high degree of high sensitivity and specificity, additional genes can be included in the gene signature if required, for example one or more of the 36 genes may be employed and/or one of more housekeeping genes may be employed.

The skilled person has the ability to customise the gene signature from the pool of 36 genes and/or known genes as required. This allows the skilled person to balance the discriminatory power of the method against the cost and speed of the method by reducing or increasing the number of genes tested.

In one embodiment the gene signature consists of only OAS1 and EMR1. In another embodiment the gene signature consists of only IFI44L and IFI27.

Thus in one embodiment the method further employs one or more housekeeping genes, such as 1, 2, 3, 4 or 5 housekeeping genes.

Housekeeping genes are not considered part of the signature in the context of the present specification.

Advantageously, in addition to a validation group (referred to herein as IRIS) the present inventors were also able to show that the disclosed method can accurately discriminate subjects having bacterial infections from subjects with viral infections or inflammatory disease in a meningococcal validation cohort, an inflammatory validation cohort, as well as in 3 published gene expression datasets which compared bacterial infection with viral infection or inflammatory disease. Accordingly, the present inventors have demonstrated that the method is applicable across a wide range of different samples and patient groups which suggests that the method is robust and reliable. In one embodiment the bacterial infection is selected from the group consisting of: *Chlamydia pneumoniae, Chlamydia trachomatis, Chlamydophila psittaci, Mycoplasma pneumonia, Corynebacterium diphtheriae, Clostridium botulinum, Clostridium difficile, Clostridium perfringens, Clostridium tetani, Enterococcus faecalis, Enterococcus faecium, Listeria monocytogenes, Staphylococcus aureus, Staphylococcus epidermidis, Staphylococcus saprophyticus*, Group B *streptococcus, Streptococcus agalactiae, Streptococcus pneumoniae, Streptococcus pyogenes*, or acid fast bacteria such as *Mycobacterium leprae, Mycobaterium tuberculosis, Mycobacterium ulcerans, Mycobacterium avium* intercellularae, *Bordetella pertussis, Borrelia burgdorferi, Brucella abortus, Brucella canis, Brucella melitensis, Brucella suis, Campylobacter jejuni, Escherichia coli, Francisella tularensis, Haemophilus influenzae, Helicobacter pylori, Legionella pneumophila, Leptospira interrogans, Neisseria gonorrhoeae, Neisseria meningitidis, Pseudomonas aeruginosa, Pseudomonas* spp, *Rickettsia rickettsii, Salmonella typhi, Salmonella typhimurium, Shigella sonnei, Treponema pallidum, Vibrio cholerae, Yersinia pestis, Kingella kingae, Stenotrophomonas* and *Klebsiella.*

In one embodiment the bacterial infection is a serious bacterial infection, for example bacterial meningitis, a respiratory infection, a urinary tract infection and/or bacteraemia.

In one embodiment the method of the present disclosure is capable of identifying a subject with bacterial infection in the presence of viral infection and/or an inflammatory disease.

In one embodiment the method of the present disclosure is capable of discriminating a subject with bacterial infection from a patient with viral infection and/or inflammatory disease only.

In one embodiment the viral infection is selected from the group comprising or consisting of: Influenza such as Influenza A, including but not limited to: H1N1, H2N2, H3N2, H5N1, H7N7, H1N2, H9N2, H7N2, H7N3, H10N7, Influenza B and Influenza C, Respiratory Syncytial Virus (RSV), rhinovirus, enterovirus, bocavirus, parainfluenza, adenovirus, metapneumovirus, herpes simplex virus, Chickenpox virus, Human papillomavirus, Hepatitis, Epstein-Barr virus, Varicella-zoster virus, Human cytomegalovirus, Human herpesvirus, type 8 BK virus, JC virus, Smallpox, Parvovirus B19, Human astrovirus, Norwalk virus, coxsackievirus, poliovirus, Severe acute respiratory syndrome virus, yellow fever virus, dengue virus. West Nile virus. Rubella virus. Human immunodeficiency virus, Guanarito virus, Junin virus, Lassa virus, Machupo virus, Sabia virus, Crimean-Congo haemorrhagic fever virus, Ebola virus, Marburg virus, Measles virus, Mumps virus, Rabies virus and Rotavirus.

In one embodiment the inflammatory disease is disease is juvenile idiopathic arthritis (JIA), Henoch-Schönlein purpura (HSP) or systemic lupus erythematosus (SLE).

In a further aspect the present disclosure provides a method of treating a subject having a bacterial or viral infection after diagnosis employing the method herein.

In one embodiment the subject is a child, for example under 17 years of age, such as 2 to 59 months old.

In one embodiment the subject is an infant, for example in the age range 0 to 59 days.

In one embodiment the subject has fever, for example is a febrile patient.

In one embodiment the method of the present disclosure is employed on a patient derived sample, for example a blood sample.

In one embodiment the analysis of gene expression modulation employs a microarray.

In one embodiment the analysis of gene expression modulation employs PCR, such as RT-PCR.

In one embodiment the PCR is multiplex PCR.

In one embodiment the PCR is quantitative.

In one embodiment the primers employed in the PCR comprise a label or a combination of labels.

In one embodiment the label is fluorescent or coloured, for example the label is coloured beads.

In one embodiment the analysis of gene expression modulation employs dual colour reverse transcriptase multiplex ligation dependent probe amplification.

In one embodiment the gene expression modulation is detected by employing fluorescence spectroscopy.

In one embodiment the gene expression modulation is detected by employing colourimetric analysis.

In one embodiment the gene expression modulation is detected employing by impedance spectroscopy.

In one embodiment the method comprises the further step of prescribing a treatment for the subject based on the results of the analysis of the gene signature.

Thus, in one aspect there is provided a method of treating a patient by administering an anti-bacterial agent, such as an antibiotic, wherein the patient is characterised in that the patient has been identified as positive for bacterial infection by the method disclosed herein.

In one aspect, there is provided a method of determining whether to administer an anti-bacterial agent to a subject, such as an antibiotic, comprising the steps of: performing the method according to the present disclosure, and administering the anti-bacterial agent to the subject if the method indicates that the subject has a bacterial infection.

In one embodiment the anti-bacterial agent is an antibiotic, for example selected from the group comprising ceftobiprole, ceflaroline, clindamycin, dalbavancin, daptomycin, linezolid, oritavancin, tedizolid, telavancin, tigecycline, vancomycin, aminoglycosides, carbapenems, ceftazidime, ceftobiprole, fluoroquinolines, piperacillin/tazobactam, ticarcillin/clavulanic acid, streptogramins, such as amikacin, gentamicin, kanamycin, netilmicin, tobramycin, paromomycin, streptomycin, geldanamycin, herbimycin, rifaximin, loracarbef, ertapenem, doripenem, imipenem/cilastatin, meropenem, cefadroxil, cefazolin, cefalotin/cefalothin, cefalexin, cefaclor, k cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, dalbavancin, oritavancin, clindamycin, linomycin, daptomycin, azithromycin, clarithromycin, dirithromycin, erythromycin, roxithromycin, troleandomycin, telithromycin, spiramycin, aztreonam, furazilidone, linezolid, posizolid, radezolid, torezolid, amoxicillin, ampicillin, azlocillin, carbenicillin, cloxacillin, dicloxacillin, flucloxacillin, mezlocillin, nafcillin, oxacillin, penicillin G, penicillin V, piperacillin, temocillin, ticarcillin, amoxicillin/clavulanate, ampicillin/sulbactam, piperacillin/tazobactam, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capremycin, cycloserine, ethambutol, ethionamide, isoniazid, pyrazinamide, rifampicin, rifapentine, streptomycin, chloramphenicol, fosfomycin, fusidic acid, metronidazole, mupirocin, platensimycin, quinupristin/dalfopristin, thiamphenicol, tigecycline, tinidazole and trimethoprim.

In another aspect there is provided a method of treating a patient by administering an anti-viral agent, such as an oseltamivir or peramivir, wherein the patient is characterised in that the patient has been identified as negative for a bacterial infection by the method disclosed herein.

In another aspect, there is provided a method of determining whether to administer an anti-viral agent to a subject, such as oseltamivir or peramivir, comprising the steps of: performing the method according to any one of the preceding claims, and administering the anti-viral agent to the subject if the method indicates that the subject has a viral infection.

Hence, the presently disclosed method can aid in the appropriate treatment of patients, such as febrile patients, for example where it is unclear if the fever is due to a bacterial infection, viral infection or both. This has the advantage of ensuring rapid and appropriate treatment without the need to wait for bacterial culture results. Importantly, this can help to ensure that antibiotics are only prescribed when the subject genuinely has a bacterial infection rather than a viral infection.

In one aspect of the disclosure, there is provided a set of primers for use in multiplex PCR, wherein the set of primers include nucleic acid sequences specific to a polynucleotide gene transcript from at least one gene from each of the following groups:

a) IFI44L, IFI27, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7 and KCNMA1; and b) FAM89A, KCNMA1, MERTK, EBI3, UPB1, EMR1, PTPN20, TMEM119, SLPI, S100P and PI3.

In one aspect of the disclosure, there is provided a set of primers for use in multiplex PCR wherein the set of primers includes nucleic acid sequences specific to a polynucleotide gene transcript for at least one gene from the group consisting of:

a) IFI44L, IFI27, IFIT1, RSAD2, IFIT3, OTOF, IFIT2, EPSTI1, OAS1, IFI6, HS.386275 and EIF2AK2; and optionally includes nucleic acid sequences specific to a polynucleotide gene transcript for one or more genes selected from the group consisting of:

b) FAM89A, KCNMA1, MERTK, EBI3, UPB1, EMR1, PTPN20, TMEM119, SLPI, S100P and PI3.

In one embodiment, the set of primers includes nucleic acid sequences specific to a polynucleotide gene transcript for at least one gene from each of the following groups:

a) IFI44L, IFI27, IFIT1, RSAD2, IFIT3, OTOF, IFIT2, EPSTI1, OAS1, IFI6, HS.386275, EIF2AK2; and b) FAM89A, KCNMA1, MERTK, EBI3, UPB1, EMR1, PTPN20, TMEM119, SLPI, S100P and PI3.

In one embodiment, the nucleic acid sequences in the set are for no more than a total of 10 genes or less, such as 5 genes, in particular 2, 3, 4 or 5 genes.

In one embodiment, the nucleic acid sequences in the set are for only IFI44L and FAM89A. In another embodiment, the nucleic acid sequences in the set are for only OAS1 and EMR1. In another embodiment, the nucleic acid sequences in the set are for only IFI44L and IFI27.

In one embodiment, the gene transcript is RNA, for example mRNA.

In one embodiment, the set of primers includes one or more nucleic acids sequences specific to a gene transcript encoded IFI44L, for example the IFI44L sequence shown in SEQ ID NO: 1. In one embodiment, the set of primers includes one or more nucleic acid sequences specific to FAM89A, for example the FAM89A sequence shown in SEQ ID NO: 2.

In one embodiment the primers for each gene are at least a pair of nucleic acid primer sequences.

In one embodiment the primer length is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 bases in length.

In one embodiment at least one primer for each gene comprises a label.

In one embodiment the labels on the primers are independently selected from selected from a fluorescent label, a coloured label, and antibody, step tag, his tag.

In one embodiment each primer in a given pair of primers is labelled, for example where one label quenches the fluorescence of the other label when said labels are within proximity of each other.

Examples of suitable primer sequences are given in Table 8. Accordingly, in one embodiment the primers comprise or consist of the sequences given in any one of SEQ ID NOs: 3 to 40.

In one aspect, there is provided a point of care test for identifying bacterial infection in a subject comprising the set of primers as defined above. Advantageously, the presently disclosed test can be performed rapidly in as little as a couple of hours without the need for complex diagnostic or lab equipment. Accordingly, the presently disclosed method can be easily implemented as part of an existing patient care program in a hospital setting as well as in more resource poor settings such as in remote villages.

In one aspect, there is provided the use of a set of primers as defined above in an assay to detect bacterial infection in a sample, for example a blood sample.

In another aspect of the disclosure there is provided a gene chip consisting of probes for detecting the modulation in gene expression levels of IFI44L and FAM89A; and optionally probes for one or more genes selected from the group consisting of: IFI27L, IFTI1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7, KCNMA1, MERTK, EBI3, UPB1, EMR1, PTPN20, TMEM119, SLPI, S100P and PI3.

In one embodiment the gene chip consists of probes for detecting the expression levels of IFI44L and FAM89A, for example Illumina transcript ID no. ILMN_9752 for IFI44L and Illumina transcript ID no. ILMN_21686 for FAM89A.

In another embodiment the gene chip consists of probes for detecting the expression levels of OAS1 and EMR1, for example Illumina transcript ID no. ILMN_2717 for OAS1 and ILMN_12984 for EMR1.

In another embodiment the gene chip consists of probes for detecting the expression levels of OAS1 and EMR1, for example Illumina transcript ID no. ILMN_2717 for OAS1 and ILMN_12984 for EMR1.

In another embodiment the gene chip consists of probes for detecting the expression levels of IFI44L and IFI27, for example Illumina transcript ID no. ILMN_9752 for IFI44L and ILMN_17548 for IFI27. Advantageously, a chip with probes for just 2 genes is able to accurately and reliably differentiate between a sample, for example whole blood derived from a subject having a bacterial infection from a sample derived from a subject having a viral infection. Such a chip can be cheaply produced, making the chip particularly suited for use in resource poor settings.

In a further embodiment the present disclosure includes use of a known or commercially available gene chip in the method of the present disclosure.

BRIEF DESCRIPTION OF THE FIGURES

FIG. 1A shows a flowchart depicting the overall flow of patients in the study showing patient recruitment and subsequent selection for microarray analysis. Febrile children with infections were recruited to the *Immunopathology of Respiratory, Inflammatory and Infectious Disease Study*, and were classified into diagnostic groups based on the symptoms shown in the flowchart in FIG. 1B.

HC Healthy Control; JIA juvenile idiopathic arthritis; ILAR International League of Associations for Rheumatology; HSP Henoch-Schönlein Purpura; SLE Systemic Lupus Erythematosus; GEO Gene Expression Omnibus; DB Definite Bacterial; PB Probable Bacterial; U Unknown; PV Probable Viral; DV Definite Viral; CRP: C-reactive protein.

Figure 2:
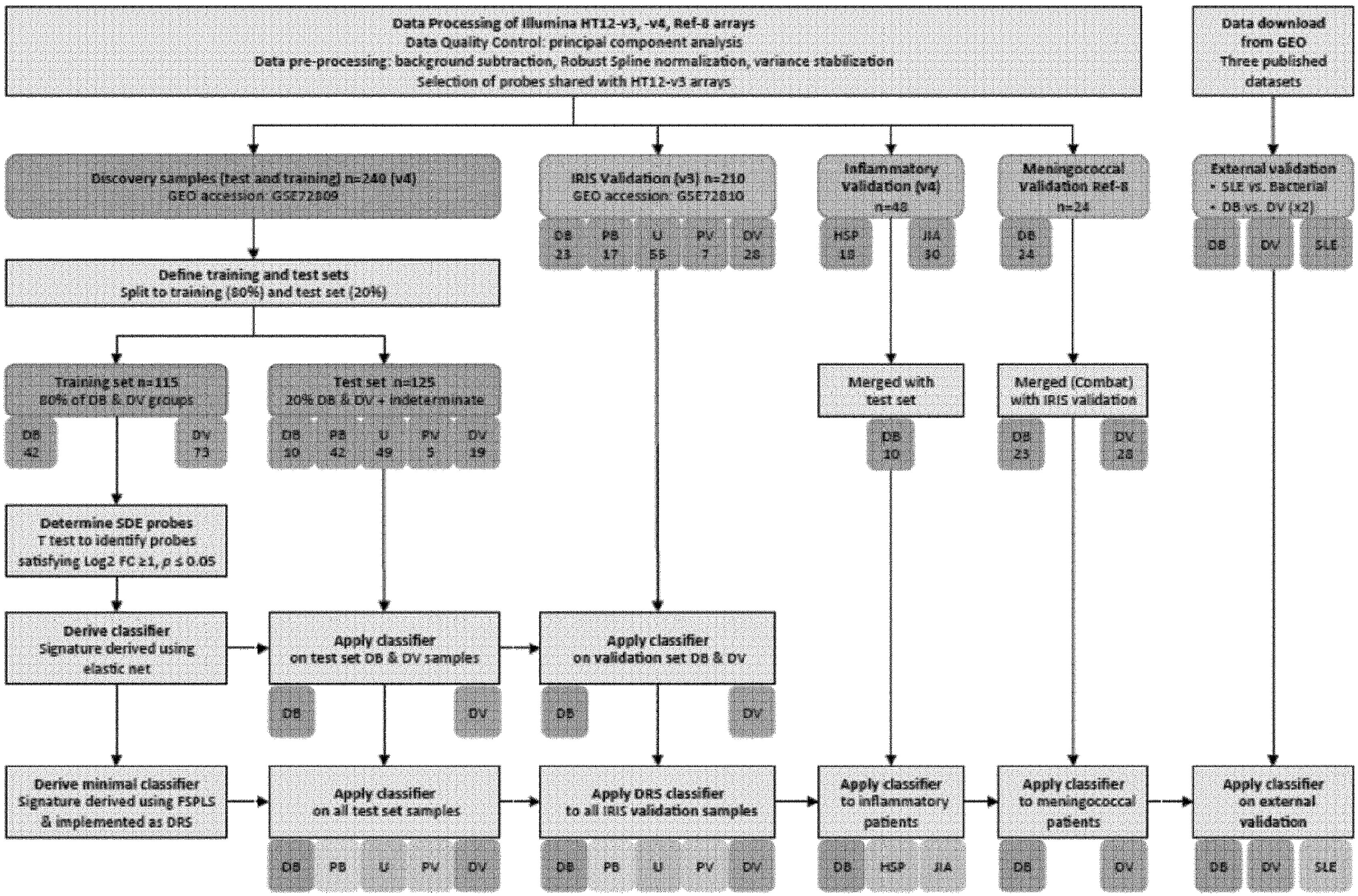

FIG. 2 shows a flowchart depicting the overall study pipeline showing sample handling, derivation of test and training datasets, data processing, and analysis pipeline including application of 38-transcript elastic net classifier and 2-transcript DRS classifier, to the test set, the validation datasets and published (external) validation datasets.

DB Definite Bacterial; PB Probable Bacterial; U Unknown; PV Probable Viral; DV Definite Viral; HSP Henoch-Schönlein Purpura; JIA Juvenile Idiopathic Arthritis; SLE Systemic Lupus Erythematosus; HC Healthy Control; SDE Significantly Differentially Expressed; FC fold change; FS-PLS Forward Selection—Partial Least Squares; DRS Disease Risk Score.

Figure 3:
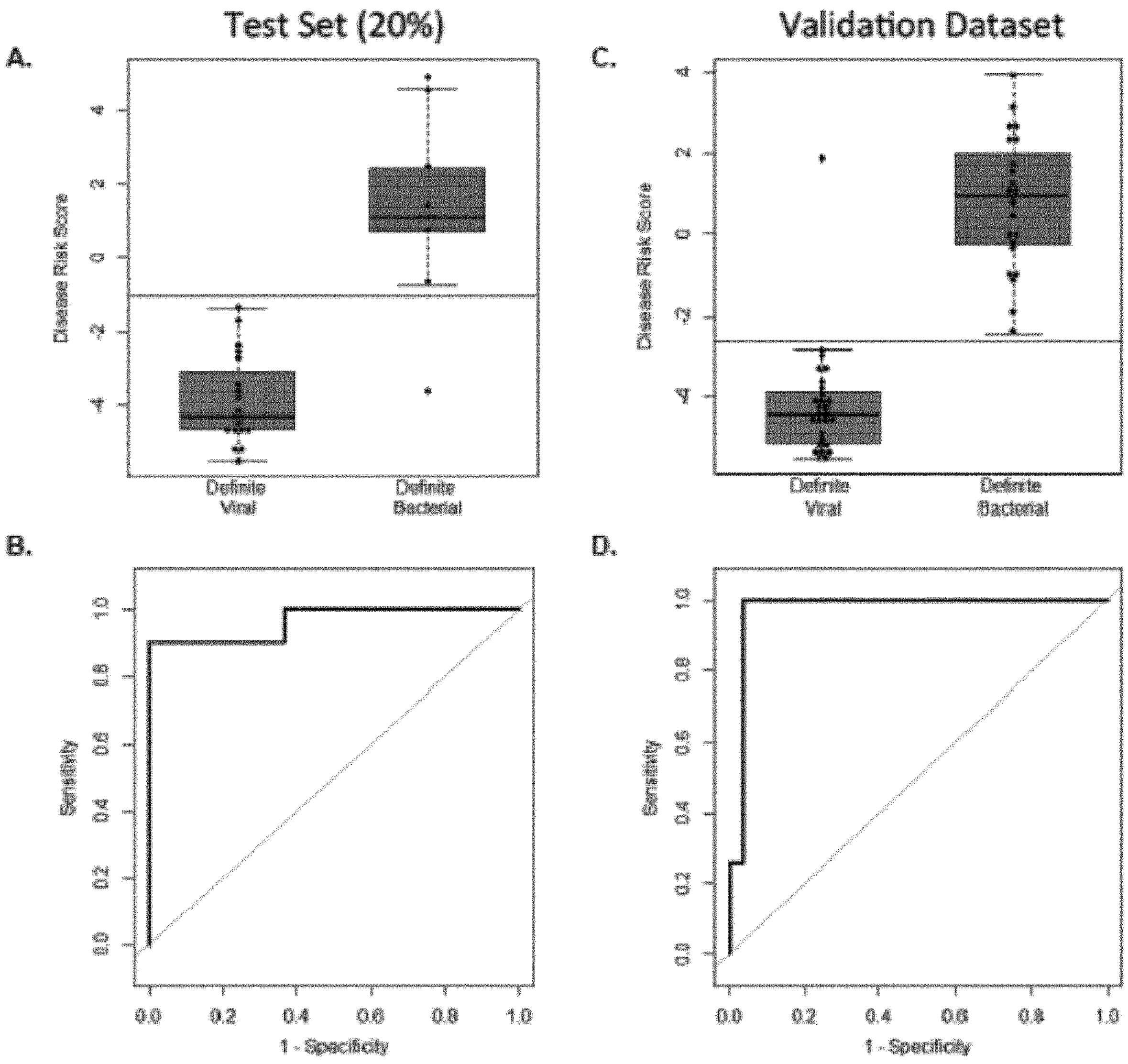

FIG. 3 shows a classification performance plot and Receiver Operating Characteristic (ROC) curve based on the 2-transcript DRS signature, applied to the Definite Bacterial and Viral groups of the 20% test set (A & B) and the IRIS validation dataset (C & D). Boxes show median with $25^{th}$ and $75^{th}$ quartiles; whiskers show ranges. Sensitivity, specificity, and AUC are reported in Table 5.

Figure 4:
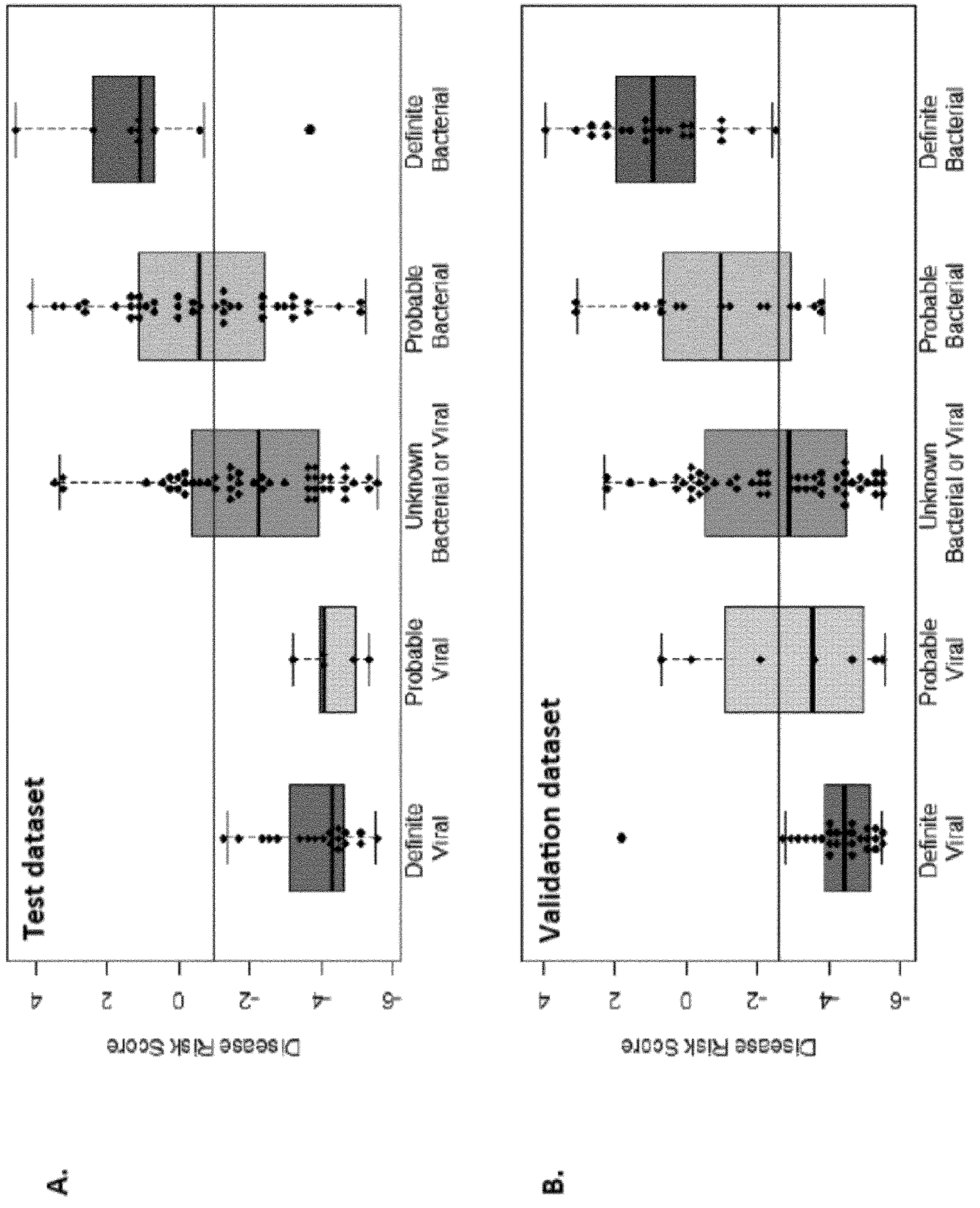

FIG. 4 shows plots indicating the performance based on the DRS signature, applied to the indeterminate groups of Probable Bacterial, Probable Viral, and Unknown of the discovery (A) and IRIS validation (B) sets. Boxes show median with $25^{th}$ and $75^{th}$ quartiles; whiskers show ranges.

Figure 5:
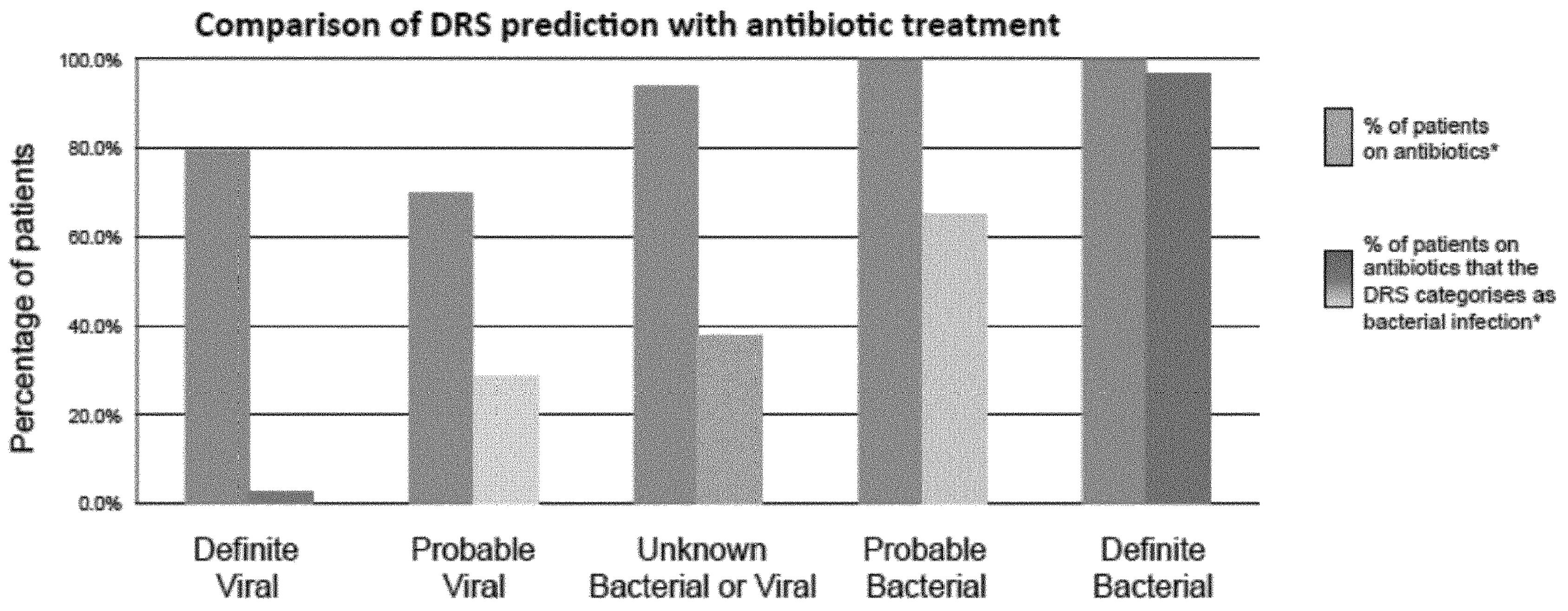

FIG. 5 shows a graph indicating the proportion of patients in the combined test and validation group receiving antibiotics, and the proportion of positive bacterial calls, as predicted by DRS. The proportion of patients classified as bacterial by the DRS and the proportion receiving antibiotics were, respectively: 2.9% and 79.5% in the Definite Viral group; 28.6% and 70.0% in the Probable Viral group; 37.7% and 93.9% in the Unknown group; 65.3% and 100.0% in the Probable Bacterial group; and 96.4% and 100% in the Definite Bacterial groups.

Figure 6:
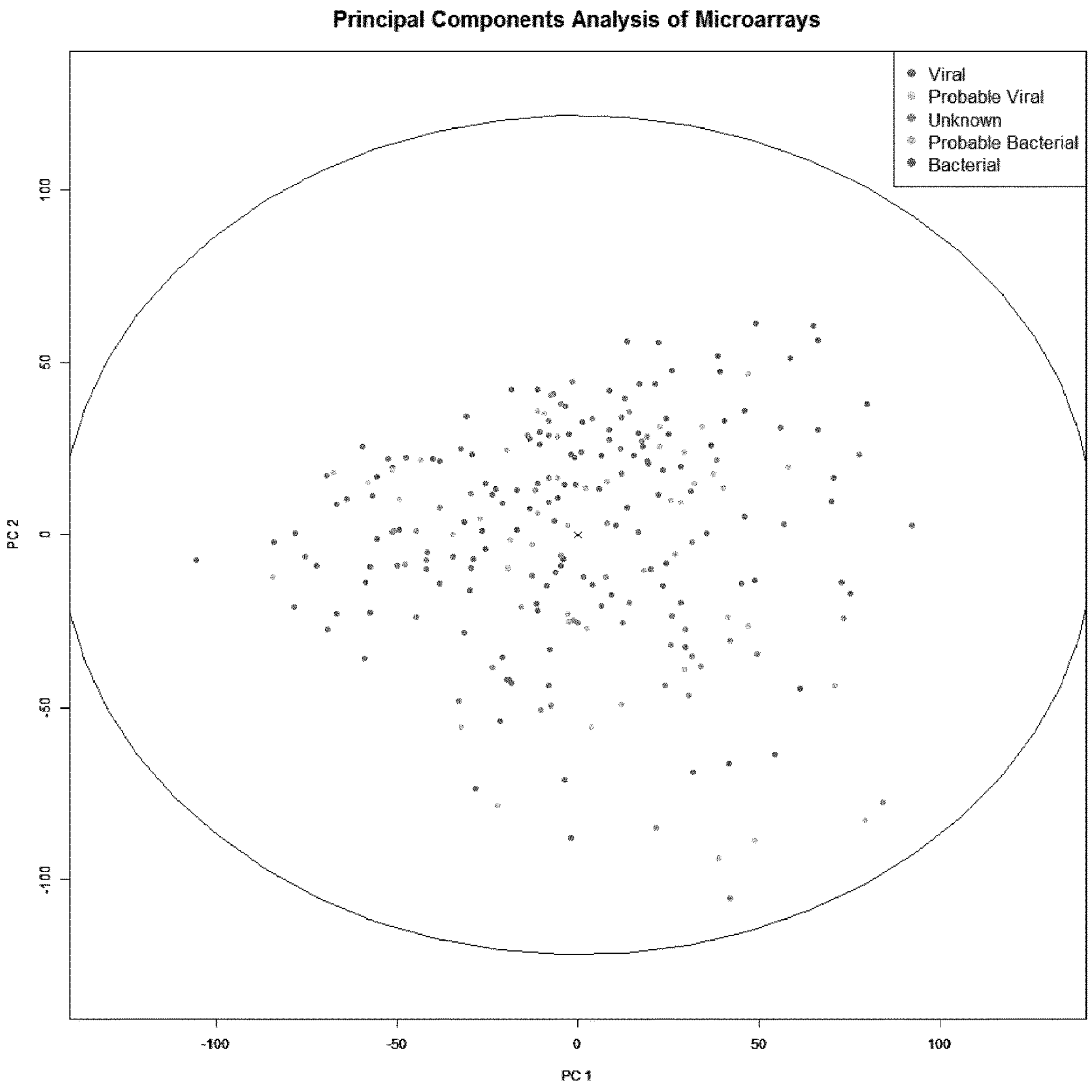

FIG. 6 shows a Principal Components analysis (PCA) of the samples in the discovery set (PC1 & PC2) based on all transcripts and samples in the discovery cohort after background adjustment and normalization. No sample was removed from the analysis at this stage. A confidence ellipse was calculated for the population mean and is shown in the plot (99%). Number of arrays for each sample are: Viral n=92, Probable Viral n=5, Unknown n=49, Probable Bacterial n=42, Bacterial n=52.

Figure 7A:
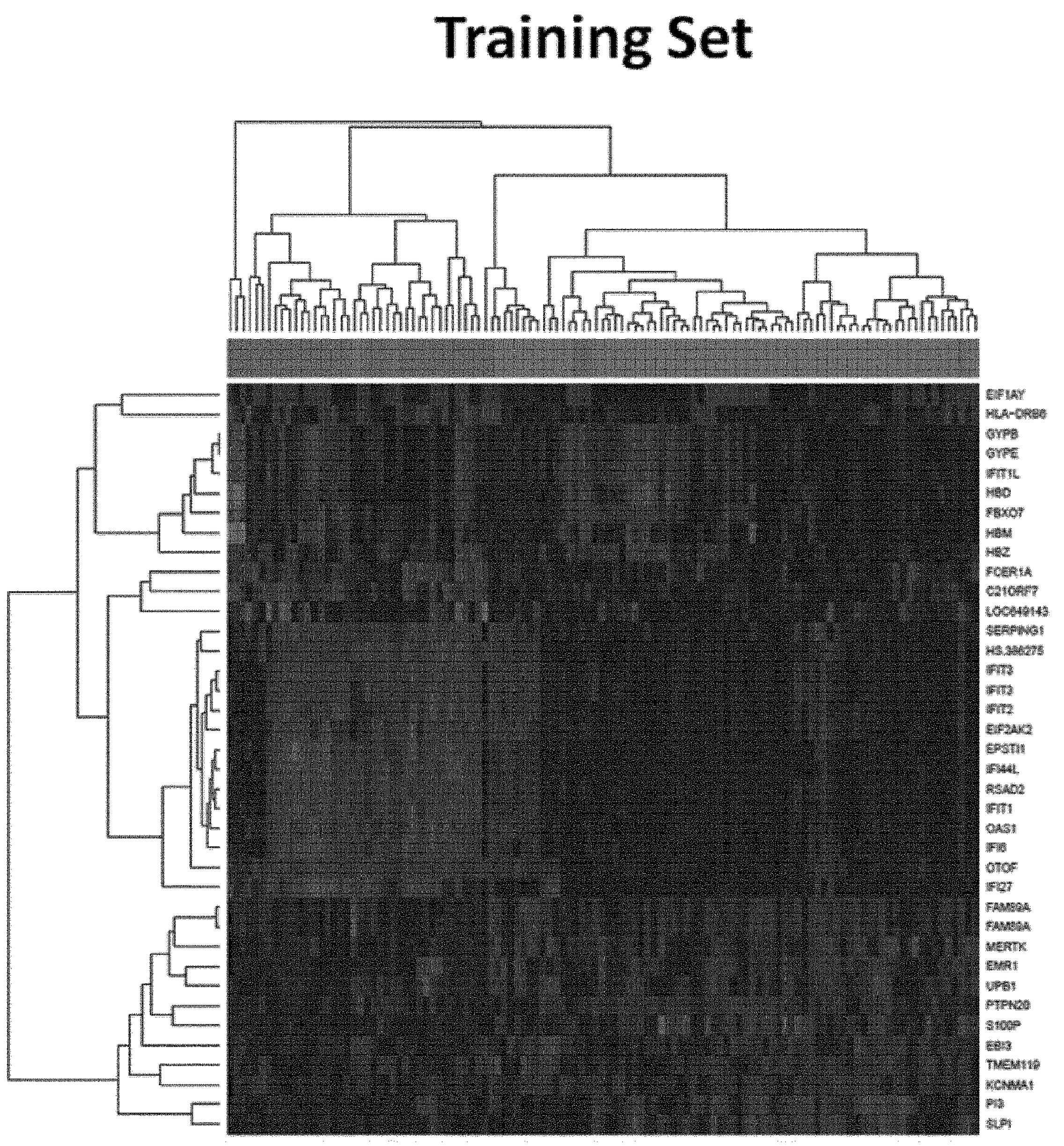
Figure 7B:
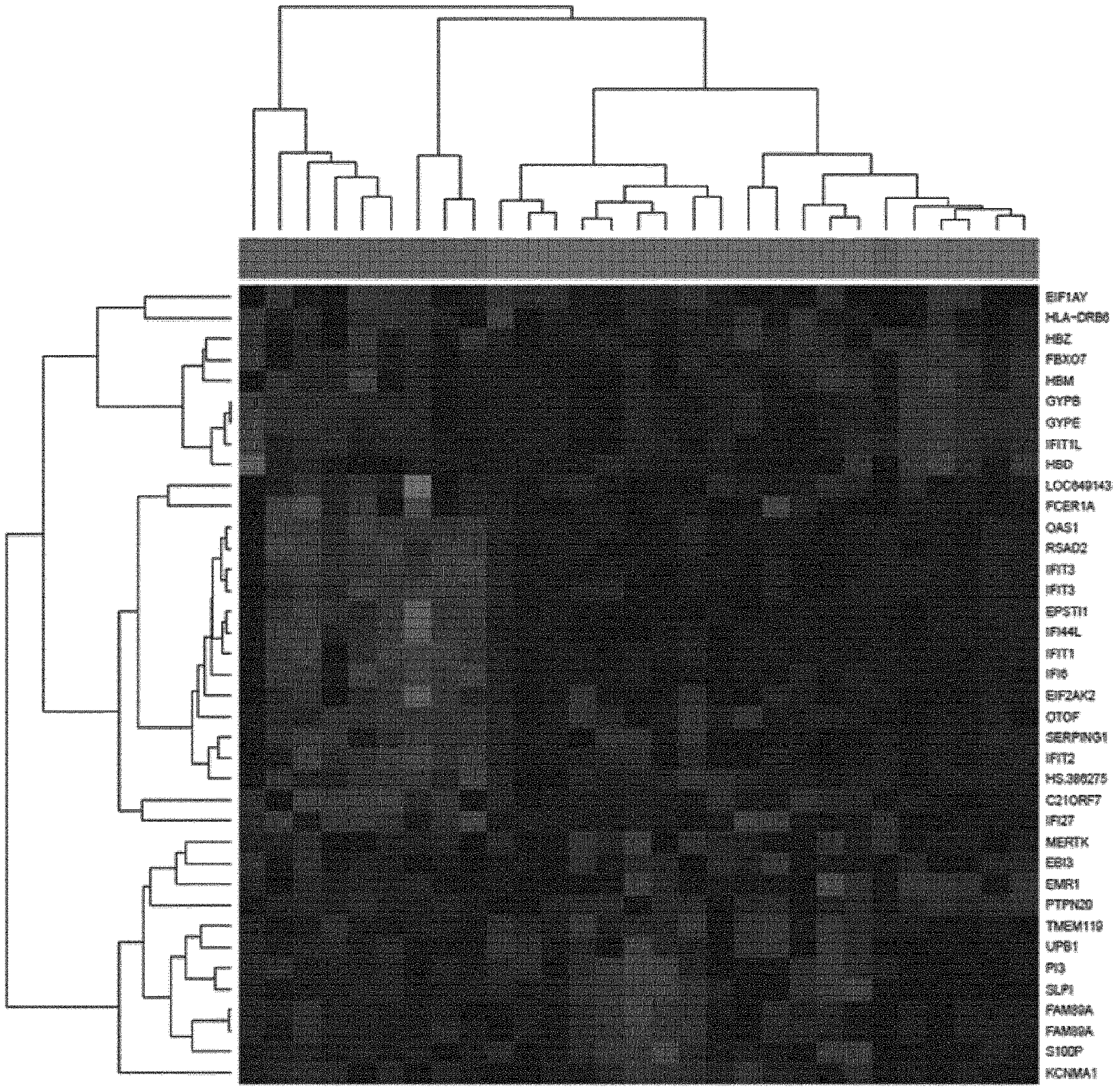

FIG. 7 shows heatmaps indicating the clustering of the training and test datasets based on the bacterial vs. viral 28-transcript signature. Patients are represented as columns (dark grey are patients with Definite Bacterial infection, light grey are patients with Definite Viral infection) and individual transcripts are shown in rows (transcripts shown in dark grey are up-regulated and those in light grey are down-regulated). The dendrograms for samples and transcripts are shown on the top and left of the heatmaps respectively, indicating hierarchical clusters of the data. Patients in the training set: Definite Bacterial n=42, Definite Viral n=92. Patients in the test set: Definite Bacterial n=10, Definite Viral n=19

Figure 8:
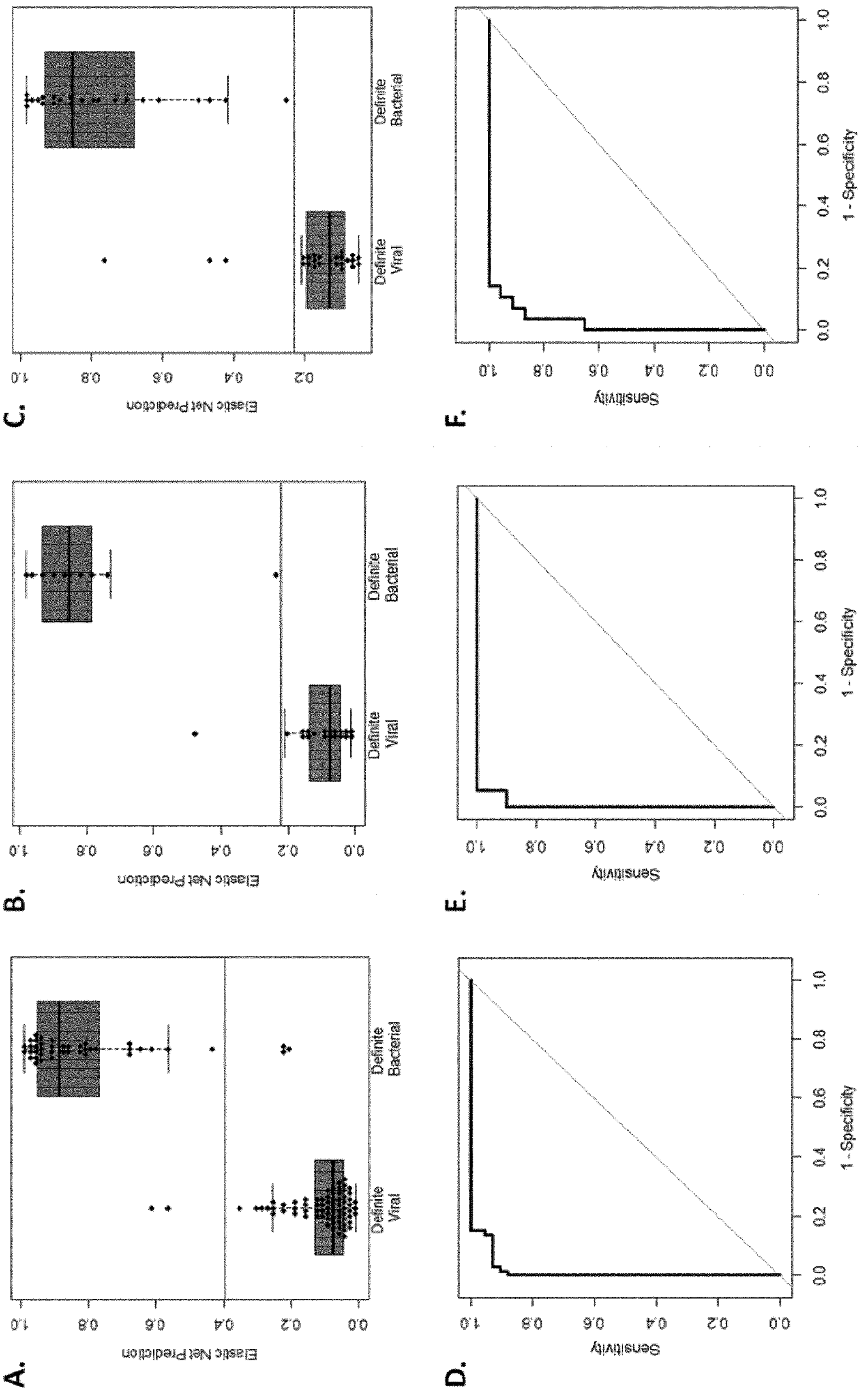

FIG. 8 shows Elastic net prediction value plots and Receiver Operating Characteristic (ROC) curves, based on the 38-transcript signature, applied to the Definite Bacterial and Definite Viral groups of the 80% training set (A & D), the 20% test set (B & E) and the IRIS validation dataset (C & F). Sensitivity, specificity and AUC are reported in Table 4. Boxes show median with $25^{th}$ and $75^{th}$ quartiles; whiskers show "range" (defined by boxplot function in R). With a "range" value set at 1, the whiskers extend no more than 1 times the interquartile range. The elastic net prediction value (the outcome variable Y obtained from fitting the elastic net model) can range from 0 (indicating viral infection) to 1 (indicating bacterial infection). Patients in the training set: Definite Bacterial n=42, Definite Viral n=92. Patients in the test set: Definite Bacterial n=10, Definite Viral n=19. Patients in IRIS validation dataset: Definite Bacterial n=23, Definite Viral n=28.

Figure 9:
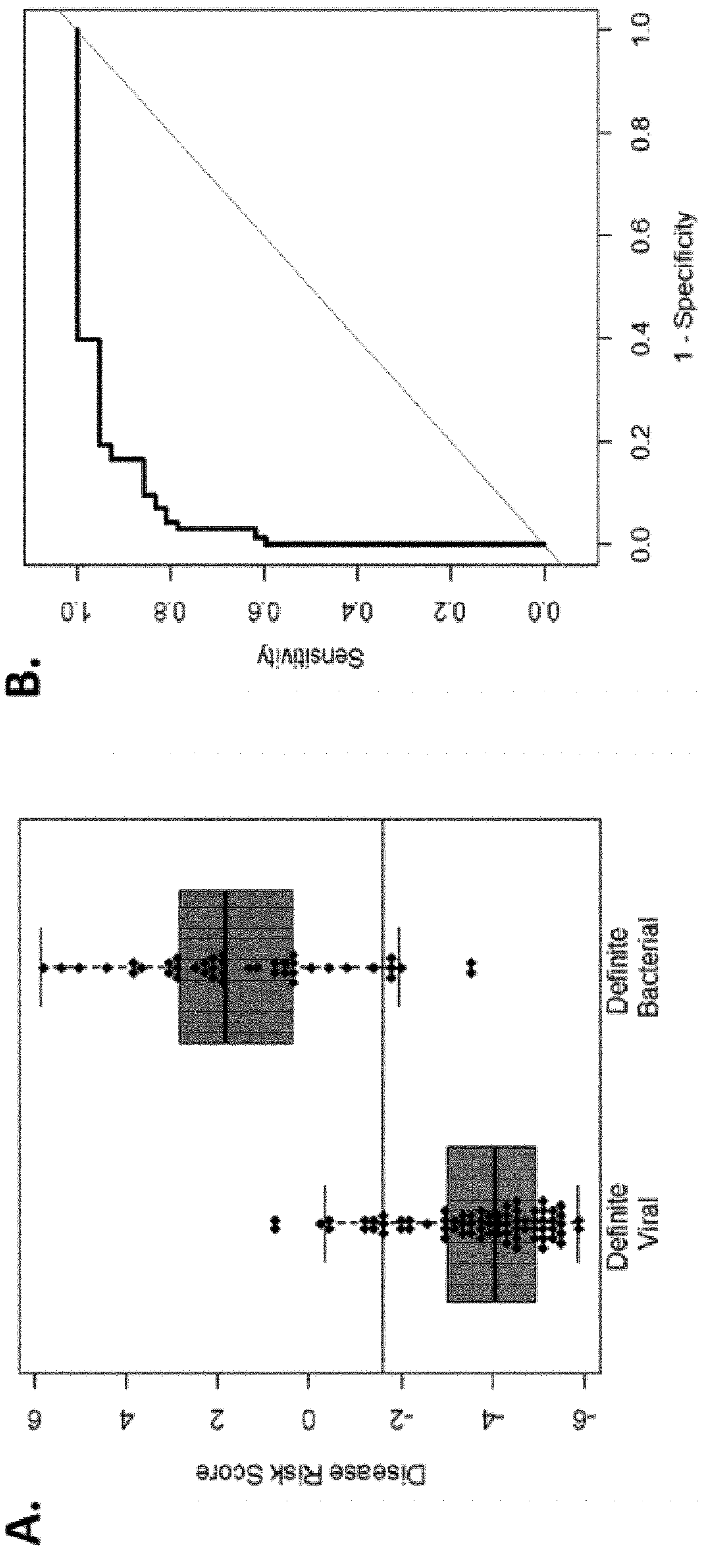

FIG. 9 shows a classification performance plot (A) and a Receiver Operating Characteristic (ROC) curve (B), based on the 2-transcript DRS signature, applied to the Definite Bacterial and Viral groups of the 80% training dataset. Sensitivity, specificity and AUC are reported in Table 5. Boxes show median with $25^{th}$ and $75^{th}$ quartiles; whiskers show ranges. Patients in the training set: Definite Bacterial n=42, Definite Viral n=92.

Figure 10:
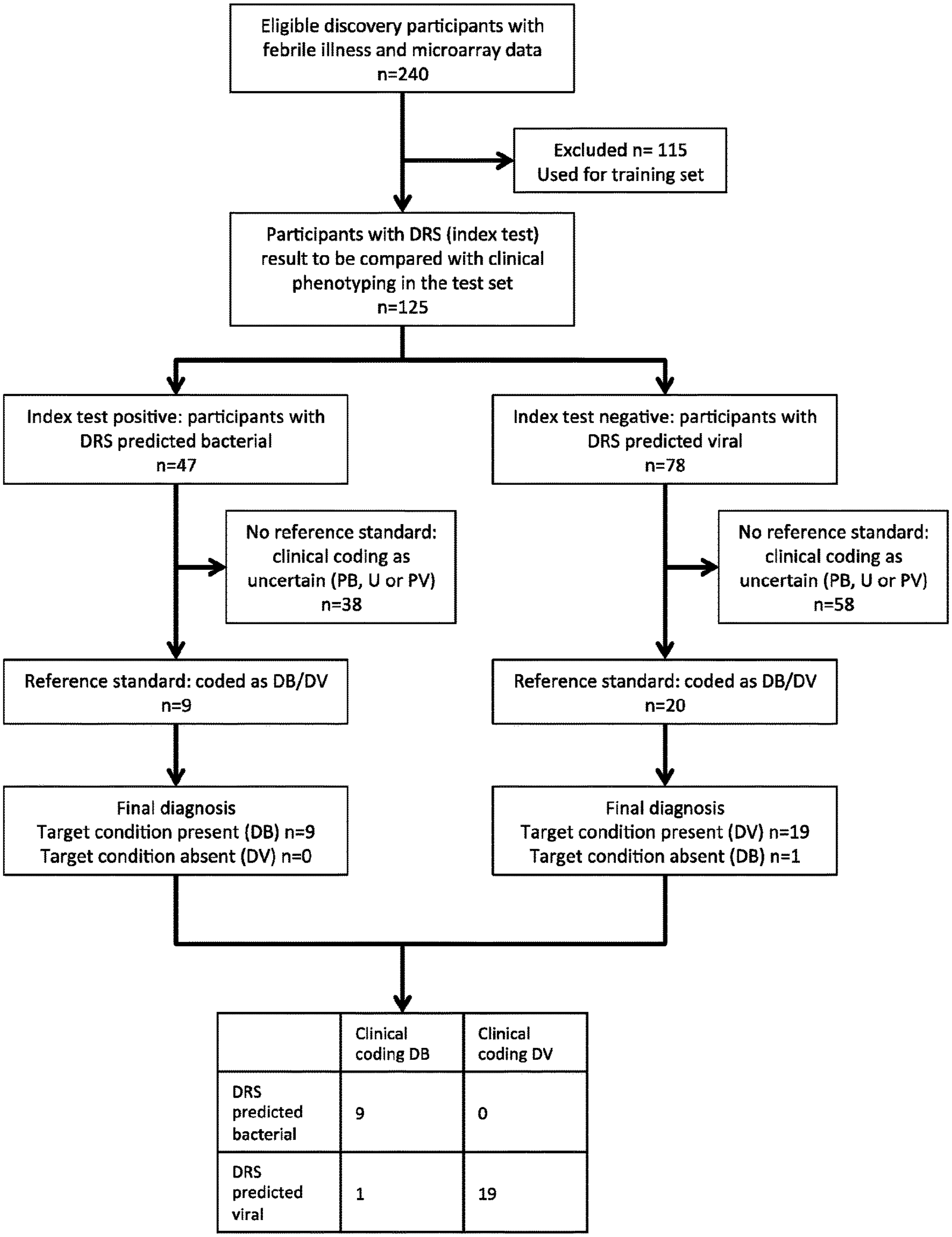
Figure 10:
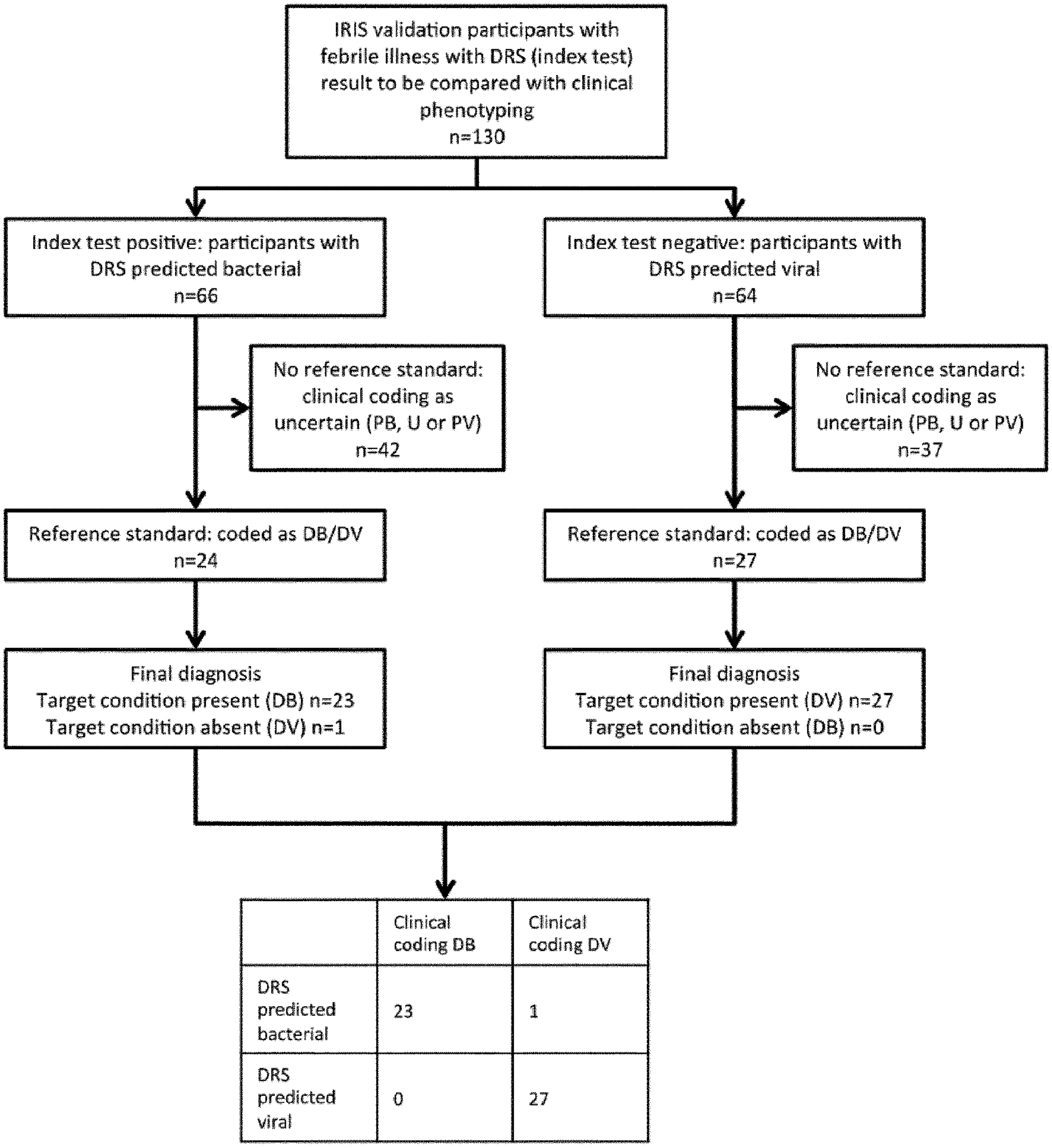

FIG. 10 shows a STARD flow diagram for assessment of diagnostic test accuracy in the test set (A) and validation set (B), including a 2×2 table of results comparing performance of the 2-transcript DRS against the clinical coding as bacterial or viral infection.

Figure 11:
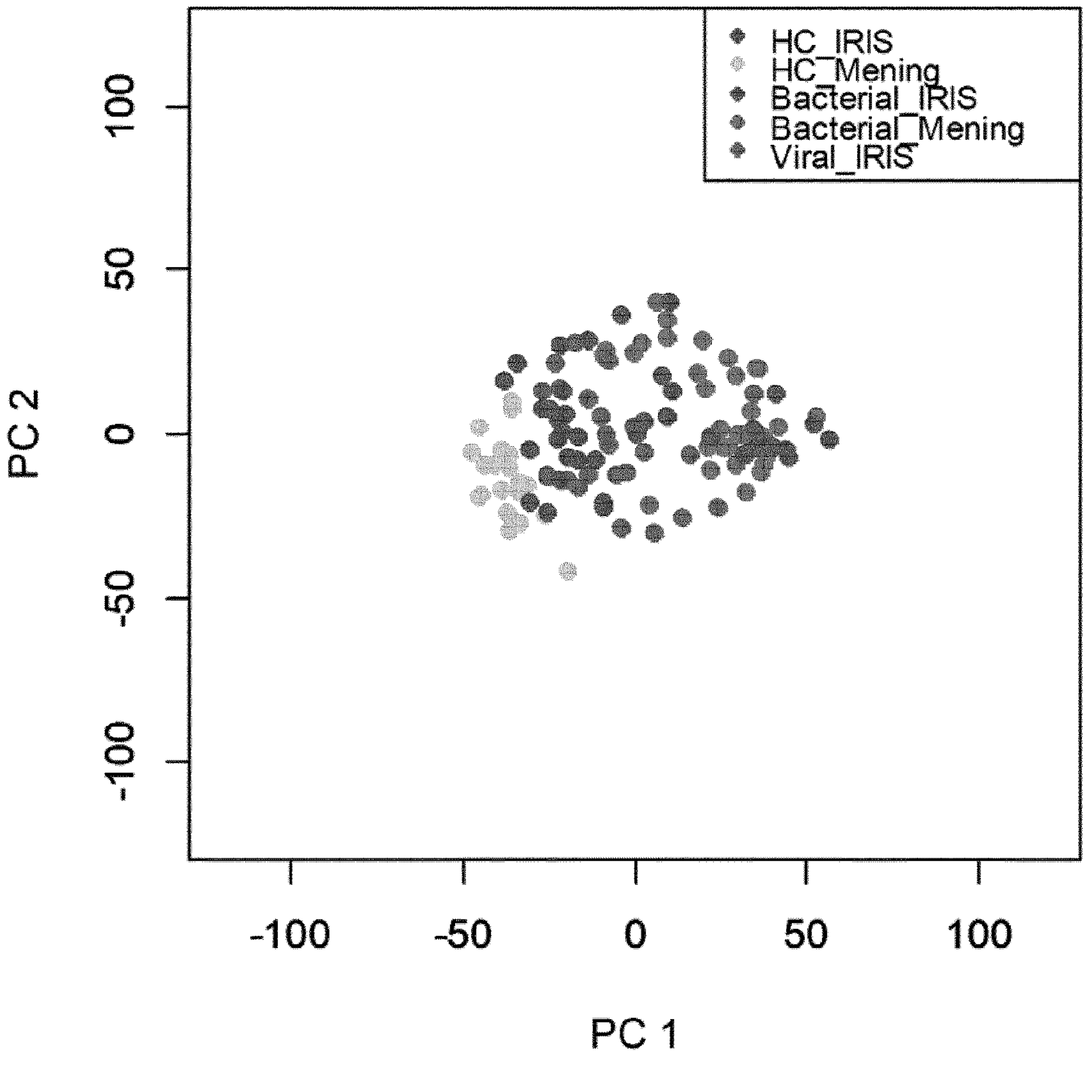

FIG. 11 shows a principal component analysis of meningococcal and IRIS validation samples after merging with ComBat. The two-transcript DRS classifier was applied on external data, and its ability to discriminate between bacterial and non-bacterial patients was assessed. In the case of the meningococcal validation data set, there were no comparator non-bacterial patients, and in order to estimate the accuracy of the DRS signature, we employed the viral group of the IRIS validation dataset. The two datasets were merged using the ComBat method to remove non-biological experimental variation, using the healthy controls from both datasets as reference. The PCA plot of the merged dataset indicates successful removal of the batch effects. The healthy controls from the IRIS dataset (HC_IRIS n=16) and the healthy controls from the meningococcal dataset (HC-_Mening n=21) are shown lying adjacent, as well as the bacterial patients from both datasets (Bacterial_IRIS n=23 and Bacterial_Mening n=24). The viral patients of the IRIS dataset lie between the bacterial patients and healthy controls (Viral IRIS n=28). The $1^{st}$ principal component was found to capture the differences in gene expression by infection status.

Figure 12:
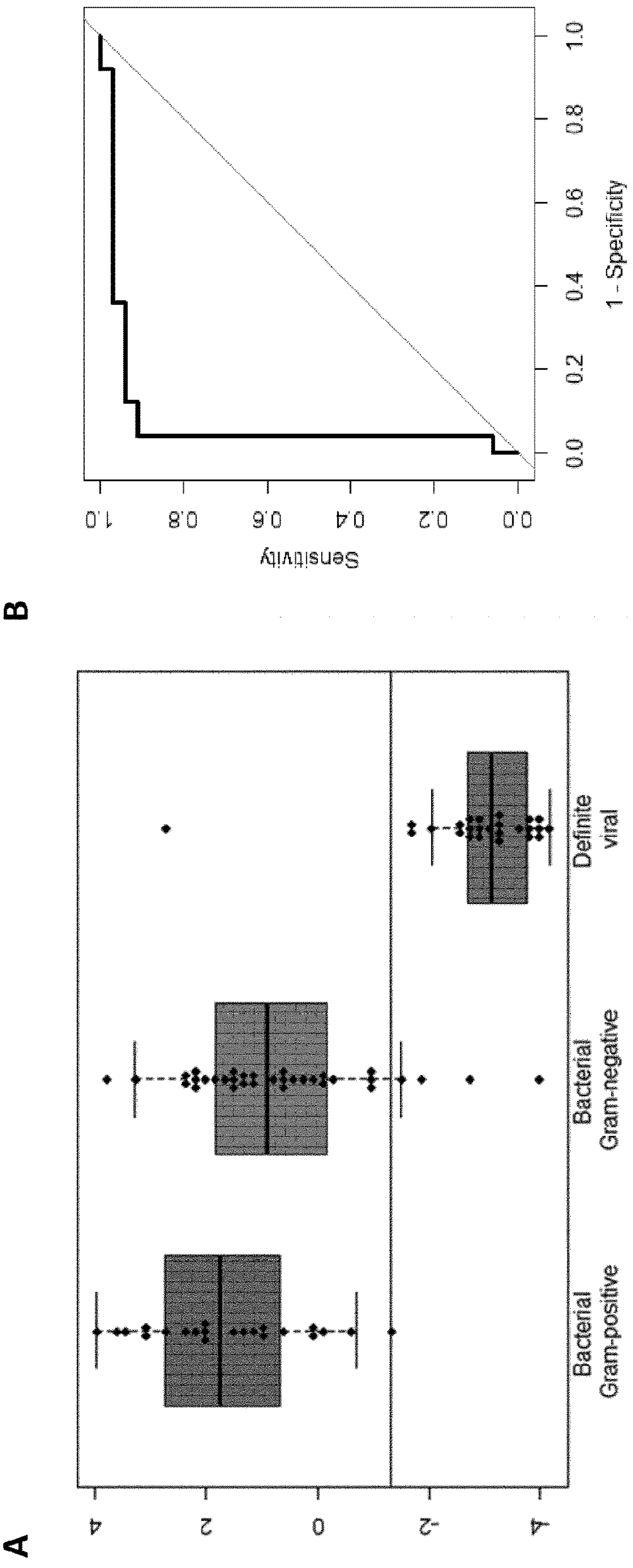

FIG. 12 shows a classification performance plot (A) and a Receiver Operating Characteristic (ROC) curve (B), based on the 2-transcript DRS signature, applied to the gram-positive (IRIS validation), gram-negative (IRIS and meningococcal validation), and viral (IRIS validation) groups of the merged datasets. Boxes show median with $25^{th}$ and $75^{th}$ quartiles; whiskers show ranges.

Sensitivity, specificity and AUC are reported in Table 7, based on discrimination of gram-negative infection and viral infection. The bacterial gram-positive group is shown on FIG. 12A for illustrative purposes.

Figure 13:
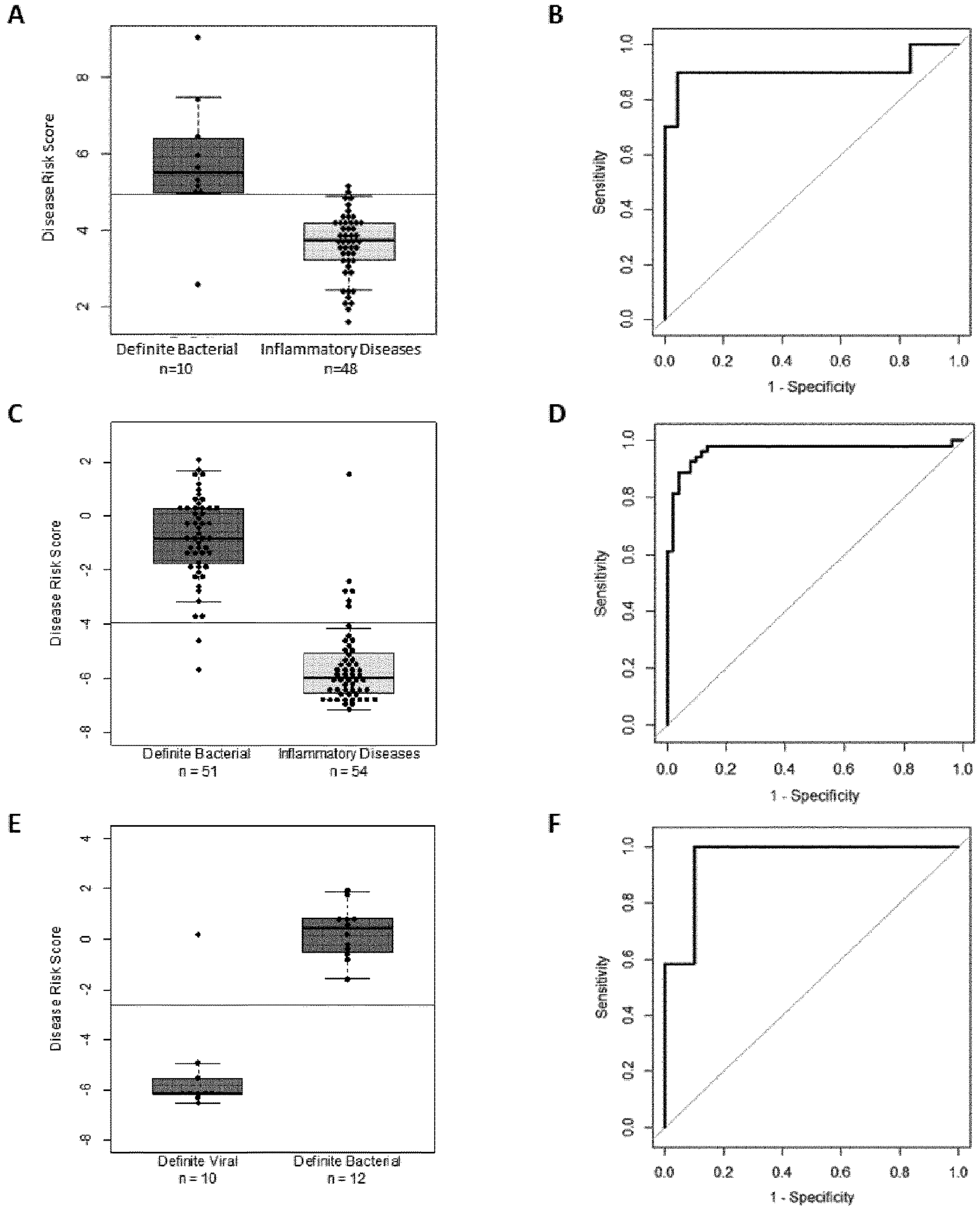
Figure 13:
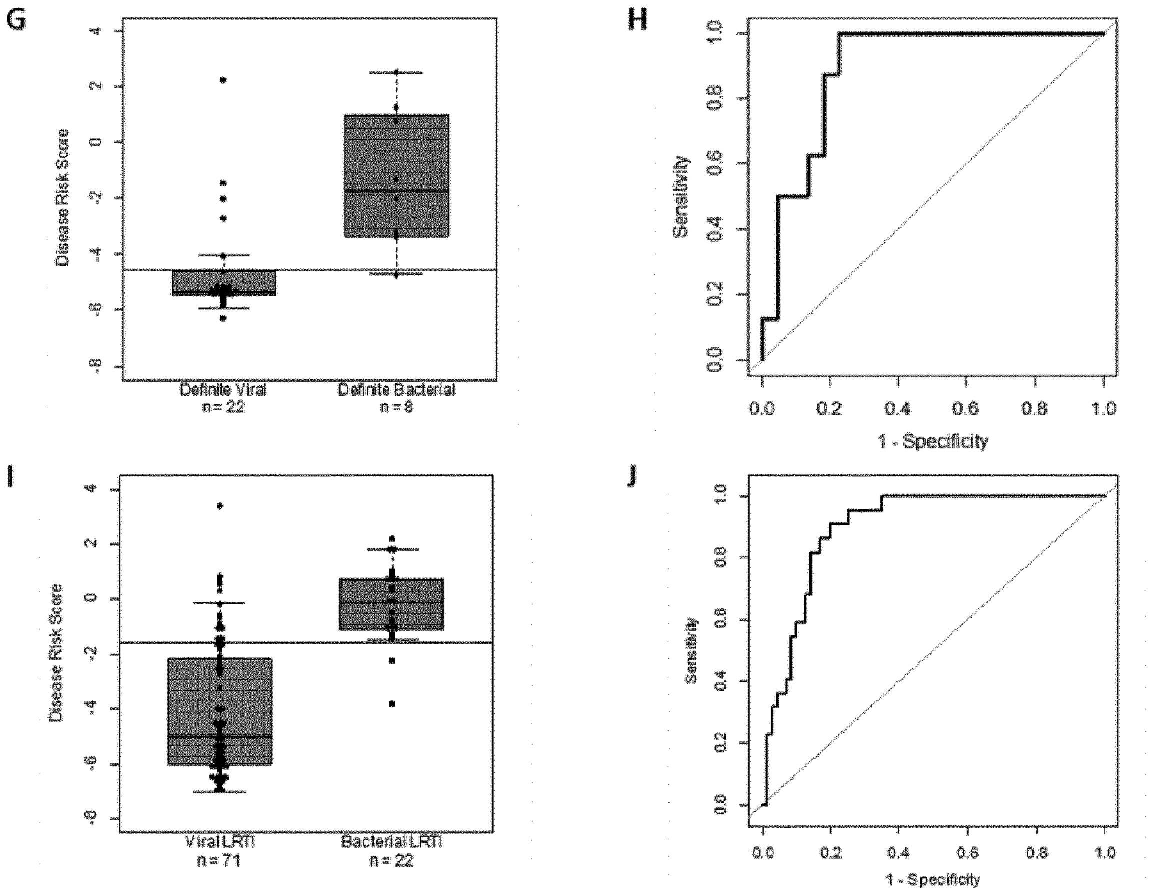

FIG. 13 shows classification performance plots and Receiver Operating Characteristic (ROC) curves, based on the 2-transcript DRS signature, applied to the inflammatory validation groups, JIA and HSP (A, B), and to 3 external published datasets: bacterial and inflammatory patients with systemic lupus erythematosus (C, D)[18]; bacterial and viral patients from the Ramilo et al study (E, F)[15]; and bacterial and viral patients from the Hu et al study (G, H)[12], and bacterial and viral adult patients from the Suarez et al study (I, J) [17]. Boxes show median with $25^{th}$ and $75^{th}$ quartiles; whiskers show ranges. Sensitivity, specificity and AUC are reported in Table 7.

Figure 14:
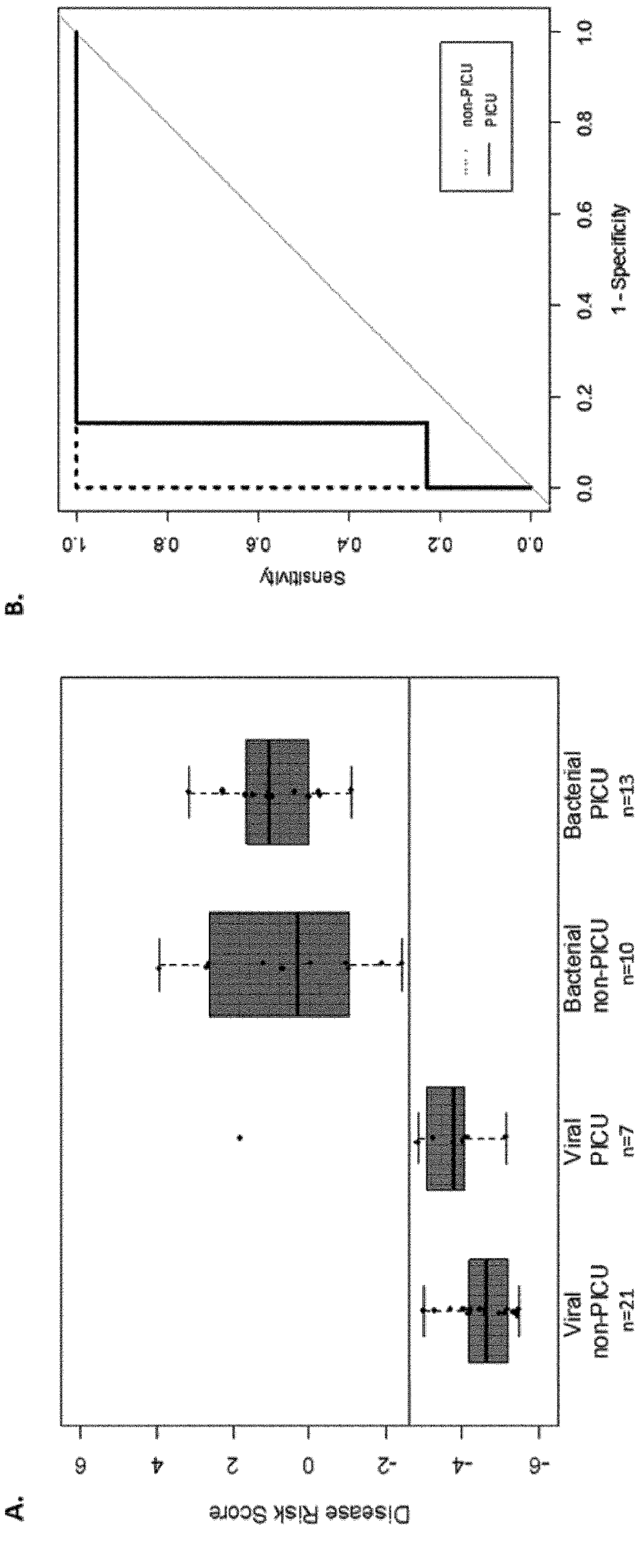

FIG. 14 shows the performance of the DRS in relation to severity of illness in the IRIS validation set. In order to investigate whether the severity of illness influenced the performance of the 2-transcript classifier, we analyzed the DRS values in the definite Viral and definite Bacterial groups by need for admission to the pediatric intensive care unit (PICU) during their illness (as shown in FIG. 4B). The horizontal DRS threshold line separates patients predicted as bacterial (above the line) or viral (below the line) (A). The 2-transcript DRS classified patients as bacterial or viral irrespective of their requirement for intensive care. The classification performance and Receiver Operating Characteristic (ROC) curve, based on the 2-transcript DRS signature is shown for patients requiring intensive care (solid line) or not requiring intensive care (dotted line) (B).

Figure 15:
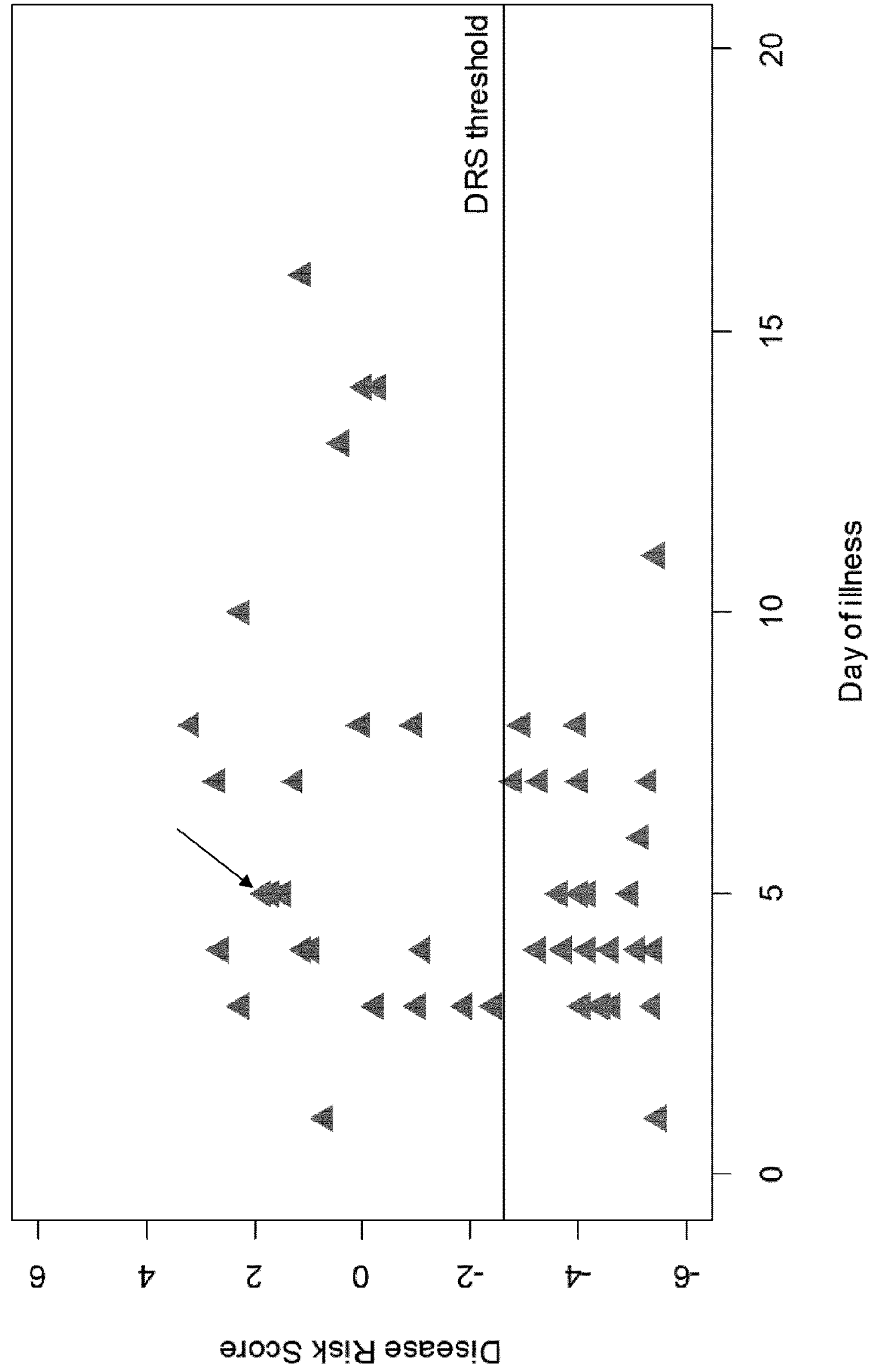

FIG. 15 shows the performance of the DRS in relation to day of illness in the IRIS validation set. In order to investigate whether the duration of illness influenced performance of the 2-transcript classifier, DRS values were plotted relative to the patient-reported day of illness (including symptomatic days before hospital admission) at the time of blood sampling. The horizontal DRS threshold line separates patients predicted as bacterial (above the line) and viral (below the line) (as shown on FIG. 4B). With the exception of one patient (see arrow), all of the DB patients were above the DRS threshold, whilst all of the DV patients were below the DRS threshold. There was no correlation of illness day with DRS. The plot does not include a single patient with a long illness. For coloured versions of the figures refer to Herberg et al [49], Distinction between bacterial and viral infection in children using a two-transcript host RNA signature (JAMA 2016)

Figure 16A:
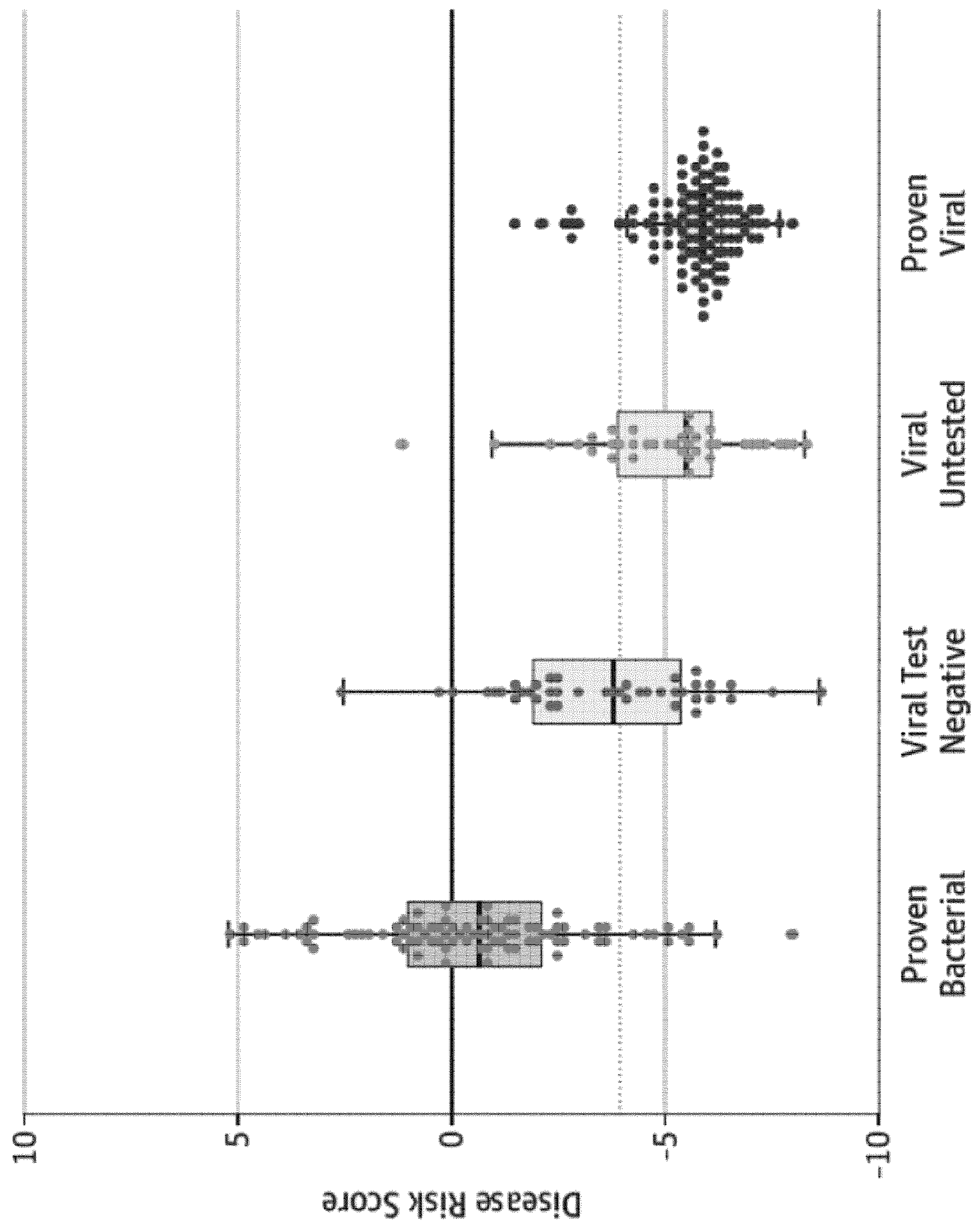
Figure 16B:
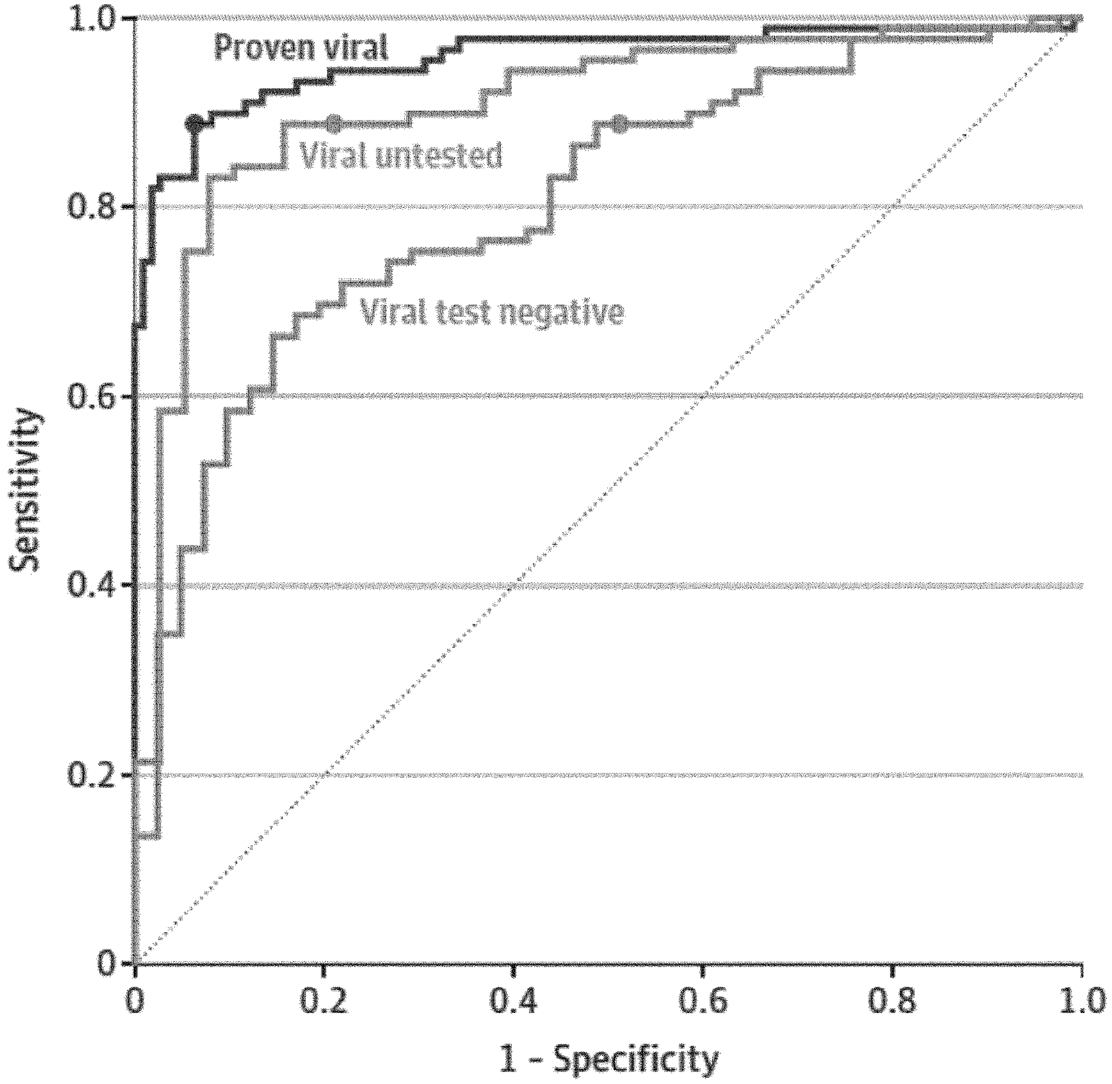

FIG. 16 shows the Disease Risk Score and Receiver Operating Characteristic (ROC) curves based on the 2-transcript signature (the combined IFI44L and FAM89A expression values). (A) Disease risk score for bacterial and viral infection groups. The dotted line indicates a disease risk score threshold of −3.79, determined by the point on the definite bacterial vs definite viral ROC curve that maximized sensitivity and specificity. This was used to calculate the quoted sensitivity and specificity. Boxes indicate the interquartile ranges and the median (bold line); whiskers represent 1 or less times the interquartile range. (B) ROC curves for proven bacterial infection group vs viral groups. Data are as reported in study by Mahajan et al [50]. Data points indicate the corresponding thresholds.

Figure 17A:
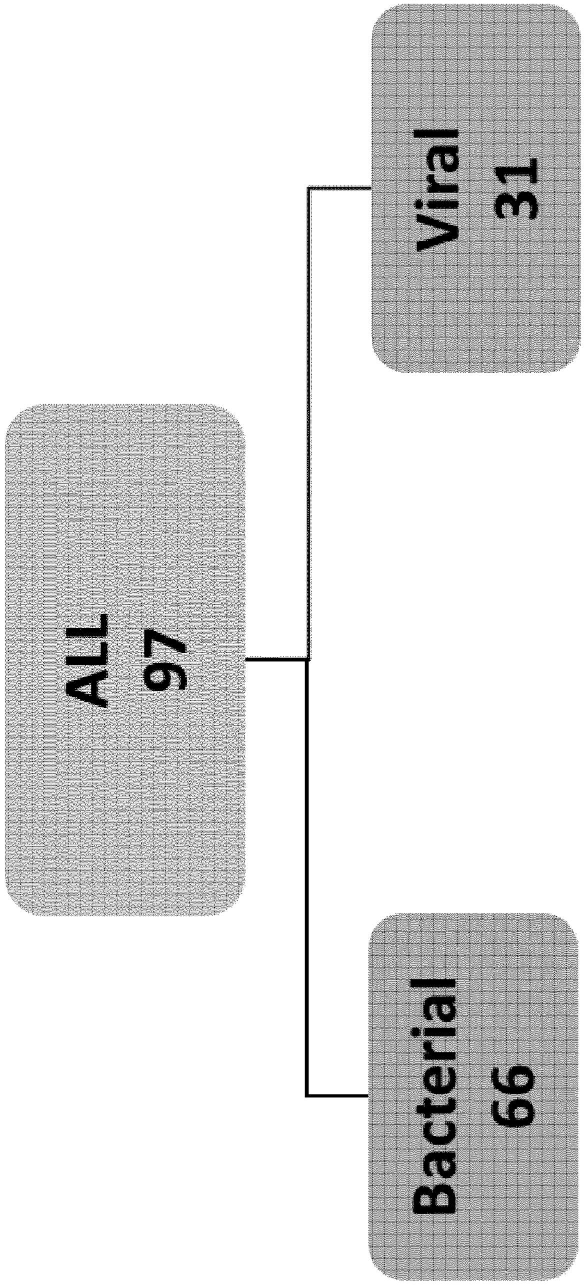
Figure 17B:
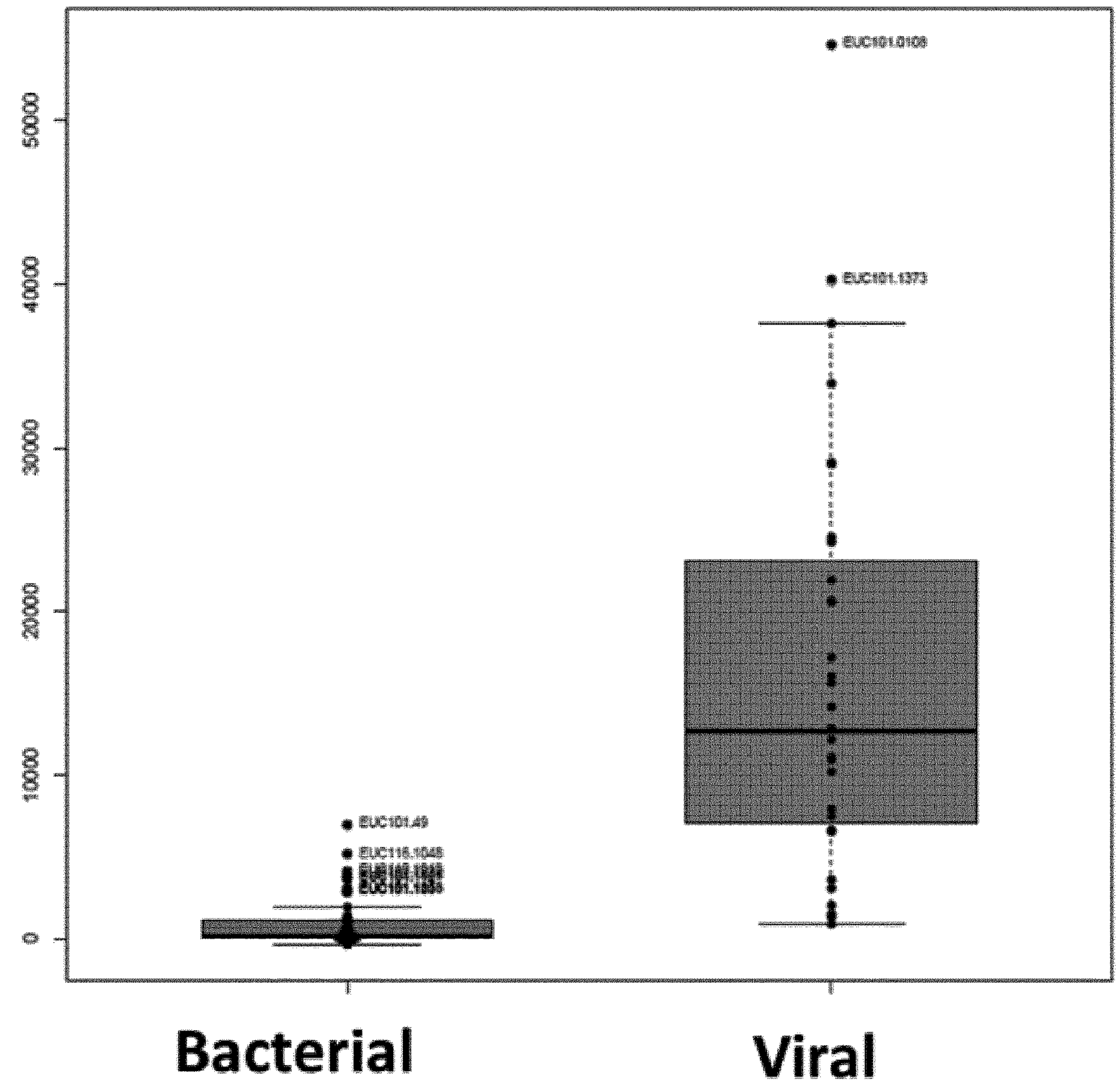
Figure 17C:
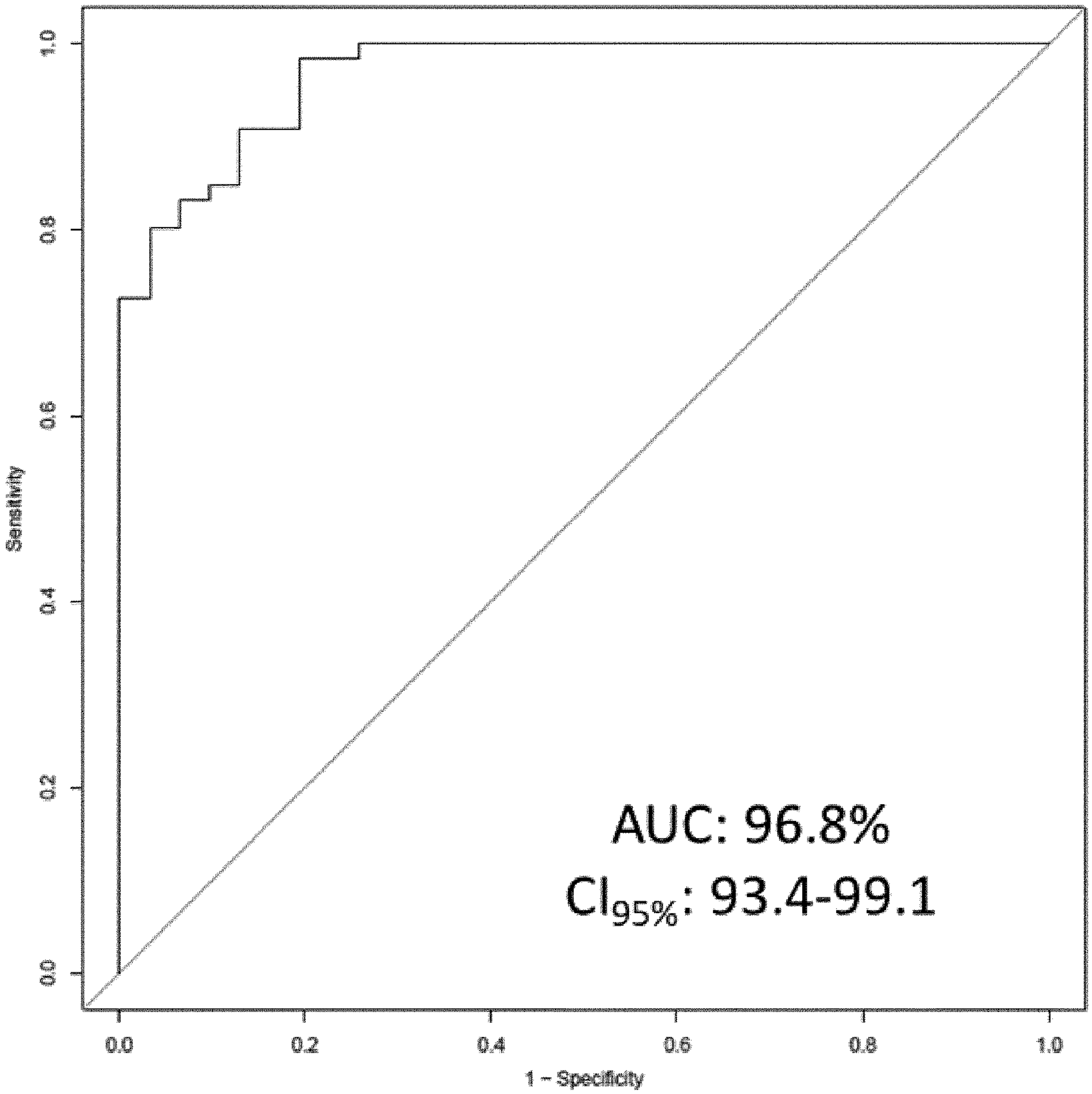

FIG. 17 shows the results of the RNA-Seq experiment using the 2-transcript signature IFI44L and FAM89A. (A) number of bacterial (66) and viral patients (31), (B) Disease Risk Score, (C) ROC curve.

DETAILED DESCRIPTION

The 36 genes/38 transcripts shown in Table 4 or Table 8 is useful for identifying a bacterial infection or discriminating a bacterial infection from a viral infection or for discriminating a bacterial infection from an inflammatory disease, such as juvenile idiopathic arthritis (JIA), Henoch-Schönlein purpura (HSP) or systemic lupus erythematosus (SLE).

In one embodiment one probe is employed for detecting the modulation in gene expression of each gene, for example selected from the list of probes shown in Table 4 or Table 8.

In another embodiment, two or more probes are employed for detecting the modulation of each gene, for example selected from the list of probes shown in Table 4 or Table 8.

In one embodiment the method of the present disclosure is able to differentiate a bacterial infection from different conditions/diseases or infections, such as a viral infection which have similar clinical symptoms.

In one embodiment the method is for discriminating a subject having a bacterial infection from a subject having a viral infection.

In one embodiment the method is for discriminating a subject having a bacterial infection from a subject having an inflammatory disease In one embodiment there is detected the gene expression levels of at least 95% of the genes in a signature such as 95, 96, 97, 98, 99 or 100% providing the signature retains the ability to detect/discriminate the relevant clinical status without significant loss of specificity and/or sensitivity. The details of the gene signature is given below.

In one embodiment the exact gene list, i.e. 100% of the genes in Table 4 or Table 8 is employed.

In one embodiment of the present disclosure the gene signature is the minimum set of genes required to optimally detect the infection or discriminate the disease, for example between a bacterial infection and a viral infection or between a bacterial infection and an inflammatory disease.

Optimally is intended to mean the smallest set of genes needed to discriminate between a bacterial infection and a viral infection or an inflammatory disease without significant loss of specificity and/or sensitivity of the signature's ability to detect or discriminate.

Detect or detecting as employed herein is intended to refer to the process of identifying a bacterial infection, a viral infection, or an inflammatory disease in a sample, in particular through detecting modulation of the relevant genes in the signature.

Discriminate refers to the ability of the signature to differentiate between different disease statuses, for example a bacterial infection vs a viral infection or a bacterial infection vs an inflammatory disease. Detect and discriminate are interchangeable in the context of the gene signature.

In one embodiment the method is able to discriminate between a bacterial infection and a viral infection or inflammatory disease in a subject derived sample.

Subject as employed herein is a human suspected of having a bacterial or viral infection from whom a sample is derived. The term patient may be used interchangeably although in one embodiment a patient has a morbidity.

In one embodiment the method of the present disclosure is performed on a sample derived from a subject having or suspected of having a bacterial infection, for example wherein the subject exhibits symptoms normally associated with a bacterial infection but not a viral infection.

In one embodiment the method of the present disclosure is performed on a sample derived from a subject having or suspected of having a viral infection, for example wherein the subject exhibits symptoms normally associated with a viral infection but not a bacterial infection. Testing a sample from such a subject can help to identify a hidden bacterial infection.

In one embodiment the subject exhibits symptoms of a viral infection. In another embodiment the subject exhibits symptoms of a bacterial infection. In yet another embodiment the subject exhibits symptoms of both a bacterial and a viral infection.

In one embodiment the method according to the present disclosure is performed on a subject having or suspected of having an acute infection, such as a severe/serious bacterial infection (SBI).

In a further embodiment the sample is a sample derived from a febrile subject; that is to say with a temperature above the normal body temperature of 37.5° C.

In yet a further embodiment the analysis is performed to establish if a fever is associated with a bacterial or viral infection. Establishing the source of the fever/infection advantageously allows the prescription and/or administration of appropriate medication, for example those with bacterial infections can be given antibiotics and those with viral infections can be given antipyretics. Efficient treatment is advantageous because it minimises hospital stays, ensures that patients obtain appropriate treatment, which may save lives, especially when the patient is an infant or child, and also ensures that resources are used appropriately.

In recent years it has become apparent that the over-use of antibiotics should be avoided because it leads to bacteria developing resistance. Therefore, the administration of antibiotics to patients who do not have bacterial infection should be avoided.

In one embodiment the subject is an adult. Adult is defined herein as a person of 18 years of age or older. The presently disclosed method is able to detect a bacterial infection in an adult, as well as discriminate between a bacterial infection and a viral infection. See for example FIG. 13 (I and J) and Table 7.

In one embodiment the subject is a child. Child as employed herein refers to a person under the age of 18, such as 5 to 17 years of age.

Modulation of gene expression as employed herein means up-regulation or down-regulation of a gene or genes.

Up-regulated as employed herein is intended to refer to a gene transcript which is expressed at higher levels in a diseased or infected patient sample relative to, for example, a control sample free from a relevant disease or infection, or in a sample with latent disease or infection or a different stage of the disease or infection, as appropriate.

Down-regulated as employed herein is intended to refer to a gene transcript which is expressed at lower levels in a diseased or infected patient sample relative to, for example, a control sample free from a relevant disease or infection or in a sample with latent disease or infection or a different stage of the disease or infection.

The modulation is measured by measuring levels of gene expression by an appropriate technique. Gene expression as employed herein is the process by which information from a gene is used in the synthesis of a functional gene product. These products are often proteins, but in non-protein coding genes such as ribosomal RNA (rRNA), transfer RNA (tRNA) or small nuclear RNA (snRNA) genes, the product is a functional RNA. That is to say, RNA with a function.

Gene expression data as employed herein is intended to refer to any data generated from a patient sample that is indicative of the expression of the two or more genes, for example 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50.

In one embodiment one or more, for example 1 to 21, such as 2, 3, 4, 5, 6, 7, 8, 9, 10, 11, 12, 13, 14, 15, 16, 17, 18, 19 or 20, genes are replaced by a gene with an equivalent function provided the signature retains the ability to detect/discriminate the relevant clinical status without significant loss in specificity and/or sensitivity.

In one embodiment the genes employed have identity with genes listed in the relevant tables, such as Table 4.

In one embodiment, one or more of the genes in the 36 gene signature are significantly differentially expressed in a sample derived from a subject having a bacterial infection compared to a sample derived from a subject having a viral infection or an inflammatory disease.

Gene signature as used herein is intended to refer to two or more genes which when tested together are able to detect/discriminate the relevant clinical status. Hence, a gene signature represents a minimal set of genes which have sufficient discriminatory power to identify a subject having a bacterial infection or to discriminate a subject having bacterial infection from a subject having a viral infection or inflammatory disease.

In one embodiment the gene signature is based on two genes of primary importance. Of primary importance as used herein means that the gene expression levels of the two genes is representative of the gene expression levels of other genes. For example, the expression levels of the first gene of primary importance may be highly correlated with the expression levels of a first group of genes, whilst the expression levels of the second gene of primary importance may be highly correlated with the expression levels of a second group of genes.

Therefore, each gene of primary importance may be used as a representative of the other highly correlated genes from their respective groups, thereby eliminating the need to test all of genes within each group. In other words, testing the expression levels of just the two genes of primary importance provides a similar sensitivity and/or specificity as testing the expression levels of all of the genes. Significantly differentially expressed as employed herein means the gene shows a log 2 fold change >0.5 or <−0.5 in a sample derived from a subject having a bacterial infection compared to a sample derived from a subject having a viral infection or an inflammatory disease.

In one embodiment, up-regulated as used herein means the gene shows a log 2 fold change >0.5.

In one embodiment, down-regulated as used herein means the gene shows a log 2 fold change <−0.5.

In one embodiment, one or more of the following genes are down-regulated in a subject having a bacterial infection: IFI27, IFI44L, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7 and KCNMA1.

In one embodiment, one or more of the following genes are up-regulated in a subject having a viral infection or an inflammatory disease: IFI27, IFI44L, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD and FBXO7.

In one embodiment, one or more of the following genes are up-regulated in a subject having a bacterial infection: KCNMA1, MERTK, EBI3, FAM89A, UPB1, EMR1, PTPN20, TMEM119, SLPI, S100P and PI3.

In one embodiment, one or more of the following genes are down-regulated in a subject having a viral infection or an inflammatory disease: KCNMA1, MERTK, EBI3, FAM89A, UPB1, EMR1, PTPN20, TMEM119, SLPI, S100P and PI3.

In one embodiment, one or more of the following genes are down-regulated in a subject having a bacterial infection: IFI27, IFI44L, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7 and KCNMA1; and one or more of the following genes are up-regulated: KCNMA1, MERTK, EBI3, FAM89A, UPB1, EMR1, PTPN20, TMEM119, SLPI, S100P and PI3.

In one embodiment, one or more of the following genes are up-regulated in a subject having a viral infection or an inflammatory disease: IFI27, IFI44L, IFIT1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7 and KCNMA1; and one or more of the following genes are down-regulated: KCNMA1, MERTK, EBI3, FAM89A, UPB1, EMR1, PTPN20, TMEM119, SLPI, S100P and PI3.

"Presented in the form of" as employed herein refers to the laying down of genes from one or more of the signatures in the form of probes on a microarray.

Accurately and robustly as employed herein refers to the fact that the method can be employed in a practical setting or low resource setting, such as Africa, and that the results of performing the method properly give a high level of confidence that a true result is obtained.

High confidence is provided by the method when it provides few results that are false positives (e.g. the result suggests that the subject has a bacterial infection when he/she does not) and also has few false negatives (e.g. the result suggests that the subject does not have a bacterial infection when he/she does).

High confidence would include 90% or greater confidence, such as 91, 92, 93, 94, 95, 96, 97, 98, 99 or 100% confidence when an appropriate statistical test is employed.

In one embodiment the method provides a sensitivity of 80% or greater such as 90% or greater in particular 95% or greater, for example where the sensitivity is calculated as below:

$$\text{sensitivity} = \frac{\text{number of true positives}}{\text{number of true positives} + \text{number of false negatives}}$$
$$= \text{probability of a positive test given that the patient is ill}$$

In one embodiment the method provides a high level of specificity, for example 80% or greater such as 90% or greater in particular 95% or greater, for example where specificity is calculated as shown below:

$$\text{sensitivity} = \frac{\text{number of true negatives}}{\text{number of true negatives} + \text{number of false positives}}$$
$$= \text{probabilityof a negative test given that the patient is well}$$

In one embodiment the sensitivity of method of the 38 transcript gene signature is 90 to 100%, such as 90, 91, 92, 93, 94, 95, 96, 97, 98 or 99%.

In one embodiment the specificity of the method of the 38 transcript gene signature is 85 to 100%, such as 86, 87, 88, 89, 90, 91, 92, 93, 94, 95, 96, 97, 98 or 99%.

In one embodiment the sensitivity of the method of the 2 transcript gene signature is 85 to 100%, such as 86, 87, 88, 89, 90, 91, 92, 93, 94, 95, 96, 97, 98 or 99%.

In one embodiment the specificity of the method of the 2 transcript gene signature is 85 to 100%, such as 86, 87, 88, 89, 90, 91, 92, 93, 94, 95, 96, 97, 98 or 99%.

There are a number of ways in which gene expression can be measured including microarrays, tiling arrays, DNA or RNA arrays for example on gene chips, RNA-seq and serial analysis of gene expression. Any suitable method of measuring gene modulation may be employed in the method of the present disclosure.

In one embodiment the gene expression measured is that of the host (e.g. human), for example the host inflammatory response, i.e. not that of the infectious agent or disease.

In one embodiment the method according to the present disclosure may be employed to detect a bacterial infection, such as *Chlamydia pneumoniae, Chlamydia trachomatis, Chlamydophila psittaci, Mycoplasma pneumonia.*

In one embodiment the disclosed method may be employed to detect a serious/severe bacterial infection (SBI), including but not limited to bacterial meningitis such as acute bacterial meningitis, septicaemia, acute respiratory infections such as tuberculosis, tuberculosis meningitis, whipple disease, nocadiosis, urinary tract infections, bacteraemia and acute cystitis.

In one embodiment the method according to the present disclosure may be employed to detect a Gram positive bacterial infection, such as but not limited to *Corynebacterium diphtheriae, Clostridium botulinum, Clostridium difficile, Clostridium perfringens, Clostridium tetani, Enterococcus faecalis, Enterococcus faecium, Listeria monocytogenes, Staphylococcus aureus, Staphylococcus epidermidis, Staphylococcus saprophyticus*, Group B *streptococcus, Streptococcus agalactiae, Streptococcus pneumoniae, Streptococcus pyogenes*, or acid fast bacteria such as *Mycobacterium leprae, Mycobaterium tuberculosis, Mycobacterium ulcerans* and *Mycobacterium avium* intercellularae.

In one embodiment the method according to the present disclosure may be employed to detect a Gram negative bacterial infection, such as but not limited to *Bordetella pertussis, Borrelia burgdorferi, Brucella abortus, Brucella canis, Brucella melitensis, Brucella suis, Campylobacter jejuni, Escherichia coli, Francisella tularensis, Haemophilus influenzae, Helicobacter pylori, Legionella pneumophila, Leptospira interrogans, Neisseria gonorrhoeae, Neisseria meningitidis, Pseudomonas aeruginosa, Pseudomonas* spp, *Rickettsia rickettsii, Salmonella typhi, Salmonella typhimurium, Shigella* sonnet *Treponema pallidum, Vibrio cholerae, Yersinia pestis, Kingella kingae, Stenotrophomonas* and *Klebsiella.*

In one embodiment the method according to the present disclosure may be employed to detect a viral infection for example, Influenza such as Influenza A, including but not limited to: H1N1, H2N2, H3N2, H5N1, H7N7, H1N2, H9N2, H7N2, H7N3, H10N7, Influenza B and Influenza C, Respiratory Syncytial Virus (RSV), rhinovirus, enterovirus, bocavirus, parainfluenza, adenovirus, metapneumovirus, herpes simplex virus, Chickenpox virus, Human papillomavirus, Hepatitis, Epstein-Barr virus, Varicella-zoster virus, Human cytomegalovirus, Human herpesvirus, type 8 BK virus, JC virus, Smallpox, Parvovirus B19, Human astrovirus, Norwalk virus, coxsackievirus, poliovirus, Severe acute respiratory syndrome virus, yellow fever virus, dengue virus. West Nile virus. Rubella virus. Human immunodeficiency virus, Guanarito virus, Junin virus, Lassa virus, Machupo virus, Sabia virus, Crimean-Congo haemorrhagic fever virus, Ebola virus, Marburg virus, Measles virus, Mumps virus, Rabies virus and Rotavirus.

In one embodiment the method according to the present disclosure may be employed to detect an inflammatory disease such as juvenile idiopathic arthritis (JIA), Henoch-Schönlein purpura (HSP) or systemic lupus erythematosus (SLE). Other examples of inflammatory diseases include asthma, chronic peptide ulcer, tuberculosis, rheumatoid arthritis, chronic periodontitis, ulcerative colitis, Crohn's disease, chronic sinusitis, chronic active hepatitis, celiac disease and vasculitis.

In one embodiment DNA or RNA from the subject sample is analysed.

In one embodiment RNA from the subject sample is analysed.

In one embodiment mRNA from the subject sample is analysed.

In one embodiment the sample is solid or fluid, for example blood or serum or a processed form of any one of the same.

A fluid sample as employed herein refers to liquids originating from inside the bodies of living people. They include fluids that are excreted or secreted from the body as well as body water that normally is not Includes amniotic fluid, aqueous humour and vitreous humour, bile, blood serum, breast milk, cerebrospinal fluid, cerumen (earwax), chyle, endolymph and perilymph, gastric juice, mucus (including nasal drainage and phlegm), sputum, peritoneal fluid, pleural fluid, saliva, sebum (skin oil), semen, sweat, tears, vaginal secretion, vomit, urine. Particularly blood and serum. Blood as employed herein refers to whole blood, that is serum, blood cells and clotting factors, typically peripheral whole blood.

Serum as employed herein refers to the component of whole blood that is not blood cells or clotting factors. It is plasma with fibrinogens removed.

In one embodiment the subject derived sample is a blood sample.

In one embodiment the sample is whole blood. Hence in one embodiment the RNA sample is derived from whole blood.

The RNA sample may be subjected to further amplification by PCR, such as whole genome amplification in order to increase the amount of starting RNA template available for analysis. Alternatively, the RNA sample may be converted into cDNA by reverse transcriptase, such as HIV-1 reverse transcriptase, moloney murine leukaemia virus (M-MLV) reverse transcriptase, AMV reverse transcriptase and telomersease reverse transcriptase. Such amplification steps may be necessary for smaller sample volumes, such as blood samples obtained from children.

In one or more embodiments the analysis is ex vivo.

Ex vivo as employed herein means that which takes place outside the body.

In one embodiment the gene expression data is generated from a microarray, such as a gene chip.

Microarray as employed herein includes RNA or DNA arrays, such as RNA arrays.

Polymerase chain reaction (PCR) as employed herein refers to a widely used molecular technique to make multiple copies of a target DNA sequence. The method relies on thermal cycling, consisting of cycles of repeated heating and cooling of the reaction for DNA melting and enzymatic replication of the DNA. Primers containing sequences complementary to the target region along with a DNA polymerase, which the method is named after, are key components to enable selective and repeated amplification. As PCR progresses, the DNA generated is itself used as a template for replication, setting in motion a chain reaction in which the DNA template is exponentially amplified.

Multiplex PCR as employed herein refers to the use of a polymerase chain reaction (PCR) to amplify two or more different DNA sequences simultaneously, i.e. as if performing many separate PCR reactions together in one reaction.

Primer as employed herein is intended to refer to a short strand of nucleic acid sequence, usually a chemically synthesised oligonucleotide, which serve as a starting point for DNA synthesis reactions. Primers are typically about 15 base pairs long but can vary from 5 to 100 bases long. It is required in processes such as PCR because DNA polymerases can only add new nucleotides or base pairs to an existing strand of DNA. During a PCR reaction, the primer hybridises to its complementary sequence in a DNA sample. Next, DNA polymerase starts replication at the 3'end of the primer and extends the primer by copying the sequence of the opposite DNA strand.

In one embodiment the primers of the present disclosure are specific for RNA, such as mRNA, i.e. they are complementary to RNA sequences. In another embodiment, the primers are specific for cDNA, i.e. they are complementary to cDNA sequences.

In one embodiment the primers of the present disclosure comprise a label which enables the primers to be detected or isolated. Examples of labels include but are not limited to a fluorescent label, a coloured label, and antibody, step tag, his tag.

In another embodiment, each primer in a given pair of primers is labelled, for example where one label (also known as a quencher) quenches the fluorescence of the other label when said labels are within proximity of each other. Such labels are particularly useful in real time PCR reactions for example. Examples of such label pairs include 6-carboxyfluorescein (FAM) and tetrachlorofluorescein, or tetramethylrhodamine and tetrachlorofluorescein.

Point of care test or bedside test as used herein is intended to refer to a medical diagnostic test which is conducted at or near the point of care, i.e. at the time and place of patient care. This is in contrast with a conventional diagnostic test which is typically confined to the medical laboratory and involves sending specimens away from the point of care to the laboratory for testing. Such diagnostic tests often require many hours or days before the results of the test can be received. In the meantime, patient care must continue without knowledge of the test results. In comparison, a point of care test is typically a simple medical test that can be performed rapidly.

A gene chip is essentially a microarray that is to say an array of discrete regions, typically nucleic acids, which are separate from one another and are, for example arrayed at a density of between, about 100/cm$^2$ to 1000/cm$^2$, but can be arrayed at greater densities such as 10000/cm$^2$.

The principle of a microarray experiment, is that mRNA from a given cell line or tissue is used to generate a labelled sample typically labelled cDNA or cRNA, termed the 'target', which is hybridised in parallel to a large number of, nucleic acid sequences, typically DNA or RNA sequences, immobilised on a solid surface in an ordered array. Tens of thousands of transcript species can be detected and quantified simultaneously. Although many different microarray systems have been developed the most commonly used systems today can be divided into two groups.

Using this technique, arrays consisting of more than 30,000 cDNAs can be fitted onto the surface of a conventional microscope slide. For oligonucleotide arrays, short 20-25 mers are synthesised in situ, either by photolithography onto silicon wafers (high-density-oligonucleotide arrays from Affymetrix) or by ink-jet technology (developed by Rosetta Inpharmatics and licensed to Agilent Technologies).

Alternatively, pre-synthesised oligonucleotides can be printed onto glass slides. Methods based on synthetic oligonucleotides offer the advantage that because sequence information alone is sufficient to generate the DNA to be arrayed, no time-consuming handling of cDNA resources is required. Also, probes can be designed to represent the most unique part of a given transcript, making the detection of closely related genes or splice variants possible. Although short oligonucleotides may result in less specific hybridization and reduced sensitivity, the arraying of pre-synthesised longer oligonucleotides (50-100 mers) has recently been developed to counteract these disadvantages.

In one embodiment the gene chip is an off the shelf, commercially available chip, for example HumanHT-12 v4 Expression BeadChip Kit, available from Illumina, NimbleGen microarrays from Roche, Agilent, Eppendorf and Genechips from Affymetrix such as HU-U133. Plus 2.0 gene chips.

In an alternate embodiment the gene chip employed in the present invention is a bespoke gene chip, that is to say the chip contains only the target genes which are relevant to the desired profile. Custom made chips can be purchased from companies such as Roche, Affymetrix and the like. In yet a further embodiment the bespoke gene chip comprises a minimal disease specific transcript set.

In one embodiment the chip consists of probes for detecting the expression levels of 95-100% of the 36 genes listed in Table 4.

In one embodiment the chip consists of 95-100% of the 38 transcript probes listed in Table 4 or 8.

In one embodiment the gene chip consisting of probes for detecting the modulation in gene expression levels of at least 95% of the genes selected from the group consisting of: IFI44L, FAM89A, IFI27L, IFTI1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7, KCNMA1, MERTK, EBI3, UPB1, EMR1, PTPN20, TMEM119, SLPI, S100P and PI3.

In one embodiment the chip consists of all the 38 Illumina probes (i.e. 100% of the probes) listed in Table 4 or Table 8.

In one embodiment the following Illumina transcript ID nos. are used to detect the modulation in gene expression levels: ILMN_9752 for IFI44L, ILMN_21686 and/or ILMN_21686 for FAM89A, ILMN_17548 for IFI27L, ILMN_1751 for IFTI1, ILMN_37168 for RSAD2, ILMN_22925 and/or ILMN_1944 for IFIT3, ILMN_27303 for OTOF, ILMN_28123 for IFIT2, ILMN_27754 for EPSTI1, ILMN_15074 for SERPING1, ILMN_2717 for OAS1, ILMN_13978 for IFI6, ILMN_5312 for HLA-DRB6, ILMN_19775 for HBZ, ILMN_89157 for HS.386275, ILMN_168435 for EIF2AK2, ILMN_5646 for IFIT1L, ILMN_18288 for FCER1A, ILMN_9078 for C21ORF7, ILMN_21264 for GYPE, ILMN_27651 for GYPB, ILMN_2819 for HBM, ILMN_14704 for EIF1AY, ILMN_43805 for LOC649143, ILMN_9543 for HBD, ILMN_28646 for FBXO7, ILMN_24236 for KCNMA1, ILMN_173016 for MERTK, ILMN_23396 for EBI3, ILMN_9777 for UPB1, ILMN_12984 for EMR1, ILMN_137356 for PTPN20, ILMN_30233 for TMEM119, ILMN_28045 for SLPI, ILMN_23476 for S100P and ILMN_13685 for PI3.

In another embodiment Illumina transcript ID nos. ILMN_21686 and ILMN_21686 are both used to detect the modulation in gene expression levels of FAM89A, and Illumina transcript ID nos. ILMN_22925 and ILMN_1944 are used to detect the gene expression levels of IFIT3.

In one embodiment the chip consists of probes for detecting the expression levels of IFI44L and FAM89A and probes for detecting one or more of the remaining 34 genes listed in Table 4.

In one embodiment the chip consists of Illumina transcript ID no. ILMN_9752 for detecting the expression levels of IFI44L and Illumina transcript ID no. ILMN_21686 for detecting the expression levels of FAM89, as well as one or more of the remaining 36 Illumina probes for detecting the expression levels of the 38 transcripts listed in Table 4 or Table 8.

In one embodiment the chip consisting of probes for detecting the modulation in gene expression levels of IFI44L and FAM89A; and optionally probes for one or more genes selected from the group consisting of: IFI27L, IFTI1, RSAD2, IFIT3, OTOF, IFIT2, EPSTI1, SERPING1, OAS1, IFI6, HLA-DRB6, HBZ, HS.386275, EIF2AK2, IFIT1L, FCER1A, C21ORF7, GYPE, GYPB, HBM, EIF1AY, LOC649143, HBD, FBXO7, KCNMA1, MERTK, EBI3, UPB1, EMR1, PTPN20, TMEM119, SLPI, S100P and PI3.

In one embodiment the chip consists of probes for detecting the expression levels of only IFI44L and FAM89A. For example, the chip consists of Illumina transcript ID no. ILMN_9752 for IFI44L and Illumina transcript ID no. ILMN_21686 for FAM89A.

In one or more embodiments above, the chip may further include 1 or more, such as 1 to 10, house-keeping genes.

In one embodiment the gene expression data is generated in solution using appropriate probes for the relevant genes.

Probe as employed herein is intended to refer to a hybridisation probe which is a fragment of DNA or RNA of variable length (usually 100-1000 bases long) which is used in DNA or RNA samples to detect the presence of nucleotide sequences (the DNA target) that are complementary to the sequence in the probe. The probe thereby hybridises to single-stranded nucleic acid (DNA or RNA) whose base sequence allows probe-target base pairing due to complementarity between the probe and target.

In one embodiment the method according to the present disclosure and for example chips employed therein may comprise one or more house-keeping genes.

House-keeping genes as employed herein is intended to refer to genes that are not directly relevant to the profile for identifying the disease or infection but are useful for statistical purposes and/or quality control purposes, for example they may assist with normalising the data, in particular a house-keeping gene is a constitutive gene i.e. one that is transcribed at a relatively constant level. The housekeeping gene's products are typically needed for maintenance of the cell.

Examples of housekeeping genes include but are not limited to actin, GAPDH, ubiquitin, 18s rRNA, RPII (POLR2A), TBP, PPIA, GUSB, HSPCB, YWHAZ, SDHA, RPS13, HPRT1 and B4GALT6.

In one embodiment minimal disease specific transcript set as employed herein means the minimum number of genes need to robustly identify the target disease state.

Minimal discriminatory gene set is interchangeable with minimal disease specific transcript set or minimal gene signature.

Normalising as employed herein is intended to refer to statistically accounting for background noise by comparison of data to control data, such as the level of fluorescence of house-keeping genes, for example fluorescent scanned data may be normalized using RMA to allow comparisons between individual chips. Irizarry et al 2003 describes this method.

Scaling as employed herein refers to boosting the contribution of specific genes which are expressed at low levels or have a high fold change but still relatively low fluorescence such that their contribution to the diagnostic signature is increased.

Fold change is often used in analysis of gene expression data in microarray and RNA-Seq experiments, for measuring change in the expression level of a gene and is calculated simply as the ratio of the final value to the initial value i.e. if the initial value is A and final value is B, the fold change is B/A. Tusher et al 2001.

In programs such as Arrayminer, fold change of gene expression can be calculated. The statistical value attached to the fold change is calculated and is the more significant in genes where the level of expression is less variable between subjects in different groups and, for example where the difference between groups is larger.

The step of obtaining a suitable sample from the subject is a routine technique, which involves taking a blood sample. This process presents little risk to donors and does not need to be performed by a doctor but can be performed by appropriately trained support staff. In one embodiment the sample derived from the subject is approximately 2.5 ml of blood, however smaller volumes can be used for example 0.5-1 ml.

Blood or other tissue fluids are immediately placed in an RNA stabilizing buffer such as included in the Pax gene tubes, or Tempus tubes.

If storage is required then it should usually be frozen within 3 hours of collections at −80° C.

In one embodiment the gene expression data is generated from RNA levels in the sample.

For microarray analysis the blood may be processed using a suitable product, such as PAX gene blood RNA extraction kits (Qiagen).

Total RNA may also be purified using the Tripure method—Tripure extraction (Roche Cat No. 1 667 165). The manufacturer's protocols may be followed. This purification may then be followed by the use of an RNeasy Mini kit—clean-up protocol with DNAse treatment (Qiagen Cat No. 74106).

Quantification of RNA may be completed using optical density at 260 nm and Quant-IT RiboGreen RNA assay kit (Invitrogen—Molecular probes Rl 1490). The Quality of the 28s and 18s ribosomal RNA peaks can be assessed by use of the Agilent bioanalyser.

In another embodiment the method further comprises the step of amplifying the RNA. Amplification may be performed using a suitable kit, for example TotalPrep RNA Amplification kits (Applied Biosystems).

In one embodiment an amplification method may be used in conjunction with the labelling of the RNA for microarray analysis. The Nugen 3' ovation biotin kit (Cat: 2300-12, 2300-60).

The RNA derived from the subject sample is then hybridised to the relevant probes, for example which may be located on a chip. After hybridisation and washing, where appropriate, analysis with an appropriate instrument is performed.

In performing an analysis to ascertain whether a subject presents a gene signature indicative of disease or infection according to the present disclosure, the following steps are performed: obtain mRNA from the sample and prepare nucleic acids targets, hybridise to the array under appropriate conditions, typically as suggested by the manufactures of the microarray (suitably stringent hybridisation conditions such as 3×SSC, 0.1% SDS, at 50<0>C) to bind corresponding probes on the array, and wash if necessary to remove unbound nucleic acid targets and analyse the results.

In one embodiment the readout from the analysis is fluorescence.

In one embodiment the readout from the analysis is colorimetric.

In one embodiment physical detection methods, such as changes in electrical impedance, nanowire technology or microfluidics may be used.

In one embodiment there is provided a method which further comprises the step of quantifying RNA from the subject sample.

If a quality control step is desired, software such as Genome Studio software may be employed.

Numeric value as employed herein is intended to refer to a number obtained for each relevant gene, from the analysis or readout of the gene expression, for example the fluorescence or colorimetric analysis. The numeric value obtained from the initial analysis may be manipulated, corrected and if the result of the processing is a still a number then it will be continue to be a numeric value.

By converting is meant processing of a negative numeric value to make it into a positive value or processing of a positive numeric value to make it into a negative value by simple conversion of a positive sign to a negative or vice versa.

Analysis of the subject-derived sample will for the genes analysed will give a range of numeric values some of which are positive (preceded by + and in mathematical terms considered greater than zero) and some of which are negative (preceded by − and in strict mathematical terms are considered to less than zero). The positive and negative in the context of gene expression analysis is a convenient mechanism for representing genes which are up-regulated and genes which are down regulated.

In the method of the present disclosure either all the numeric values of genes which are down-regulated and represented by a negative number are converted to the corresponding positive number (i.e. by simply changing the sign) for example −1 would be converted to 1 or all the positive numeric values for the up-regulated genes are converted to the corresponding negative number.

The present inventors have established that this step of rendering the numeric values for the gene expressions positive or alternatively all negative allows the summating of the values to obtain a single value that is indicative of the presence of disease or infection or the absence of the same.

This is a huge simplification of the processing of gene expression data and represents a practical step forward thereby rendering the method suitable for routine use in the clinic.

By discriminatory power is meant the ability to distinguish between a bacterial infected and a viral infected sample/subject or between a bacterial infection and an inflammatory disease, such as SLE, JIA and HSP.

The discriminatory power of the method according to the present disclosure may, for example, be increased by attaching greater weighting to genes which are more significant in the signature, even if they are expressed at low or lower absolute levels.

As employed herein, raw numeric value is intended to, for example refer to unprocessed fluorescent values from the gene chip, either absolute fluorescence or relative to a house keeping gene or genes. Summating as employed herein is intended to refer to act or process of adding numerical values.

Composite expression score as employed herein means the sum (aggregate number) of all the individual numerical values generated for the relevant genes by the analysis, for example the sum of the fluorescence data for all the relevant up and down regulated genes. The score may or may not be normalised and/or scaled and/or weighted.

In one embodiment the composite expression score is normalised.

In one embodiment the composite expression score is scaled.

In one embodiment the composite expression score is weighted.

Weighted or statistically weighted as employed herein is intended to refer to the relevant value being adjusted to more appropriately reflect its contribution to the signature.

In one embodiment the method employs a simplified risk score as employed in the examples herein. Simplified risk score is also known as disease risk score (DRS).

Control as employed herein is intended to refer to a positive (control) sample and/or a negative (control) sample which, for example is used to compare the subject sample to, and/or a numerical value or numerical range which has been defined to allow the subject sample to be designated as positive or negative for disease/infection by reference thereto.

Positive control sample as employed herein is a sample known to be positive for the pathogen or disease in relation to which the analysis is being performed, such as a bacterial infection.

Negative control sample as employed herein is intended to refer to a sample known to be negative for the pathogen or disease in relation to which the analysis is being performed.

In one embodiment the control is a sample, for example a positive control sample or a negative control sample, such as a negative control sample.

In one embodiment the control is a numerical value, such as a numerical range, for example a statistically determined range obtained from an adequate sample size defining the cut-offs for accurate distinction of disease cases from controls.

Conversion of Multi-Gene Transcript Disease Signatures into a Single Number Disease Score Once the RNA expression signature of the disease has been identified by variable selection, the transcripts are separated based on their up- or down-regulation relative to the comparator group. The two groups of transcripts are selected and collated separately.

Summation of Up-Regulated and Down-Regulated RNA Transcripts

To identify the single disease risk score for any individual patient, the raw intensities, for example fluorescent intensities (either absolute or relative to housekeeping standards) of all the up-regulated RNA transcripts associated with the disease are summated. Similarly summation of all down-regulated transcripts for each individual is achieved by combining the raw values (for example fluorescence) for each transcript relative to the unchanged housekeeping gene standards. Since the transcripts have various levels of expression and respectively their fold changes differ as well, instead of summing the raw expression values, they can be scaled and normalised between 0,1. Alternatively they can be weighted to allow important genes to carry greater effect. Then, for every sample the expression values of the signature's transcripts are summated, separately for the up- and down-regulated transcripts.

The total disease score incorporating the summated fluorescence of up- and down-regulated genes is calculated by adding the summated score of the down-regulated transcripts (after conversion to a positive number) to the summated score of the up-regulated transcripts, to give a single number composite expression score. This score maximally distinguishes the cases and controls and reflects the contribution of the up- and down-regulated transcripts to this distinction.

Comparison of the Disease Risk Score in Cases and Controls

The composite expression scores for patients and the comparator group may be compared, in order to derive the means and variance of the groups, from which statistical cut-offs are defined for accurate distinction of cases from controls. Using the disease subjects and comparator populations, sensitivities and specificities for the disease risk score may be calculated using, for example a Support Vector Machine and internal elastic net classification.

Disease risk score as employed herein is an indicator of the likelihood that patient has a bacterial infection when comparing their composite expression score to the comparator group's composite expression score.

Development of the Disease Risk Score into a Simple Clinical Test for Disease Severity or Disease Risk Prediction The approach outlined above in which complex RNA expression signatures of disease or disease processes are converted into a single score which predicts disease risk can be used to develop simple, cheap and clinically applicable tests for disease diagnosis or risk prediction.

The procedure is as follows: For tests based on differential gene expression between cases and controls (or between different categories of cases such as severity), the up- and down-regulated transcripts identified as relevant may be printed onto a suitable solid surface such as microarray slide, bead, tube or well.

Up-regulated transcripts may be co-located separately from down-regulated transcripts either in separate wells or separate tubes. A panel of unchanged housekeeping genes may also be printed separately for normalisation of the results.

RNA recovered from individual patients using standard recovery and quantification methods (with or without amplification) is hybridised to the pools of up- and down-regulated transcripts and the unchanged housekeeping transcripts.

Control RNA is hybridised in parallel to the same pools of up- or down-regulated transcripts.

Total value, for example fluorescence for the subject sample and optionally the control sample is then read for up- and down-regulated transcripts and the results combined to give a composite expression score for patients and controls, which is/are then compared with a reference range of a suitable number of healthy controls or comparator subjects.

Correcting the Detected Signal for the Relative Abundance of RNA Species in the Subject Sample The details above explain how a complex signature of many transcripts can be reduced to the minimum set that is maximally able to distinguish between patients and other phenotypes. For example, within the up-regulated transcript set, there will be some transcripts that have a total level of expression many fold lower than that of others. However, these transcripts may be highly discriminatory despite their overall low level of expression. The weighting derived from the elastic net coefficient can be included in the test, in a number of different ways. Firstly, the number of copies of individual transcripts included in the assay can be varied. Secondly, in order to ensure that the signal from rare, important transcripts are not swamped by that from transcripts expressed at a higher level, one option would be to select probes for a test that are neither overly strongly nor too weakly expressed, so that the contribution of multiple probes is maximised. Alternatively, it may be possible to adjust the signal from low-abundance transcripts by a scaling factor.

Whilst this can be done at the analysis stage using current transcriptomic technology as each signal is measured separately, in a simple colorimetric test only the total colour change will be measured, and it would not therefore be possible to scale the signal from selected transcripts. This problem can be circumnavigated by reversing the chemistry usually associated with arrays. In conventional array chemistry, the probes are coupled to a solid surface, and the amount of biotin-labelled, patient-derived target that binds is measured. Instead, we propose coupling the biotin-labelled cRNA derived from the patient to an avidin-coated surface, and then adding DNA probes coupled to a chromogenic enzyme via an adaptor system. At the design and manufacturing stage, probes for low-abundance but important transcripts are coupled to greater numbers, or more potent forms of the chromogenic enzyme, allowing the signal for these transcripts to be 'scaled-up' within the final single-channel colorimetric readout. This approach would be used to normalise the relative input from each probe in the up-regulated, down-regulated and housekeeping channels of the kit, so that each probe makes an appropriately weighted contribution to the final reading, which may take account of its discriminatory power, suggested by the weights of variable selection methods.

The detection system for measuring multiple up or down regulated genes may also be adapted to use rTPCR to detect the transcripts comprising the diagnostic signature, with summation of the separate pooled values for up and down regulated transcripts, or physical detection methods such as changes in electrical impedance. In this approach, the transcripts in question are printed on nanowire surfaces or within microfluidic cartridges, and binding of the corresponding ligand for each transcript is detected by changes in impedance or other physical detection system In one embodiment the gene chip is a fluorescent gene chip that is to say the readout is fluorescence. Fluorescence as employed herein refers to the emission of light by a substance that has absorbed light or other electromagnetic radiation.

Thus in an alternate embodiment the gene chip is a colorimetric gene chip, for example colorimetric gene chip uses microarray technology wherein avidin is used to attach enzymes such as peroxidase or other chromogenic substrates to the biotin probe currently used to attach fluorescent markers to DNA. The present disclosure extends to a microarray chip adapted to be read by colorimetric analysis and adapted to discriminate a subject having a bacterial infection from a subject having a viral infection or an inflammatory disease. The present disclosure also extends to use of a colorimetric chip to analyse a subject sample for discriminating a subject having a bacterial infection from a subject having a viral infection or an inflammatory disease.

Colorimetric as employed herein refers to as assay wherein the output is in the human visible spectrum.

In an alternative embodiment, a gene set or probe set for discriminating a subject having a bacterial infection from a subject having a viral infection or an inflammatory disease may be detected by physical detection methods including nanowire technology, changes in electrical impedance, or microfluidics.

The readout for the assay can be converted from a fluorescent readout as used in current microarray technology into a simple colorimetric format or one using physical detection methods such as changes in impedance, which can be read with minimal equipment. For example, this is achieved by utilising the Biotin currently used to attach fluorescent markers to DNA. Biotin has high affinity for avidin which can be used to attach enzymes such as peroxidase or other chromogenic substrates. This process will allow the quantity of cRNA binding to the target transcripts to be quantified using a chromogenic process rather than fluorescence. Simplified assays providing yes/no indications of disease status can then be developed by comparison of the colour intensity of the up- and down-regulated pools of transcripts with control colour standards. Similar approaches can enable detection of multiple gene signatures using physical methods such as changes in electrical impedance.

This aspect of the invention is likely to be particularly advantageous for use in remote or under-resourced settings or for rapid diagnosis in "near patient" tests. For example, places in Africa because the equipment required to read the chip is likely to be simpler.

Multiplex assay as employed herein refers to a type of assay that simultaneously measures several analytes (often dozens or more) in a single run/cycle of the assay. It is distinguished from procedures that measure one analyte at a time.

In one embodiment there is provided a bespoke gene chip for use in the method, in particular as described herein.

In one embodiment there is provided use of a known gene chip for use in the method described herein in particular to identify one or more gene signatures described herein.

In one embodiment there is provided a method of determining whether to administer an anti-bacterial agent to a subject, such as a subject suspected of having a bacterial infection for example a subject exhibiting symptoms of having a bacterial infection, by employing the method disclosed therein, and administering the anti-bacterial agent to the subject if the method indicates that the subject has a bacterial infection.

In one embodiment the subject exhibits clinical symptoms of having only a viral infection.

In another embodiment the subject exhibits clinical symptoms of having both a viral and a bacterial infection.

In one embodiment there is provided a method of treating a bacterial infection after diagnosis employing the method disclosed herein.

In one embodiment the bacterial infection is treated by administering one or more anti-bacterial agents to the subject.

In one embodiment the one or more anti-bacterial agents are selected from the group consisting of: erythromycin, clindamucin, gentamicin, tetracycline, meclocycline, sulfacetamide, benzoyl peroxide, azelaic acid, ceftobiprole, ceftaroline, dalbavancin, daptomycin, linezolid, mupirocin, oritavancin, tedizolid, telavancin, tigecycline, vancomycin, aminoglycosides, carbapenems, ceftazidime, cefepime, ceftobiprole, fluorquinolones, piperacillin/tazobactam, ticarcillin/clavulanic acid, linezolid, streptogramins, daptomycin, amikacin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, telavancin, dalbavancin, oritavancin, clindamycin, lincomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin, penicillin, G, penicillin V, piperacillin, temocillin, ticarcillin, amoxicillin/clavulanate, ampicillin/sulbactam, pieracillin/tazobactam, ticarcillin/clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofoxacin, trovafloxacin, grepafloxacin, sparfloxacin, temafloxacin, mafenide, sulfacetamide, sulfadiazine, silversulfadiazine, sulfadimethoxine, sulfamethizole, sulfamethoxazole, sulfanilimide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, arsphenamine, chloramphenicol, fosfomycin, fusidic acid, metronidazole, mupirocin, platensimycin, quinupristin/dalfopristin, thiamphenicol, tinidazole and trimethoprim.

In one embodiment there is provided a method of determining whether to administer an anti-viral agent to a subject, such as a subject suspected of having a viral infection (for example a subject exhibiting symptoms of having a viral infection), by employing the method disclosed therein, and administering the anti-viral agent to the subject if the method indicates that the subject has a viral infection.

In one embodiment the subject exhibits clinical symptoms of having only a bacterial infection.

In another embodiment the subject exhibits clinical symptoms of having both a viral and a bacterial infection.

In one embodiment there is provided a method of treating a viral infection after diagnosis employing the method disclosed herein.

In one embodiment the viral infection is treated by administering one or more anti-viral agents to the subject.

In one embodiment the one or more anti-viral agents are selected from the group consisting of:

amantadine, rimantadine, ritonavir, cobicistat, interferon alfa-2b/ribavirin, ombitasvir/paritaprevir/ritonavir, peginterferon alfa-2a, peginterferon alfa-2b, maraviroc, raltegravir, dolutegravir, elvitegravir, sofosbuvir, enfuvirtide, foscarnet, fomivirsen, zanamivir, oseltamivir, peramivir, nevirapine, etravirine, efavirenz, rilpivirine, delavirdine, nevirapine, daclatasvir, entacavir, lamivudine, adefovir, didanosine, tenofovir, abacavir, lamivudine, zidovudine, stavudine, emtricitabine, zalcitabine, telbivudine, didanosine, boceprevir, simeprevir, telaprevir, lopinavir, fosamprenavir, darunavir, ritonavir, tipranavir, atazanavir, nelfinavir, amprenavir, indinavir, saquinavir, ribavirin, valacyclovir, famciclovir, acyclovir, ganciclovir, valganciclovir and cidofovir.

In one embodiment there is provided a method of treating an inflammatory disease, such as JIA, HSP or SLE after diagnosis employing the method disclosed herein.

Gene signature, gene set, disease signature, diagnostic signature and gene profile are used interchangeably throughout and should be interpreted to mean gene signature.

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

EXAMPLES

Example 1

Method

Patient Groups—Discovery and Validation Groups

Figure 1:
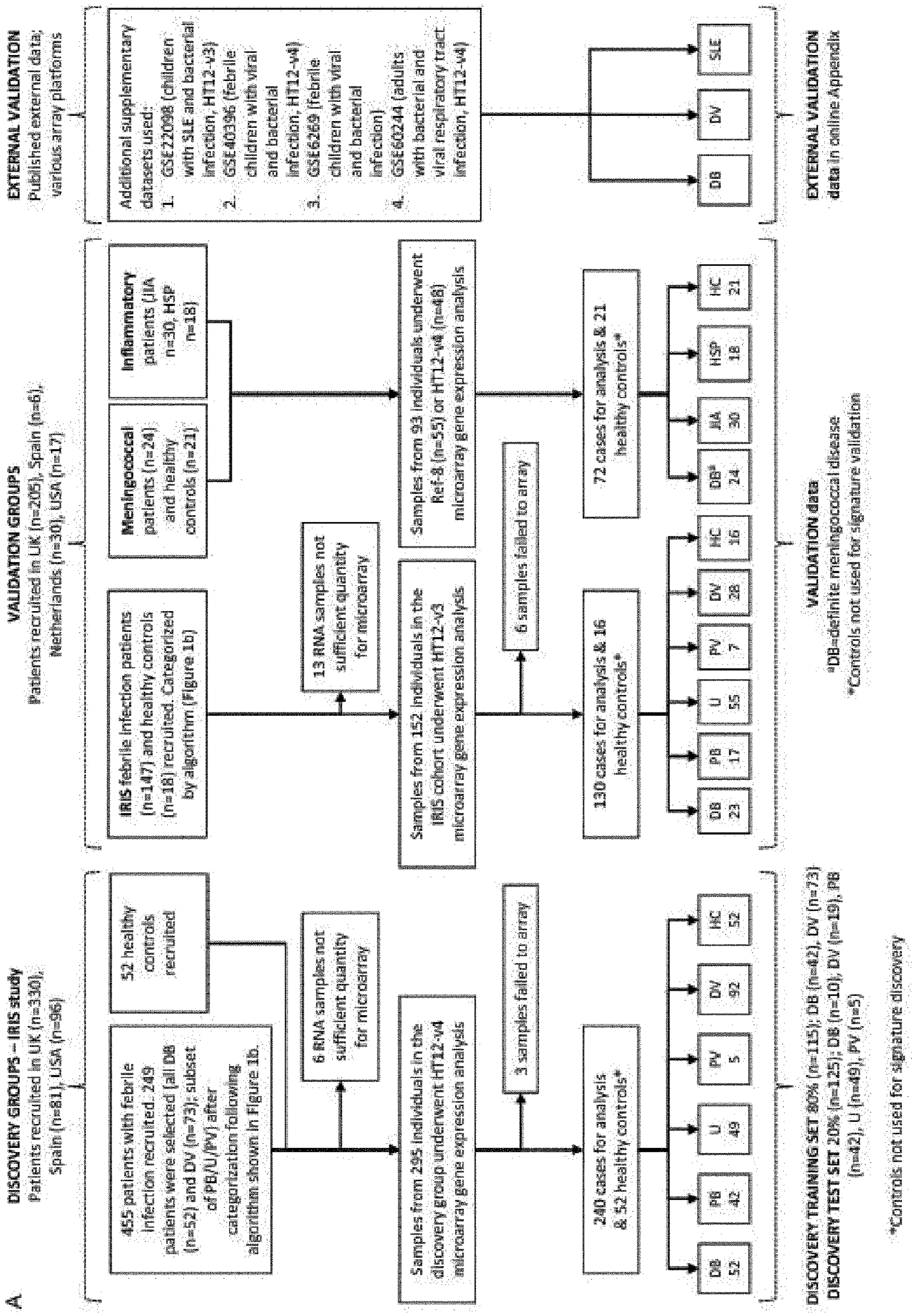
FIG. 1 shows an overview of the study.
Figure 1:
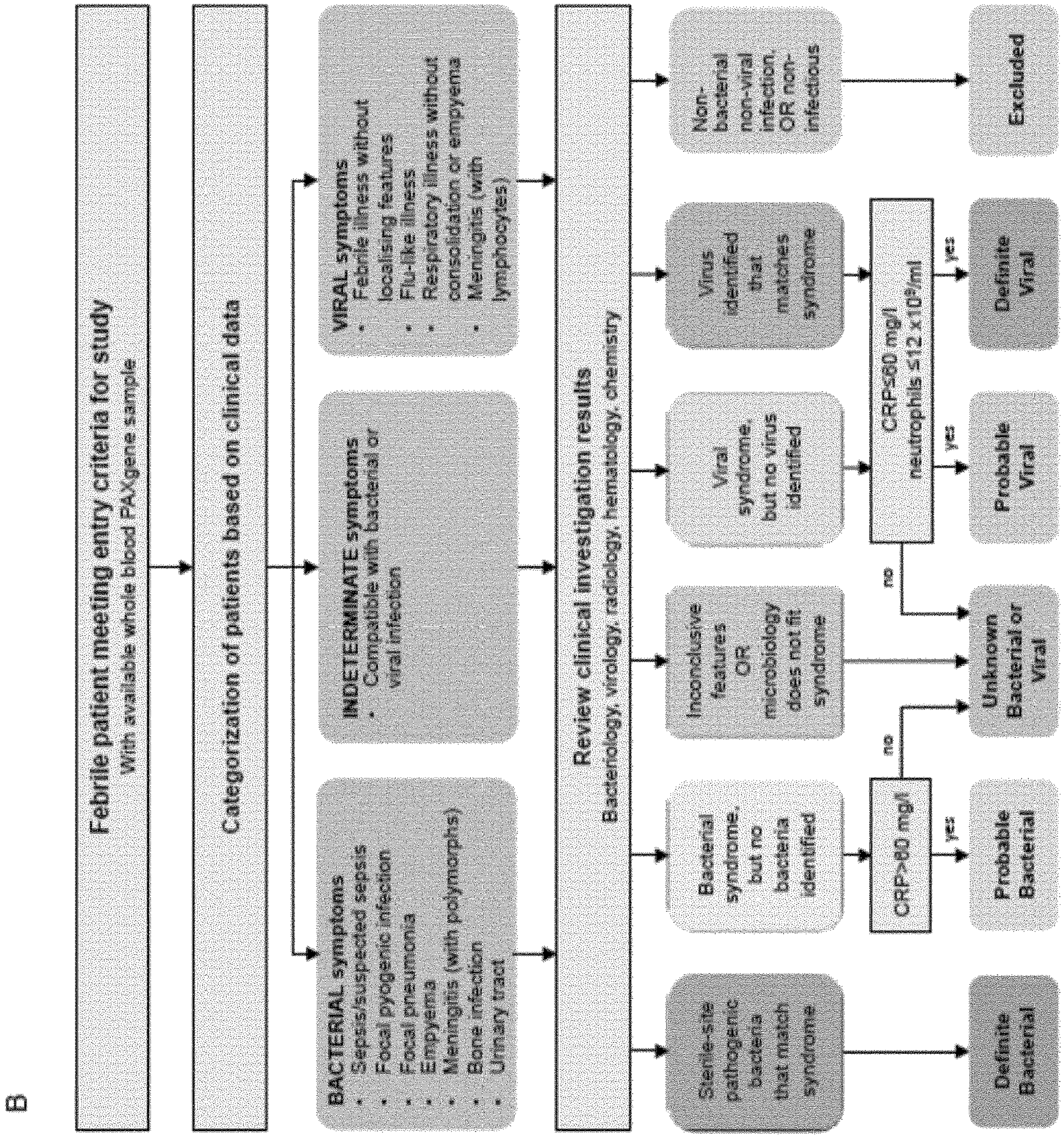

The overall design of the study is shown in FIGS. 1 and 2. Patients were recruited prospectively as part of a UK National Institute of Health Research-supported study (NIHR ID 8209), the Immunopathology of Respiratory, Inflammatory and Infectious Disease Study (IRIS), which recruited children at three UK hospitals; patients were also recruited in Spain (GENDRES network, Santiago de Compostela), and USA (Rady Children's Hospital, San Diego). Inclusion criteria were fever (axillary temperature ≥38° C.) and perceived illness of sufficient severity to warrant blood testing in children <17 years of age. Patients with co-morbidities likely to affect gene expression (bone marrow transplant, immunodeficiency, or immunosuppressive treatment) were excluded. Blood samples for RNA analysis were collected together with clinical blood tests at, or as close as possible to, presentation to hospital, irrespective of antibiotic use at the time of collection.

Additional Validation Groups

Additional validation groups (see also Table 2) included children with meningococcal sepsis,[16] inflammatory diseases (Juvenile Idiopathic Arthritis and Henoch-Schönlein purpura) and published gene expression datasets which compared bacterial infection with viral infection,[12,15,11] or inflammatory disease.[18] Healthy children were recruited from out-patient departments. Data from healthy controls were not utilized in identification or validation of gene expression signatures, and were only used for interpretation of direction of gene regulation.

IRIS Discovery and IRIS Validation Groups

Children were classified as Definite Bacterial if they had a clinical syndrome consistent with SBI (sepsis with shock or severe focal infection), and if pathogenic bacteria were detected at a usually sterile site (such as blood or CSF, excluding surface swabs, endotracheal secretions, or broncho-alveolar lavage samples); patients without sterile-site bacteria but with the other features listed above were categorized as Probable Bacterial. Children were classified as Definite Viral if they had a viral clinical syndrome, displayed no bacterial features, and matching virus was identified; patients without detected viruses but with clinical features of viral infection were classified as Probable Viral. In the absence of sterile site bacteria, children with inconclusive clinical features were classified as Unknown Bacterial or Viral. We used a CRP cut-off of above 60 mg/L for inclusion into the Probable Bacterial group, or exclusion from the Probable and Definite Viral groups; otherwise patients were categorized as Unknown. Inclusion in the Definite Bacterial group was irrespective of CRP. The indeterminate infection patients not selected for array were those with the most missing clinical data (FIG. 1B).

Healthy Controls

In order to compare expression of identified biomarker genes with the healthy state and understand the direction of expression (up- or down-regulation), healthy children without intercurrent infection or recent immunization were recruited from the outpatient phlebotomy department (n=52). Data from healthy controls were not utilized in identification or validation of RNA expression signatures.

Meningococcal Validation Cohort

We validated our expression signatures on children with meningococcal (gram-negative) infection (n=24), recruited to an earlier study at St Mary's Hospital, London, UK [29]. Following informed parental consent, and with approval of the hospital Local Research Ethics Committee (EC3263), venous blood was collected on admission and within 24 hours of onset of symptoms from patients admitted to PICU at St Mary's hospital between December 2002 and May 2005 with suspected meningococcal sepsis, meningococcal meningitis or both. Group B meningococcus was detected in blood or CSF by culture or by bacterial DNA PCR amplification. Controls (used only for removal of array data batch effects) were healthy white adults recruited following informed consent [11 males, 10 females age median (IQR) 35.6 (30.8-44.5)].

Inflammatory Validation Cohort

In order to establish if gene expression signatures could also distinguish children with bacterial infection from childhood inflammatory or vasculitic diseases, we used data from children with inflammatory diseases (Table 2). Patients were recruited at pediatric centers in the Netherlands and USA under approvals by the Research Ethics Committees of UCSD (Human Research Protection Program #140220), Amsterdam (NL41846.018.12 and NL34230.018.10). The inflammatory syndromes in the cohort were a) Henoch Schönlein Purpura (HSP) that was diagnosed in children presenting with palpable purpura, typically over the buttocks and extensor surfaces in association with abdominal pain, arthralgia or renal abnormalities (hematuria and proteinuria); and b) Juvenile Idiopathic arthritis (JIA) that was defined according to International League of Associations for Rheumatology [30]. Patients for the JIA cohort were recruited at initial presentation with early arthritis. They were not treated with DMARDs, corticosteroids or biologicals. Some patients used simple non-steroidal anti-inflammatory drugs.

Diagnostic Process

All patients underwent routine diagnostic investigations as part of clinical care in each hospital's microbiology and virology laboratories, including blood count and differential, C-reactive protein (CRP), blood chemistry, blood, and urine cultures, and cerebrospinal fluid (CSF) analysis where indicated. Throat swabs were cultured for bacteria, and viral diagnostics were undertaken on nasopharyngeal aspirates using multiplex PCR for common respiratory viruses. Chest radiographs and other tests were undertaken as clinically indicated. Patients were assigned to diagnostic groups using predefined criteria (FIG. 1B). The Definite Bacterial group included only patients with culture confirmed infection, and the Definite Viral group included only patients with culture, PCR or immunofluorescent test-confirmed viral infection and no features of co-existing bacterial infection. Children in whom definitive diagnosis was not established (indeterminate infection) were categorized into Probable Bacterial, Unknown Bacterial or Viral, and Probable Viral groups based on level of clinical suspicion (FIG. 1B). Detection of virus did not prevent inclusion in the Definite, Probable Bacterial, or Unknown groups, as bacterial infection can occur in children co-infected with viruses.

Study Conduct and Oversight

Clinical data and samples were identified only by study number. Assignment of patients to clinical groups was made by consensus of two experienced clinicians independent of those managing the patient, after review of the investigation results and using previously agreed definitions (FIG. 1B). Statistical analysis was conducted after the gene expression data and clinical assignment databases had been locked.

Written, informed consent was obtained from parents or guardians at all sites using locally approved research ethics committee permissions (St Mary's Research Ethics Committee (REC 09/H0712/58 and EC3263); Ethical Committee of Clinical Investigation of Galicia (CEIC ref 2010/015); UCSD Human Research Protection Program #140220; and Academic Medical Centre, University of Amsterdam (NL41846.018.12 and NL34230.018.10).

Peripheral Blood Gene Expression by Microarray

Whole blood (2.5 ml) was collected at the time of recruitment into PAXgene blood RNA tubes (PreAnalytiX, Germany), incubated for two hours, frozen at −20° C. within six hours of collection, before storage at −80° C. Total RNA was extracted using PAXgene blood RNA kits (PreAnalytiX, Germany) according to the manufacturer's instructions. The integrity and yield of the total RNA was assessed using an Agilent 2100 Bioanalyser and a NanoDrop 1000 spectrophotometer. After quantification and quality control, biotin-labeled cRNA was prepared using Illumina TotalPrep RNA Amplification kits (Applied Biosystems) from 500 ng RNA. Labeled cRNA was hybridized overnight to Human HT12-V4 Expression BeadChip arrays (Illumina) [Discovery cohort, Inflammatory Validation cohort] or Human HT12-V3 Expression BeadChip arrays (Illumina) [IRIS validation cohort] or Human Ref-8 V3 Beadchip (Meningococcal validation cohort). After washing blocking, and staining, the arrays were scanned using an Illumina BeadArray Reader according to the manufacturer's instructions. Using Genome Studio software, the microarray images were inspected for artifacts and QC parameters were assessed. No arrays were excluded at this stage.

Statistical Analysis

Microarray Pre-Processing

Expression Data was analyzed using 'R' Language and Environment for Statistical Computing (R) 3.1.2 [31]. Expression values were transformed to a logarithmic scale (base 2). Mean raw intensity values for each probe were corrected for local background intensities and robust spline normalization [32] (combining quantile normalization and spline interpolation) was applied. Principal Component Analysis (PCA) was used as part of the quality control process. PCA is an approach that allowed us to summarize our data and reduce the dimensionality (240 arrays×48,000 probes, down to 240 arrays×no of principal components) in order to explore variance in the expression level [33]. Transcript expression profiles of all samples in the discovery dataset clustered together on PCA; regardless of the diagnostic group (FIG. 6). All the samples were within the confidence ellipse (level: 0.999). The arrays in the discovery dataset that correspond to patients with definite diagnosis were divided into 80%-20% for the identification and validation of expression signatures, resulting in a balanced training set ($n_{adenovirus}$=18, $n_{flu}$=18, $n_{RSV}$=22, $n_{other\ viral}$=15, $n_{bacterial\ gram\text{-}negative}$=20, $n_{bacterial\ gram\text{-}positive}$=22) and test set ($n_{adenovirus}$=5, $n_{flu}$=5, $n_{RSV}$=S, $n_{other\ viral}$=4, $n_{bacterial\ gram\text{-}negative}$=5, $n_{bacterial\ gram\text{-}positive}$=5).

Identification of Expression Signatures

For the discovery dataset, we used transcripts that were measured on both V3 and V4 Illumina BeadChips (the intersection array IDs). Using the training set, we identified the transcripts that were significantly differentially expressed between the definite viral and definite bacterial groups with |log 2 FC|>1 and adjusted P-value <0.05, using a linear model for expression, conditional on recruitment site. These thresholds were chosen to ensure that differential expression for selected variables could be distinguished using the resolution of other validation techniques (i.e. qPCR). The transcripts that fulfilled the above criteria were taken forward to variable selection with elastic net, using glmnet [34] package in R. The parameters of elastic net, which control the size of the selected model, were optimized via ten-fold cross-validation (CV).

In order to identify a smaller signature, we applied a novel in-house forward selection algorithm to discover a transcript signature, Forward Selection-Partial Least Squares (FS-PLS) which was then implemented as a Disease Risk Score (DRS) in order to translate the minimal multi-transcript signature into a value that could be assigned to each individual to form the basis of a simple diagnostic test. The DRS is calculated by adding the total intensity of the up-regulated transcripts (relative to comparator group) and subtracting the total intensity of the down-regulated transcripts (relative to comparator group) in the signature [11, 20]. The disease risk score for individual i is:

$$\text{Disease Risk } Score^i = \sum_{k=0}^{n} expr.value_k^i - \sum_{l=0}^{m} expr.value_l^i \tag{1}$$

where:

n the number of up-regulated probes in the signature in disease of interest (bacterial infection) compared to comparator group (viral infection) and m the number of down-regulated probes in the signature in disease of interest (bacterial infection) compared to comparator group (viral infection).

In order to discover gene expression signatures using FS-PLS, the first iteration of the algorithm considers the expression levels of all transcripts (N) and initially fits N univariate regression models. The regression coefficient for each model is estimated using the Maximum Likelihood Estimation (MLE) function, and the goodness of fit is assessed by means of a t-test. The variable with the highest MLE and smallest p-value is selected first (SV1). Before selecting which of the N−1 remaining variables to use next, the algorithm projects the variation explained by SV1 using Singular Value Decomposition. The algorithm iteratively fits up to N−1 models, at each step projecting the variation corresponding to the already selected variables, and selecting new variables based on the residual variation. This process terminates when the MLE p-value exceeds a predefined threshold. The final model includes regression coefficients for all selected variables.

The performance of both the signatures was assessed on the 20% test and the IRIS validation dataset. The probable viral and bacterial groups as well as the unknown bacterial or viral infection group from the discovery cohort were assessed with the 20% test dataset. The thresholds for the classification throughout were calculated using the pROC package in R [35], employing the Youden's J statistic [36].

The optimal threshold was determined by the point in the ROC curve that maximizes the distance to the identity line (maximum of (sensitivities+specificities)).

In the boxplots, boxes show median with 25$^{th}$ and 75$^{th}$ quartiles and whiskers show "range" (defined by boxplot function in R). With a "range" value set at 1, the whiskers extend no more than 1 times the interquartile range. For the 2-transcript signature, the DRS was calculated by subtracting the $\log_2$ transformed expression value of IFI44L from the $\log_2$ transformed FAM89A expression value for every patient. The range of DRS in the population can be between: [the minimum FAM89A value−the maximum IFI44L, the maximum FAM89A value−the minimum IFI44L value].

The signatures identified in the discovery group were then externally validated on our previously published validation group [13] additional patient groups with meningococcal disease and inflammatory diseases, and three published pediatric data sets (FIG. 2).

Analysis of IRIS Validation Dataset

The IRIS validation dataset (analysed using HT-12-V3 Illumina BeadChip arrays) was pre-processed and analysed separately to the discovery dataset, using the same approach.

Analysis of Additional Validation Datasets

To assess the performance of the signature in gram-negative bacterial infection, the IRIS validation dataset was merged with a dataset containing pediatric meningococcal infection and healthy controls. As the meningococcal and IRIS validation cohorts had been run on different versions of the Illumina chip, the data were merged for analysis using the ComBat method [37] to remove unwanted batch effects using transcripts common to the 2 platforms. The healthy controls in the IRIS validation set (Illumina HT12-V3), and the healthy controls in the meningococcal validation set (Illumina Ref-8) were used for the adjustment One binary covariate was passed to ComBat which assigned samples to two groups—healthy, and disease. (FIG. 11)

The inflammatory validation dataset contained JIA and HSP patients run on Illumina HT12-V4 arrays. These arrays were processed and normalized alongside the Discovery arrays, and the discriminatory power of the 2-transcript signature was applied without further pre-processing of array data.

To further validate the performance of the disease risk score based on the 2-transcript signature, we used publicly available microarray expression datasets with bacterial infections and comparator groups run simultaneously on the same platform to avoid the introduction of batch effects, as follows:

1. GPL570 [HG-U133_Plus_2] Affymetrix Human Genome U133 Plus 2.0 [15] (accession series GSE6269) dataset. The dataset consists of 22 pediatric cases, 10 viral and 12 bacterial; 7 children were diagnosed with Influenza A, 3 with Influenza B, 6 with *S. pneumoniae* and 6 with *S. aureus* infection. Gene identities for the two genes in our signature from the Illumina arrays were mapped to the Affymetrix dataset and "204439_at" for IFI44L and "226448_at" for FAM89A transcript ids were used. Despite differences in experimental design—the GSE6269 gene expression dataset was acquired from peripheral blood mononuclear cells using a non-Illumina platform, the 2-transcript signature DRS had a sensitivity of 100% (95% CI, 100 to 100) and a specificity of 90% (95% CI, 70 to 100), misclassifying only one viral patient with Influenza A (patient id: GSM173316). The AUC was 96% (95% CI, 85 to 100) (FIG. 12).
2. GSE40396 dataset. This includes 30 febrile children with viral infection (8 with adenovirus, 6 with enterovirus and 8 with HHV6) and 8 with bacterial infection (MRSA, MSSA, *Salmonella* and *E. coli*) [12]. As the arrays used were Illumina HT12-V4, the same probe ids for IFI44L and FAM89A were identified. The 2-transcript signature had a sensitivity of 100% (95% CI, 100 to 100) and a specificity of 77.3% (95% CI, 59.1 to 95.5) and an AUC of 89.2% (95% CI, 75.6 to 98.3).
3. GSE22098 dataset. This includes 48 children (aged <17 years) with bacterial infection (*S. pneumoniae* and *S. aureus*) and 31 children with systemic lupus erythematosus [18], run on Illumina Beadchip HT12-V3 arrays. The same probe IDs for the two-transcript signature were available on both HT12-V3 and V4 arrays, and were applied to the data. The 2-transcript signature had a sensitivity for detection of bacterial infection of 93.5% (95% CI, 83.9 to 100) and a specificity of 96.1% (95% CI, 96.9 to 100) and an AUC of 96.6% (95% CI, 91.9 to 100).
4. GSE60244 dataset. This dataset includes patients with bacterial lower respiratory tract infection (LRTI) n=22 and viral LRTI n=71 run on Illumina Beadchip HT12-V4 arrays. As the arrays used were Illumina HT12-V4, the same probe ids for IFI44L and FAM89A were identified. The 2-transcript signature had a sensitivity for detection of bacterial infection of 90.1 (95% CI, 77.3 to 100) and a specificity of 80.3 (95% CI, 70.4 to 88.7) and an AUC of 89.8 (95% CI, 83.4-95.5).

Results 240 patients were recruited to the discovery group, including a Definite Bacterial group with 52 patients and Definite Viral group with 92 patients. These were subdivided into 80% and 20%—forming a training set and test set respectively (FIGS. 1A, 2). The test set (20%) also included 96 children whose infection was not definitively diagnosed (indeterminate) (FIGS. 1A, 2). The validation groups comprised 130 children previously recruited[13] (IRIS validation—with 23 Definite Bacterial, 28 Definite Viral patients and 79 patients with indeterminate infection) and 72 other children (additional validation—with 24 meningococcal infection, 30 juvenile idiopathic arthritis, and 18 patients with Henoch-Schönlein purpura) (FIGS. 1A, 2). The numbers in each diagnostic category in the discovery, IRIS validation and additional validation groups and their clinical features are shown in Table 1 and Table 2. Details of the types of infection are shown in Table 3. Gene expression profiles of children in the discovery group clustered together on Principal Component Analysis (FIG. 6).

Identification of Minimal Transcript Signatures

Of the 8565 transcripts differentially expressed between bacterial and viral infections, we identified 285 transcripts as potential biomarkers after applying the screening filters based on log fold change and statistical significance (see methods). Variable selection using elastic net identified 38 of these transcripts (Table 4) as best discriminators of bacterial and viral infection in the discovery test set with sensitivity of 100% (95% CI, 100-100) and specificity of 95% (95% CI, 84-100) (Table 5). In the IRIS validation group, this signature had an area under the curve (AUC) of 98% (95% CI, 94-100), sensitivity of 100% (95% CI, 100-100), and specificity of 86% (95% CI, 71-96) for distinguishing bacterial from viral infection (Table 5, FIGS. 7, 8). The putative function of the 38 transcripts in our signature, as defined by Gene Ontology is shown in Table 6.

After using the novel forward selection process (FS-PLS) to remove highly correlated transcripts, a two-transcript gene signature which distinguished bacterial from viral infections: interferon-induced protein 44-like (IFI44L, RefSeq ID: NM 006820.1), and family with sequence similarity 89, member A (FAM89A, RefSeq ID: NM 198552.1). Both transcripts were also included in the larger 38 transcript signature.

Implementation of a Simplified Disease Risk Score

The expression data of both genes in the signature was combined into a single Disease Risk Score for each patient, using the reported DRS method which simplifies application of multi transcript signatures as a diagnostic test [20] The sensitivity (95% CI) of the DRS in the training, test and validation sets respectively was: 86% (74-95), 90% (70-100), and 100% (100-100) (FIG. 3A-D, FIG. 9 and Table 5). Expression of IFI44L was increased in viral patients and FAM89A was increased in bacterial patients relative to healthy children (Table 4). The summary of diagnostic test accuracy including STARD flow diagrams are shown in FIG. 10.

For additional validation the 2-transcript signature was applied to patients with meningococcal disease (FIG. 11), inflammatory diseases (Juvenile Idiopathic arthritis and Henoch-Schönlein purpura), and published datasets for children and adults with bacterial or viral infection, and inflammatory disease (pediatric SLE).[12, 15, 17, 18] The 2-transcript signature distinguished bacterial infection from viral infection and inflammatory disease in all these datasets with AUC ranging from 89% to 98% (Table 7 and FIG. 12-13).

Effect of Viral and Bacterial Co-Infection

The effect of viral co-infection on the signatures was investigated (Table 1). 30 of 47 (64%) of the definite bacterial infection group who were tested had a virus isolated from nasopharyngeal samples. There was no significant difference in DRS score between those with and without viral co-infection.

DRS Score in Patients with Indeterminate Infection Status

The classification performance of the DRS was investigated in patients with indeterminate viral or bacterial infection status. Patients were separated into those with clinical features strongly suggestive of bacterial infection (Probable Bacterial), those with features consistent with either bacterial or viral infection (Unknown), and those with clinical features and results suggestive of viral infection (Probable Viral) as in FIG. 1B. The Probable Bacterial and Unknown groups included patients with DRS values that indicated viral infection, despite having clinical features that justified initiation of antibiotics by the clinical team. The median DRS showed a gradient of assignment that followed the degree of certainty in the clinical diagnosis, although many of the indeterminate group DRS values overlapped with those of Definite Bacterial and Definite Viral groups (FIG. 4A, 4B).

For patients in the indeterminate groups, we compared DRS assignment as 'viral' or 'bacterial' to clinical variables (Table 8). CRP is widely used to aid distinction of bacterial from viral infection and was included in the categorization of Definite Viral, Probable Bacterial, and Probable Viral infection in this study; patients assigned as bacterial by DRS had higher CRP levels than those assigned as viral infection (median [IQR]: 101 [48-192] and 71 [27-120] mg/l; p=0.015 respectively). They also had increased incidence of shock (p=0.006), requirement for ventilator support (p=0.048) and intensive care admission (p=0.066). There was a non-significant increase in white cell and neutrophil counts in patients assigned by DRS as bacterial or viral respectively: (median [IQR] 14.1 [8.3-19.4] and 11.1 [7.3-16.0] for white cells; 8.7 [5.0-13.8] and 6.8 [3.5-11.4] for neutrophils), (p=0.079 and 0.114 respectively).

Antibiotic Use

The number of children treated with antibiotics was compared with DRS prediction of bacterial or viral infection. There were high rates of antibiotic use in all groups, including >90% in the Unknown group. The high rate of antibiotic use in the indeterminate groups contrasted with the low numbers predicted to have bacterial infection by both DRS and clinical assignment (FIG. 5).

Illness Severity and Duration

The study recruited a high proportion of seriously ill patients needing intensive care, thus raising concern that selection bias might have influenced performance of the signature. To exclude bias based on severity or duration of illness, performance of the DRS was evaluated after stratification of patients into those with milder illness or severe illness requiring intensive care, and by duration of reported illness before presentation. The DRS distinguished bacterial from viral infection in both severe and milder groups (FIG. 14), and irrespective of day of illness (FIG. 15).

Discussion

We have identified a host whole blood RNA transcriptomic signature that distinguishes bacterial from viral infection with only two transcripts. The signature also distinguishes bacterial infection from childhood inflammatory diseases, SLE, HA and FISP and discriminates bacterial from viral infection in published adult studies [12, 15, 17, 18]. The design of our study with recruitment of febrile patients to a discovery set and then evaluation of the diagnostic signature in a separate validation set and in multiple additional datasets, recruited in different centres and analysed on various microarray platforms, ensures that our findings are robust. The results extend previous gene expression studies in single infections that suggest that bacterial and viral infections have different signatures, and that this approach is superior to non-specific markers such as CRP or procalcitonin alone [12, 13, 17, 21].

The transcripts identified in the larger 38-transcript elastic net gene signature comprise a combination of transcripts up-regulated by viruses or by bacteria. The two transcripts IFI44L and FAM89A in the smaller 2 transcript signature show reciprocal expression in viral and bacterial infection, and are differentially expressed when bacterial or viral patients were compared to healthy controls [20].

An obstacle in the development of improved tests to distinguish bacterial from viral infection is the lack of a gold standard. Some studies include patients with "clinically diagnosed bacterial infection" who have features of bacterial infection but cultures remain negative. Negative cultures may reflect prior antibiotic use, low numbers of bacteria, or inaccessible sites of infection. If patients with indeterminate status are included in biomarker discovery, there is a risk that the identified biomarker will not be specific for "true" infection. This study adopted the rigorous approach of identifying the signature in culture-confirmed cases, and using the signature to explore likely proportions of "true" infection in the indeterminate groups.

The proportion of children predicted by DRS signature to have bacterial infection follows the level of clinical suspicion (greater in Probable Bacterial and less in the Probable Viral groups), thus supporting the hypothesis that the signatures may be an indication of the true proportion of bacterial infection in each group. Furthermore, a higher proportion of patients in the indeterminate group, assigned as bacterial by the signature (Probable and Unknown groups) had clinical features normally associated with severe bacterial infection, including increased need for intensive care, and higher neutrophil counts, and CRP, suggesting that the signature may be providing additional clues to the presence of bacterial infection.

The decision to initiate antibiotics in febrile children is largely driven by fear of missing bacterial infection. A test that correctly distinguishes children with bacterial infection from those with viral infections would reduce inappropriate antibiotic prescription and investigation. The DRS predicts that many children who were prescribed antibiotics did not have a bacterial illness (see FIG. 5). If the score reflects the true likelihood of bacterial infection, its implementation could reduce unnecessary investigation, hospitalization, and treatment with antibiotics. Confirmation that the DRS provides an accurate estimate of bacterial infection in the large group of patients with negative cultures, for whom there is no gold standard, can only be achieved in prospective clinical trials. Careful consideration will be needed to design an ethically acceptable and safe trial in which observation without antibiotic administration is undertaken for febrile children predicted by DRS to be at low risk of bacterial infection.

In comparison with the high frequency of common viral infections in febrile children presenting to healthcare, inflammatory and vasculitic illness are very rare.[24-27] However, children presenting with inflammatory or vasculitic conditions commonly undergo extensive investigation to exclude bacterial infection and treatment with antibiotics before the correct diagnosis is made. Although children with inflammatory conditions were not included in the discovery process, the 2-transcript signature was able to distinguish bacterial infection from SLE, JIA and HSP.

A major challenge in using transcriptomic signatures as diagnostic tools is the translation of multi-transcript signatures into clinical tests suitable for use in hospital laboratories or at the bedside. The DRS gene signature, distinguishing viral from bacterial infections with only two transcripts, has potential to be translated into a clinically applicable test using current technology such as real-time PCR.[28] Furthermore, new methods for rapid detection of nucleic acids including nanoparticles, and electrical impedance have potential for low-cost direct and rapid analysis of multi-transcript signatures. This may be particularly advantageous for the implementation of the DRS based test in resource poor settings such as in remote villages.

In summary, our work provides proof of principle that as few as two gene transcripts can discriminate between bacterial and viral infection in children with a high degree of sensitivity and specificity. A rapid test based on our signatures could potentially reduce unnecessary investigation, admission, and antibiotic prescription.

Example 2

Herberg and colleagues (49), in a preliminary, cross-sectional study of 370 febrile children (aged <17 years) in Europe and the United States, reported that children with bacterial infection may be characterized by the difference in blood RNA expression values of 2 genes. In a recent study, Mahajan and colleagues [50] reported a 66-transcript blood RNA signature that distinguished bacterial from viral infection in 279 febrile infants younger than 60 days. To provide further validation of the 2-transcript signature (IFI44L and FAM89A) and to evaluate its performance in an infant population, the 2-transcript signature was further applied to the RNA expression data of Mahajan et al.

Methods

Institutional review board approval was obtained from all 22 sites in the Pediatric Emergency Care Applied Research Network included in the study by Mahajan et al. Parents or guardians provided written informed consent. The RNA expression data of Mahajan et al were downloaded from the Gene Expression Omnibus database accession GSE64456 (51), obtained from a convenience sample of febrile neonates and infants less than 60 days who were recruited from 22 US emergency departments between 2008 and 2010. 89 infants had culture-positive bacterial infections (32 with bacteremia and 57 with urinary tract infection) and 190 had negative bacterial cultures (111 with proven viral infection, 38 not tested for viruses, and 41 with negative test results). After logarithmic transformation, robust spline normalization and quality control using the lumi Bioconductor package in R (R Foundation), version 3.3.1, the expression values for the 2-signature transcripts IFI441, (RefSeq ID NO: NM_006820.1) and FAM89A (RefSeq ID NO: NM_198552.1) were extracted for each patient. These values were combined into a single disease risk score (DRS) as described in Kaforou et al [20], by subtracting the intensity of the IFI44L transcript from the intensity of the FAM89A transcript. We evaluated the predictive accuracy of the DRS first in patients with microbiologically confirmed diagnoses, and then in patients without definite clinical diagnosis. Using the pROC package in R [35], we calculated the area under the characteristic curve (AUC), sensitivity, specificity, and their 95% CIs under the negative binomial distribution.

Results

When the 2-transcript DRS signature was applied to infants with definite bacterial diagnoses (n=89) and proven viral infections (n=111), sensitivity was 88.8% (95% CI, 80.3%-94.5%), specificity was 93.7% (95% CI, 87.4%-97.4%) and AUC was 95.7% (95% CI, 92.6%-98.3%) See FIG. 16. The signature distinguished patients with a definite bacterial diagnosis from those with negative results for viruses (n=41) or no viral tests performed (n=38) with specificities of 48.8% (95% CI, 32.8%-64.9%) and 78.9% (95% CI, 62.7%-90.5%), whereas the sensitivities remained unchanged. The AUC was 80.5% (95% CI, 72.4%-87.5%) for those with negative results and 90.9% (95% CI, 84.8%-95.9%) for those with no viral test Discussion The studies by Herberg et al and Mahajan et al reported sensitivities of 100% (95% CI, 85%-100%) and 87% (95% CI, 73%-95%), respectively, and specificities of 96.4% (95% CI, 89.3%-100%) and 89% (95% CI, 81%-93%), respectively, for the discrimination of bacterial from viral and non-bacterial infections. In this study, the 2-transcript RNA signature, which was originally identified and validated in children with a mean age of 19 months, also had high sensitivity and specificity in the specific population of infants younger than 60 days.

Accordingly, the 2-gene DRS has the potential to translate into a simple bedside diagnostic test for infants.

Example 3

Paired-end and stranded RNA-Seq of RNA extracted from the whole blood of 97 patients (see FIG. 17A) was performed. The data has been analysed and some of the results are shown in FIGS. 17B & C. The dataset included 66 bacterial (culture confirmed) and 31 viral patients. Raw reads were trimmed using Trimmomatic, aligned to the Ensembl reference genome 38 using the STAR aligner and Samtools was used for the manipulation of alignments. Expression quantification was performed using Feature-Counts.

The counts for IFI44L and FAM89A were employed to calculate a Disease Risk Score for each one of the patients in the dataset. The AUC was 96.8% and the CI 95% (93.4-99.1%). As the counts are more comparable to the measures which would be obtained as part of a point-of-care test vs microarray expression values, the validation of the 2-gene signature using RNA-seq highlights even more its point-of-care potential.

TABLE 1

Demographic and clinical features of the study groups

| | Discovery | | | IRIS Validation | | |
|---|---|---|---|---|---|---|
| | Definite Bacterial | Definite Viral | Indeterminate [a] | Definite Bacterial | Definite Viral | Indeterminate [a] |
| Number of patients | 52 | 92 | 96 | 23 | 28 | 79 |
| Age-mo. median (IQR) | 22 (9-46) | 14 (2-39) | 27 (7-71) | 22 (13-52) | 18 (7-48) | 15 (2-44) |
| Male, No. (%) | 22 (42%) | 65 (71%) | 62 (65%) | 10 (43%) | 17 (61%) | 47 (59%) |
| White ethnicity[b]-no. (%) | 35/48 (73%) | 46/87 (53%) | 47/85 (55%) | 12/22 (55%) | 14/27 (51%) | 42/71 (59%) |
| Days from symptons[c]-median (IQR) | 5 (2-8.8) | 4.5 (3.0-6.0) | 5 (4.8-8) | 4 (2.5-8) | 3.5 (2.8-5.3) | 4 (3-7) |
| Intensive car-no. (%) | 36 (69%) | 32 (35%) | 57 (59%) | 13 (57%) | 7 (23%) | 42 (53%) |
| Deaths-no. | 10 | 0 | 2 | 1 | 1 | 8 |
| CRP[d] (mg/dl)-median (IQR) | 17.6 (9.8-27.5) | 1.6 (0.6-2.7) | 10.2 (4.7-17.6) | 21.7 (16.8-28.5) | 0.7 (0.1-2.0) | 6.7 (2.5-12.8) |
| Neutrophil %: median (IQR) | 75 (49-85) | 50 (36-63) | 63 (46-79) | 82 (71-88) | 53 (41-69) | 64 (43-82) |
| Lymphocytes %: median (IQR) | 19 (10-36) | 34 (20-44) | 22 (15-42) | 15 (8-23) | 32 (26-48) | 30 (14-42) |
| Monocyte %: median (IQR) | 5 (3-8) | 10 (4-14) | 6 (2-12) | 3 (0-7) | 7 (5-10) | 5 (2-8) |
| Main clinical syndrome | | | | | | |
| Bone, joint, soft tissue infection | 5 | 0 | 0 | 1 | 0 | 0 |
| Fever without source/sepsis | 21 | 7 | 9 | 5 | 2 | 6 |
| Gastroenteritis | 0 | 0 | 1 | 0 | 1 | 2 |
| Meningitis/encephalitis | 14 | 3 | 3 | 5 | 1 | 1 |
| Respiratory (upper + lower) | 10 | 81 | 83 | 11 | 23 | 68 |
| Other | 2 | 1 | 0 | 1 | 1 | 2 |
| Virus detected [e] (%) | 22/34 (65%) | 92/92 (100%) | 62/87 (71%) | 8/13 (62%) | 28/28 (100%) | 52/77 (68%) |

IQR = interquartile range

[a] The indeterminate group in the discovery set comprised 42 Probable Bacterial, 49 Unknown bacterial or viral, and 5 Probable Viral patients. The intermediate group in the validation cohort comprised 17 Probable Bacterial, 55 Unknown bacterial or viral, and 7 Probable Viral patients respectively.

[b]self-reported ethnicity, where stated,

[c]until sampling,

[d]maximum value of CRP in illness is reported,

[e] Denominator denotes number of patients with viral investigations.

TABLE 2

Demographic and clinical features of the validation groups.

| | Meningococcal Disease[a] | Juvenile Idiopathic Arthritis[b] | Henoch-Schönlein purpura[c] |
|---|---|---|---|
| Number of patients | 24 | 30 | 18 |
| Age-mo. median (IQR) | 23 (17-35) | 163 (124-187) | 56 (43-81) |
| Male, No. (%) | 16 (66%) | 11 (37%) | 9 (50%) |
| White ethnicity-no. (%) | 24/24 (100%) | 27/30 (90%) | 4/18 (22%) |
| Days from symptoms-median (IQR) | 1 (1-1) | n/a | 3.5 (2-6) |
| Intensive care, No. (%) | 24 (100%) | 0 | 0 |
| Deaths, No. (%) | 3 (12.5%) | 0 | 0 |
| CRP (mg/dl)-median (IQR) | 6.8 (3.4-10) | 0.1 (0.0-0.2) | 2.2 (0.8-2.4) |
| Neutrophil %: median (IQR) | 71 (56-83) | 51 (45-57) | 60 (45-68) |
| Lymphocyte %: median (IQR) | 23 (12-53) | 37 (33-45) | 26 (16-34) |
| Monocyte %: median (IQR) | ND | 7 (6-8) | 7 (5-8) |

[a]sample size for data fields: % neutrophil n = 20, % lymphocyte n = 12, CRP n = 22.

[b]sample size for JIA (juvenile idiopathic arthritis) disease categories: enthesitis-related arthritis n = 6, extended oligoarthritis n = 4, persistent oligoarthritis n = 4, polyarthritis rheumatoid factor (RF)-negative n = 12, polyarthritis RF-positive n = 1, psoriatic n = 3. Sample size for data fields: % neutrophil n = 27, % lymphocyte n = 27, % monocyte n = 27.

[c]HSP (Henoch-Schönlein purpura). Sample size for data fields: % neutrophil n = 15, % monocyte n = 15, CRP n = 8

TABLE 3

Viral and Bacterial causative pathogens in patients in the Definite Bacterial and Viral groups in the discovery and IRIS validation cohorts.

| | Definite Viral | | Definite Bacterial | |
|---|---|---|---|---|
| | Discovery (n) | Validation (n) | Discovery (n) | Validation (n) |
| Viral causative pathogen | | | | |
| Adenovirus | 23 | 2 | | |
| Influenza A or B | 23 | 13 | | |
| RSV | 27 | 10 | | |
| Other | 19 | 3 | | |
| Bacterial causative pathogen | | | | |
| *S.pneumonioe* | | | 10 | 15 |
| *S.aureus* | | | 2 | 2 |
| *S.pyogenes* | | | 10 | 5 |
| Group B *streptococcus* | | | 4 | |
| *E.coli* | | | 2 | |
| *N.meningitidis* | | | 17 | 24 |
| *Enterococcus* | | | 1 | |
| *Kingella* | | | 1 | |
| *H.influenzae* | | | 1 | |
| *Pseudomonas* spp | | | 3 | |
| *Stenotrophomonas* | | | 1 | |
| *Klebsiella* | | | | 1 |
| Total number of patients | 92 | 28 | 52 | 47 |

TABLE 4

38-transcript signature for distinguishing bacterial from viral infection.

| Array ID | Elastic net co-efficient | Transcript ID | Official Symbol (HGNC) | Definition | Definite Bacterial vs. Definite Viral log$_2$ FC | Definite Bacterial vs. Definite Viral q-value[a] | Definite Bacterial vs. Healthy Control log$_2$ FC | Definite Bacterial vs. Healthy Control q-value[a] | Definite Viral vs. Healthy Control log$_2$ FC | Definite Viral vs. Healthy Control q-value[a] |
|---|---|---|---|---|---|---|---|---|---|---|
| 3990170 | −0.18 | ILMN_17548 | IFI27 | *Homo sapiens* interferon, alpha-inducible protein 27, transcript variant 2, mRNA. | −4.32 | 4.78E−21 | 1.08 | 7.06E−02 | 5.40 | 3.15E−23 |
| 3870338* | −0.02 | ILMN_9752 | IFI44L | *Homo sapiens* interferon-induced protein 44-like, mRNA. | −3.79 | 1.36E−22 | −1.11 | 1.98E−02 | 2.68 | 4.45E−10 |
| 2000148 | −0.06 | ILMN_1751 | IFIT1 | *Homo sapiens* interferon-induced protein with tetratricopeptide repeats 1, transcript variant 2, mRNA. | −3.49 | 2.90E−20 | −1.15 | 1.48E−02 | 2.35 | 3.89E−08 |
| 3360343 | −0.03 | ILMN_37168 | RSAD2 | *Homo sapiens* radical S-adenosyl methionine domain containing 2, mRNA. | −3.28 | 5.14E−19 | −0.75 | 1.48E−01 | 2.53 | 2.11E−09 |
| 6510170 | −0.04 | ILMN_22925 | IFIT3 | *Homo sapiens* interferon-induced protein with tetratricopeptide repeats 3, mRNA. | −2.66 | 2.47E−16 | −0.90 | 3.77E−02 | 1.77 | 3.25E−06 |
| 520408 | −0.04 | ILMN_1944 | IFIT3 | *Homo sapiens* interferon-induced protein with tetratricopeptide repeats 3, mRNA. | −2.56 | 1.20E−16 | −0.94 | 1.90E−02 | 1.62 | 7.09E−06 |
| 1440615 | −0.05 | ILMN_27303 | OTOF | *Homo sapiens* otoferlin, transcript variant 4, mRNA. | −2.53 | 1.73E−14 | 0.08 | 9.22E−01 | 2.61 | 4.01E−11 |
| 2600747 | −0.07 | ILMN_28123 | IFIT2 | *Homo sapiens* interferon-induced protein with tetratricopeptide repeats 2, mRNA. | −2.40 | 7.83E−17 | −1.15 | 1.22E−03 | 1.25 | 2.33E−04 |
| 5700725 | −0.05 | ILMN_27754 | EPSTI1 | *Homo sapiens* epithelial stromal interaction 1 (breast), transcript variant 2, mRNA. | −2.23 | 1.90E−20 | −0.55 | 8.77E−02 | 1.69 | 5.76E−10 |
| 2030309 | −0.05 | ILMN_15074 | SERPING1 | *Homo sapiens* serpin peptidase inhibitor, clade G (C1 inhibitor), member 1, transcript variant 2, mRNA. | −2.19 | 4.14E−12 | −0.18 | 7.94E−01 | 2.01 | 9.82E−08 |
| 1090390 | −0.04 | ILMN_2717 | OAS1 | *Homo sapiens* 2',5'-oligoadenylate synthetase 1, 40/46 kDa, transcript variant 3, mRNA. | −2.13 | 2.10E−18 | −0.27 | 5.13E−01 | 1.86 | 5.60E−11 |
| 5090215 | −0.17 | ILMN_13978 | IFI6 | *Homo sapiens* interferon, alpha-inducible protein 6, transcript variant 3, mRNA. | −1.55 | 1.23E−18 | −0.41 | 8.55E−02 | 1.14 | 1.53E−08 |
| 620544 | −0.13 | ILMN_5312 | HLA-DR86 | *Homo sapiens* major histocompatibility complex, class II, DR beta 6 (pseudogene), non-coding RNA. | −1.42 | 8.94E−05 | −1.93 | 2.02E−05 | −0.51 | 4.40E−01 |
| 6980192 | −0.02 | ILMN_19775 | HBZ | *Homo sapiens* hemoglobin, zeta, mRNA. | −1.33 | 2.85E−03 | −0.43 | 5.97E−01 | 0.90 | 1.69E−01 |
| 1030100 | −0.22 | ILMN_89157 | HS.386275 | cl02h05.z1 Hembase; Erythroid Precursor Cells (LCB:cl library) *Homo sapiens* cDNA clone cl02h05 5, mRNA sequence | −1.31 | 2.84E−14 | −0.42 | 8.24E−02 | 0.89 | 1.19E−05 |
| 2120079 | −0.11 | ILMN_516843 | EIF2AK2 | *Homo sapiens* eukaryotic translation initiation factor 2-alpha kinase 2, mRNA. | −1.24 | 1.25E−12 | −0.08 | 8.48E−01 | 1.16 | 2.55E−08 |

TABLE 4-continued 38-transcript signature for distinguishing bacterial from viral infection.

| Array ID | Elastic net co-efficient | Transcript ID | Official Symbol (HGNC) | Definition | Definite Bacterial vs. Definite Viral log$_2$ FC | Definite Bacterial vs. Definite Viral q-value[a] | Definite Bacterial vs. Healthy Control log$_2$ FC | Definite Bacterial vs. Healthy Control q-value[a] | Definite Viral vs. Healthy Control log$_2$ FC | Definite Viral vs. Healthy Control q-value[a] |
|---|---|---|---|---|---|---|---|---|---|---|
| 3780452 | −0.01 | ILMN_5646 | IFIT1L | *Homo sapiens* interferon-induced protein with tetratricopeptide repeats 1-like, mRNA. | −1.18 | 5.13E−03 | 0.29 | 7.22E−01 | 1.47 | 3.89E−03 |
| 3360615 | −0.04 | ILMN_18288 | FCER1A | *Homo sapiens* Fc fragment of IgE, high affinity I, receptor for; alpha polypeptide, mRNA. | −1.13 | 6.50E−07 | −2.80 | 2.28E−19 | −1.66 | 2.24E−09 |
| 150315 | −0.18 | ILMN_9078 | C21ORF7 | *Homo sapiens* chromosome 21 open reading frame 7, mRNA. | −1.12 | 3.53E−11 | −1.11 | 1.18E−07 | 0.01 | 9.86E−01 |
| 6940086 | −0.02 | ILMN_21264 | GYPE | *Homo sapiens* glycophorin E, transcript variant 1, mRNA. | −1.11 | 2.37E−03 | 0.33 | 6.31E−01 | 1.44 | 1.06E−03 |
| 3780187 | −0.06 | ILMN_27651 | GYPB | *Homo sapiens* glycophorin B (MNS blood group), mRNA. | −1.09 | 3.03E−03 | 0.46 | 4.56E−01 | 1.55 | 3.76E−04 |
| 4480730 | −0.12 | ILMN_2819 | HBM | *Homo sapiens* hemoglobin, mu, mRNA. | −1.02 | 1.03E−04 | 0.08 | 8.98E−01 | 1.10 | 6.73E−04 |
| 4150600 | −0.19 | ILMN_14704 | EIF1AY | *Homo sapiens* eukaryotic translation initiation factor 1A, Y-linked, mRNA. | −1.00 | 1.61E−02 | 0.24 | 7.73E−01 | 1.24 | 1.43E−02 |
| 1010546 | −0.02 | ILMN _43805 | LOC649143 | PREDICTED: *Homo sapiens* similar to HLA class II histocompatibility antigen, DRB1-9 beta chain precursor (MHC class I antigen DRB1*9) (DR-9) (DR9), transcript variant | −0.95 | 2.37E−04 | −1.33 | 3.83E−05 | −0.37 | 4.16E−01 |
| 1450358 | −0.02 | ILMN_9543 | HBD | *Homo sapiens* hemoglobin, delta, mRNA. | −0.69 | 2.79E−02 | −0.44 | 3.66E−01 | 0.26 | 6.76E−01 |
| 4670327 | −0.11 | ILMN_28646 | FBXO7 | *Homo sapiens* F-box protein 7, transcript variant 2, mRNA. | −0.65 | 1.09E−02 | −0.65 | 5.11E−02 | 0.00 | 9.98E−01 |
| 5550452 | 0.07 | ILMN_24236 | KCNMA1 | *Homo sapiens* potassium large conductance calcium-activated channel, subfamily M, alpha member 1, transcript variant 2, mRNA. | 0.95 | 2.01E−09 | 1.13 | 1.29E−08 | 0.18 | 5.69E−01 |
| 7550066 | 0.00 | ILMN_173016 | MERTK | *Homo sapiens* c-mer proto-oncogene tyrosine kinase, mRNA. | 1.04 | 3.04E−09 | 1.59 | 1.53E−12 | 0.55 | 1.85E−02 |
| 2810767 | 0.45 | ILMN_23396 | EBI3 | *Homo sapiens* Epstein-Barr virus induced 3, mRNA. | 1.10 | 8.79E−13 | 0.81 | 1.71E−05 | −0.28 | 2.41E−01 |
| 4040242* | 0.24 | ILMN_21686 | FAM89A | *Homo sapiens* family with sequence similarity 89, member A, mRNA. | 1.21 | 2.97E−14 | 1.56 | 1.42E−14 | 0.34 | 1.37E−01 |
| 3830735 | 0.03 | ILMN_9777 | UPB1 | *Homo sapiens* ureidopropionase, beta, mRNA. | 1.23 | 5.27E−13 | 1.67 | 2.14E−14 | 0.43 | 6.51E−02 |
| 7400747 | 0.22 | ILMN_21686 | FAM89A | *Homo sapiens* family with sequence similarity 89, member A, mRNA. | 1.26 | 7.65E−14 | 1.65 | 1.13E−14 | 0.40 | 9.38E−02 |
| 2510356 | 0.02 | ILMN_12984 | EMR1 | *Homo sapiens* egf-like module containing, mucin-like, hormone receptor-like 1, mRNA. | 1.33 | 1.50E−11 | 1.32 | 6.00E−08 | −0.01 | 9.91E−01 |
| 3850647 | 0.14 | ILMN_137356 | PTPN20 | PREDICTED: *Homo sapiens* protein | 1.35 | 1.88E−11 | 1.98 | 2.35E−14 | 0.63 | 1.77E−02 |

TABLE 4-continued 38-transcript signature for distinguishing bacterial from viral infection.

| Array ID | Elastic net co-efficient | Transcript ID | Official Symbol (HGNC) | Definition | Definite Bacterial vs. Definite Viral log$_2$ FC | Definite Bacterial vs. Definite Viral q-value[a] | Definite Bacterial vs. Healthy Control log$_2$ FC | Definite Bacterial vs. Healthy Control q-value[a] | Definite Viral vs. Healthy Control log$_2$ FC | Definite Viral vs. Healthy Control q-value[a] |
|---|---|---|---|---|---|---|---|---|---|---|
| | | | | tyrosine phosphatase, non-receptor type 20, mRNA. | | | | | | |
| 3830762 | 0.04 | ILMN_30233 | TMEM119 | *Homo sapiens* transmembrane protein 119, mRNA. | 1.35 | 1.76E−08 | 2.10 | 8.55E−12 | 0.74 | 2.07E−02 |
| 2140707 | 0.08 | ILMN_28045 | SLPI | *Homo sapiens* secretory leukocyte peptidase inhibitor, mRNA. | 1.84 | 2.44E−12 | 2.78 | 4.34E−16 | 0.94 | 4.79E−03 |
| 1510424 | 0.06 | ILMN_23476 | S100P | *Homo sapiens* S100 calcium binding protein P, mRNA. | 2.35 | 1.39E−16 | 2.91 | 6.99E−16 | 0.56 | 1.85E−01 |
| 1050168 | 0.03 | ILMN_13685 | PI3 | *Homo sapiens* peptidase inhibitor 3, skin-derived, mRNA. | 2.58 | 4.52E−10 | 0.77 | 2.39E−01 | −1.82 | 3.76E−04 |

*Transcripts that comprise the 2-transcript DRS signature.
HGNC = HUGO Gene Nomenclature Committee, FC = Fold Change.
[a]This is the P-value corrected for false discovery, using Benjamin-Hochberg [38], for the difference in expression between the 2 comparator groups for each transcript using a moderated t-test in R using limma [39].

TABLE 5

Diagnostic performance of the bacterial vs. viral 38-transcript elastic net and DRS 2-transcript signatures in the training, test and IRIS validation datasets.

| | Training Set | Test Set | IRIS Validation Set |
|---|---|---|---|
| Definite Bacterial patients (n) | 42 | 10 | 23 |
| Definite Viral patients (n) | 73 | 19 | 28 |
| | 38-transcript signature derived from elastic net model | | |
| Area under ROC curve (95% CI) | 98.9 (97.4-99.9) | 99.5 (96.8-100-0) | 97.8 (93.8-100.0) |
| Sensitivity % (95% CI) | 92.9 (83.3-100.0) | 100.0 (100.0-100.0) | 100.0 (100.0-100.0) |
| Specificity % (95% CI) | 97.3 (93.2-100.0) | 94.7 (84.2-100.0) | 85.71 (71.4-96.4) |
| | 2-transcript signature derived from DRS model | | |
| Area under ROC curve (95% CI) | 95.5 (91.8-98.4) | 96.3 (87.4-100.0) | 97.4 (91.2-100.0) |
| Sensitivity % (95% CI) | 85.7 (73.8-95.2) | 90.0 (70.0-100.0) | 100.0 (100.0-100.0) |
| Specificity % (95% CI) | 84.9 (76.7-91.8) | 100 (100.0-100.0) | 96.4 (89.3-100.0) |

TABLE 6

GO biological process terms analysis.
Overrepresentation test for the genes in the 38-transcript signature for the GO: biological process *Homo sapiens* terms using the PANTHER Pathway resource (Bonferroni corrected). [48, 49]

| GO Term (Biological Process) | Number of genes mapped: Background Reference[a] | Number of genes mapped: Signature[b] | Expected value[c] | Over (+) or under (−) representation[d] | Fold enrichment[e] | P-value[f] | Genes associated with the GO Term |
|---|---|---|---|---|---|---|---|
| Cellular response to interferon-alpha (GO:0035457) | 9 | 3 | 0.01 | + | >5 | 3.09E−03 | IFIT2; OAS1; IFIT3 |
| Response to interferon-alpha (GO:0035455) | 18 | 4 | 0.03 | + | >5 | 1.53E−04 | IFIT2; OAS1; IFIT3; EIF2AK2 |
| Oxygen transport (GO:0015671) | 15 | 3 | 0.02 | + | >5 | 1.42E−02 | HBD; HBM; HBZ |
| Gas transport (GO:0015669) | 19 | 3 | 0.03 | + | >5 | 2.88E−02 | HBD; HBM; HBZ |
| Negative regulation of viral genome replication (GO:0045071) | 46 | 5 | 0.07 | + | >5 | 7.86E−05 | SLPI; IFIT1; OAS1; RSAD2; EIF2AK2 |

TABLE 6-continued

GO biological process terms analysis.
Overrepresentation test for the genes in the 38-transcript signature for the GO: biological process *Homo sapiens* terms using the PANTHER Pathway resource (Bonferroni corrected). [48, 49]

| GO Term (Biological Process) | Number of genes mapped Background Reference[a] | Signature[b] | Expected value[c] | Over (+) or under (−) representation[d] | Fold enrichment[e] | P-value[f] | Genes associated with the GO Term |
|---|---|---|---|---|---|---|---|
| Type I interferon signalling pathway (GO:0060337) | 68 | 7 | 0.1 | + | >5 | 9.68E−08 | IFIT2; IFIT1; OAS1; IFI27; RSAD2; IFI6; IFIT3 |
| Cellular response to type I interferon (GO:0071357) | 68 | 7 | 0.1 | + | >5 | 9.68E−08 | IFIT2; IFIT1; OAS1; IFI27; RSAD2; IFI6; IFIT3 |
| Response to type I interferon (GO:0034340) | 69 | 7 | 0.11 | + | >5 | 1.07E−07 | IFIT2; IFIT1; OAS1; IFI27; RSAD2; IFI6; IFIT3 |
| Regulation of viral genome replication (GO:0045069) | 70 | 5 | 0.11 | + | >5 | 6.25E−04 | SLPI; IFIT1; OAS1; RSAD2; EIF2AK2 |
| Negative regulation of viral life cycle (GO:1903901) | 84 | 5 | 0.13 | + | >5 | 1.53E−03 | SLPI; IFIT1; OAS1; RSAD2; EIF2AK2 |
| Negative regulation of viral process (GO:0048525) | 87 | 5 | 0.13 | + | >5 | 1.82E−03 | SLPI; IFIT1; OAS1; RSAD2; EIF2AK2 |
| Defence response to virus (GO:0051607) | 159 | 7 | 0.24 | + | >5 | 3.36E−05 | IFIT2; IFIT1; OAS1; IFI44L; RSAD2; EIF2AK2; IFIT3 |
| Negative regulation of multi-organism process (GO:0043901) | 150 | 5 | 0.23 | + | >5 | 2.59E−02 | SLPI; IFIT1; OAS1; RSAD2; EIF2AK2 |
| Response to virus (GO:0009615) | 240 | 7 | 0.37 | + | >5 | 5.51E−04 | IFIT2; IFIT1; OAS1; IFI44L; RSAD2; EIF2AK2; IFIT3 |
| Defence response to other organism (GO:0098542) | 371 | 8 | 0.57 | + | >5 | 5.69E−04 | SLPI; IFIT2; IFIT1; OAS1; IFI44L; RSAD2; EIF2AK2; IFIT3 |
| Immune effector process (GO:0002252) | 447 | 8 | 0.69 | + | >5 | 2.33E−03 | IFIT2; IFIT1; OAS1; IFI44L; RSAD2; EIF2AK2; SERPING1; IFIT3 |
| Cytokine-mediated signalling pathway (GO:0019221) | 487 | 8 | 0.75 | + | >5 | 4.44E−03 | IFIT2; IFIT1; OAS1; IFI27; RSAD2; IFI6; IFIT3; EBI3 |
| Cellular response to cytokine stimulus (GO:0071345) | 632 | 8 | 0.97 | + | >5 | 3.07E−02 | IFIT2; IFIT1; OAS1; IFI27; RSAD2; IFI6; IFIT3; EBI3 |
| Response to cytokine (GO:0034097) | 730 | 9 | 1.12 | + | >5 | 8.40E−03 | IFIT2; IFIT1; OAS1; IFI27; RSAD2; IFI6; EIF2AK2; IFIT3; EBI3 |
| Innate immune response (GO:0045087) | 1012 | 10 | 1.56 | + | >5 | 1.38E−02 | IFIT2; IFIT1; OAS1; IFI27; RSAD2; IFI6; EIF2AK2; SERPING1; IFIT3; FCER1A |
| Immune response (GO:0006955) | 1430 | 14 | 2.2 | + | >5 | 5.82E−05 | SLPI; IFIT2; IFIT1; EMR1; OAS1; IFI44L; IFI27; RSAD2; IFI6; EIF2AK2; IFIT3; SERPING1; EBI3; FCER1A |
| Defence response (GO:0006952) | 1507 | 12 | 2.32 | + | >5 | 9.19E−03 | SLPI; IFIT2; IFIT1; OAS1; IFI27; IFI44L; RSAD2; IFI6; EIF2AK2; SERPING1; IFIT3; FCER1A |

TABLE 6-continued

GO biological process terms analysis.
Overrepresentation test for the genes in the 38-transcript signature for the GO: biological process *Homo sapiens* terms using the PANTHER Pathway resource (Bonferroni corrected). [48, 49]

| GO Term (Biological Process) | Number of genes mapped: Background Reference[a] | Signature[b] | Expected value[c] | Over (+) or under (−) representation[d] | Fold enrichment[e] | P-value[f] | Genes associated with the GO Term |
|---|---|---|---|---|---|---|---|
| Immune system process (GO:0002376) | 2163 | 16 | 3.33 | + | 4.81 | 1.67E−04 | SLPI; IFIT2; HBZ; IFIT1; EMR1; MERTK; OAS1; IFI44L; IFI27; RSAD2; IFI6; EIF2AK2; IFIT3; SERPING1; EBI3; FCER1A; |
| Unclassified (Unclassified) | 4272 | 6 | 6.57 | − | 0.91 | 0.00E+00 | GYPB; EPSTI1; FAM89A; MAP3K7CL; GYPE; IFIT1B |

[a]number of genes mapped to GO terms when using the background reference dataset of *Homo Sapiens*. The total number of genes in this dataset is 20814.
[b]number of genes mapped to GO terms when using genes in the 38-transcript signature. The total number of genes in the signature is 36.
[c]number of genes expected to be in signature for this category, based on the background reference dataset.
[d]+ indicates an over-representation of the GO term in the signature, − indicates an under-representation of the GO term in the signature.
[e]GO term over-represented if >1, under-represented if <1
[f]Probability that the number of genes from the signature in the GO term occurred randomly.

TABLE 7

Additional validation and external microarray datasets. Overview of the gene expression microarray datasets used for assessment of the 2-transcript DRS signature. Study and experimental details, as well as the metrics for classification accuracy (i.e. Sensitivity, Specificity and AUC with 95% CIs) are shown.

| | | | | | | Results after application of the 2-transcript DRS signature | | | |
|---|---|---|---|---|---|---|---|---|---|
| 1$^{st}$ group | 2$^{nd}$ group | GEO accession | Reference | Age (years) | Platform | Sensitivity % (95% Cl) | Specificity % (95% Cl) | AUC % (95% Cl) | Related eFigure |
| Meningococcal validation: 24 children | Viral group of the IRIS validation set (after data merging) | GSE80496 | Unpublished | <3 | Illumina Ref8-V3 | 91.7 (79.2-100) | 96.0 (88.0-100) | 92.6 (81.3-100) | FIG. 11 |
| Inflammatory validation: 30 JIA & 18 HSP | 20% Discovery Bacterial set (after data merging) | GSE80412 | Unpublished | <18 | Illumina HT12-V4 | 90.0 (70.0-100) | 95.8 (89.6-100) | 90.8 (73-100) | FIG. 12 |
| 48 bacterial: (*S.aureus*, *streptococcus*) | 31 Pediatric SLE | GSE22098 | Berry M (2010) [13] | <17 | Illumina HT12-V3 | 93.5 (83.9-100) | 96.1 (90.2-100) | 96.6 (91.9-100) | FIG. 12 |
| 12 bacterial (*S.pneumoniae*, *S.aureus*) | 10 viral (Influenza A and B) | GSE6269-GPL570 | Ramilo O (2007) [11] | <16 | Affymetrix | 100 (100-100) | 90 (70-100) | 96 (85-100) | FIG. 12 |
| 8 bacterial-mixed gram positive & gram negative | 22-viral-mixed adenovirus, HHV6, enterovirus | GSE40396 | Hu X (2013) [12] | <3 | Illumina HT12-V4 | 100 (100-100) | 77.3 (59.1-95.5) | 89.2 (75.6-98.3) | FIG. 12 |
| 15 bacterial LTRI | 64 Viral LTRI | GSE60244 | Suarez N (2015) [14] | Adults | Illumina HT12-V4 | 90.1 (77.3-100) | 80.3 (70.4-88.7) | 89.8 (83.4-95.5) | FIG. 12 |

TABLE 8

Performance of clinical features in relation to DRS score in patients with indeterminate infection status (combined Probable Bacterial, Unknown, and Probable Viral groups).

| | Patients split by DRS score | | |
|---|---|---|---|
| | DRS predicts viral infection | DRS predicts bacterial infection | P value |
| Number of patients | 95 | 80 | |
| Shock (needed inotropes) | 22 of 95 | 35 of 80 | 0.006 |
| % | (23%) | (44%) | |
| Respiratory failure requiring ventilation | 46 of 95 | 51 of 80 | 0.048 |
| % | (48%) | (64%) | |
| Requiring intensive care admission | 51 of 95 | 54 of 80 | 0.066 |
| % | (54%) | (68%) | |
| White blood count ($\times10^3/mm^3$): median | 11.1 | 14.1 | 0.079 |
| (IQR) [a] | (7.3-16.0) | (8.3-19.4) | |
| Neutrophil count ($\times10^3/mm^3$): median | 6.8 | 8.7 | 0.114 |
| (IQR) [a] | (3.5-11.4) | (5.0-13.8) | |

TABLE 8-continued

Performance of clinical features in relation to DRS score in patients with indeterminate infection status (combined Probable Bacterial, Unknown, and Probable Viral groups).

| | Patients split by DRS score | | |
|---|---|---|---|
| | DRS predicts viral infection | DRS predicts bacterial infection | P value |
| CRP during illness (mg/l) [a] | 71 | 101 | 0.015 |
| (IQR) | (27-120) | (48-192) | |
| Respiratory infection: CXR consolidation | 43 of 69 | 47 of 66 | 0.3612 |
| % | (62%) | (71%) | |
| Respiratory infection: no CXR focal change | 24 of 69 | 18 of 66 | 0.3599 |
| % | (35%) | (27%) | |

[a] with available data. Maximum values in illness used.

IQR-interquartile range; CRP-C reactive protein; CXR-chest X-ray

Clinical features of children in the three indeterminate groups (Probable Bacterial, Unknown and Probable Viral) were classified. For each clinical feature, the proportion of children with a DRS predictive of viral or of bacterial infection was compared using Fisher exact test and two tailed t-tests. DRS predictive of bacterial infection was significantly associated with shock, ventilation and higher CRP.

TABLE 9

Sequences of probes in 38 and 2 transcript gene signatures

| Array ID | Transcript ID | Entrez Symbol | Sequence (5' to 3') |
|---|---|---|---|
| 3990170 | ILMN_17548 | IFI27 | CCAAGTTCATCCTGGGCTCCATTGGGTCTGCCATTGCGGCTGT CATTGCG (SEQ ID NO: 3) |
| 3870338* | ILMN_9752 | IFI44L | GTGGGCTAAGATAGGTCCTACTGCAAACCACCCCTCCATATTT CCGTACC (SEQ ID NO: 4) |
| 2000148 | ILMN_1751 | IFIT1 | TGAATGAAGCCCTGGAGTACTATGAGCGGGCCCTGAGACTGG CTGCTGAC (SEQ ID NO: 5) |
| 3360343 | ILMN_37168 | RSAD2 | CGCTGGAACCTTGGGCAAGGAAGAATGTGAGCAAGAGTAGA GAGAGTGCC (SEQ ID NO: 6) |
| 6510170 | ILMN_22925 | IFIT3 | AAAACAAAATCAACCGGGACCCCAGCTTTTCAGAACTGCAGG GAAACAGC (SEQ ID NO: 7) |
| 520408 | ILMN_1944 | IFIT3 | ACAAATCAGCCTGGTCACCAGCTTTTCGGAACAGCAGAGACA CAGAGGGC (SEQ ID NO: 8) |
| 1440615 | ILMN_27303 | OTOF | GCCCGTCAAGTGCTGCCCCTGCCTGTGTCTGGGTTTCTGTTGG CTGTTTT (SEQ ID NO: 9) |
| 2600747 | ILMN_28123 | IFIT2 | GCTGACCCAGCATCAGCCACACTCTGGGTTGGAAAATGTTTGC CTGTTGG (SEQ ID NO: 10) |
| 5700725 | ILMN_27754 | EPSTI1 | GGGAGTCACTTGATGCTTTCAGGTTAATCAGAGCTATGGGTG CTACAGGC (SEQ ID NO: 11) |
| 2030309 | ILMN_15074 | SERPING1 | TGGGACCAGCAGCACAAGTTCCCTGTCTTCATGGGGCGAGTA TATGACCC (SEQ ID NO: 12) |
| 1090390 | ILMN_2717 | OAS1 | AGAGAGACTTCCTGAAGCAGCGCCCCACCAAGCTCAAGAGCC TCATCCGC (SEQ ID NO: 13) |
| 5090215 | ILMN_13978 | IFI6 | TGCGCCGACGATGCCCAGAATCCAGAACTTTGTCTATCACTCT CCCCAAC (SEQ ID NO: 14) |
| 620544 | ILMN_5312 | HLA-DR86 | AACCCCACAGCCTTGATGGCAGCGCCTCGTCTTCAACTTTTGT GCTTCCT (SEQ ID NO: 15) |
| 6980192 | ILMN_19775 | HBZ | GTCCTGGAGGTTCCCCAGCCCCACTTACCGCGTAATGCGCCAA TAAACCA (SEQ ID NO: 16) |
| 1030100 | ILMN_89157 | HS.386275 | TGTTCTTCCCCATGTCCTGGATGCCACTGGAAGTGCACACTGC TTGTATG (SEQ ID NO: 17) |

TABLE 9-continued

Sequences of probes in 38 and 2 transcript gene signatures

| Array ID | Transcript ID | Entrez Symbol | Sequence (5' to 3') |
|---|---|---|---|
| 2120079 | ILMN_168435 | EIF2AK2 | CGTTCTCTGCCTCACATAGCTTACAAGCCAGCTGGAGAAATAT GGTACTC (SEQ ID NO: 18) |
| 3780452 | ILMN_5646 | IFIT1L | AGGCCTTGTGGCACCAGACATAAGACCCCCTGAAAGTATCATC CCTCCTG (SEQ ID NO: 19) |
| 3360615 | ILMN_18288 | FCER1A | GAACCAGGAAAGGCTTCAGACTTCTGAACCCACATCCTAAGCC AAACCCC (SEQ ID NO: 20) |
| 150315 | ILMN_9078 | C21ORF7 | GTGACCTCACAGTAAACATCTCTGCCTTTGCCTGTGTGTGTTCT GGGGGA (SEQ ID NO: 21) |
| 6940086 | ILMN_21264 | GYPE | AGGATGTGGCCTGCATGCTGCCTGATCTTGCCTAGAACCAGCT GCACCTG (SEQ ID NO: 22) |
| 3780187 | ILMN_27651 | GYP8 | TGGAGAAACGGGACAACTTGTCCATCGTTTCACTGTACCAGCT CCTGTAG (SEQ ID NO: 23) |
| 4480730 | ILMN_2819 | HBM | TCGTGCTGCGCGTGGACCCAGCCAACTTTCCGCTGCTAATCCA GTGTTTC (SEQ ID NO: 24) |
| 4150600 | ILMN_14704 | EIF1AY | CTGAGGATGGTTCTACAGTTGGGATTTTGGCCATCATCAACCA AGAAGAG (SEQ ID NO: 25) |
| 1010546 | ILMN_43805 | LOC649143 | GGTTGGTGAGAGCTTCACAGTGCAGAGGCGAGTCCATCCTGA GGTGACTG (SEQ ID NO: 26) |
| 1450358 | ILMN_9543 | HBD | GGCTAATGCCCTGGCTCACAAGTACCATTGAGATCCTGGACTG TTTCCTG (SEQ ID NO: 27) |
| 4670327 | ILMN_28646 | FBXO7 | AGGCGACGGGAAGCGCGGGTGGTCGGCTGGGGTCCGGCTCC TGGAGAACA (SEQ ID NO: 28) |
| 5550452 | ILMN_24236 | KCNMA1 | GGTTCTGCATGACCTAGCCACTGCTGGGGGTTTTCTTCTATAA CGTTGTC (SEQ ID NO: 29) |
| 7550066 | ILMN_173016 | MERTK | CTTCCTTACCAAGTGAACTCCATGGCCCCAAAGCACCAGATGA ATGTTGT (SEQ ID NO: 30) |
| 2810767 | ILMN_23396 | EBI3 | GAGCTGCCGGGCAACCTCAGATGACCGACTTTTCCCTTTGAGC CTCAGTT (SEQ ID NO: 31) |
| 4040242* | ILMN_21686 | FAM89A | CAGGGGATGAGCGCTACCAGTTTCATTTGTAGGCAGGGAGTT CTCCGCGG (SEQ ID NO: 32) |
| 3830735 | ILMN_9777 | UP81 | GAAATTCTGCCTGAGGACAGCAGCCCAGTGCTTGGCGAGAGT TCCTGACA (SEQ ID NO: 33) |
| 7400747 | ILMN_21686 | FAM89A | GATCTCGGTGAAAGGCCTTAGTGGGTGTTTTGTGTGAGGTGG CTTGTAGC (SEQ ID NO: 34) |
| 2510356 | ILMN_12984 | EMR1 | TCTCAGCTTAACATGGAAATGAGGATCCCACCAGCCCCAGAAC CCTCTGG (SEQ ID NO: 35) |
| 3850647 | ILMN_137356 | PTPN20 | GCATCCTGAGGTGGCCAAGGGCAGTGGTGCTCCAGATGTTTC TGTTTCTG (SEQ ID NO: 36) |
| 3830762 | ILMN_30233 | TMEM119 | GTCTGGCAGCCTGTGTCCACAATATTCGTCAGTCCTCGACAGG GAGCCTG (SEQ ID NO: 37) |
| 2140707 | ILMN_28045 | SLPI | GGATCCTGTTGACACCCCAAACCCAACAAGGAGGAAGCCTGG GAAGTGCC (SEQ ID NO: 38) |
| 1510424 | ILMN_23476 | S100P | AATGATGCCCTGGAGATGTCACAGATTCCTGGCAGAGCCATG GTCCCAGG (SEQ ID NO: 39) |
| 1050168 | ILMN_13685 | PI3 | CTGACTGCCCAGGAATCAAGAAGTGCTGTGAAGGCTCTTGCG GGATGGCC (SEQ ID NO: 40) |

*Probe used in 2 transcript/gene signature

TABLE 10

Performance of different 2 transcript signatures

| Combi ID | Array ID | 1st gene | expression level * | Array ID | 2nd gene | expression level * |
|---|---|---|---|---|---|---|
| 489 | 1090390 | OAS1 | DOWN | 2510356 | EMR1 | UP |
| 80 | 3870338 | IFI44L | DOWN | 7400747 | FAM89A | UP |
| 267 | 2510356 | EMR1 | UP | 3870338 | IFI44L | DOWN |
| 467 | 1090390 | OAS1 | DOWN | 7400747 | FAM89A | UP |
| 224 | 2810767 | EBI3 | UP | 3870338 | IFI44L | DOWN |
| 399 | 1510424 | S100P | UP | 3360343 | RSAD2 | DOWN |
| 290 | 2140707 | SLPI | UP | 3870338 | IFI44L | DOWN |
| 384 | 1510424 | S100P | UP | 5700725 | EPSTI1 | DOWN |
| 392 | 1510424 | S100P | UP | 3870338 | IFI44L | DOWN |
| 477 | 1090390 | OAS1 | DOWN | 4040242 | FAM89A | UP |
| 90 | 3870338 | IFI44L | DOWN | 4040242 | FAM89A | UP |
| 274 | 2510356 | EMR1 | UP | 3360343 | RSAD2 | DOWN |
| 632 | 520408 | IFIT3 | DOWN | 7400747 | FAM89A | UP |
| 119 | 3830762 | TMEM119 | UP | 3870338 | IFI44L | DOWN |
| 654 | 520408 | IFIT3 | DOWN | 2510356 | EMR1 | UP |
| 23 | 5090215 | IFI6 | DOWN | 7400747 | FAM89A | UP |
| 12 | 5700725 | EPSTI1 | DOWN | 7400747 | FAM89A | UP |
| 642 | 520408 | IFIT3 | DOWN | 4040242 | FAM89A | UP |
| 134 | 3830735 | UPB1 | UP | 3870338 | IFI44L | DOWN |
| 406 | 1510424 | S100P | UP | 2000148 | IFIT1 | DOWN |
| 192 | 3360343 | RSAD2 | DOWN | 7400747 | FAM89A | UP |
| 259 | 2510356 | EMR1 | UP | 5700725 | EPSTI1 | DOWN |
| 404 | 1510424 | S100P | UP | 2120079 | EIF2AK2 | DOWN |
| 202 | 3360343 | RSAD2 | DOWN | 4040242 | FAM89A | UP |
| 8 | 6510170 | IFIT3 | DOWN | 7400747 | FAM89A | UP |
| 490 | 1090390 | OAS1 | DOWN | 2140707 | SLPI | UP |
| 353 | 2000148 | IFIT1 | DOWN | 7400747 | FAM89A | UP |
| 655 | 520408 | IFIT3 | DOWN | 2140707 | SLPI | UP |
| 258 | 2510356 | EMR1 | UP | 6510170 | IFIT3 | DOWN |
| 494 | 1090390 | OAS1 | DOWN | 1510424 | S100P | UP |
| 376 | 2000148 | IFIT1 | DOWN | 2140707 | SLPI | UP |
| 375 | 2000148 | IFIT1 | DOWN | 2510356 | EMR1 | UP |
| 61 | 4040242 | FAM89A | UP | 5700725 | EPSTI1 | DOWN |
| 297 | 2140707 | SLPI | UP | 3360343 | RSAD2 | DOWN |
| 401 | 1510424 | S100P | UP | 2600747 | IFIT2 | DOWN |
| 367 | 2000148 | IFIT1 | DOWN | 3830762 | TMEM119 | UP |
| 363 | 2000148 | IFIT1 | DOWN | 4040242 | FAM89A | UP |
| 282 | 2140707 | SLPI | UP | 5700725 | EPSTI1 | DOWN |
| 60 | 4040242 | FAM89A | UP | 6510170 | IFIT3 | DOWN |
| 517 | 1050168 | PI3 | UP | 3360343 | RSAD2 | DOWN |
| 487 | 1090390 | OAS1 | DOWN | 2810767 | EBI3 | UP |
| 302 | 2120079 | EIF2AK2 | DOWN | 7400747 | FAM89A | UP |
| 216 | 2810767 | EBI3 | UP | 5700725 | EPSTI1 | DOWN |
| 659 | 520408 | IFIT3 | DOWN | 1510424 | S100P | UP |
| 510 | 1050168 | PI3 | UP | 3870338 | IFI44L | DOWN |
| 386 | 1510424 | S100P | UP | 5090215 | IFI6 | DOWN |
| 464 | 1440615 | OTOF | DOWN | 1510424 | S100P | UP |
| 481 | 1090390 | OAS1 | DOWN | 3830762 | TMEM119 | UP |
| 206 | 3360343 | RSAD2 | DOWN | 3830762 | TMEM119 | UP |
| 231 | 2810767 | EBI3 | UP | 3360343 | RSAD2 | DOWN |
| 457 | 1440615 | OTOF | DOWN | 2810767 | EBI3 | UP |
| 383 | 1510424 | S100P | UP | 6510170 | IFIT3 | DOWN |
| 437 | 1440615 | OTOF | DOWN | 7400747 | FAM89A | UP |
| 243 | 2600747 | IFIT2 | DOWN | 4040242 | FAM89A | UP |
| 451 | 1440615 | OTOF | DOWN | 3830762 | TMEM119 | UP |
| 233 | 2600747 | IFIT2 | DOWN | 7400747 | FAM89A | UP |
| 68 | 3990170 | IFI27 | DOWN | 7400747 | FAM89A | UP |
| 482 | 1090390 | OAS1 | DOWN | 3830735 | UPB1 | UP |
| 447 | 1440615 | OTOF | DOWN | 4040242 | FAM89A | UP |
| 368 | 2000148 | IFIT1 | DOWN | 3830735 | UPB1 | UP |
| 530 | 1030100 | HS.386275 | DOWN | 7400747 | FAM89A | UP |
| 312 | 2120079 | EIF2AK2 | DOWN | 4040242 | FAM89A | UP |
| 207 | 3360343 | RSAD2 | DOWN | 3830735 | UPB1 | UP |
| 524 | 1050168 | PI3 | UP | 2000148 | IFIT1 | DOWN |
| 652 | 520408 | IFIT3 | DOWN | 2810767 | EBI3 | UP |
| 299 | 2140707 | SLPI | UP | 2600747 | IFIT2 | DOWN |
| 460 | 1440615 | OTOF | DOWN | 2140707 | SLPI | UP |
| 281 | 2140707 | SLPI | UP | 6510170 | IFIT3 | DOWN |
| 276 | 2510356 | EMR1 | UP | 2600747 | IFIT2 | DOWN |
| 550 | 1030100 | HS.386275 | DOWN | 2810767 | EBI3 | UP |
| 545 | 1030100 | HS.386275 | DOWN | 3830735 | UPB1 | UP |
| 647 | 520408 | IFIT3 | DOWN | 3830735 | UPB1 | UP |
| 553 | 1030100 | HS.386275 | DOWN | 2140707 | SLPI | UP |
| 63 | 4040242 | FAM89A | UP | 5090215 | IFI6 | DOWN |
| 540 | 1030100 | HS.386275 | DOWN | 4040242 | FAM89A | UP |

TABLE 10-continued

| | | | | | | |
|---|---|---|---|---|---|---|
| 289 | 2140707 | SLPI | UP | 3990170 | IFI27 | DOWN |
| 105 | 3850647 | PTPN20 | UP | 3870338 | IFI44L | DOWN |
| 452 | 1440615 | OTOF | DOWN | 3830735 | UPB1 | UP |
| 557 | 1030100 | HS.386275 | DOWN | 1510424 | S100P | UP |
| 391 | 1510424 | S100P | UP | 3990170 | IFI27 | DOWN |
| 317 | 2120079 | EIF2AK2 | DOWN | 3830735 | UPB1 | UP |
| 325 | 2120079 | EIF2AK2 | DOWN | 2140707 | SLPI | UP |
| 223 | 2810767 | EBI3 | UP | 3990170 | IFI27 | DOWN |
| 85 | 3870338 | IFI44L | DOWN | 5550452 | KCNMA1 | UP |
| 111 | 3830762 | TMEM119 | UP | 5700725 | EPSTI1 | DOWN |
| 247 | 2600747 | IFIT2 | DOWN | 3830762 | TMEM119 | UP |
| 284 | 2140707 | SLPI | UP | 5090215 | IFI6 | DOWN |
| 646 | 520408 | IFIT3 | DOWN | 3830762 | TMEM119 | UP |
| 126 | 3830735 | UPB1 | UP | 5700725 | EPSTI1 | DOWN |
| 78 | 3990170 | IFI27 | DOWN | 4040242 | FAM89A | UP |
| 373 | 2000148 | IFIT1 | DOWN | 2810767 | EBI3 | UP |
| 205 | 3360343 | RSAD2 | DOWN | 3850647 | PTPN20 | UP |
| 215 | 2810767 | EBI3 | UP | 6510170 | IFIT3 | DOWN |
| 79 | 3870338 | IFI44L | DOWN | 7550066 | MERTK | UP |
| 218 | 2810767 | EBI3 | UP | 5090215 | IFI6 | DOWN |
| 133 | 3830735 | UPB1 | UP | 3990170 | IFI27 | DOWN |
| 509 | 1050168 | PI3 | UP | 3990170 | IFI27 | DOWN |
| 248 | 2600747 | IFIT2 | DOWN | 3830735 | UPB1 | UP |
| 544 | 1030100 | HS.386275 | DOWN | 3830762 | TMEM119 | UP |
| 118 | 3830762 | TMEM119 | UP | 3990170 | IFI27 | DOWN |
| 253 | 2600747 | IFIT2 | DOWN | 2810767 | EBI3 | UP |
| 110 | 3830762 | TMEM119 | UP | 6510170 | IFIT3 | DOWN |
| 232 | 2600747 | IFIT2 | DOWN | 7550066 | MERTK | UP |
| 322 | 2120079 | EIF2AK2 | DOWN | 2810767 | EBI3 | UP |
| 405 | 1510424 | S100P | UP | 2030309 | SERPING1 | DOWN |
| 695 | 150315 | C21ORF7 | DOWN | 1510424 | S100P | UP |
| 542 | 1030100 | HS.386275 | DOWN | 3870338 | IFI44L | DOWN |
| 191 | 3360343 | RSAD2 | DOWN | 7550066 | MERTK | UP |
| 631 | 520408 | IFIT3 | DOWN | 7550066 | MERTK | UP |
| 663 | 520408 | IFIT3 | DOWN | 1050168 | PI3 | UP |
| 125 | 3830735 | UPB1 | UP | 6510170 | IFIT3 | DOWN |
| 528 | 1050168 | PI3 | UP | 1090390 | OAS1 | DOWN |
| 466 | 1090390 | OAS1 | DOWN | 7550066 | MERTK | UP |
| 104 | 3850647 | PTPN20 | UP | 3990170 | IFI27 | DOWN |
| 327 | 2030309 | SERPING1 | DOWN | 7400747 | FAM89A | UP |
| 261 | 2510356 | EMR1 | UP | 5090215 | IFI6 | DOWN |
| 352 | 2000148 | IFIT1 | DOWN | 7550066 | MERTK | UP |
| 501 | 1050168 | PI3 | UP | 6510170 | IFIT3 | DOWN |
| 645 | 520408 | IFIT3 | DOWN | 3850647 | PTPN20 | UP |
| 21 | 5550452 | KCNMA1 | UP | 5700725 | EPSTI1 | DOWN |
| 637 | 520408 | IFIT3 | DOWN | 5550452 | KCNMA1 | UP |
| 519 | 1050168 | PI3 | UP | 2600747 | IFIT2 | DOWN |
| 337 | 2030309 | SERPING1 | DOWN | 4040242 | FAM89A | UP |
| 197 | 3360343 | RSAD2 | DOWN | 5550452 | KCNMA1 | UP |
| 314 | 2120079 | EIF2AK2 | DOWN | 3870338 | IFI44L | DOWN |
| 358 | 2000148 | IFIT1 | DOWN | 5550452 | KCNMA1 | UP |
| 324 | 2120079 | EIF2AK2 | DOWN | 2510356 | EMR1 | UP |
| 238 | 2600747 | IFIT2 | DOWN | 5550452 | KCNMA1 | UP |
| 316 | 2120079 | EIF2AK2 | DOWN | 3830762 | TMEM119 | UP |
| 84 | 3870338 | IFI44L | DOWN | 5700725 | EPSTI1 | DOWN |
| 480 | 1090390 | OAS1 | DOWN | 3850647 | PTPN20 | UP |
| 472 | 1090390 | OAS1 | DOWN | 5550452 | KCNMA1 | UP |
| 527 | 1050168 | PI3 | UP | 1440615 | OTOF | DOWN |
| 97 | 3850647 | PTPN20 | UP | 5700725 | EPSTI1 | DOWN |
| 436 | 1440615 | OTOF | DOWN | 7550066 | MERTK | UP |
| 366 | 2000148 | IFIT1 | DOWN | 3850647 | PTPN20 | UP |
| 350 | 2030309 | SERPING1 | DOWN | 2140707 | SLPI | UP |
| 128 | 3830735 | UPB1 | UP | 5090215 | IFI6 | DOWN |
| 442 | 1440615 | OTOF | DOWN | 5550452 | KCNMA1 | UP |
| 502 | 1050168 | PI3 | UP | 5700725 | EPSTI1 | DOWN |
| 459 | 1440615 | OTOF | DOWN | 2510356 | EMR1 | UP |
| 7 | 6510170 | IFIT3 | DOWN | 7550066 | MERTK | UP |
| 535 | 1030100 | HS.386275 | DOWN | 5550452 | KCNMA1 | UP |
| 11 | 5700725 | EPSTI1 | DOWN | 7550066 | MERTK | UP |
| 266 | 2510356 | EMR1 | UP | 3990170 | IFI27 | DOWN |
| 96 | 3850647 | PTPN20 | UP | 6510170 | IFIT3 | DOWN |
| 552 | 1030100 | C | DOWN | 2510356 | EMR1 | UP |
| 246 | 2600747 | IFIT2 | DOWN | 3850647 | PTPN20 | UP |
| 73 | 3990170 | IFI27 | DOWN | 5550452 | KCNMA1 | UP |
| 301 | 2120079 | EIF2AK2 | DOWN | 7550066 | MERTK | UP |
| 450 | 1440615 | OTOF | DOWN | 3850647 | PTPN20 | UP |
| 307 | 2120079 | EIF2AK2 | DOWN | 5550452 | KCNMA1 | UP |
| 86 | 3870338 | IFI44L | DOWN | 5090215 | IFI6 | DOWN |
| 67 | 3990170 | IFI27 | DOWN | 7550066 | MERTK | UP |
| 349 | 2030309 | SERPING1 | DOWN | 2510356 | EMR1 | UP |

TABLE 10-continued

| | | | | | | |
|---|---|---|---|---|---|---|
| 691 | 150315 | C21ORF7 | DOWN | 2140707 | SLPI | UP |
| 347 | 2030309 | SERPING1 | DOWN | 2810767 | EBI3 | UP |
| 20 | 5550452 | KCNMA1 | UP | 6510170 | IFIT3 | DOWN |
| 523 | 1050168 | PI3 | UP | 2030309 | SERPING1 | DOWN |
| 549 | 1030100 | HS.386275 | DOWN | 3360343 | RSAD2 | DOWN |
| 341 | 2030309 | SERPING1 | DOWN | 3830762 | TMEM119 | UP |
| 398 | 1510424 | S100P | UP | 3360615 | FCER1A | DOWN |
| 113 | 3830762 | TMEM119 | UP | 5090215 | IFI6 | DOWN |
| 561 | 1030100 | HS.386275 | DOWN | 1050168 | PI3 | UP |
| 522 | 1050168 | PI3 | UP | 2120079 | EIF2AK2 | DOWN |
| 529 | 1030100 | HS.386275 | DOWN | 7550066 | MERTK | UP |
| 543 | 1030100 | HS.386275 | DOWN | 3850647 | PTPN20 | UP |
| 22 | 5090215 | IFI6 | DOWN | 7550066 | MERTK | UP |
| 296 | 2140707 | SLPI | UP | 3360615 | FCER1A | DOWN |
| 377 | 2000148 | IFIT1 | DOWN | 2120079 | EIF2AK2 | DOWN |
| 688 | 150315 | C21ORF7 | DOWN | 2810767 | EBI3 | UP |
| 315 | 2120079 | EIF2AK2 | DOWN | 3850647 | PTPN20 | UP |
| 76 | 3990170 | IFI27 | DOWN | 4480730 | HBM | DOWN |
| 556 | 1030100 | HS.386275 | DOWN | 2000148 | IFIT1 | DOWN |
| 28 | 5090215 | IFI6 | DOWN | 5550452 | KCNMA1 | UP |
| 690 | 150315 | C21ORF7 | DOWN | 2510356 | EMR1 | UP |
| 342 | 2030309 | SERPING1 | DOWN | 3830735 | UPB1 | UP |
| 504 | 1050168 | PI3 | UP | 5090215 | IFI6 | DOWN |
| 99 | 3850647 | PTPN20 | UP | 5090215 | IFI6 | DOWN |
| 75 | 3990170 | IFI27 | DOWN | 4670327 | FBXO7 | DOWN |
| 673 | 150315 | C21ORF7 | DOWN | 5550452 | KCNMA1 | UP |
| 326 | 2030309 | SERPING1 | DOWN | 7550066 | MERTK | UP |
| 479 | 1090390 | OAS1 | DOWN | 3870338 | IFI44L | DOWN |
| 339 | 2030309 | SERPING1 | DOWN | 3870338 | IFI44L | DOWN |
| 664 | 520408 | IFIT3 | DOWN | 1030100 | HS.386275 | DOWN |
| 387 | 1510424 | S100P | UP | 4670327 | FBXO7 | DOWN |
| 668 | 150315 | C21ORF7 | DOWN | 7400747 | FAM89A | UP |
| 678 | 150315 | C21ORF7 | DOWN | 4040242 | FAM89A | UP |
| 683 | 150315 | C21ORF7 | DOWN | 3830735 | UPB1 | UP |
| 699 | 150315 | C21ORF7 | DOWN | 1050168 | PI3 | UP |
| 332 | 2030309 | SERPING1 | DOWN | 5550452 | KCNMA1 | UP |
| 516 | 1050168 | PI3 | UP | 3360615 | FCER1A | DOWN |
| 419 | 1450358 | HBD | DOWN | 3990170 | IFI27 | DOWN |
| 590 | 1010546 | LOC649143 | DOWN | 1510424 | S100P | UP |
| 198 | 3360343 | RSAD2 | DOWN | 5090215 | IFI6 | DOWN |
| 575 | 1010546 | LOC649143 | DOWN | 3870338 | IFI44L | DOWN |
| 359 | 2000148 | IFIT1 | DOWN | 5090215 | IFI6 | DOWN |
| 681 | 150315 | C21ORF7 | DOWN | 3850647 | PTPN20 | UP |
| 682 | 150315 | C21ORF7 | DOWN | 3830762 | TMEM119 | UP |
| 166 | 3780187 | GYPB | DOWN | 3990170 | IFI27 | DOWN |
| 628 | 620544 | HLA-DRB6 | DOWN | 1050168 | PI3 | UP |
| 340 | 2030309 | SERPING1 | DOWN | 3850647 | PTPN20 | UP |
| 667 | 150315 | C21ORF7 | DOWN | 7550066 | MERTK | UP |
| 321 | 2120079 | EIF2AK2 | DOWN | 3360343 | RSAD2 | DOWN |
| 594 | 1010546 | LOC649143 | DOWN | 1050168 | PI3 | UP |
| 185 | 3360615 | FCER1A | DOWN | 3870338 | IFI44L | DOWN |
| 230 | 2810767 | EBI3 | UP | 3360615 | FCER1A | DOWN |
| 624 | 620544 | HLA-DRB6 | DOWN | 1510424 | S100P | UP |
| 378 | 2000148 | IFIT1 | DOWN | 2030309 | SERPING1 | DOWN |
| 533 | 1030100 | HS.386275 | DOWN | 6510170 | IFIT3 | DOWN |
| 586 | 1010546 | LOC649143 | DOWN | 2140707 | SLPI | UP |
| 88 | 3870338 | IFI44L | DOWN | 4480730 | HBM | DOWN |
| 173 | 3360615 | FCER1A | DOWN | 7400747 | FAM89A | UP |
| 560 | 1030100 | HS.386275 | DOWN | 1090390 | OAS1 | DOWN |
| 273 | 2510356 | EMR1 | UP | 3360615 | FCER1A | DOWN |
| 346 | 2030309 | SERPING1 | DOWN | 3360343 | RSAD2 | DOWN |
| 188 | 3360615 | FCER1A | DOWN | 3830735 | UPB1 | UP |
| 381 | 1510424 | S100P | UP | 6980192 | HBZ | DOWN |
| 680 | 150315 | C21ORF7 | DOWN | 3870338 | IFI44L | DOWN |
| 70 | 3990170 | IFI27 | DOWN | 6940086 | GYPE | DOWN |
| 323 | 2120079 | EIF2AK2 | DOWN | 2600747 | IFIT2 | DOWN |
| 551 | 1030100 | HS.386275 | DOWN | 2600747 | IFIT2 | DOWN |
| 388 | 1510424 | S100P | UP | 4480730 | HBM | DOWN |
| 486 | 1090390 | OAS1 | DOWN | 3360343 | RSAD2 | DOWN |
| 87 | 3870338 | IFI44L | DOWN | 4670327 | FBXO7 | DOWN |
| 493 | 1090390 | OAS1 | DOWN | 2000148 | IFIT1 | DOWN |
| 74 | 3990170 | IFI27 | DOWN | 5090215 | IFI6 | DOWN |
| 149 | 3780452 | IFIT1L | DOWN | 3990170 | IFI27 | DOWN |
| 541 | 1030100 | HS.386275 | DOWN | 3990170 | IFI27 | DOWN |
| 183 | 3360615 | FCER1A | DOWN | 4040242 | FAM89A | UP |
| 385 | 1510424 | S100P | UP | 5550452 | KCNMA1 | UP |
| 534 | 1030100 | HS.386275 | DOWN | 5700725 | EPSTI1 | DOWN |
| 620 | 620544 | HLA-DRB6 | DOWN | 2140707 | SLPI | UP |
| 420 | 1450358 | HBD | DOWN | 3870338 | IFI44L | DOWN |
| 184 | 3360615 | FCER1A | DOWN | 3990170 | IFI27 | DOWN |

TABLE 10-continued

| | | | | | | |
|---|---|---|---|---|---|---|
| 285 | 2140707 | SLPI | UP | 4670327 | FBXO7 | DOWN |
| 379 | 1510424 | S100P | UP | 7550066 | MERTK | UP |
| 574 | 1010546 | LOC649143 | DOWN | 3990170 | IFI27 | DOWN |
| 357 | 2000148 | IFIT1 | DOWN | 5700725 | EPSTI1 | DOWN |
| 679 | 150315 | C21ORF7 | DOWN | 3990170 | IFI27 | DOWN |
| 589 | 1010546 | LOC649143 | DOWN | 2000148 | IFIT1 | DOWN |
| 199 | 3360343 | RSAD2 | DOWN | 4670327 | FBXO7 | DOWN |
| 694 | 150315 | C21ORF7 | DOWN | 2000148 | IFIT1 | DOWN |
| 200 | 3360343 | RSAD2 | DOWN | 4480730 | HBM | DOWN |
| 656 | 520408 | IFIT3 | DOWN | 2120079 | EIF2AK2 | DOWN |
| 69 | 3990170 | IFI27 | DOWN | 6980192 | HBZ | DOWN |
| 371 | 2000148 | IFIT1 | DOWN | 3360615 | FCER1A | DOWN |
| 286 | 2140707 | SLPI | UP | 4480730 | HBM | DOWN |
| 187 | 3360615 | FCER1A | DOWN | 3830762 | TMEM119 | UP |
| 435 | 1450358 | HBD | DOWN | 1510424 | S100P | UP |
| 397 | 1510424 | S100P | UP | 3780187 | GYPB | DOWN |
| 313 | 2120079 | EIF2AK2 | DOWN | 3990170 | IFI27 | DOWN |
| 360 | 2000148 | IFIT1 | DOWN | 4670327 | FBXO7 | DOWN |
| 195 | 3360343 | RSAD2 | DOWN | 6510170 | IFIT3 | DOWN |
| 505 | 1050168 | PI3 | UP | 4670327 | FBXO7 | DOWN |
| 506 | 1050168 | PI3 | UP | 4480730 | HBM | DOWN |
| 582 | 1010546 | LOC649143 | DOWN | 3360343 | RSAD2 | DOWN |
| 687 | 150315 | C21ORF7 | DOWN | 3360343 | RSAD2 | DOWN |
| 361 | 2000148 | IFIT1 | DOWN | 4480730 | HBM | DOWN |
| 559 | 1030100 | HS.386275 | DOWN | 1440615 | OTOF | DOWN |
| 583 | 1010546 | LOC649143 | DOWN | 2810767 | EBI3 | UP |
| 77 | 3990170 | IFI27 | DOWN | 4150600 | EIF1AY | DOWN |
| 172 | 3360615 | FCER1A | DOWN | 7550066 | MERTK | UP |
| 210 | 3360343 | RSAD2 | DOWN | 3360615 | FCER1A | DOWN |
| 585 | 1010546 | LOC649143 | DOWN | 2510356 | EMR1 | UP |
| 608 | 620544 | HLA-DRB6 | DOWN | 3990170 | IFI27 | DOWN |
| 389 | 1510424 | S100P | UP | 4150600 | EIF1AY | DOWN |
| 563 | 1010546 | LOC649143 | DOWN | 7400747 | FAM89A | UP |
| 83 | 3870338 | IFI44L | DOWN | 6510170 | IFIT3 | DOWN |
| 186 | 3360615 | FCER1A | DOWN | 3850647 | PTPN20 | UP |
| 434 | 1450358 | HBD | DOWN | 2000148 | IFIT1 | DOWN |
| 382 | 1510424 | S100P | UP | 6940086 | GYPE | DOWN |
| 178 | 3360615 | FCER1A | DOWN | 5550452 | KCNMA1 | UP |
| 279 | 2140707 | SLPI | UP | 6980192 | HBZ | DOWN |
| 499 | 1050168 | PI3 | UP | 6980192 | HBZ | DOWN |
| 396 | 1510424 | S100P | UP | 3780452 | IFIT1L | DOWN |
| 89 | 3870338 | IFI44L | DOWN | 4150600 | EIF1AY | DOWN |
| 245 | 2600747 | IFIT2 | DOWN | 3870338 | IFI44L | DOWN |
| 427 | 1450358 | HBD | DOWN | 3360343 | RSAD2 | DOWN |
| 578 | 1010546 | LOC649143 | DOWN | 3830735 | UPB1 | UP |
| 196 | 3360343 | RSAD2 | DOWN | 5700725 | EPSTI1 | DOWN |
| 167 | 3780187 | GYPB | DOWN | 3870338 | IFI44L | DOWN |
| 639 | 520408 | IFIT3 | DOWN | 4670327 | FBXO7 | DOWN |
| 390 | 1510424 | S100P | UP | 4040242 | FAM89A | UP |
| 393 | 1510424 | S100P | UP | 3850647 | PTPN20 | UP |
| 597 | 620544 | HLA-DRB6 | DOWN | 7400747 | FAM89A | UP |
| 507 | 1050168 | PI3 | UP | 4150600 | EIF1AY | DOWN |
| 82 | 3870338 | IFI44L | DOWN | 6940086 | GYPE | DOWN |
| 356 | 2000148 | IFIT1 | DOWN | 6510170 | IFIT3 | DOWN |
| 619 | 620544 | HLA-DRB6 | DOWN | 2510356 | EMR1 | UP |
| 262 | 2510356 | EMR1 | UP | 4670327 | FBXO7 | DOWN |
| 362 | 2000148 | IFIT1 | DOWN | 4150600 | EIF1AY | DOWN |
| 644 | 520408 | IFIT3 | DOWN | 3870338 | IFI44L | DOWN |
| 263 | 2510356 | EMR1 | UP | 4480730 | HBM | DOWN |
| 395 | 1510424 | S100P | UP | 3830735 | UPB1 | UP |
| 33 | 4670327 | FBXO7 | DOWN | 6510170 | IFIT3 | DOWN |
| 287 | 2140707 | SLPI | UP | 4150600 | EIF1AY | DOWN |
| 240 | 2600747 | IFIT2 | DOWN | 4670327 | FBXO7 | DOWN |
| 638 | 520408 | IFIT3 | DOWN | 5090215 | IFI6 | DOWN |
| 665 | 520408 | IFIT3 | DOWN | 1010546 | LOC649143 | DOWN |
| 449 | 1440615 | OTOF | DOWN | 3870338 | IFI44L | DOWN |
| 526 | 1050168 | PI3 | UP | 1450358 | HBD | DOWN |
| 617 | 620544 | HLA-DRB6 | DOWN | 2810767 | EBI3 | UP |
| 306 | 2120079 | EIF2AK2 | DOWN | 5700725 | EPSTI1 | DOWN |
| 573 | 1010546 | LOC649143 | DOWN | 4040242 | FAM89A | UP |
| 612 | 620544 | HLA-DRB6 | DOWN | 3830735 | UPB1 | UP |
| 256 | 2510356 | EMR1 | UP | 6980192 | HBZ | DOWN |
| 611 | 620544 | HLA-DRB6 | DOWN | 3830762 | TMEM119 | UP |
| 431 | 1450358 | HBD | DOWN | 2140707 | SLPI | UP |
| 515 | 1050168 | PI3 | UP | 3780187 | GYPB | DOWN |
| 577 | 1010546 | LOC649143 | DOWN | 3830762 | TMEM119 | UP |
| 239 | 2600747 | IFIT2 | DOWN | 5090215 | IFI6 | DOWN |
| 30 | 4670327 | FBXO7 | DOWN | 7400747 | FAM89A | UP |
| 609 | 620544 | HLA-DRB6 | DOWN | 3870338 | IFI44L | DOWN |
| 294 | 2140707 | SLPI | UP | 3780452 | IFIT1L | DOWN |

TABLE 10-continued

| | | | | | | |
|---|---|---|---|---|---|---|
| 478 | 1090390 | OAS1 | DOWN | 3990170 | IFI27 | DOWN |
| 607 | 620544 | HLA-DRB6 | DOWN | 4040242 | FAM89A | UP |
| 584 | 1010546 | LOC649143 | DOWN | 1010546 | IFIT2 | DOWN |
| 338 | 2030309 | SERPING1 | DOWN | 3990170 | IFI27 | DOWN |
| 295 | 2140707 | SLPI | UP | 3780187 | GYPB | DOWN |
| 689 | 150315 | C21ORF7 | DOWN | 2600747 | IFIT2 | DOWN |
| 500 | 1050168 | PI3 | UP | 6940086 | GYPE | DOWN |
| 209 | 3360343 | RSAD2 | DOWN | 3780187 | GYPB | DOWN |
| 514 | 1050168 | PI3 | UP | 3780452 | IFIT1L | DOWN |
| 201 | 3360343 | RSAD2 | DOWN | 4150600 | EIF1AY | DOWN |
| 38 | 4480730 | HBM | DOWN | 7400747 | FAM89A | UP |
| 491 | 1090390 | OAS1 | DOWN | 2120079 | EIF2AK2 | DOWN |
| 355 | 2000148 | IFIT1 | DOWN | 6940086 | GYPE | DOWN |
| 150 | 3780452 | IFIT1L | DOWN | 3870338 | IFI44L | DOWN |
| 34 | 4670327 | FBXO7 | DOWN | 5700725 | EPSTI1 | DOWN |
| 280 | 2140707 | SLPI | UP | 6940086 | GYPE | DOWN |
| 370 | 2000148 | IFIT1 | DOWN | 3780187 | GYPB | DOWN |
| 3 | 6980192 | HBZ | DOWN | 7400747 | FAM89A | UP |
| 400 | 1510424 | S100P | UP | 2810767 | EBI3 | UP |
| 194 | 3360343 | RSAD2 | DOWN | 6940086 | GYPE | DOWN |
| 658 | 520408 | IFIT3 | DOWN | 2000148 | IFIT1 | DOWN |
| 463 | 1440615 | OTOF | DOWN | 2000148 | IFIT1 | DOWN |
| 640 | 520408 | IFIT3 | DOWN | 4480730 | HBM | DOWN |
| 241 | 2600747 | IFIT2 | DOWN | 4480730 | HBM | DOWN |
| 602 | 620544 | HLA-DRB6 | DOWN | 5550452 | KCNMA1 | UP |
| 129 | 3830735 | UPB1 | UP | 4670327 | FBXO7 | DOWN |
| 474 | 1090390 | OAS1 | DOWN | 4670327 | FBXO7 | DOWN |
| 660 | 520408 | IFIT3 | DOWN | 1450358 | HBD | DOWN |
| 72 | 3990170 | IFI27 | DOWN | 5700725 | EPSTI1 | DOWN |
| 64 | 4040242 | FAM89A | UP | 4670327 | FBXO7 | DOWN |
| 283 | 2140707 | SLPI | UP | 5550452 | KCNMA1 | UP |
| 610 | 620544 | HLA-DRB6 | DOWN | 3850647 | PTPN20 | UP |
| 41 | 4480730 | HBM | DOWN | 6510170 | IFIT3 | DOWN |
| 562 | 1010546 | LOC649143 | DOWN | 7550066 | MERTK | UP |
| 81 | 3870338 | IFI44L | DOWN | 6980192 | HBZ | DOWN |
| 291 | 2140707 | SLPI | UP | 3850647 | PTPN20 | UP |
| 155 | 3780187 | GYPB | DOWN | 7400747 | FAM89A | UP |
| 703 | 150315 | C21ORF7 | DOWN | 520408 | IFIT3 | DOWN |
| 429 | 1450358 | HBD | DOWN | 2600747 | IFIT2 | DOWN |
| 567 | 1010546 | LOC649143 | DOWN | 5700725 | EPSTI1 | DOWN |
| 475 | 1090390 | OAS1 | DOWN | 4480730 | HBM | DOWN |
| 566 | 1010546 | LOC649143 | DOWN | 6510170 | IFIT3 | DOWN |
| 623 | 620544 | HLA-DRB6 | DOWN | 2000148 | IFIT1 | DOWN |
| 220 | 2810767 | EBI3 | UP | 4480730 | HBM | DOWN |
| 374 | 2000148 | IFIT1 | DOWN | 2600747 | IFIT2 | DOWN |
| 65 | 4040242 | FAM89A | UP | 4480730 | HBM | DOWN |
| 58 | 4040242 | FAM89A | UP | 6980192 | HBZ | DOWN |
| 123 | 3830735 | UPB1 | UP | 6980192 | HBZ | DOWN |
| 130 | 3830735 | UPB1 | UP | 4480730 | HBM | DOWN |
| 219 | 2810767 | EBI3 | UP | 4670327 | FBXO7 | DOWN |
| 42 | 4480730 | HBM | DOWN | 5700725 | EPSTI1 | DOWN |
| 651 | 520408 | IFIT3 | DOWN | 3360343 | RSAD2 | DOWN |
| 27 | 5090215 | IFI6 | DOWN | 5700725 | EPSTI1 | DOWN |
| 26 | 5090215 | IFI6 | DOWN | 6510170 | IFIT3 | DOWN |
| 5 | 6940086 | GYPE | DOWN | 7400747 | FAM89A | UP |
| 272 | 2510356 | EMR1 | UP | 3780187 | GYPB | DOWN |
| 503 | 1050168 | PI3 | UP | 5550452 | KCNMA1 | UP |
| 448 | 1440615 | OTOF | DOWN | 3990170 | IFI27 | DOWN |
| 411 | 1450358 | HBD | DOWN | 6510170 | IFIT3 | DOWN |
| 47 | 4150600 | EIF1AY | DOWN | 7400747 | FAM89A | UP |
| 208 | 3360343 | RSAD2 | DOWN | 3780452 | IFIT1L | DOWN |
| 596 | 620544 | HLA-DRB6 | DOWN | 7550066 | MERTK | UP |
| 108 | 3830762 | TMEM119 | UP | 6980192 | HBZ | DOWN |
| 165 | 3780187 | GYPB | DOWN | 4040242 | FAM89A | UP |
| 354 | 2000148 | IFIT1 | DOWN | 6980192 | HBZ | DOWN |
| 305 | 2120079 | EIF2AK2 | DOWN | 6510170 | IFIT3 | DOWN |
| 369 | 2000148 | IFIT1 | DOWN | 3780452 | IFIT1L | DOWN |
| 576 | 1010546 | LOC649143 | DOWN | 3850647 | PTPN20 | UP |
| 593 | 1010546 | LOC649143 | DOWN | 1090390 | OAS1 | DOWN |
| 221 | 2810767 | EBI3 | UP | 4150600 | EIF1AY | DOWN |
| 445 | 1440615 | OTOF | DOWN | 4480730 | HBM | DOWN |
| 568 | 1010546 | LOC649143 | DOWN | 5550452 | KCNMA1 | UP |
| 251 | 2600747 | IFIT2 | DOWN | 3360615 | FCER1A | DOWN |
| 444 | 1440615 | OTOF | DOWN | 4670327 | FBXO7 | DOWN |
| 592 | 1010546 | LOC649143 | DOWN | 1440614 | OTOF | DOWN |
| 138 | 3780452 | IFIT1L | DOWN | 7400747 | FAM89A | UP |
| 513 | 1050168 | PI3 | UP | 3830735 | UPB1 | UP |
| 271 | 2510356 | EMR1 | UP | 3780452 | IFIT1L | DOWN |
| 114 | 3830762 | TMEM119 | UP | 4670327 | FBXO7 | DOWN |
| 380 | 1510424 | S100P | UP | 7400747 | FAM89A | UP |

TABLE 10-continued

| | | | | | | |
|---|---|---|---|---|---|---|
| 71 | 3990170 | IFI27 | DOWN | 6510170 | IFIT3 | DOWN |
| 497 | 1050168 | PI3 | UP | 7550066 | MERTK | UP |
| 456 | 1440615 | OTOF | DOWN | 3360343 | RSAD2 | DOWN |
| 257 | 2510356 | EMR1 | UP | 6940086 | GYPE | DOWN |
| 402 | 1510424 | S100P | UP | 2510356 | EMR1 | UP |
| 495 | 1090390 | OAS1 | DOWN | 1450358 | HBD | DOWN |
| 671 | 150315 | C21ORF7 | DOWN | 6510170 | IFIT3 | DOWN |
| 59 | 4040242 | FAM89A | UP | 6940086 | GYPE | DOWN |
| 151 | 3780452 | IFIT1L | DOWN | 3850647 | PTPN20 | UP |
| 511 | 1050168 | PI3 | UP | 3850647 | PTPN20 | UP |
| 412 | 1450358 | HBD | DOWN | 5700725 | EPSTI1 | DOWN |
| 213 | 2810767 | EBI3 | UP | 6980192 | HBZ | DOWN |
| 616 | 620544 | HLA-DRB6 | DOWN | 3360343 | RSAD2 | DOWN |
| 229 | 2810767 | EBI3 | UP | 3780187 | GYPB | DOWN |
| 170 | 3780187 | GYPB | DOWN | 3830735 | UPB1 | UP |
| 168 | 3780187 | GYPB | DOWN | 3850647 | PTPN20 | UP |
| 650 | 520408 | IFIT3 | DOWN | 3360615 | FCER1A | DOWN |
| 264 | 2510356 | EMR1 | UP | 4150600 | EIF1AY | DOWN |
| 641 | 520408 | IFIT3 | DOWN | 4150600 | EIF1AY | DOWN |
| 193 | 3360343 | RSAD2 | DOWN | 6980192 | HBZ | DOWN |
| 35 | 4670327 | FBXO7 | DOWN | 5550452 | KCNMA1 | UP |
| 95 | 3850647 | PTPN20 | UP | 6940086 | GYPE | DOWN |
| 465 | 1440615 | OTOF | DOWN | 1450358 | HBD | DOWN |
| 512 | 1050168 | PI3 | UP | 3830762 | TMEM119 | UP |
| 115 | 3830762 | TMEM119 | UP | 4480730 | HBM | DOWN |
| 116 | 3830762 | TMEM119 | UP | 4150600 | EIF1AY | DOWN |
| 29 | 4670327 | FBXO7 | DOWN | 7550066 | MERTK | UP |
| 277 | 2140707 | SLPI | UP | 7550066 | MERTK | UP |
| 124 | 3830735 | UPB1 | UP | 6940086 | GYPE | DOWN |
| 101 | 3850647 | PTPN20 | UP | 4480730 | HBM | DOWN |
| 461 | 1440615 | OTOF | DOWN | 2120079 | EIF2AK2 | DOWN |
| 148 | 3780452 | IFIT1L | DOWN | 4040242 | FAM89A | UP |
| 214 | 2810767 | EBI3 | UP | 6940086 | GYPE | DOWN |
| 228 | 2810767 | EBI3 | UP | 3780452 | IFIT1L | DOWN |
| 662 | 520408 | IFIT3 | DOWN | 1090390 | OAS1 | DOWN |
| 2 | 6980192 | HBZ | DOWN | 7550066 | MERTK | UP |
| 66 | 4040242 | FAM89A | UP | 4150600 | EIF1AY | DOWN |
| 18 | 5550452 | KCNMA1 | UP | 6980192 | HBZ | DOWN |
| 169 | 3780187 | GYPB | DOWN | 3830762 | TMEM119 | UP |
| 153 | 3780452 | IFIT1L | DOWN | 3830735 | UPB1 | UP |
| 473 | 1090390 | OAS1 | DOWN | 5090215 | IFI6 | DOWN |
| 242 | 2600747 | IFIT2 | DOWN | 4150600 | EIF1AY | DOWN |
| 109 | 3830762 | TMEM119 | UP | 6940086 | GYPE | DOWN |
| 176 | 3360615 | FCER1A | DOWN | 6510170 | IFIT3 | DOWN |
| 100 | 3850647 | PTPN20 | UP | 4670327 | FBXO7 | DOWN |
| 154 | 3780187 | GYPB | DOWN | 7550066 | MERTK | UP |
| 643 | 520408 | IFIT3 | DOWN | 3990170 | IFI27 | DOWN |
| 408 | 1450358 | HBD | DOWN | 7400747 | FAM89A | UP |
| 394 | 1510424 | S100P | UP | 3830762 | TMEM119 | UP |
| 94 | 3850647 | PTPN20 | UP | 6980192 | HBZ | DOWN |
| 152 | 3780452 | IFIT1L | DOWN | 3830762 | TMEM119 | UP |
| 160 | 3780187 | GYPB | DOWN | 5550452 | KCNMA1 | UP |
| 1 | 7400747 | FAM89A | UP | 7550066 | MERTK | UP |
| 293 | 2140707 | SLPI | UP | 3830735 | UPB1 | UP |
| 697 | 150315 | C21ORF7 | DOWN | 1440615 | OTOF | DOWN |
| 50 | 4150600 | EIF1AY | DOWN | 6510170 | IFIT3 | DOWN |
| 672 | 150315 | C21ORF7 | DOWN | 5700725 | EPSTI1 | DOWN |
| 698 | 150315 | C21ORF7 | DOWN | 1090390 | OAS1 | DOWN |
| 131 | 3830735 | UPB1 | UP | 4150600 | EIF1AY | DOWN |
| 177 | 3360615 | FCER1A | DOWN | 5700725 | EPSTI1 | DOWN |
| 334 | 2030309 | SERPING1 | DOWN | 4670327 | FBXO7 | DOWN |
| 470 | 1090390 | OAS1 | DOWN | 6510170 | IFIT3 | DOWN |
| 649 | 520408 | IFIT3 | DOWN | 3780187 | GYPB | DOWN |
| 17 | 5550452 | KCNMA1 | UP | 7400747 | FAM89A | UP |
| 657 | 520408 | IFIT3 | DOWN | 2030309 | SERPING1 | DOWN |
| 236 | 2600747 | IFIT2 | DOWN | 6510170 | IFIT3 | DOWN |
| 4 | 6940086 | GYPE | DOWN | 7550066 | MERTK | UP |
| 518 | 1050168 | PI3 | UP | 2810767 | EBI3 | UP |
| 443 | 1440615 | OTOF | DOWN | 5090215 | IFI6 | DOWN |
| 634 | 520408 | IFIT3 | DOWN | 6940086 | GYPE | DOWN |
| 37 | 4480730 | HBM | DOWN | 7550066 | MERTK | UP |
| 520 | 1050168 | PI3 | UP | 2510356 | EMR1 | UP |
| 555 | 1030100 | HS.386275 | DOWN | 2030309 | SERPING1 | DOWN |
| 143 | 3780452 | IFIT1L | DOWN | 5550452 | KCNMA1 | UP |
| 421 | 1450358 | HBD | DOWN | 3850647 | PTPN20 | UP |
| 137 | 3780452 | IFIT1L | DOWN | 7550066 | MERTK | UP |
| 252 | 2600747 | IFIT2 | DOWN | 3360343 | RSAD2 | DOWN |
| 418 | 1450358 | HBD | DOWN | 4040242 | FAM89A | UP |
| 298 | 2140707 | SLPI | UP | 2810767 | EBI3 | UP |
| 423 | 1450358 | HBD | DOWN | 3830735 | UPB1 | UP |

TABLE 10-continued

| | | | | | | |
|---|---|---|---|---|---|---|
| 250 | 2600747 | IFIT2 | DOWN | 3780187 | GYPB | DOWN |
| 633 | 520408 | IFIT3 | DOWN | 6980192 | HBZ | DOWN |
| 488 | 1090390 | OAS1 | DOWN | 2600747 | IFIT2 | DOWN |
| 348 | 2030309 | SERPING1 | DOWN | 2600747 | IFIT2 | DOWN |
| 235 | 2600747 | IFIT2 | DOWN | 6940086 | GYPE | DOWN |
| 351 | 2030309 | SERPING1 | DOWN | 2120079 | EIF2AK2 | DOWN |
| 19 | 5550452 | KCNMA1 | UP | 6940086 | GYPE | DOWN |
| 446 | 1440615 | OTOF | DOWN | 4150600 | EIF1AY | DOWN |
| 244 | 2600747 | IFIT2 | DOWN | 3990170 | IFI27 | DOWN |
| 43 | 4480730 | HBM | DOWN | 5550452 | KCNMA1 | UP |
| 9 | 6510170 | IFIT3 | DOWN | 6980192 | HBZ | DOWN |
| 422 | 1450358 | HBD | DOWN | 3830762 | TMEM119 | UP |
| 430 | 1450358 | HBD | DOWN | 2510356 | EMR1 | UP |
| 508 | 1050168 | PI3 | UP | 4040242 | FAM89A | UP |
| 485 | 1090390 | OAS1 | DOWN | 3360615 | FCER1A | DOWN |
| 648 | 520408 | IFIT3 | DOWN | 3780452 | IFIT1L | DOWN |
| 428 | 1450358 | HBD | DOWN | 2810767 | EBI3 | UP |
| 52 | 4150600 | EIF1AY | DOWN | 5550452 | KCNMA1 | UP |
| 335 | 2030309 | SERPING1 | DOWN | 4480730 | HBM | DOWN |
| 10 | 6510170 | IFIT3 | DOWN | 6940086 | GYPE | DOWN |
| 158 | 3780187 | GYPB | DOWN | 6510170 | IFIT3 | DOWN |
| 476 | 1090390 | OAS1 | DOWN | 4150600 | EIF1AY | DOWN |
| 433 | 1450358 | HBD | DOWN | 2030309 | SERPING1 | DOWN |
| 249 | 2600747 | IFIT2 | DOWN | 3780452 | IFIT1L | DOWN |
| 141 | 3780452 | IFIT1L | DOWN | 6510170 | IFIT3 | DOWN |
| 107 | 3830762 | TMEM119 | UP | 7400747 | FAM89A | UP |
| 51 | 4150600 | EIF1AY | DOWN | 5700725 | EPSTI1 | DOWN |
| 618 | 620544 | HLA-DRB6 | DOWN | 2600747 | IFIT2 | DOWN |
| 57 | 4040242 | FAM89A | UP | 7400747 | FAM89A | UP |
| 46 | 4150600 | EIF1AY | DOWN | 7550066 | MERTK | UP |
| 204 | 3360343 | RSAD2 | DOWN | 3870338 | IFI44L | DOWN |
| 269 | 2510356 | EMR1 | UP | 3830762 | TMEM119 | UP |
| 234 | 2600747 | IFIT2 | DOWN | 6980192 | HBZ | DOWN |
| 484 | 1090390 | OAS1 | DOWN | 3780187 | GYPB | DOWN |
| 635 | 520408 | IFIT3 | DOWN | 6510170 | IFIT3 | DOWN |
| 588 | 1010546 | LOC649143 | DOWN | 2030309 | SERPING1 | DOWN |
| 469 | 1090390 | OAS1 | DOWN | 6940086 | GYPE | DOWN |
| 102 | 3850647 | PTPN20 | UP | 4150600 | EIF1AY | DOWN |
| 454 | 1440615 | OTOF | DOWN | 3780187 | GYPB | DOWN |
| 439 | 1440615 | OTOF | DOWN | 6940086 | GYPE | DOWN |
| 36 | 4670327 | FBXO7 | DOWN | 5090215 | IFI6 | DOWN |
| 308 | 2120079 | EIF2AK2 | DOWN | 5090215 | IFI6 | DOWN |
| 309 | 2120079 | EIF2AK2 | DOWN | 4670327 | FBXO7 | DOWN |
| 292 | 2140707 | SLPI | UP | 3830762 | TMEM119 | UP |
| 330 | 2030309 | SERPING1 | DOWN | 6510170 | IFIT3 | DOWN |
| 536 | 1030100 | HS.386275 | DOWN | 5090215 | IFI6 | DOWN |
| 44 | 4480730 | HBM | DOWN | 5090215 | IFI6 | DOWN |
| 569 | 1010546 | LOC649143 | DOWN | 5090215 | IFI6 | DOWN |
| 56 | 4040242 | FAM89A | UP | 7550066 | MERTK | UP |
| 414 | 1450358 | HBD | DOWN | 5090215 | IFI6 | DOWN |
| 237 | 2600747 | IFIT2 | DOWN | 5700725 | EPSTI1 | DOWN |
| 498 | 1050168 | PI3 | UP | 7400747 | FAM89A | UP |
| 413 | 1450358 | HBD | DOWN | 5550452 | KCNMA1 | UP |
| 483 | 1090390 | OAS1 | DOWN | 3780452 | IFIT1L | DOWN |
| 453 | 1440615 | OTOF | DOWN | 3780452 | IFIT1L | DOWN |
| 666 | 520408 | IFIT3 | DOWN | 620544 | HLA-DRB6 | DOWN |
| 203 | 3360343 | RSAD2 | DOWN | 3990170 | IFI27 | DOWN |
| 626 | 620544 | HLA-DRB6 | DOWN | 1440615 | OTOF | DOWN |
| 455 | 1440615 | OTOF | DOWN | 3360615 | FCER1A | DOWN |
| 103 | 3850647 | PTPN20 | UP | 4040242 | FAM89A | UP |
| 407 | 1450358 | HBD | DOWN | 7550066 | MERTK | UP |
| 62 | 4040242 | FAM89A | UP | 5550452 | KCNMA1 | UP |
| 278 | 2140707 | SLPI | UP | 7400747 | FAM89A | UP |
| 468 | 1090390 | OAS1 | DOWN | 6980192 | HBZ | DOWN |
| 93 | 3850647 | PTPN20 | UP | 7400747 | FAM89A | UP |
| 675 | 150315 | C21ORF7 | DOWN | 4670327 | FBXO7 | DOWN |
| 225 | 2810767 | EBI3 | UP | 3850647 | PTPN20 | UP |
| 320 | 2120079 | EIF2AK2 | DOWN | 3360615 | FCER1A | DOWN |
| 142 | 3780452 | IFIT1L | DOWN | 5700725 | EPSTI1 | DOWN |
| 438 | 1440615 | OTOF | DOWN | 6980192 | HBZ | DOWN |
| 300 | 2140707 | SLPI | UP | 2510356 | EMR1 | UP |
| 600 | 620544 | HLA-DRB6 | DOWN | 6510170 | IFIT3 | DOWN |
| 365 | 2000148 | IFIT1 | DOWN | 3870338 | IFI44L | DOWN |
| 310 | 2120079 | EIF2AK2 | DOWN | 4480730 | HBM | DOWN |
| 117 | 3830762 | TMEM119 | UP | 4040242 | FAM89A | UP |
| 15 | 5700725 | EPSTI1 | DOWN | 6510170 | IFIT3 | DOWN |
| 601 | 620544 | HLA-DRB6 | DOWN | 5700725 | EPSTI1 | DOWN |
| 521 | 1050168 | PI3 | UP | 2140707 | SLPI | UP |
| 98 | 3850647 | PTPN20 | UP | 5550452 | KCNMA1 | UP |
| 554 | 1030100 | HS.386275 | DOWN | 2120079 | EIF2AK2 | DOWN |

TABLE 10-continued

| | | | | | | |
|---|---|---|---|---|---|---|
| 344 | 2030309 | SERPING1 | DOWN | 3780187 | GYPB | DOWN |
| 92 | 3850647 | PTPN20 | UP | 7550066 | MERTK | UP |
| 410 | 1450358 | HBD | DOWN | 6940086 | GYPE | DOWN |
| 432 | 1450358 | HBD | DOWN | 2120079 | EIF2AK2 | DOWN |
| 548 | 1030100 | HS.386275 | DOWN | 3360615 | FCER1A | DOWN |
| 537 | 1030100 | HS.386275 | DOWN | 4670327 | FBXO7 | DOWN |
| 329 | 2030309 | SERPING1 | DOWN | 6940086 | GYPE | DOWN |
| 403 | 1510424 | S100P | UP | 2140707 | SLPI | UP |
| 492 | 1090390 | OAS1 | DOWN | 2030309 | SERPING1 | DOWN |
| 336 | 2030309 | SERPING1 | DOWN | 4150600 | EIF1AY | DOWN |
| 653 | 520408 | IFIT3 | DOWN | 2600747 | IFIT2 | DOWN |
| 13 | 5700725 | EPSTI1 | DOWN | 6980192 | HBZ | DOWN |
| 458 | 1440615 | OTOF | DOWN | 2600747 | IFIT2 | DOWN |
| 372 | 2000148 | IFIT1 | DOWN | 3360343 | RSAD2 | DOWN |
| 180 | 3360615 | FCER1A | DOWN | 4670327 | FBXO7 | DOWN |
| 288 | 2140707 | SLPI | UP | 4040242 | FAM89A | UP |
| 159 | 3780187 | GYPB | DOWN | 5700725 | EPSTI1 | DOWN |
| 136 | 3830735 | UPB1 | UP | 3830762 | TMEM119 | UP |
| 627 | 620544 | HLA-DRB6 | DOWN | 1090390 | OAS1 | DOWN |
| 255 | 2510356 | EMR1 | UP | 7400747 | FAM89A | UP |
| 425 | 1450358 | HBD | DOWN | 3780187 | GYPB | DOWN |
| 440 | 1440615 | OTOF | DOWN | 6510170 | IFIT3 | DOWN |
| 424 | 1450358 | HBD | DOWN | 3780452 | IFIT1L | DOWN |
| 14 | 5700725 | EPSTI1 | DOWN | 6940086 | GYPE | DOWN |
| 636 | 520408 | IFIT3 | DOWN | 5700725 | EPSTI1 | DOWN |
| 254 | 2510356 | EMR1 | UP | 7550066 | MERTK | UP |
| 686 | 150315 | C21ORF7 | DOWN | 3360615 | FCER1A | DOWN |
| 693 | 150315 | C21ORF7 | DOWN | 2030309 | SERPING1 | DOWN |
| 270 | 2510356 | EMR1 | UP | 3830735 | UPB1 | UP |
| 268 | 2510356 | EMR1 | UP | 3850647 | PTPN20 | UP |
| 343 | 2030309 | SERPING1 | DOWN | 3780452 | IFIT1L | DOWN |
| 179 | 3360615 | FCER1A | DOWN | 5090215 | IFI6 | DOWN |
| 122 | 3830735 | UPB1 | UP | 7400747 | FAM89A | UP |
| 692 | 150315 | C21ORF7 | DOWN | 2120079 | EIF2AK2 | DOWN |
| 112 | 3830762 | TMEM119 | UP | 5550452 | KCNMA1 | UP |
| 587 | 1010546 | LOC649143 | DOWN | 2120079 | EIF2AK2 | DOWN |
| 701 | 150315 | C21ORF7 | DOWN | 1010546 | LOC649143 | DOWN |
| 135 | 3830735 | UPB1 | UP | 3850647 | PTPN20 | UP |
| 226 | 2810767 | EBI3 | UP | 3830762 | TMEM119 | UP |
| 333 | 2030309 | SERPING1 | DOWN | 5090215 | IFI6 | DOWN |
| 106 | 3830762 | TMEM119 | UP | 7550066 | MERTK | UP |
| 345 | 2030309 | SERPING1 | DOWN | 3360615 | FCER1A | DOWN |
| 676 | 150315 | C21ORF7 | DOWN | 4480730 | HBM | DOWN |
| 331 | 2030309 | SERPING1 | DOWN | 5700725 | EPSTI1 | DOWN |
| 328 | 2030309 | SERPING1 | DOWN | 6980192 | HBZ | DOWN |
| 120 | 3830762 | TMEM119 | UP | 3850647 | PTPN20 | UP |
| 181 | 3360615 | FCER1A | DOWN | 4480730 | HBM | DOWN |
| 145 | 3780452 | IFIT1L | DOWN | 4670327 | FBXO7 | DOWN |
| 132 | 3830735 | UPB1 | UP | 4040242 | FAM89A | UP |
| 604 | 620544 | HLA-DRB6 | DOWN | 4670327 | FBXO7 | DOWN |
| 319 | 2120079 | EIF2AK2 | DOWN | 3780187 | GYPB | DOWN |
| 625 | 620544 | HLA-DRB6 | DOWN | 1450358 | HBD | DOWN |
| 311 | 2120079 | EIF2AK2 | DOWN | 4150600 | EIF1AY | DOWN |
| 260 | 2510356 | EMR1 | UP | 5550452 | KCNMA1 | UP |
| 558 | 1030100 | HS.386275 | DOWN | 1450358 | HBD | DOWN |
| 217 | 2810767 | EBI3 | UP | 5550452 | KCNMA1 | UP |
| 31 | 4670327 | FBXO7 | DOWN | 6980192 | HBZ | DOWN |
| 304 | 2120079 | EIF2AK2 | DOWN | 6940086 | GYPE | DOWN |
| 275 | 2510356 | EMR1 | UP | 2810767 | EBI3 | UP |
| 661 | 520408 | IFIT3 | DOWN | 1440615 | OTOF | DOWN |
| 547 | 1030100 | HS.386275 | DOWN | 3780187 | GYPB | DOWN |
| 415 | 1450358 | HBD | DOWN | 4670327 | FBXO7 | DOWN |
| 144 | 3780452 | IFIT1L | DOWN | 5090215 | IFI6 | DOWN |
| 364 | 2000148 | IFIT1 | DOWN | 3990170 | IFI27 | DOWN |
| 622 | 620544 | HLA-DRB6 | DOWN | 2030309 | SERPING1 | DOWN |
| 32 | 4670327 | FBXO7 | DOWN | 6940086 | GYPE | DOWN |
| 700 | 150315 | C21ORF7 | DOWN | 1030100 | HS.386275 | DOWN |
| 91 | 3870338 | IFI44L | DOWN | 3990170 | IFI27 | DOWN |
| 409 | 1450358 | HBD | DOWN | 6980192 | HBZ | DOWN |
| 162 | 3780187 | GYPB | DOWN | 4670327 | FBXO7 | DOWN |
| 121 | 3830735 | UPB1 | UP | 7550066 | MERTK | UP |
| 25 | 5090215 | IFI6 | DOWN | 6940086 | GYPE | DOWN |
| 212 | 2810767 | EBI3 | UP | 7400747 | FAM89A | UP |
| 161 | 3780187 | GYPB | DOWN | 5090215 | IFI6 | DOWN |
| 615 | 620544 | HLA-DRB6 | DOWN | 3360615 | FCER1A | DOWN |
| 595 | 1010546 | LOC649143 | DOWN | 1030100 | HS.386275 | DOWN |
| 416 | 1450358 | HBD | DOWN | 4480730 | HBM | DOWN |
| 674 | 150315 | C21ORF7 | DOWN | 5090215 | IFI6 | DOWN |
| 318 | 2120079 | EIF2AK2 | DOWN | 3780452 | IFIT1L | DOWN |
| 605 | 620544 | HLA-DRB6 | DOWN | 4480730 | HBM | DOWN |

TABLE 10-continued

| | | | | | |
|---|---|---|---|---|---|
| 1563780187 | GYPB | DOWN | 6980192 | HBZ | DOWN |
| 4961090390 | OAS1 | DOWN | 1440615 | OTOF | DOWN |
| 394480730 | HBM | DOWN | 6980192 | HBZ | DOWN |
| 534150600 | EIF1AY | DOWN | 5090215 | IFI6 | DOWN |
| 630 620544 | HLA-DRB6 | DOWN | 1010546 | LOC649143 | DOWN |
| 454480730 | HBM | DOWN | 4670327 | FBXO7 | DOWN |
| 3032120079 | EIF2AK2 | DOWN | 6980192 | HBZ | DOWN |
| 66940086 | GYPE | DOWN | 6980192 | HBZ | DOWN |
| 5321030100 | HS.386275 | DOWN | 6940086 | GYPE | DOWN |
| 5811010546 | LOC649143 | DOWN | 3360615 | FCER1A | DOWN |
| 4621440615 | OTOF | DOWN | 2030309 | SERPING1 | DOWN |
| 2652510356 | EMR1 | UP | 4040242 | FAM89A | UP |
| 685 150315 | C21ORF7 | DOWN | 3780187 | GYPB | DOWN |
| 621 620544 | HLA-DRB6 | DOWN | 2120079 | EIF2AK2 | DOWN |
| 669 150315 | C21ORF7 | DOWN | 6980192 | HBZ | DOWN |
| 245090215 | IFI6 | DOWN | 6980192 | HBZ | DOWN |
| 4261450358 | HBD | DOWN | 3360615 | FCER1A | DOWN |
| 5651010546 | LOC649143 | DOWN | 6940086 | GYPE | DOWN |
| 5801010546 | LOC649143 | DOWN | 3780187 | GYPB | DOWN |
| 5461030100 | HS.386275 | DOWN | 3780452 | IFIT1L | DOWN |
| 1903360615 | FCER1A | DOWN | 3780187 | GYPB | DOWN |
| 5701010546 | LOC649143 | DOWN | 4670327 | FBXO7 | DOWN |
| 2222810767 | EBI3 | UP | 4040242 | FAM89A | UP |
| 599 620544 | HLA-DRB6 | DOWN | 6940086 | GYPE | DOWN |
| 484150600 | EIF1AY | DOWN | 6980192 | HBZ | DOWN |
| 1633780187 | GYPB | DOWN | 4480730 | HBM | DOWN |
| 1573780187 | GYPB | DOWN | 6940086 | GYPE | DOWN |
| 1393780452 | IFIT1L | DOWN | 6980192 | HBZ | DOWN |
| 670 150315 | C21ORF7 | DOWN | 6940086 | GYPE | DOWN |
| 5311030100 | HS.386275 | DOWN | 6980192 | HBZ | DOWN |
| 1713780187 | GYPB | DOWN | 3780452 | IFIT1L | DOWN |
| 614 620544 | HLA-DRB6 | DOWN | 3780187 | GYPB | DOWN |
| 5381030100 | HS.386275 | DOWN | 4480730 | HBM | DOWN |
| 603 620544 | HLA-DRB6 | DOWN | 5090215 | IFI6 | DOWN |
| 4411440615 | OTOF | DOWN | 5700725 | EPSTI1 | DOWN |
| 684 150315 | C21ORF7 | DOWN | 3780452 | IFIT1L | DOWN |
| 404480730 | HBM | DOWN | 6940086 | GYPE | DOWN |
| 5251050168 | PI3 | UP | 1510424 | S100P | UP |
| 4171450358 | HBD | DOWN | 4150600 | EIF1AY | DOWN |
| 1273830735 | UPB1 | UP | 5550452 | KCNMA1 | UP |
| 1403780452 | IFIT1L | DOWN | 6940086 | GYPE | DOWN |
| 4711090390 | OAS1 | DOWN | 5700725 | EPSTI1 | DOWN |
| 5641010546 | LOC649143 | DOWN | 6980192 | HBZ | DOWN |
| 1463780452 | IFIT1L | DOWN | 4480730 | HBM | DOWN |
| 5911010546 | LOC649143 | DOWN | 1450358 | HBD | DOWN |
| 702 150315 | C21ORF7 | DOWN | 620544 | HLA-DRB6 | DOWN |
| 5791010546 | LOC649143 | DOWN | 3780452 | IFIT1L | DOWN |
| 1473780452 | IFIT1L | DOWN | 4150600 | EIF1AY | DOWN |
| 165550452 | KCNMA1 | UP | 7550066 | MERTK | UP |
| 696 150315 | C21ORF7 | DOWN | 1450358 | HBD | DOWN |
| 1753360615 | FCER1A | DOWN | 6940086 | GYPE | DOWN |
| 2112810767 | EBI3 | UP | 7550066 | MERTK | UP |
| 554150600 | EIF1AY | DOWN | 4480730 | HBM | DOWN |
| 613 620544 | HLA-DRB6 | DOWN | 3780452 | IFIT1L | DOWN |
| 5721010546 | LOC649143 | DOWN | 4150600 | EIF1AY | DOWN |
| 1823360615 | FCER1A | DOWN | 4150600 | EIF1AY | DOWN |
| 1643780187 | GYPB | DOWN | 4150600 | EIF1AY | DOWN |
| 598 620544 | HLA-DRB6 | DOWN | 6980192 | HBZ | DOWN |
| 2272810767 | EBI3 | UP | 3830735 | UPB1 | UP |
| 1893360615 | FCER1A | DOWN | 3780452 | IFIT1L | DOWN |
| 544150600 | EIF1AY | DOWN | 4670327 | FBXO7 | DOWN |
| 494150600 | EIF1AY | DOWN | 6940086 | GYPE | DOWN |
| 606 620544 | HLA-DRB6 | DOWN | 4150600 | EIF1AY | DOWN |
| 1743360615 | FCER1A | DOWN | 6980192 | HBZ | DOWN |
| 5711010546 | LOC649143 | DOWN | 4480730 | HBM | DOWN |
| 629 620544 | HLA-DRB6 | DOWN | 1030100 | HS.386275 | DOWN |
| 677 150315 | C21ORF7 | DOWN | 4150600 | EIF1AY | DOWN |
| 5391030100 | HS.386275 | DOWN | 4150600 | EIF1AY | DOWN |

| Combi | Performance of different 2 transcript signatures | | | | | | | |
|---|---|---|---|---|---|---|---|---|
| | AUC training dataset | | AUC Test dataset | | AUC IRIS validation dataset | | Total AUC (training + test + iris) | |
| ID | opposite^ | same# | opposite^ | same# | opposite^ | same# | opposite^ | same# |
| 489 | 0.94032 | 0.65333 | 0.95789 | 0.66842 | 0.98609 | 0.70435 | 2.88430 | 2.02610 |
| 80 | 0.94921 | 0.78667 | 0.96316 | 0.60000 | 0.97043 | 0.73391 | 2.88280 | 2.12058 |
| 267 | 0.93365 | 0.79524 | 0.97368 | 0.63158 | 0.97217 | 0.86261 | 2.87951 | 2.28943 |

TABLE 10-continued

| | | | | | | | | |
|---|---|---|---|---|---|---|---|---|
| 467 | 0.96063 | 0.69048 | 0.93684 | 0.71579 | 0.97913 | 0.59478 | 2.87661 | 2.00105 |
| 224 | 0.93397 | 0.81810 | 0.96842 | 0.66316 | 0.97391 | 0.83478 | 2.87630 | 2.31604 |
| 399 | 0.94413 | 0.65524 | 0.94737 | 0.72105 | 0.98435 | 0.62261 | 2.87584 | 1.99890 |
| 290 | 0.92317 | 0.75778 | 0.98947 | 0.61053 | 0.96174 | 0.83826 | 2.87439 | 2.20656 |
| 384 | 0.94381 | 0.51968 | 0.96316 | 0.90000 | 0.96522 | 0.48348 | 2.87218 | 1.90316 |
| 392 | 0.93968 | 0.70063 | 0.95789 | 0.65263 | 0.97217 | 0.70087 | 2.86975 | 2.05414 |
| 477 | 0.96159 | 0.70032 | 0.93158 | 0.73158 | 0.97565 | 0.70261 | 2.86882 | 2.13451 |
| 90 | 0.94540 | 0.79683 | 0.95789 | 0.59474 | 0.96522 | 0.80000 | 2.86851 | 2.19156 |
| 274 | 0.92952 | 0.74952 | 0.95263 | 0.55789 | 0.98609 | 0.83478 | 2.86824 | 2.14220 |
| 632 | 0.95016 | 0.69619 | 0.93684 | 0.62632 | 0.98087 | 0.66261 | 2.86787 | 1.98511 |
| 119 | 0.92317 | 0.80444 | 1.00000 | 0.48947 | 0.94435 | 0.96000 | 2.86752 | 2.25392 |
| 654 | 0.92571 | 0.67111 | 0.95789 | 0.57368 | 0.98261 | 0.74087 | 2.86622 | 1.98566 |
| 23 | 0.96286 | 0.60444 | 0.96316 | 0.83684 | 0.93913 | 0.53913 | 2.86515 | 1.98042 |
| 12 | 0.96095 | 0.70159 | 0.94211 | 0.68947 | 0.96174 | 0.56696 | 2.86480 | 1.95802 |
| 642 | 0.94825 | 0.70540 | 0.93684 | 0.61579 | 0.97913 | 0.76000 | 2.86423 | 2.08119 |
| 134 | 0.93619 | 0.80254 | 0.96316 | 0.58421 | 0.96348 | 0.92696 | 2.86283 | 2.31371 |
| 406 | 0.94571 | 0.67556 | 0.94211 | 0.66316 | 0.97391 | 0.70783 | 2.86173 | 2.04654 |
| 192 | 0.95365 | 0.74413 | 0.93158 | 0.50000 | 0.97565 | 0.72522 | 2.86088 | 1.96934 |
| 259 | 0.94000 | 0.67175 | 0.95789 | 0.65263 | 0.96174 | 0.69739 | 2.85963 | 2.02177 |
| 404 | 0.94095 | 0.67841 | 0.95263 | 0.98421 | 0.96522 | 0.58261 | 2.85880 | 2.24523 |
| 202 | 0.95016 | 0.75429 | 0.93158 | 0.49474 | 0.97565 | 0.81217 | 2.85739 | 2.06120 |
| 8 | 0.94794 | 0.69587 | 0.92632 | 0.56316 | 0.98261 | 0.55652 | 2.85686 | 1.81555 |
| 490 | 0.91556 | 0.59016 | 0.97895 | 0.89474 | 0.96174 | 0.65391 | 2.85624 | 2.13881 |
| 353 | 0.95397 | 0.76825 | 0.92632 | 0.53158 | 0.97391 | 0.76348 | 2.85420 | 2.06331 |
| 655 | 0.91524 | 0.63016 | 0.97895 | 0.78421 | 0.96000 | 0.70435 | 2.85419 | 2.11872 |
| 258 | 0.92381 | 0.69079 | 0.94737 | 0.47368 | 0.98261 | 0.67304 | 2.85379 | 1.83752 |
| 494 | 0.94095 | 0.51016 | 0.94211 | 0.92632 | 0.97043 | 0.54783 | 2.85349 | 1.98430 |
| 376 | 0.92667 | 0.74317 | 0.96316 | 0.64737 | 0.96348 | 0.83652 | 2.85330 | 2.22706 |
| 375 | 0.93206 | 0.77206 | 0.94211 | 0.60526 | 0.97913 | 0.85391 | 2.85330 | 2.23124 |
| 61 | 0.95778 | 0.72095 | 0.94211 | 0.67895 | 0.95304 | 0.67130 | 2.85293 | 2.07120 |
| 297 | 0.91746 | 0.71746 | 0.96842 | 0.68947 | 0.96696 | 0.77913 | 2.85284 | 2.18606 |
| 401 | 0.94444 | 0.46825 | 0.93684 | 0.82632 | 0.97043 | 0.65739 | 2.85172 | 1.95196 |
| 367 | 0.92127 | 0.78413 | 0.97895 | 0.50000 | 0.95130 | 0.93565 | 2.85152 | 2.21978 |
| 363 | 0.95048 | 0.77778 | 0.92632 | 0.52632 | 0.97391 | 0.81217 | 2.85071 | 2.11627 |
| 282 | 0.91587 | 0.60190 | 0.98421 | 0.85789 | 0.94957 | 0.64174 | 2.84965 | 2.10154 |
| 60 | 0.94381 | 0.70921 | 0.92632 | 0.56842 | 0.97913 | 0.68000 | 2.84926 | 1.95763 |
| 517 | 0.89397 | 0.57810 | 1.00000 | 0.73158 | 0.95130 | 0.69217 | 2.84527 | 2.00185 |
| 487 | 0.94095 | 0.73556 | 0.93158 | 0.70000 | 0.97217 | 0.77043 | 2.84471 | 2.20599 |
| 302 | 0.95460 | 0.53968 | 0.91053 | 0.87895 | 0.97913 | 0.55826 | 2.84426 | 1.97689 |
| 216 | 0.93841 | 0.76667 | 0.95263 | 0.65789 | 0.95304 | 0.72174 | 2.84409 | 2.14630 |
| 659 | 0.94317 | 0.55429 | 0.93684 | 0.82632 | 0.96348 | 0.48522 | 2.84349 | 1.86582 |
| 510 | 0.89778 | 0.63651 | 0.99474 | 0.67368 | 0.94957 | 0.80870 | 2.84208 | 2.11889 |
| 386 | 0.93968 | 0.63397 | 0.96842 | 0.97368 | 0.93391 | 0.65565 | 2.84202 | 2.26330 |
| 464 | 0.92571 | 0.56825 | 0.94737 | 0.89474 | 0.96870 | 0.50435 | 2.84178 | 1.96734 |
| 481 | 0.91460 | 0.69873 | 1.00000 | 0.76316 | 0.92696 | 0.89739 | 2.84156 | 2.35928 |
| 206 | 0.91905 | 0.76667 | 0.98947 | 0.55789 | 0.93043 | 0.95478 | 2.83896 | 2.27934 |
| 231 | 0.92603 | 0.79810 | 0.93158 | 0.60000 | 0.98087 | 0.84522 | 2.83848 | 2.24331 |
| 457 | 0.92032 | 0.74190 | 0.94737 | 0.64737 | 0.97043 | 0.79652 | 2.83812 | 2.18579 |
| 383 | 0.94222 | 0.57079 | 0.93684 | 0.82105 | 0.95826 | 0.57565 | 2.83733 | 1.96750 |
| 437 | 0.93683 | 0.70730 | 0.93158 | 0.65789 | 0.96870 | 0.62087 | 2.83710 | 1.98607 |
| 243 | 0.95079 | 0.70476 | 0.91579 | 0.61579 | 0.97043 | 0.80000 | 2.83702 | 2.12055 |
| 451 | 0.92222 | 0.70444 | 1.00000 | 0.76842 | 0.91478 | 0.89043 | 2.83700 | 2.36330 |
| 233 | 0.95365 | 0.69270 | 0.91053 | 0.61053 | 0.97217 | 0.73913 | 2.83635 | 2.04236 |
| 68 | 0.94222 | 0.80286 | 0.94737 | 0.68421 | 0.94435 | 0.73391 | 2.83394 | 2.22098 |
| 482 | 0.93683 | 0.68857 | 0.93684 | 0.74737 | 0.96000 | 0.87130 | 2.83367 | 2.30724 |
| 447 | 0.93302 | 0.71968 | 0.93684 | 0.67368 | 0.96348 | 0.74609 | 2.83334 | 2.13945 |
| 368 | 0.93111 | 0.78889 | 0.93684 | 0.56842 | 0.96522 | 0.90435 | 2.83317 | 2.26166 |
| 530 | 0.94921 | 0.55460 | 0.90000 | 0.87895 | 0.98261 | 0.62957 | 2.83182 | 2.06312 |
| 312 | 0.95079 | 0.55238 | 0.90526 | 0.86842 | 0.97565 | 0.66609 | 2.83171 | 2.08689 |
| 207 | 0.92603 | 0.76952 | 0.93684 | 0.52105 | 0.96696 | 0.92174 | 2.82983 | 2.21232 |
| 524 | 0.89429 | 0.60413 | 0.98947 | 0.64737 | 0.94435 | 0.74957 | 2.82811 | 2.00106 |
| 652 | 0.91778 | 0.74222 | 0.92632 | 0.56316 | 0.98261 | 0.80000 | 2.82670 | 2.10538 |
| 299 | 0.91683 | 0.61079 | 0.95789 | 0.78421 | 0.95130 | 0.77043 | 2.82602 | 2.16544 |
| 460 | 0.89048 | 0.67365 | 0.97895 | 0.88421 | 0.95652 | 0.65739 | 2.82595 | 2.21525 |
| 281 | 0.90952 | 0.64825 | 0.97895 | 0.74211 | 0.93739 | 0.58783 | 2.82586 | 1.97819 |
| 276 | 0.92857 | 0.65587 | 0.92105 | 0.58947 | 0.97565 | 0.81913 | 2.82528 | 2.06448 |
| 550 | 0.93206 | 0.60825 | 0.91579 | 0.89474 | 0.97739 | 0.61739 | 2.82524 | 2.12038 |
| 545 | 0.93651 | 0.48476 | 0.92632 | 0.90526 | 0.96000 | 0.67652 | 2.82282 | 2.06655 |
| 647 | 0.92381 | 0.69492 | 0.93684 | 0.63158 | 0.96174 | 0.87652 | 2.82239 | 2.20302 |
| 553 | 0.90698 | 0.46413 | 0.96842 | 0.96842 | 0.94609 | 0.61043 | 2.82149 | 2.04298 |
| 63 | 0.96508 | 0.62254 | 0.95263 | 0.81579 | 0.90261 | 0.57217 | 2.82032 | 2.01050 |
| 540 | 0.94921 | 0.56952 | 0.90000 | 0.87895 | 0.97043 | 0.49217 | 2.81964 | 1.94065 |
| 289 | 0.92254 | 0.81111 | 0.95789 | 0.56842 | 0.93913 | 0.78609 | 2.81956 | 2.16562 |
| 105 | 0.93143 | 0.78603 | 0.93158 | 0.56842 | 0.95652 | 0.96522 | 2.81953 | 2.31967 |
| 452 | 0.92730 | 0.70476 | 0.93684 | 0.71053 | 0.95478 | 0.85217 | 2.81893 | 2.26746 |
| 557 | 0.93746 | 0.67587 | 0.93684 | 0.99474 | 0.94435 | 0.76696 | 2.81865 | 2.43757 |
| 391 | 0.93016 | 0.73079 | 0.96842 | 0.52105 | 0.92000 | 0.66261 | 2.81858 | 1.91445 |
| 317 | 0.91206 | 0.50825 | 0.94737 | 0.90526 | 0.95826 | 0.79304 | 2.81769 | 2.20656 |
| 325 | 0.89143 | 0.56063 | 0.97368 | 0.95789 | 0.95130 | 0.44870 | 2.81642 | 1.96723 |
| 223 | 0.94095 | 0.84190 | 0.95263 | 0.70000 | 0.92174 | 0.83304 | 2.81532 | 2.37495 |

TABLE 10-continued

| | | | | | | | | |
|---|---|---|---|---|---|---|---|---|
| 85 | 0.92508 | 0.82254 | 0.93158 | 0.65263 | 0.95826 | 0.94435 | 2.81492 | 2.41952 |
| 111 | 0.91048 | 0.70984 | 0.99474 | 0.72632 | 0.90957 | 0.88870 | 2.81478 | 2.32485 |
| 247 | 0.90190 | 0.70349 | 0.97368 | 0.67895 | 0.93913 | 0.92348 | 2.81472 | 2.30592 |
| 284 | 0.90317 | 0.50857 | 0.98421 | 0.95789 | 0.92696 | 0.51304 | 2.81434 | 1.97951 |
| 646 | 0.90190 | 0.72095 | 0.98421 | 0.66842 | 0.92696 | 0.90609 | 2.81307 | 2.29546 |
| 126 | 0.93270 | 0.70603 | 0.94737 | 0.71579 | 0.93217 | 0.84000 | 2.81224 | 2.26182 |
| 78 | 0.94254 | 0.81302 | 0.94211 | 0.67368 | 0.92522 | 0.78261 | 2.80986 | 2.26931 |
| 373 | 0.92635 | 0.80730 | 0.90526 | 0.59474 | 0.97739 | 0.85043 | 2.80900 | 2.25247 |
| 205 | 0.92889 | 0.74984 | 0.92105 | 0.46842 | 0.95826 | 0.96522 | 2.80820 | 2.18348 |
| 215 | 0.91492 | 0.76413 | 0.92105 | 0.50526 | 0.97217 | 0.73913 | 2.80815 | 2.00852 |
| 79 | 0.92730 | 0.81270 | 0.91579 | 0.64737 | 0.96348 | 0.90783 | 2.80657 | 2.36789 |
| 218 | 0.93810 | 0.67524 | 0.96316 | 0.83158 | 0.90261 | 0.64174 | 2.80386 | 2.14856 |
| 133 | 0.94825 | 0.80984 | 0.95789 | 0.72105 | 0.89565 | 0.86087 | 2.80180 | 2.39176 |
| 509 | 0.91143 | 0.69873 | 0.96842 | 0.70526 | 0.92174 | 0.71478 | 2.80159 | 2.11878 |
| 248 | 0.92730 | 0.68508 | 0.92105 | 0.64737 | 0.95130 | 0.88870 | 2.79966 | 2.22114 |
| 544 | 0.90698 | 0.56635 | 0.96316 | 0.90526 | 0.92870 | 0.72696 | 2.79884 | 2.19857 |
| 118 | 0.92413 | 0.82762 | 0.98421 | 0.53158 | 0.88870 | 0.89217 | 2.79703 | 2.25137 |
| 253 | 0.92159 | 0.74222 | 0.91579 | 0.57368 | 0.95826 | 0.82957 | 2.79564 | 2.14547 |
| 110 | 0.90381 | 0.71905 | 0.97895 | 0.64211 | 0.91130 | 0.83652 | 2.79406 | 2.19767 |
| 232 | 0.92952 | 0.69968 | 0.91053 | 0.43158 | 0.95304 | 0.87478 | 2.79309 | 2.00604 |
| 322 | 0.91175 | 0.59810 | 0.91053 | 0.92632 | 0.97043 | 0.72000 | 2.79271 | 2.24441 |
| 405 | 0.91397 | 0.54063 | 0.93158 | 0.86842 | 0.94609 | 0.64174 | 2.79163 | 2.05080 |
| 695 | 0.89397 | 0.70317 | 0.96316 | 0.97368 | 0.93391 | 0.76696 | 2.79104 | 2.44382 |
| 542 | 0.86032 | 0.90825 | 0.97895 | 0.77895 | 0.94957 | 0.95826 | 2.78883 | 2.64546 |
| 191 | 0.92127 | 0.77429 | 0.90526 | 0.58947 | 0.96174 | 0.89565 | 2.78827 | 2.25941 |
| 631 | 0.92286 | 0.70063 | 0.90526 | 0.56316 | 0.96000 | 0.85913 | 2.78812 | 2.12292 |
| 663 | 0.89016 | 0.51841 | 0.96316 | 0.78947 | 0.93391 | 0.60696 | 2.78723 | 1.91484 |
| 125 | 0.91460 | 0.71810 | 0.92632 | 0.58421 | 0.94609 | 0.80870 | 2.78701 | 2.11100 |
| 528 | 0.87968 | 0.55841 | 0.97895 | 0.85263 | 0.92696 | 0.54261 | 2.78559 | 1.95365 |
| 466 | 0.93651 | 0.68349 | 0.88421 | 0.65789 | 0.96348 | 0.84522 | 2.78420 | 2.18660 |
| 104 | 0.94095 | 0.78190 | 0.94737 | 0.68421 | 0.89391 | 0.88348 | 2.78223 | 2.34959 |
| 327 | 0.91587 | 0.67143 | 0.92105 | 0.66316 | 0.94435 | 0.52000 | 2.78127 | 1.85459 |
| 261 | 0.93302 | 0.53333 | 0.96316 | 0.76316 | 0.88348 | 0.56522 | 2.77965 | 1.86171 |
| 352 | 0.92190 | 0.79619 | 0.89474 | 0.61579 | 0.96000 | 0.91652 | 2.77664 | 2.32850 |
| 501 | 0.88540 | 0.50032 | 0.98421 | 0.76842 | 0.90609 | 0.49391 | 2.77569 | 1.76265 |
| 645 | 0.91175 | 0.69270 | 0.91579 | 0.66842 | 0.94783 | 0.95304 | 2.77536 | 2.31416 |
| 21 | 0.92603 | 0.76921 | 0.90526 | 0.65263 | 0.94261 | 0.84174 | 2.77390 | 2.26358 |
| 637 | 0.91905 | 0.72984 | 0.90526 | 0.53158 | 0.94783 | 0.91130 | 2.77214 | 2.17272 |
| 519 | 0.88349 | 0.53968 | 0.95263 | 0.79474 | 0.93565 | 0.71652 | 2.77178 | 2.05094 |
| 337 | 0.91556 | 0.68254 | 0.92105 | 0.67368 | 0.93217 | 0.56696 | 2.76878 | 1.92318 |
| 197 | 0.91873 | 0.79556 | 0.89474 | 0.60000 | 0.95478 | 0.93739 | 2.76825 | 2.33295 |
| 314 | 0.89556 | 0.89460 | 0.94211 | 0.78947 | 0.92870 | 0.94783 | 2.76636 | 2.63190 |
| 358 | 0.92444 | 0.81524 | 0.89474 | 0.61053 | 0.94609 | 0.92696 | 2.76527 | 2.35272 |
| 324 | 0.90508 | 0.53143 | 0.89474 | 0.83158 | 0.96348 | 0.63826 | 2.76329 | 2.00127 |
| 238 | 0.92349 | 0.72698 | 0.88421 | 0.55789 | 0.95478 | 0.91304 | 2.76249 | 2.19792 |
| 316 | 0.88032 | 0.58032 | 0.97895 | 0.88421 | 0.90261 | 0.85217 | 2.76187 | 2.31670 |
| 84 | 0.87333 | 0.90063 | 0.94737 | 0.81579 | 0.94087 | 0.94783 | 2.76157 | 2.66425 |
| 480 | 0.92381 | 0.66317 | 0.91053 | 0.78421 | 0.92522 | 0.93565 | 2.75955 | 2.38304 |
| 472 | 0.93556 | 0.74000 | 0.88421 | 0.68947 | 0.93739 | 0.90783 | 2.75716 | 2.33730 |
| 527 | 0.86889 | 0.47651 | 0.94737 | 0.86316 | 0.93913 | 0.56870 | 2.75539 | 1.90836 |
| 97 | 0.92444 | 0.70413 | 0.91053 | 0.73158 | 0.92000 | 0.92000 | 2.75497 | 2.35571 |
| 436 | 0.91683 | 0.71302 | 0.88947 | 0.60000 | 0.94783 | 0.84348 | 2.75413 | 2.15649 |
| 366 | 0.92889 | 0.78095 | 0.87895 | 0.52632 | 0.94609 | 0.94087 | 2.75392 | 2.24814 |
| 350 | 0.89143 | 0.61873 | 0.95263 | 0.80526 | 0.90957 | 0.52696 | 2.75363 | 1.95095 |
| 128 | 0.93111 | 0.44698 | 0.95263 | 0.85263 | 0.86609 | 0.67652 | 2.74983 | 1.97614 |
| 442 | 0.90825 | 0.76349 | 0.90526 | 0.62632 | 0.93391 | 0.89043 | 2.74743 | 2.28024 |
| 502 | 0.87111 | 0.54317 | 0.97368 | 0.82105 | 0.90261 | 0.54087 | 2.74740 | 1.90510 |
| 459 | 0.90635 | 0.69778 | 0.86842 | 0.67368 | 0.97043 | 0.74783 | 2.74521 | 2.11929 |
| 7 | 0.91048 | 0.72540 | 0.90000 | 0.51579 | 0.93043 | 0.79304 | 2.74091 | 2.03423 |
| 535 | 0.92952 | 0.61714 | 0.85263 | 0.86316 | 0.95826 | 0.76696 | 2.74042 | 2.24726 |
| 11 | 0.92159 | 0.72857 | 0.88421 | 0.66316 | 0.93391 | 0.79826 | 2.73971 | 2.18999 |
| 266 | 0.93143 | 0.79651 | 0.92105 | 0.68947 | 0.88696 | 0.82609 | 2.73944 | 2.31207 |
| 96 | 0.91556 | 0.69841 | 0.91053 | 0.64737 | 0.91304 | 0.90435 | 2.73913 | 2.25013 |
| 552 | 0.91937 | 0.51683 | 0.86316 | 0.87368 | 0.95652 | 0.55130 | 2.73904 | 1.94181 |
| 246 | 0.90825 | 0.69333 | 0.88421 | 0.69474 | 0.94609 | 0.93739 | 2.73855 | 2.32546 |
| 73 | 0.92921 | 0.84159 | 0.92632 | 0.78947 | 0.87478 | 0.90261 | 2.73030 | 2.53367 |
| 301 | 0.89873 | 0.53238 | 0.87895 | 0.84211 | 0.95130 | 0.79130 | 2.72898 | 2.16579 |
| 450 | 0.90635 | 0.71302 | 0.90000 | 0.70526 | 0.92174 | 0.93043 | 2.72809 | 2.34871 |
| 307 | 0.91333 | 0.60444 | 0.88947 | 0.83158 | 0.91826 | 0.85391 | 2.72107 | 2.28994 |
| 86 | 0.89365 | 0.90063 | 0.91579 | 0.80526 | 0.91130 | 0.93913 | 2.72074 | 2.64503 |
| 67 | 0.92794 | 0.83619 | 0.91579 | 0.73684 | 0.87652 | 0.85739 | 2.72025 | 2.43042 |
| 349 | 0.90095 | 0.65905 | 0.88421 | 0.66316 | 0.93391 | 0.45565 | 2.71908 | 1.77786 |
| 691 | 0.86190 | 0.61651 | 0.96842 | 0.97368 | 0.88870 | 0.57043 | 2.71902 | 2.16063 |
| 347 | 0.89810 | 0.71556 | 0.90526 | 0.67895 | 0.91478 | 0.62783 | 2.71814 | 2.02233 |
| 20 | 0.91937 | 0.74286 | 0.86316 | 0.50526 | 0.92870 | 0.84696 | 2.71122 | 2.09508 |
| 523 | 0.87143 | 0.52540 | 0.97368 | 0.81053 | 0.86087 | 0.59652 | 2.70598 | 1.93244 |
| 549 | 0.84730 | 0.90000 | 0.92105 | 0.76842 | 0.93043 | 0.96348 | 2.69879 | 2.63190 |
| 341 | 0.88603 | 0.68222 | 0.98421 | 0.76316 | 0.82609 | 0.71652 | 2.69633 | 2.16190 |
| 398 | 0.86413 | 0.71778 | 0.94211 | 0.98421 | 0.88348 | 0.84348 | 2.68971 | 2.54547 |
| 113 | 0.89111 | 0.61492 | 1.00000 | 0.85263 | 0.79826 | 0.76696 | 2.68937 | 2.23451 |

TABLE 10-continued

| | | | | | | | | |
|---|---|---|---|---|---|---|---|---|
| 561 | 0.85397 | 0.63206 | 0.95263 | 0.91579 | 0.88174 | 0.66435 | 2.68834 | 2.21220 |
| 522 | 0.83683 | 0.64921 | 0.94737 | 0.88947 | 0.90261 | 0.52348 | 2.68680 | 2.06216 |
| 529 | 0.91460 | 0.55873 | 0.83684 | 0.85789 | 0.93217 | 0.66261 | 2.68362 | 2.07923 |
| 543 | 0.89841 | 0.49111 | 0.86316 | 0.91053 | 0.91826 | 0.94087 | 2.67983 | 2.34251 |
| 22 | 0.92063 | 0.60349 | 0.89474 | 0.78421 | 0.86087 | 0.67478 | 2.67624 | 2.06249 |
| 296 | 0.83746 | 0.60571 | 0.97895 | 0.88947 | 0.85913 | 0.69565 | 2.67554 | 2.19084 |
| 377 | 0.89365 | 0.89079 | 0.86316 | 0.73158 | 0.91826 | 0.94087 | 2.67507 | 2.56324 |
| 688 | 0.86825 | 0.48635 | 0.91053 | 0.87895 | 0.89565 | 0.61217 | 2.67443 | 1.97747 |
| 315 | 0.89556 | 0.51048 | 0.85789 | 0.86842 | 0.91130 | 0.91478 | 2.66475 | 2.29368 |
| 76 | 0.82127 | 0.91460 | 0.90000 | 0.77895 | 0.93565 | 0.77391 | 2.65692 | 2.46746 |
| 556 | 0.85683 | 0.90317 | 0.87368 | 0.75263 | 0.92522 | 0.94783 | 2.65573 | 2.60363 |
| 28 | 0.92095 | 0.67302 | 0.91053 | 0.76842 | 0.82087 | 0.74261 | 2.65235 | 2.18405 |
| 690 | 0.83968 | 0.61048 | 0.90526 | 0.85789 | 0.89739 | 0.52870 | 2.64234 | 1.99707 |
| 342 | 0.88444 | 0.67492 | 0.89474 | 0.71579 | 0.86261 | 0.67826 | 2.64179 | 2.06897 |
| 504 | 0.84889 | 0.63429 | 0.95789 | 0.88947 | 0.83478 | 0.58957 | 2.64157 | 2.11332 |
| 99 | 0.92159 | 0.56921 | 0.91579 | 0.84211 | 0.79304 | 0.80696 | 2.63042 | 2.21827 |
| 75 | 0.83746 | 0.92159 | 0.88421 | 0.82105 | 0.90783 | 0.85913 | 2.62950 | 2.60177 |
| 673 | 0.83778 | 0.53238 | 0.93684 | 0.81053 | 0.85217 | 0.72348 | 2.62679 | 2.06639 |
| 326 | 0.88095 | 0.68603 | 0.86842 | 0.62105 | 0.87652 | 0.68348 | 2.62590 | 1.99056 |
| 479 | 0.83079 | 0.90413 | 0.94737 | 0.81579 | 0.84696 | 0.95478 | 2.62512 | 2.67470 |
| 339 | 0.80698 | 0.88349 | 0.91053 | 0.80000 | 0.90609 | 0.92696 | 2.62360 | 2.61045 |
| 664 | 0.79524 | 0.89175 | 0.90526 | 0.73684 | 0.92174 | 0.95304 | 2.62224 | 2.58163 |
| 387 | 0.87968 | 0.72254 | 0.89474 | 0.97368 | 0.84348 | 0.84696 | 2.61790 | 2.54318 |
| 668 | 0.84571 | 0.54413 | 0.86842 | 0.92632 | 0.90261 | 0.64348 | 2.61674 | 2.11392 |
| 678 | 0.84476 | 0.52825 | 0.86842 | 0.92105 | 0.89739 | 0.47826 | 2.61057 | 1.92757 |
| 683 | 0.82571 | 0.55556 | 0.90526 | 0.94737 | 0.87652 | 0.73217 | 2.60750 | 2.23510 |
| 699 | 0.82889 | 0.67905 | 0.91579 | 0.93684 | 0.86087 | 0.61217 | 2.60555 | 2.22806 |
| 332 | 0.89238 | 0.71651 | 0.84737 | 0.61053 | 0.85913 | 0.72174 | 2.59888 | 2.04877 |
| 516 | 0.84635 | 0.64444 | 0.95263 | 0.85789 | 0.79304 | 0.67826 | 2.59202 | 2.18060 |
| 419 | 0.80952 | 0.91714 | 0.86316 | 0.77895 | 0.91652 | 0.77043 | 2.58920 | 2.46653 |
| 590 | 0.87206 | 0.74159 | 0.91053 | 0.97368 | 0.80348 | 0.82783 | 2.58607 | 2.54310 |
| 198 | 0.86889 | 0.89460 | 0.85789 | 0.80526 | 0.85391 | 0.95478 | 2.58070 | 2.65465 |
| 575 | 0.81143 | 0.91397 | 0.89474 | 0.80526 | 0.86957 | 0.91652 | 2.57573 | 2.63575 |
| 359 | 0.86889 | 0.89714 | 0.81579 | 0.78421 | 0.88870 | 0.94783 | 2.57337 | 2.62918 |
| 681 | 0.85079 | 0.55873 | 0.86842 | 0.91053 | 0.84348 | 0.85391 | 2.56269 | 2.32317 |
| 682 | 0.81556 | 0.52825 | 0.92632 | 0.95789 | 0.81913 | 0.72000 | 2.56100 | 2.20615 |
| 166 | 0.80540 | 0.89714 | 0.84737 | 0.77895 | 0.90783 | 0.78957 | 2.56059 | 2.46566 |
| 628 | 0.86000 | 0.58413 | 0.89474 | 0.91579 | 0.80522 | 0.61565 | 2.55995 | 2.11557 |
| 340 | 0.88317 | 0.66667 | 0.88421 | 0.71579 | 0.79130 | 0.80870 | 2.55869 | 2.19115 |
| 667 | 0.84222 | 0.50762 | 0.85789 | 0.83158 | 0.85739 | 0.68348 | 2.55751 | 2.02268 |
| 321 | 0.87714 | 0.88762 | 0.82105 | 0.77895 | 0.85913 | 0.95478 | 2.55733 | 2.62135 |
| 594 | 0.83175 | 0.66444 | 0.94737 | 0.87368 | 0.77565 | 0.68174 | 2.55477 | 2.21987 |
| 185 | 0.81302 | 0.90889 | 0.83684 | 0.82632 | 0.90261 | 0.94435 | 2.55247 | 2.67955 |
| 230 | 0.79587 | 0.52603 | 0.95263 | 0.75789 | 0.80174 | 0.54783 | 2.55024 | 1.83175 |
| 624 | 0.86413 | 0.58762 | 0.87368 | 0.97895 | 0.81217 | 0.71652 | 2.54999 | 2.28309 |
| 378 | 0.78413 | 0.88444 | 0.83158 | 0.76316 | 0.93043 | 0.92522 | 2.54614 | 2.57282 |
| 533 | 0.80190 | 0.89587 | 0.89474 | 0.75789 | 0.84870 | 0.92174 | 2.54534 | 2.57551 |
| 586 | 0.83016 | 0.62794 | 0.94737 | 0.93158 | 0.76348 | 0.66087 | 2.54101 | 2.22039 |
| 88 | 0.77651 | 0.94000 | 0.85263 | 0.80526 | 0.91130 | 0.86783 | 2.54044 | 2.61309 |
| 173 | 0.79968 | 0.56921 | 0.91053 | 0.81053 | 0.82957 | 0.81913 | 2.53977 | 2.19886 |
| 560 | 0.78127 | 0.90063 | 0.86316 | 0.68421 | 0.89391 | 0.94609 | 2.53834 | 2.53093 |
| 273 | 0.82349 | 0.60825 | 0.92105 | 0.72105 | 0.79304 | 0.68000 | 2.53759 | 2.00931 |
| 346 | 0.77651 | 0.87937 | 0.81579 | 0.80526 | 0.94435 | 0.92348 | 2.53665 | 2.60811 |
| 188 | 0.82032 | 0.57460 | 0.94737 | 0.78947 | 0.76870 | 0.54783 | 2.53638 | 1.91190 |
| 381 | 0.84698 | 0.58508 | 0.86316 | 0.86316 | 0.82609 | 0.69739 | 2.53623 | 2.14563 |
| 680 | 0.80698 | 0.93619 | 0.84737 | 0.85789 | 0.88000 | 0.96174 | 2.53435 | 2.75582 |
| 70 | 0.80063 | 0.89810 | 0.83158 | 0.78947 | 0.90087 | 0.76348 | 2.53308 | 2.45105 |
| 323 | 0.82762 | 0.86889 | 0.84211 | 0.67368 | 0.85913 | 0.94609 | 2.52885 | 2.48866 |
| 551 | 0.75016 | 0.88889 | 0.86316 | 0.68947 | 0.91130 | 0.94957 | 2.52462 | 2.52793 |
| 388 | 0.89460 | 0.64000 | 0.87895 | 0.99474 | 0.74435 | 0.78435 | 2.51790 | 2.41908 |
| 486 | 0.78476 | 0.90476 | 0.90526 | 0.81053 | 0.82783 | 0.95826 | 2.51785 | 2.67355 |
| 87 | 0.80889 | 0.92794 | 0.79474 | 0.87368 | 0.91130 | 0.96174 | 2.51493 | 2.76336 |
| 493 | 0.82444 | 0.90730 | 0.80000 | 0.79474 | 0.89043 | 0.95652 | 2.51488 | 2.65856 |
| 74 | 0.84825 | 0.92794 | 0.84737 | 0.89474 | 0.81913 | 0.89913 | 2.51475 | 2.72180 |
| 149 | 0.78794 | 0.89492 | 0.84211 | 0.76316 | 0.88174 | 0.75304 | 2.51178 | 2.41112 |
| 541 | 0.83746 | 0.93016 | 0.87368 | 0.88421 | 0.79652 | 0.94609 | 2.50767 | 2.76046 |
| 183 | 0.80730 | 0.55968 | 0.91053 | 0.81579 | 0.78783 | 0.69565 | 2.50565 | 2.07112 |
| 385 | 0.74254 | 0.87492 | 0.89474 | 1.00000 | 0.86435 | 0.89217 | 2.50162 | 2.76709 |
| 534 | 0.77365 | 0.90190 | 0.91053 | 0.70000 | 0.81739 | 0.94261 | 2.50157 | 2.54451 |
| 620 | 0.83746 | 0.50540 | 0.86842 | 0.96842 | 0.79304 | 0.56348 | 2.49892 | 2.03730 |
| 420 | 0.78381 | 0.92825 | 0.82632 | 0.82105 | 0.88522 | 0.85913 | 2.49534 | 2.60844 |
| 184 | 0.83810 | 0.93048 | 0.82105 | 0.90000 | 0.83478 | 0.88870 | 2.49393 | 2.71917 |
| 285 | 0.80286 | 0.66063 | 0.87895 | 0.97368 | 0.81043 | 0.75130 | 2.49224 | 2.38562 |
| 379 | 0.71397 | 0.88286 | 0.88947 | 0.98947 | 0.88696 | 0.88696 | 2.49040 | 2.75929 |
| 574 | 0.84254 | 0.92698 | 0.83684 | 0.87368 | 0.80696 | 0.87652 | 2.48634 | 2.67719 |
| 357 | 0.83333 | 0.89968 | 0.77368 | 0.78421 | 0.87826 | 0.94957 | 2.48528 | 2.63346 |
| 679 | 0.82540 | 0.94952 | 0.87368 | 0.88947 | 0.78609 | 0.93043 | 2.48517 | 2.76943 |
| 589 | 0.80444 | 0.90825 | 0.81053 | 0.74211 | 0.86957 | 0.91304 | 2.48454 | 2.56340 |
| 199 | 0.79333 | 0.91270 | 0.77368 | 0.77895 | 0.91652 | 0.92000 | 2.48354 | 2.61165 |
| 694 | 0.79683 | 0.92762 | 0.76842 | 0.81053 | 0.91652 | 0.93913 | 2.48177 | 2.67728 |

TABLE 10-continued

| | | | | | | | | |
|---|---|---|---|---|---|---|---|---|
| 200 | 0.75492 | 0.92984 | 0.84211 | 0.70526 | 0.88000 | 0.85565 | 2.47703 | 2.49076 |
| 656 | 0.84159 | 0.86921 | 0.89474 | 0.73158 | 0.72348 | 0.94957 | 2.45980 | 2.55035 |
| 69 | 0.76349 | 0.88413 | 0.86316 | 0.81053 | 0.82957 | 0.83130 | 2.45622 | 2.52596 |
| 371 | 0.80317 | 0.90317 | 0.75789 | 0.77368 | 0.89391 | 0.94435 | 2.45498 | 2.62121 |
| 286 | 0.84032 | 0.56000 | 0.88421 | 0.97368 | 0.73043 | 0.69391 | 2.45496 | 2.22760 |
| 187 | 0.77079 | 0.53460 | 0.95789 | 0.79474 | 0.72348 | 0.57043 | 2.45217 | 1.89977 |
| 435 | 0.85937 | 0.67810 | 0.84737 | 0.95789 | 0.74435 | 0.76348 | 2.45108 | 2.39947 |
| 397 | 0.85683 | 0.61619 | 0.83158 | 0.90000 | 0.76174 | 0.78087 | 2.45014 | 2.29706 |
| 313 | 0.84857 | 0.92984 | 0.85263 | 0.91053 | 0.74783 | 0.95826 | 2.44903 | 2.79863 |
| 360 | 0.80381 | 0.92222 | 0.73158 | 0.78421 | 0.91304 | 0.95826 | 2.44843 | 2.66469 |
| 195 | 0.77365 | 0.89143 | 0.76316 | 0.82105 | 0.90957 | 0.94957 | 2.44637 | 2.66205 |
| 505 | 0.79460 | 0.68857 | 0.85789 | 0.95263 | 0.79130 | 0.73043 | 2.44380 | 2.37164 |
| 506 | 0.82540 | 0.64508 | 0.89474 | 0.94211 | 0.72348 | 0.71304 | 2.44361 | 2.30023 |
| 582 | 0.78032 | 0.90857 | 0.79474 | 0.77895 | 0.86783 | 0.89913 | 2.44288 | 2.58665 |
| 687 | 0.77683 | 0.92857 | 0.77895 | 0.83684 | 0.88696 | 0.96000 | 2.44273 | 2.72541 |
| 361 | 0.76381 | 0.93651 | 0.78421 | 0.73684 | 0.88522 | 0.88000 | 2.43324 | 2.55335 |
| 559 | 0.78889 | 0.89905 | 0.78421 | 0.62632 | 0.85913 | 0.94783 | 2.43223 | 2.47319 |
| 583 | 0.81619 | 0.51619 | 0.90526 | 0.82632 | 0.70957 | 0.56000 | 2.43102 | 1.90251 |
| 77 | 0.77079 | 0.92190 | 0.84211 | 0.75789 | 0.81565 | 0.82783 | 2.42855 | 2.50763 |
| 172 | 0.80857 | 0.48857 | 0.86316 | 0.80000 | 0.75304 | 0.48696 | 2.42477 | 1.77553 |
| 210 | 0.78571 | 0.90540 | 0.74737 | 0.82632 | 0.88870 | 0.94087 | 2.42178 | 2.67258 |
| 585 | 0.83143 | 0.59746 | 0.87368 | 0.81053 | 0.71652 | 0.60522 | 2.42163 | 2.01320 |
| 608 | 0.76349 | 0.92159 | 0.86842 | 0.83158 | 0.78957 | 0.86087 | 2.42148 | 2.61404 |
| 389 | 0.84000 | 0.62603 | 0.81579 | 0.94211 | 0.76174 | 0.80000 | 2.41753 | 2.36814 |
| 563 | 0.81683 | 0.57270 | 0.82632 | 0.86842 | 0.77391 | 0.72696 | 2.41705 | 2.16808 |
| 83 | 0.77873 | 0.89746 | 0.77368 | 0.82105 | 0.86435 | 0.94435 | 2.41676 | 2.66286 |
| 186 | 0.79556 | 0.58190 | 0.88947 | 0.77368 | 0.73043 | 0.74087 | 2.41546 | 2.09646 |
| 434 | 0.77556 | 0.91905 | 0.77895 | 0.74211 | 0.85913 | 0.87130 | 2.41363 | 2.53246 |
| 382 | 0.85429 | 0.61079 | 0.84211 | 0.90000 | 0.71652 | 0.77043 | 2.41291 | 2.28123 |
| 178 | 0.78540 | 0.49714 | 0.86842 | 0.81053 | 0.75652 | 0.56870 | 2.41034 | 1.87636 |
| 279 | 0.80603 | 0.48000 | 0.82632 | 0.88421 | 0.77217 | 0.63652 | 2.40452 | 2.00073 |
| 499 | 0.80032 | 0.58667 | 0.82632 | 0.91053 | 0.77565 | 0.62609 | 2.40229 | 2.12328 |
| 396 | 0.84190 | 0.60921 | 0.81579 | 0.85789 | 0.74261 | 0.75652 | 2.40030 | 2.22362 |
| 89 | 0.73302 | 0.92032 | 0.78947 | 0.70526 | 0.87652 | 0.86087 | 2.39901 | 2.48645 |
| 245 | 0.79873 | 0.90540 | 0.87895 | 0.83158 | 0.72000 | 0.95478 | 2.39768 | 2.69176 |
| 427 | 0.75651 | 0.91873 | 0.81053 | 0.71053 | 0.82783 | 0.81391 | 2.39486 | 2.44317 |
| 578 | 0.82857 | 0.58032 | 0.89474 | 0.85789 | 0.65565 | 0.53739 | 2.37896 | 1.97560 |
| 196 | 0.78635 | 0.89746 | 0.78421 | 0.81579 | 0.80522 | 0.94435 | 2.37578 | 2.65760 |
| 167 | 0.75111 | 0.92063 | 0.74211 | 0.83158 | 0.88174 | 0.89739 | 2.37496 | 2.64961 |
| 639 | 0.75841 | 0.88571 | 0.74211 | 0.66842 | 0.87304 | 0.90609 | 2.37356 | 2.46022 |
| 390 | 0.71873 | 0.89238 | 0.84737 | 0.98947 | 0.80174 | 0.89565 | 2.36784 | 2.77751 |
| 393 | 0.69048 | 0.87143 | 0.77895 | 0.98947 | 0.89739 | 0.89739 | 2.36681 | 2.75829 |
| 597 | 0.82159 | 0.55651 | 0.76316 | 0.85263 | 0.78087 | 0.65043 | 2.36561 | 2.05957 |
| 507 | 0.79810 | 0.62635 | 0.87368 | 0.87895 | 0.69043 | 0.65739 | 2.36221 | 2.16269 |
| 82 | 0.75397 | 0.92190 | 0.74211 | 0.83158 | 0.86609 | 0.85565 | 2.36216 | 2.60914 |
| 356 | 0.77556 | 0.89397 | 0.68947 | 0.80000 | 0.89391 | 0.93739 | 2.35894 | 2.63136 |
| 619 | 0.85238 | 0.51651 | 0.75263 | 0.83158 | 0.75304 | 0.52696 | 2.35806 | 1.87504 |
| 262 | 0.81333 | 0.62222 | 0.80526 | 0.82105 | 0.73913 | 0.74087 | 2.35773 | 2.18414 |
| 362 | 0.72413 | 0.90159 | 0.74211 | 0.67368 | 0.89043 | 0.85739 | 2.35667 | 2.43266 |
| 644 | 0.77683 | 0.90571 | 0.80526 | 0.83158 | 0.77391 | 0.96870 | 2.35600 | 2.70599 |
| 263 | 0.85778 | 0.52889 | 0.85789 | 0.83684 | 0.63652 | 0.65739 | 2.35219 | 2.02312 |
| 395 | 0.69587 | 0.87873 | 0.78947 | 0.99474 | 0.86609 | 0.89913 | 2.35143 | 2.77260 |
| 33 | 0.75778 | 0.89270 | 0.76842 | 0.67895 | 0.82261 | 0.86435 | 2.34881 | 2.43599 |
| 287 | 0.78794 | 0.55238 | 0.83158 | 0.91053 | 0.72870 | 0.65565 | 2.34821 | 2.11856 |
| 240 | 0.73937 | 0.89841 | 0.71053 | 0.69474 | 0.89739 | 0.94609 | 2.34728 | 2.53924 |
| 638 | 0.76730 | 0.88921 | 0.82632 | 0.78421 | 0.75304 | 0.92870 | 2.34666 | 2.60211 |
| 665 | 0.73111 | 0.89175 | 0.78421 | 0.66842 | 0.83130 | 0.84000 | 2.34663 | 2.40017 |
| 449 | 0.72286 | 0.90159 | 0.85263 | 0.80526 | 0.76870 | 0.95826 | 2.34418 | 2.66511 |
| 526 | 0.79492 | 0.67397 | 0.85263 | 0.95263 | 0.69217 | 0.68522 | 2.33973 | 2.31182 |
| 617 | 0.82063 | 0.58540 | 0.77368 | 0.82105 | 0.74261 | 0.49043 | 2.33693 | 1.89688 |
| 306 | 0.82667 | 0.88286 | 0.87895 | 0.70526 | 0.63130 | 0.92348 | 2.33692 | 2.51160 |
| 573 | 0.81683 | 0.56127 | 0.80526 | 0.86316 | 0.71478 | 0.63304 | 2.33687 | 2.05747 |
| 612 | 0.84317 | 0.53016 | 0.78947 | 0.85263 | 0.70261 | 0.55652 | 2.33526 | 1.93931 |
| 256 | 0.79238 | 0.52317 | 0.77895 | 0.74737 | 0.76174 | 0.60000 | 2.33307 | 1.87054 |
| 611 | 0.80063 | 0.56254 | 0.84737 | 0.91053 | 0.68348 | 0.58609 | 2.33148 | 2.05915 |
| 431 | 0.79016 | 0.61333 | 0.84211 | 0.97368 | 0.69739 | 0.65217 | 2.32966 | 2.23919 |
| 515 | 0.79238 | 0.63810 | 0.84211 | 0.90000 | 0.69391 | 0.70783 | 2.32840 | 2.24592 |
| 577 | 0.76825 | 0.54127 | 0.93158 | 0.87368 | 0.62435 | 0.52696 | 2.32418 | 1.94191 |
| 239 | 0.74698 | 0.88730 | 0.73158 | 0.77895 | 0.84522 | 0.94261 | 2.32378 | 2.60886 |
| 30 | 0.79937 | 0.60159 | 0.74211 | 0.89474 | 0.78087 | 0.81391 | 2.32234 | 2.31024 |
| 609 | 0.72921 | 0.90952 | 0.78947 | 0.80526 | 0.80348 | 0.93217 | 2.32216 | 2.64696 |
| 294 | 0.78794 | 0.55079 | 0.82105 | 0.88947 | 0.70783 | 0.63652 | 2.31682 | 2.07679 |
| 478 | 0.77873 | 0.92825 | 0.83158 | 0.88947 | 0.70087 | 0.95826 | 2.31118 | 2.77599 |
| 607 | 0.82254 | 0.56444 | 0.75263 | 0.83684 | 0.73565 | 0.54261 | 2.31082 | 1.94390 |
| 584 | 0.72571 | 0.88476 | 0.73684 | 0.62632 | 0.84348 | 0.89565 | 2.30603 | 2.40673 |
| 338 | 0.75016 | 0.91365 | 0.77895 | 0.88947 | 0.77565 | 0.92000 | 2.30476 | 2.72312 |
| 295 | 0.79016 | 0.56635 | 0.81053 | 0.92105 | 0.70261 | 0.70087 | 2.30329 | 2.18827 |
| 689 | 0.71810 | 0.91651 | 0.69474 | 0.75789 | 0.89043 | 0.93913 | 2.30327 | 2.61353 |
| 500 | 0.79302 | 0.64032 | 0.84211 | 0.91053 | 0.66435 | 0.69391 | 2.29947 | 2.24476 |
| 209 | 0.72095 | 0.90825 | 0.72632 | 0.73684 | 0.85217 | 0.84522 | 2.29944 | 2.49031 |

TABLE 10-continued

| | | | | | | | | |
|---|---|---|---|---|---|---|---|---|
| 514 | 0.78190 | 0.62317 | 0.82632 | 0.90000 | 0.69043 | 0.64522 | 2.29866 | 2.16839 |
| 201 | 0.70889 | 0.90413 | 0.73158 | 0.67895 | 0.85739 | 0.82261 | 2.29786 | 2.40568 |
| 38 | 0.85365 | 0.51333 | 0.73158 | 0.90526 | 0.70957 | 0.75826 | 2.29479 | 2.17686 |
| 491 | 0.83206 | 0.89143 | 0.80000 | 0.69474 | 0.66261 | 0.94435 | 2.29467 | 2.53051 |
| 355 | 0.73302 | 0.91937 | 0.71053 | 0.74211 | 0.85043 | 0.83478 | 2.29398 | 2.49625 |
| 150 | 0.72381 | 0.91873 | 0.72632 | 0.83158 | 0.84348 | 0.86609 | 2.29360 | 2.61640 |
| 34 | 0.73968 | 0.92476 | 0.70000 | 0.64737 | 0.85043 | 0.90957 | 2.29012 | 2.48170 |
| 280 | 0.79302 | 0.56508 | 0.82632 | 0.91579 | 0.66957 | 0.66957 | 2.28890 | 2.15043 |
| 370 | 0.73460 | 0.91778 | 0.68947 | 0.74211 | 0.86435 | 0.88348 | 2.28842 | 2.54336 |
| 3 | 0.77333 | 0.53873 | 0.73684 | 0.77895 | 0.77565 | 0.66087 | 2.28583 | 1.97855 |
| 400 | 0.70127 | 0.91238 | 0.78947 | 1.00000 | 0.79478 | 0.90783 | 2.28553 | 2.82021 |
| 194 | 0.72127 | 0.91048 | 0.72105 | 0.74211 | 0.84174 | 0.79478 | 2.28406 | 2.44736 |
| 658 | 0.77429 | 0.89587 | 0.70000 | 0.81053 | 0.80870 | 0.96870 | 2.28298 | 2.67509 |
| 463 | 0.69302 | 0.90540 | 0.76842 | 0.75789 | 0.81913 | 0.95652 | 2.28057 | 2.61981 |
| 640 | 0.70508 | 0.91683 | 0.77368 | 0.61053 | 0.80174 | 0.82783 | 2.28050 | 2.35518 |
| 241 | 0.69175 | 0.91714 | 0.73684 | 0.63684 | 0.85043 | 0.87130 | 2.27902 | 2.42529 |
| 602 | 0.81143 | 0.58921 | 0.77895 | 0.77895 | 0.68522 | 0.41043 | 2.27559 | 1.77859 |
| 129 | 0.79016 | 0.60413 | 0.79474 | 0.92632 | 0.69043 | 0.65391 | 2.27533 | 2.18436 |
| 474 | 0.73841 | 0.92413 | 0.67895 | 0.58421 | 0.85565 | 0.89739 | 2.27301 | 2.40573 |
| 660 | 0.72698 | 0.89333 | 0.77368 | 0.63158 | 0.77217 | 0.78435 | 2.27284 | 2.30926 |
| 72 | 0.78571 | 0.93238 | 0.77895 | 0.90526 | 0.70609 | 0.95652 | 2.27075 | 2.79417 |
| 64 | 0.80952 | 0.59492 | 0.72632 | 0.88421 | 0.73391 | 0.75478 | 2.26975 | 2.23391 |
| 283 | 0.62794 | 0.82984 | 0.85789 | 1.00000 | 0.78087 | 0.88870 | 2.26670 | 2.71854 |
| 610 | 0.82159 | 0.53492 | 0.79474 | 0.82105 | 0.64870 | 0.65043 | 2.26502 | 2.00641 |
| 41 | 0.72413 | 0.92286 | 0.79474 | 0.65789 | 0.74609 | 0.76870 | 2.26495 | 2.34945 |
| 562 | 0.82095 | 0.54222 | 0.81053 | 0.80526 | 0.63130 | 0.51826 | 2.26278 | 1.86575 |
| 81 | 0.72349 | 0.91810 | 0.73684 | 0.81579 | 0.80174 | 0.90783 | 2.26207 | 2.64171 |
| 291 | 0.55968 | 0.84698 | 0.82105 | 0.97895 | 0.88000 | 0.85217 | 2.26074 | 2.67811 |
| 155 | 0.79429 | 0.48508 | 0.74737 | 0.76842 | 0.71826 | 0.74609 | 2.25992 | 1.99959 |
| 703 | 0.72063 | 0.92159 | 0.74211 | 0.79474 | 0.79478 | 0.95826 | 2.25752 | 2.67459 |
| 429 | 0.70794 | 0.89270 | 0.74211 | 0.61053 | 0.80348 | 0.84348 | 2.25352 | 2.34670 |
| 567 | 0.71429 | 0.89841 | 0.77368 | 0.65263 | 0.76174 | 0.83130 | 2.24971 | 2.38235 |
| 475 | 0.70349 | 0.92730 | 0.75263 | 0.52105 | 0.79130 | 0.80000 | 2.24743 | 2.24835 |
| 566 | 0.73270 | 0.89365 | 0.76316 | 0.71053 | 0.75130 | 0.79304 | 2.24716 | 2.39722 |
| 623 | 0.71492 | 0.90857 | 0.72632 | 0.77368 | 0.80522 | 0.93391 | 2.24645 | 2.61617 |
| 220 | 0.87365 | 0.56381 | 0.72105 | 0.88421 | 0.64870 | 0.42087 | 2.24340 | 1.86889 |
| 374 | 0.81206 | 0.89746 | 0.78947 | 0.78421 | 0.64174 | 0.94261 | 2.24328 | 2.62428 |
| 65 | 0.85556 | 0.52095 | 0.75263 | 0.90000 | 0.63478 | 0.66957 | 2.24297 | 2.09052 |
| 58 | 0.77365 | 0.54127 | 0.73684 | 0.75789 | 0.73043 | 0.59826 | 2.24093 | 1.89743 |
| 123 | 0.79175 | 0.52444 | 0.76842 | 0.79474 | 0.68000 | 0.52870 | 2.24017 | 1.84788 |
| 130 | 0.84095 | 0.51683 | 0.79474 | 0.93158 | 0.60174 | 0.57217 | 2.23743 | 2.02058 |
| 219 | 0.81365 | 0.56413 | 0.71579 | 0.88421 | 0.70783 | 0.67304 | 2.23727 | 2.12138 |
| 42 | 0.71429 | 0.92730 | 0.74211 | 0.58947 | 0.77739 | 0.78783 | 2.23378 | 2.30460 |
| 651 | 0.77524 | 0.89746 | 0.71579 | 0.83158 | 0.74261 | 0.96348 | 2.23364 | 2.69252 |
| 27 | 0.81492 | 0.89206 | 0.72632 | 0.78421 | 0.69217 | 0.90087 | 2.23341 | 2.57714 |
| 26 | 0.78952 | 0.88571 | 0.79474 | 0.78421 | 0.64870 | 0.91130 | 2.23296 | 2.58123 |
| 5 | 0.79429 | 0.49333 | 0.74737 | 0.76842 | 0.69043 | 0.72174 | 2.23209 | 1.98349 |
| 272 | 0.79302 | 0.51683 | 0.73684 | 0.71053 | 0.69739 | 0.70435 | 2.22725 | 1.93170 |
| 503 | 0.65651 | 0.83048 | 0.82105 | 0.98947 | 0.74957 | 0.80522 | 2.22713 | 2.62517 |
| 448 | 0.72381 | 0.90730 | 0.82632 | 0.89474 | 0.67652 | 0.96348 | 2.22665 | 2.76552 |
| 411 | 0.72921 | 0.90540 | 0.80000 | 0.67895 | 0.69565 | 0.74609 | 2.22486 | 2.33043 |
| 47 | 0.77016 | 0.47651 | 0.72105 | 0.78947 | 0.73217 | 0.73565 | 2.22339 | 2.00163 |
| 208 | 0.69968 | 0.90095 | 0.71053 | 0.75789 | 0.81043 | 0.81565 | 2.22064 | 2.47450 |
| 596 | 0.81937 | 0.56413 | 0.70526 | 0.83684 | 0.69565 | 0.54957 | 2.22028 | 1.95053 |
| 108 | 0.74825 | 0.53175 | 0.82105 | 0.86316 | 0.65043 | 0.48174 | 2.21974 | 1.87664 |
| 165 | 0.79460 | 0.49873 | 0.73684 | 0.76316 | 0.68522 | 0.69043 | 2.21666 | 1.95232 |
| 354 | 0.70000 | 0.90540 | 0.72105 | 0.71053 | 0.79478 | 0.90261 | 2.21584 | 2.51853 |
| 305 | 0.83556 | 0.87397 | 0.81053 | 0.77368 | 0.56870 | 0.93217 | 2.21478 | 2.57983 |
| 369 | 0.70444 | 0.90825 | 0.68421 | 0.75263 | 0.82609 | 0.86435 | 2.21474 | 2.52523 |
| 576 | 0.80952 | 0.57492 | 0.83684 | 0.84211 | 0.56696 | 0.58261 | 2.21332 | 1.99963 |
| 593 | 0.71714 | 0.88921 | 0.71053 | 0.61053 | 0.78435 | 0.83652 | 2.21202 | 2.33625 |
| 221 | 0.78381 | 0.49016 | 0.74211 | 0.75263 | 0.68174 | 0.61913 | 2.20765 | 1.86192 |
| 445 | 0.70825 | 0.93238 | 0.72632 | 0.52105 | 0.77217 | 0.85565 | 2.20674 | 2.30909 |
| 568 | 0.78730 | 0.48159 | 0.77368 | 0.87895 | 0.64522 | 0.48348 | 2.20620 | 1.84401 |
| 251 | 0.71683 | 0.88508 | 0.61579 | 0.77368 | 0.87304 | 0.92000 | 2.20566 | 2.57876 |
| 444 | 0.73683 | 0.93333 | 0.64737 | 0.55789 | 0.81913 | 0.92870 | 2.20332 | 2.41992 |
| 592 | 0.73492 | 0.88381 | 0.66842 | 0.62105 | 0.79823 | 0.85043 | 2.20160 | 2.35530 |
| 138 | 0.77556 | 0.50444 | 0.72632 | 0.77368 | 0.69913 | 0.70609 | 2.20100 | 1.98422 |
| 513 | 0.66095 | 0.82127 | 0.83158 | 0.98421 | 0.70783 | 0.85565 | 2.20036 | 2.66113 |
| 271 | 0.78317 | 0.49778 | 0.72632 | 0.68947 | 0.69043 | 0.61913 | 2.19993 | 1.80638 |
| 114 | 0.73778 | 0.58825 | 0.82632 | 0.96316 | 0.63478 | 0.57913 | 2.19888 | 2.13054 |
| 380 | 0.70222 | 0.89397 | 0.84737 | 0.98947 | 0.64870 | 0.91304 | 2.19829 | 2.79649 |
| 71 | 0.72000 | 0.92825 | 0.77895 | 0.91053 | 0.69913 | 0.96348 | 2.19808 | 2.80226 |
| 497 | 0.65778 | 0.82889 | 0.83684 | 0.98421 | 0.70261 | 0.83826 | 2.19723 | 2.65136 |
| 456 | 0.66349 | 0.90127 | 0.78421 | 0.77895 | 0.74783 | 0.96348 | 2.19553 | 2.64370 |
| 257 | 0.79143 | 0.51333 | 0.73158 | 0.71053 | 0.67130 | 0.66783 | 2.19431 | 1.89169 |
| 402 | 0.65841 | 0.88349 | 0.77368 | 1.00000 | 0.76000 | 0.89739 | 2.19210 | 2.78088 |
| 495 | 0.70698 | 0.90286 | 0.75789 | 0.52105 | 0.72522 | 0.76522 | 2.19010 | 2.18913 |
| 671 | 0.73270 | 0.91905 | 0.73684 | 0.80526 | 0.71826 | 0.93217 | 2.18780 | 2.65648 |
| 59 | 0.79429 | 0.50222 | 0.73158 | 0.76842 | 0.66087 | 0.64870 | 2.18673 | 1.91934 |

TABLE 10-continued

| | | | | | | | | |
|---|---|---|---|---|---|---|---|---|
| 151 | 0.81270 | 0.48349 | 0.80526 | 0.71579 | 0.56870 | 0.59478 | 2.18666 | 1.79406 |
| 511 | 0.61873 | 0.85111 | 0.76842 | 0.95789 | 0.79826 | 0.80348 | 2.18541 | 2.61248 |
| 412 | 0.71524 | 0.89968 | 0.76842 | 0.58947 | 0.70087 | 0.76174 | 2.18453 | 2.25090 |
| 213 | 0.76603 | 0.56984 | 0.71579 | 0.76842 | 0.70261 | 0.57391 | 2.18443 | 1.91218 |
| 616 | 0.69079 | 0.90159 | 0.73158 | 0.79474 | 0.76174 | 0.92000 | 2.18411 | 2.61632 |
| 229 | 0.78476 | 0.52667 | 0.70526 | 0.73684 | 0.69391 | 0.59304 | 2.18394 | 1.85655 |
| 170 | 0.77905 | 0.49238 | 0.74211 | 0.79474 | 0.66261 | 0.59826 | 2.18376 | 1.88538 |
| 168 | 0.83175 | 0.53079 | 0.78421 | 0.73684 | 0.56522 | 0.57391 | 2.18117 | 1.84155 |
| 650 | 0.71937 | 0.89333 | 0.64737 | 0.79474 | 0.81391 | 0.92174 | 2.18065 | 2.60981 |
| 264 | 0.77619 | 0.46698 | 0.71579 | 0.75263 | 0.68522 | 0.66261 | 2.17720 | 1.88222 |
| 641 | 0.65048 | 0.87302 | 0.70000 | 0.61579 | 0.82261 | 0.79652 | 2.17308 | 2.28533 |
| 193 | 0.67683 | 0.90000 | 0.72105 | 0.70000 | 0.77217 | 0.90087 | 2.17005 | 2.50087 |
| 35 | 0.76635 | 0.57016 | 0.74737 | 0.82632 | 0.65565 | 0.60174 | 2.16937 | 1.99821 |
| 95 | 0.83270 | 0.47079 | 0.79474 | 0.73684 | 0.54087 | 0.56348 | 2.16830 | 1.77111 |
| 465 | 0.70000 | 0.92952 | 0.72632 | 0.53158 | 0.74087 | 0.80696 | 2.16719 | 2.26806 |
| 512 | 0.67048 | 0.81683 | 0.72105 | 0.96842 | 0.77565 | 0.78957 | 2.16718 | 2.57481 |
| 115 | 0.78730 | 0.51587 | 0.82105 | 0.95789 | 0.55826 | 0.54957 | 2.16662 | 2.02333 |
| 116 | 0.74190 | 0.50698 | 0.83158 | 0.82105 | 0.59304 | 0.53739 | 2.16653 | 1.86543 |
| 29 | 0.78254 | 0.57365 | 0.71579 | 0.81053 | 0.66609 | 0.63130 | 2.16442 | 2.01548 |
| 277 | 0.58762 | 0.85365 | 0.86316 | 0.99474 | 0.71304 | 0.87652 | 2.16382 | 2.72491 |
| 124 | 0.77810 | 0.48984 | 0.74737 | 0.80000 | 0.63826 | 0.56522 | 2.16372 | 1.85506 |
| 101 | 0.87175 | 0.50667 | 0.76842 | 0.89474 | 0.52348 | 0.51478 | 2.16365 | 1.91619 |
| 461 | 0.80603 | 0.88730 | 0.70000 | 0.64211 | 0.65565 | 0.93217 | 2.16168 | 2.46158 |
| 148 | 0.77524 | 0.50571 | 0.70526 | 0.75263 | 0.68000 | 0.63478 | 2.16050 | 1.89313 |
| 214 | 0.78349 | 0.53206 | 0.71053 | 0.73158 | 0.66435 | 0.57391 | 2.15837 | 1.83756 |
| 228 | 0.76921 | 0.54222 | 0.70000 | 0.75789 | 0.68696 | 0.44000 | 2.15616 | 1.74012 |
| 662 | 0.65206 | 0.89937 | 0.80526 | 0.80526 | 0.69739 | 0.94957 | 2.15472 | 2.65419 |
| 2 | 0.77270 | 0.55873 | 0.71579 | 0.76316 | 0.66609 | 0.52870 | 2.15457 | 1.85058 |
| 66 | 0.76857 | 0.47841 | 0.70000 | 0.78421 | 0.68522 | 0.67304 | 2.15379 | 1.93567 |
| 18 | 0.75810 | 0.56825 | 0.73684 | 0.73158 | 0.65739 | 0.51826 | 2.15233 | 1.81809 |
| 169 | 0.73683 | 0.50952 | 0.81053 | 0.87368 | 0.60000 | 0.58783 | 2.14735 | 1.97103 |
| 153 | 0.76762 | 0.50286 | 0.71579 | 0.77895 | 0.66261 | 0.48522 | 2.14602 | 1.76702 |
| 473 | 0.75556 | 0.90127 | 0.68947 | 0.77895 | 0.70087 | 0.91826 | 2.14590 | 2.59848 |
| 242 | 0.63270 | 0.86571 | 0.66842 | 0.59474 | 0.84000 | 0.84174 | 2.14112 | 2.30219 |
| 109 | 0.73714 | 0.49238 | 0.81053 | 0.86316 | 0.59130 | 0.54261 | 2.13897 | 1.89815 |
| 176 | 0.73492 | 0.89397 | 0.65789 | 0.80000 | 0.74609 | 0.89391 | 2.13890 | 2.58788 |
| 100 | 0.83524 | 0.60635 | 0.77368 | 0.85263 | 0.52870 | 0.56174 | 2.13762 | 2.02072 |
| 154 | 0.76571 | 0.51206 | 0.72105 | 0.73684 | 0.65043 | 0.59130 | 2.13720 | 1.84021 |
| 643 | 0.73048 | 0.92730 | 0.75789 | 0.92105 | 0.64870 | 0.95652 | 2.13707 | 2.80488 |
| 408 | 0.78286 | 0.55524 | 0.66842 | 0.94211 | 0.68174 | 0.71652 | 2.13302 | 2.21387 |
| 394 | 0.68286 | 0.87619 | 0.58421 | 1.00000 | 0.86261 | 0.87826 | 2.12968 | 2.75445 |
| 94 | 0.79587 | 0.51016 | 0.75789 | 0.76842 | 0.57565 | 0.61913 | 2.12942 | 1.89771 |
| 152 | 0.73048 | 0.50571 | 0.78421 | 0.83684 | 0.61391 | 0.51130 | 2.12860 | 1.85386 |
| 160 | 0.74825 | 0.51651 | 0.73158 | 0.66842 | 0.64870 | 0.56000 | 2.12853 | 1.74493 |
| 1 | 0.56222 | 0.83016 | 0.67895 | 0.97368 | 0.88696 | 0.82609 | 2.12813 | 2.62993 |
| 293 | 0.58508 | 0.83587 | 0.83158 | 1.00000 | 0.70783 | 0.90087 | 2.12448 | 2.73674 |
| 697 | 0.71746 | 0.93016 | 0.63684 | 0.71579 | 0.76870 | 0.95478 | 2.12300 | 2.60073 |
| 50 | 0.66381 | 0.88032 | 0.71053 | 0.66316 | 0.74609 | 0.74087 | 2.12042 | 2.28434 |
| 672 | 0.71651 | 0.93683 | 0.66842 | 0.77895 | 0.73391 | 0.93739 | 2.11884 | 2.65316 |
| 698 | 0.71778 | 0.94762 | 0.63684 | 0.74737 | 0.76348 | 0.95304 | 2.11810 | 2.64803 |
| 131 | 0.76825 | 0.49492 | 0.72105 | 0.78947 | 0.62783 | 0.42261 | 2.11713 | 1.70700 |
| 177 | 0.71175 | 0.89746 | 0.61579 | 0.74737 | 0.78783 | 0.89565 | 2.11536 | 2.54048 |
| 334 | 0.72190 | 0.87937 | 0.65789 | 0.61053 | 0.73043 | 0.76696 | 2.11023 | 2.25685 |
| 470 | 0.67143 | 0.89619 | 0.77895 | 0.79474 | 0.65913 | 0.93043 | 2.10951 | 2.62136 |
| 649 | 0.66921 | 0.90000 | 0.62632 | 0.69474 | 0.81043 | 0.83304 | 2.10596 | 2.42778 |
| 17 | 0.60603 | 0.83968 | 0.66316 | 0.99474 | 0.83304 | 0.89217 | 2.10223 | 2.72659 |
| 657 | 0.57238 | 0.87238 | 0.64211 | 0.76316 | 0.88696 | 0.91130 | 2.10144 | 2.54684 |
| 236 | 0.62444 | 0.87810 | 0.62105 | 0.79474 | 0.85391 | 0.93565 | 2.09941 | 2.60848 |
| 4 | 0.76635 | 0.51683 | 0.69474 | 0.74211 | 0.63478 | 0.57391 | 2.09587 | 1.83284 |
| 518 | 0.64508 | 0.84921 | 0.81579 | 0.97368 | 0.63478 | 0.86783 | 2.09565 | 2.69072 |
| 443 | 0.74540 | 0.90000 | 0.63684 | 0.68947 | 0.71304 | 0.92696 | 2.09528 | 2.51643 |
| 634 | 0.67111 | 0.89841 | 0.63158 | 0.68947 | 0.79130 | 0.78609 | 2.09399 | 2.37397 |
| 37 | 0.84222 | 0.51143 | 0.67895 | 0.88947 | 0.57043 | 0.58609 | 2.09160 | 1.98699 |
| 520 | 0.64413 | 0.82095 | 0.84737 | 0.95789 | 0.60000 | 0.86957 | 2.09150 | 2.64841 |
| 555 | 0.73651 | 0.87206 | 0.73684 | 0.61053 | 0.61739 | 0.87130 | 2.09074 | 2.35389 |
| 143 | 0.74381 | 0.47333 | 0.71053 | 0.66842 | 0.63478 | 0.50609 | 2.08912 | 1.64784 |
| 421 | 0.80381 | 0.56730 | 0.74211 | 0.86316 | 0.54261 | 0.54957 | 2.08852 | 1.98002 |
| 137 | 0.75683 | 0.52413 | 0.67895 | 0.70000 | 0.65217 | 0.46957 | 2.08795 | 1.69369 |
| 252 | 0.75397 | 0.89683 | 0.80000 | 0.82632 | 0.53391 | 0.94957 | 2.08788 | 2.67271 |
| 418 | 0.78444 | 0.54444 | 0.66842 | 0.93158 | 0.63478 | 0.65913 | 2.08765 | 2.13515 |
| 298 | 0.59111 | 0.88381 | 0.80526 | 1.00000 | 0.69043 | 0.92000 | 2.08681 | 2.80381 |
| 423 | 0.76730 | 0.57206 | 0.71053 | 0.95263 | 0.60696 | 0.54087 | 2.08478 | 2.06556 |
| 250 | 0.65048 | 0.90159 | 0.60526 | 0.67368 | 0.82783 | 0.87826 | 2.08357 | 2.45353 |
| 633 | 0.62317 | 0.88254 | 0.69474 | 0.61579 | 0.76522 | 0.89739 | 2.08313 | 2.39572 |
| 488 | 0.57810 | 0.89778 | 0.70000 | 0.76842 | 0.80174 | 0.95826 | 2.07983 | 2.62446 |
| 348 | 0.49587 | 0.86762 | 0.67368 | 0.72632 | 0.90957 | 0.92000 | 2.07912 | 2.51393 |
| 235 | 0.65302 | 0.90222 | 0.60000 | 0.65789 | 0.82261 | 0.83652 | 2.07562 | 2.39664 |
| 351 | 0.74540 | 0.85365 | 0.70000 | 0.63684 | 0.62783 | 0.88348 | 2.07322 | 2.37397 |
| 19 | 0.75048 | 0.51905 | 0.71053 | 0.66316 | 0.61217 | 0.54261 | 2.07318 | 1.72481 |
| 446 | 0.67270 | 0.87333 | 0.62105 | 0.45789 | 0.77739 | 0.79652 | 2.07114 | 2.12775 |

TABLE 10-continued

| | | | | | | | | |
|---|---|---|---|---|---|---|---|---|
| 244 | 0.73397 | 0.93587 | 0.74737 | 0.92105 | 0.58957 | 0.97739 | 2.07090 | 2.83432 |
| 43 | 0.82952 | 0.54190 | 0.69474 | 0.94737 | 0.54435 | 0.45739 | 2.06861 | 1.94666 |
| 9 | 0.63302 | 0.88571 | 0.70526 | 0.64211 | 0.72870 | 0.84870 | 2.06697 | 2.37652 |
| 422 | 0.72476 | 0.55714 | 0.77895 | 0.96316 | 0.56174 | 0.49913 | 2.06545 | 2.01943 |
| 430 | 0.78127 | 0.59270 | 0.64737 | 0.89474 | 0.63478 | 0.62261 | 2.06342 | 2.11004 |
| 508 | 0.64698 | 0.84952 | 0.80526 | 0.96316 | 0.60696 | 0.89391 | 2.05920 | 2.70659 |
| 485 | 0.70476 | 0.89175 | 0.55789 | 0.70000 | 0.79304 | 0.92522 | 2.05570 | 2.51696 |
| 648 | 0.64032 | 0.87968 | 0.63684 | 0.67895 | 0.77739 | 0.80000 | 2.05455 | 2.35863 |
| 428 | 0.78032 | 0.50921 | 0.63684 | 0.95263 | 0.63652 | 0.57565 | 2.05368 | 2.03749 |
| 52 | 0.75683 | 0.51016 | 0.69474 | 0.71579 | 0.60174 | 0.46087 | 2.05330 | 1.68682 |
| 335 | 0.68889 | 0.89333 | 0.67368 | 0.54737 | 0.69043 | 0.70783 | 2.05301 | 2.14853 |
| 10 | 0.68190 | 0.90571 | 0.63158 | 0.71053 | 0.73913 | 0.73739 | 2.05261 | 2.35363 |
| 158 | 0.67937 | 0.90603 | 0.62105 | 0.72105 | 0.74609 | 0.78087 | 2.04650 | 2.40795 |
| 476 | 0.62635 | 0.85619 | 0.64211 | 0.45263 | 0.77565 | 0.77565 | 2.04411 | 2.08447 |
| 433 | 0.69968 | 0.88476 | 0.70526 | 0.47368 | 0.63826 | 0.70087 | 2.04321 | 2.05932 |
| 249 | 0.62635 | 0.89048 | 0.60526 | 0.66316 | 0.80870 | 0.86087 | 2.04031 | 2.41450 |
| 141 | 0.64825 | 0.89810 | 0.66842 | 0.70526 | 0.71652 | 0.75826 | 2.03320 | 2.36162 |
| 107 | 0.54381 | 0.82984 | 0.67368 | 0.98421 | 0.81565 | 0.85217 | 2.03315 | 2.66623 |
| 51 | 0.62603 | 0.86286 | 0.66842 | 0.39474 | 0.73739 | 0.77739 | 2.03184 | 2.03499 |
| 618 | 0.60159 | 0.88317 | 0.67368 | 0.68421 | 0.75304 | 0.92870 | 2.02831 | 2.49608 |
| 57 | 0.56508 | 0.82444 | 0.59474 | 0.96842 | 0.86435 | 0.86261 | 2.02416 | 2.65547 |
| 46 | 0.75460 | 0.50730 | 0.65263 | 0.74211 | 0.61565 | 0.57043 | 2.02289 | 1.81984 |
| 204 | 0.68254 | 0.89683 | 0.65789 | 0.84211 | 0.68174 | 0.96870 | 2.02217 | 2.70763 |
| 269 | 0.57524 | 0.82000 | 0.71053 | 0.97895 | 0.73565 | 0.74783 | 2.02142 | 2.54677 |
| 234 | 0.60349 | 0.87651 | 0.65789 | 0.61579 | 0.76000 | 0.88696 | 2.02139 | 2.37925 |
| 484 | 0.64095 | 0.90254 | 0.58421 | 0.62105 | 0.79304 | 0.81043 | 2.01821 | 2.33403 |
| 635 | 0.59968 | 0.88190 | 0.56316 | 0.81053 | 0.85043 | 0.94261 | 2.01328 | 2.63504 |
| 588 | 0.69873 | 0.87302 | 0.64737 | 0.56316 | 0.66609 | 0.71652 | 2.01219 | 2.15270 |
| 469 | 0.64000 | 0.90349 | 0.57895 | 0.62632 | 0.79304 | 0.76348 | 2.01199 | 2.29329 |
| 102 | 0.77238 | 0.52857 | 0.72632 | 0.78947 | 0.51130 | 0.52348 | 2.01000 | 1.84152 |
| 454 | 0.65810 | 0.90540 | 0.56316 | 0.62105 | 0.78609 | 0.84696 | 2.00734 | 2.37341 |
| 439 | 0.65810 | 0.90857 | 0.57895 | 0.61579 | 0.76870 | 0.77043 | 2.00574 | 2.29480 |
| 36 | 0.67619 | 0.88984 | 0.61579 | 0.51579 | 0.71304 | 0.76000 | 2.00502 | 2.16563 |
| 308 | 0.64254 | 0.87365 | 0.73158 | 0.65263 | 0.62609 | 0.88174 | 2.00021 | 2.40802 |
| 309 | 0.62825 | 0.86508 | 0.56316 | 0.59474 | 0.80522 | 0.89739 | 1.99663 | 2.35721 |
| 292 | 0.61619 | 0.81206 | 0.60526 | 0.98947 | 0.77391 | 0.84696 | 1.99537 | 2.64849 |
| 330 | 0.64381 | 0.86857 | 0.66842 | 0.78421 | 0.67826 | 0.87304 | 1.99049 | 2.52583 |
| 536 | 0.61048 | 0.89968 | 0.79474 | 0.59474 | 0.57913 | 0.89739 | 1.98434 | 2.39181 |
| 44 | 0.62095 | 0.89905 | 0.65789 | 0.54737 | 0.70261 | 0.69217 | 1.98146 | 2.13859 |
| 569 | 0.63968 | 0.88603 | 0.67368 | 0.53684 | 0.66783 | 0.76348 | 1.98119 | 2.18635 |
| 56 | 0.55302 | 0.83238 | 0.63158 | 0.97368 | 0.79652 | 0.77043 | 1.98112 | 2.57650 |
| 414 | 0.64381 | 0.86063 | 0.70000 | 0.55789 | 0.63652 | 0.65913 | 1.98033 | 2.07766 |
| 237 | 0.56254 | 0.89492 | 0.57895 | 0.76316 | 0.83826 | 0.94087 | 1.97975 | 2.59895 |
| 498 | 0.63778 | 0.85460 | 0.80526 | 0.95789 | 0.53043 | 0.91478 | 1.97348 | 2.72728 |
| 413 | 0.74254 | 0.53778 | 0.64737 | 0.91053 | 0.57739 | 0.47652 | 1.96730 | 1.92483 |
| 483 | 0.61778 | 0.88095 | 0.58947 | 0.62632 | 0.76000 | 0.78435 | 1.96725 | 2.29162 |
| 453 | 0.64032 | 0.89270 | 0.57368 | 0.56316 | 0.75304 | 0.78957 | 1.96705 | 2.24542 |
| 666 | 0.60921 | 0.88762 | 0.65789 | 0.73158 | 0.69913 | 0.88696 | 1.96623 | 2.50615 |
| 203 | 0.66413 | 0.92952 | 0.71053 | 0.92632 | 0.58957 | 0.97217 | 1.96422 | 2.82801 |
| 626 | 0.63937 | 0.88381 | 0.64211 | 0.67368 | 0.68174 | 0.88348 | 1.96321 | 2.44097 |
| 455 | 0.71556 | 0.89238 | 0.43684 | 0.73158 | 0.80870 | 0.92000 | 1.96109 | 2.54396 |
| 103 | 0.57524 | 0.84921 | 0.53158 | 0.97368 | 0.85391 | 0.79652 | 1.96073 | 2.61941 |
| 407 | 0.76603 | 0.56317 | 0.60000 | 0.91053 | 0.59304 | 0.44696 | 1.95908 | 1.92066 |
| 62 | 0.58794 | 0.84095 | 0.63684 | 0.99474 | 0.73043 | 0.84522 | 1.95521 | 2.68091 |
| 278 | 0.56159 | 0.87143 | 0.82105 | 0.99474 | 0.57217 | 0.93043 | 1.95481 | 2.79660 |
| 468 | 0.58190 | 0.87333 | 0.62105 | 0.57368 | 0.75130 | 0.86435 | 1.95426 | 2.31137 |
| 93 | 0.56349 | 0.84317 | 0.50526 | 0.96842 | 0.88522 | 0.87130 | 1.95397 | 2.68290 |
| 675 | 0.57937 | 0.77841 | 0.63684 | 0.47895 | 0.73739 | 0.75826 | 1.95360 | 2.01562 |
| 225 | 0.55333 | 0.84063 | 0.53684 | 0.97895 | 0.85739 | 0.79652 | 1.94757 | 2.61610 |
| 320 | 0.54984 | 0.86317 | 0.65789 | 0.57368 | 0.73913 | 0.90957 | 1.94687 | 2.34642 |
| 142 | 0.62222 | 0.88603 | 0.58421 | 0.65263 | 0.73043 | 0.76870 | 1.93687 | 2.30736 |
| 438 | 0.62254 | 0.88794 | 0.61579 | 0.59474 | 0.69739 | 0.89739 | 1.93572 | 2.38006 |
| 300 | 0.55238 | 0.83778 | 0.81579 | 1.00000 | 0.56000 | 0.90783 | 1.92817 | 2.74560 |
| 600 | 0.63333 | 0.88540 | 0.66316 | 0.72632 | 0.62957 | 0.84696 | 1.92606 | 2.45867 |
| 365 | 0.61016 | 0.90349 | 0.71053 | 0.82105 | 0.60174 | 0.96348 | 1.92242 | 2.68802 |
| 310 | 0.55492 | 0.88984 | 0.61579 | 0.62105 | 0.74783 | 0.78435 | 1.91854 | 2.29524 |
| 117 | 0.52571 | 0.83397 | 0.67368 | 0.98421 | 0.71652 | 0.79826 | 1.91592 | 2.61644 |
| 15 | 0.65429 | 0.89048 | 0.69474 | 0.81579 | 0.56348 | 0.92870 | 1.91250 | 2.63496 |
| 601 | 0.58571 | 0.88190 | 0.65263 | 0.67895 | 0.67130 | 0.87130 | 1.90965 | 2.43216 |
| 521 | 0.65333 | 0.79492 | 0.66316 | 0.96842 | 0.59304 | 0.85217 | 1.90953 | 2.61552 |
| 98 | 0.57365 | 0.84000 | 0.61579 | 0.98947 | 0.71652 | 0.59826 | 1.90596 | 2.42773 |
| 554 | 0.54762 | 0.87683 | 0.57368 | 0.51053 | 0.78261 | 0.94435 | 1.90391 | 2.33170 |
| 344 | 0.63937 | 0.89206 | 0.56842 | 0.61053 | 0.69565 | 0.72000 | 1.90344 | 2.22259 |
| 92 | 0.57048 | 0.83746 | 0.61053 | 0.98421 | 0.72000 | 0.71130 | 1.90100 | 2.53298 |
| 410 | 0.57968 | 0.67873 | 0.72632 | 0.55789 | 0.58957 | 0.56174 | 1.89556 | 1.79836 |
| 432 | 0.58540 | 0.84476 | 0.62632 | 0.63684 | 0.68348 | 0.73391 | 1.89519 | 2.21552 |
| 548 | 0.56667 | 0.87333 | 0.66842 | 0.58421 | 0.65913 | 0.86609 | 1.89422 | 2.32363 |
| 537 | 0.63873 | 0.90889 | 0.52632 | 0.62632 | 0.72870 | 0.82435 | 1.89374 | 2.35955 |
| 329 | 0.63651 | 0.89048 | 0.57368 | 0.61053 | 0.68348 | 0.68522 | 1.89367 | 2.18622 |
| 403 | 0.64222 | 0.87492 | 0.55263 | 0.99474 | 0.69739 | 0.91478 | 1.89225 | 2.78444 |

TABLE 10-continued

| | | | | | | | | |
|---|---|---|---|---|---|---|---|---|
| 492 | 0.55079 | 0.87937 | 0.53684 | 0.71579 | 0.80348 | 0.88870 | 1.89111 | 2.48385 |
| 336 | 0.62508 | 0.85079 | 0.61053 | 0.43684 | 0.65391 | 0.68174 | 1.88952 | 1.96937 |
| 653 | 0.58635 | 0.87556 | 0.58947 | 0.79474 | 0.70957 | 0.96000 | 1.88539 | 2.63029 |
| 13 | 0.58603 | 0.87619 | 0.58421 | 0.59474 | 0.70957 | 0.85565 | 1.87981 | 2.32658 |
| 458 | 0.56825 | 0.89810 | 0.59474 | 0.71579 | 0.71304 | 0.95478 | 1.87603 | 2.56867 |
| 372 | 0.60762 | 0.89524 | 0.52105 | 0.81053 | 0.74435 | 0.96000 | 1.87302 | 2.66576 |
| 180 | 0.55587 | 0.76159 | 0.64737 | 0.46316 | 0.66957 | 0.68348 | 1.87281 | 1.90822 |
| 288 | 0.57492 | 0.86571 | 0.82105 | 0.99474 | 0.47130 | 0.91826 | 1.86728 | 2.77871 |
| 159 | 0.64444 | 0.89810 | 0.42632 | 0.66842 | 0.79478 | 0.79652 | 1.86554 | 2.36304 |
| 136 | 0.55429 | 0.79937 | 0.67895 | 0.98947 | 0.62957 | 0.73391 | 1.86280 | 2.52275 |
| 627 | 0.58508 | 0.88317 | 0.60526 | 0.65789 | 0.66609 | 0.87478 | 1.85643 | 2.41585 |
| 255 | 0.55746 | 0.83333 | 0.57895 | 0.98947 | 0.71826 | 0.87130 | 1.85467 | 2.69411 |
| 425 | 0.56984 | 0.67873 | 0.71579 | 0.55263 | 0.56696 | 0.56870 | 1.85259 | 1.80006 |
| 440 | 0.51683 | 0.90540 | 0.67368 | 0.75789 | 0.66087 | 0.94783 | 1.85138 | 2.61112 |
| 424 | 0.59683 | 0.67270 | 0.71579 | 0.45263 | 0.53739 | 0.56870 | 1.85001 | 1.69403 |
| 14 | 0.64508 | 0.89968 | 0.43158 | 0.66842 | 0.77217 | 0.76174 | 1.84883 | 2.32984 |
| 636 | 0.61397 | 0.89778 | 0.60000 | 0.81053 | 0.63130 | 0.94087 | 1.84527 | 2.64917 |
| 254 | 0.60000 | 0.81683 | 0.55789 | 0.97368 | 0.68348 | 0.77565 | 1.84137 | 2.56616 |
| 686 | 0.55714 | 0.82603 | 0.56316 | 0.63158 | 0.71826 | 0.81913 | 1.83856 | 2.27674 |
| 693 | 0.68889 | 0.88889 | 0.58421 | 0.71579 | 0.56348 | 0.89739 | 1.83658 | 2.50207 |
| 270 | 0.54635 | 0.82159 | 0.54737 | 0.99474 | 0.73739 | 0.79130 | 1.83111 | 2.60763 |
| 268 | 0.47619 | 0.83143 | 0.53684 | 0.97368 | 0.81565 | 0.79304 | 1.82868 | 2.59816 |
| 343 | 0.61397 | 0.88667 | 0.57368 | 0.60526 | 0.63652 | 0.69913 | 1.82417 | 2.19106 |
| 179 | 0.61810 | 0.87460 | 0.55263 | 0.64211 | 0.65217 | 0.81043 | 1.82290 | 2.32714 |
| 122 | 0.50381 | 0.84603 | 0.48947 | 1.00000 | 0.82957 | 0.87826 | 1.82285 | 2.72429 |
| 692 | 0.55524 | 0.90286 | 0.56316 | 0.59474 | 0.70261 | 0.93565 | 1.82100 | 2.43325 |
| 112 | 0.53651 | 0.78159 | 0.70000 | 0.99474 | 0.58435 | 0.68174 | 1.82086 | 2.45806 |
| 587 | 0.58349 | 0.85397 | 0.52105 | 0.58947 | 0.70957 | 0.83478 | 1.81411 | 2.27822 |
| 701 | 0.55429 | 0.81492 | 0.63158 | 0.50000 | 0.62261 | 0.69565 | 1.80847 | 2.01057 |
| 135 | 0.49302 | 0.83238 | 0.52105 | 0.98421 | 0.78435 | 0.74435 | 1.79842 | 2.56094 |
| 226 | 0.50730 | 0.81111 | 0.68947 | 0.99474 | 0.60000 | 0.82435 | 1.79678 | 2.63020 |
| 333 | 0.68667 | 0.86127 | 0.60526 | 0.71053 | 0.50087 | 0.82957 | 1.79280 | 2.40136 |
| 106 | 0.53206 | 0.81714 | 0.70526 | 0.98421 | 0.55478 | 0.70783 | 1.79211 | 2.50918 |
| 345 | 0.69079 | 0.86889 | 0.44211 | 0.68421 | 0.65913 | 0.83826 | 1.79203 | 2.39136 |
| 676 | 0.48317 | 0.83206 | 0.66842 | 0.54211 | 0.64000 | 0.67826 | 1.79160 | 2.05243 |
| 331 | 0.52317 | 0.87111 | 0.56842 | 0.71579 | 0.69913 | 0.88870 | 1.79073 | 2.47560 |
| 328 | 0.57968 | 0.86476 | 0.58947 | 0.45263 | 0.62087 | 0.77565 | 1.79003 | 2.09305 |
| 120 | 0.55841 | 0.82127 | 0.55789 | 0.97368 | 0.67304 | 0.59826 | 1.78935 | 2.39321 |
| 181 | 0.52889 | 0.80413 | 0.66316 | 0.53158 | 0.59478 | 0.59478 | 1.78683 | 1.93049 |
| 145 | 0.61333 | 0.67492 | 0.57895 | 0.49474 | 0.59304 | 0.57913 | 1.78532 | 1.74879 |
| 132 | 0.51333 | 0.84317 | 0.53684 | 1.00000 | 0.73217 | 0.83652 | 1.78235 | 2.67970 |
| 604 | 0.61111 | 0.79365 | 0.57368 | 0.57368 | 0.59304 | 0.65565 | 1.77784 | 2.02299 |
| 319 | 0.53429 | 0.84095 | 0.48421 | 0.52632 | 0.75304 | 0.76696 | 1.77154 | 2.13422 |
| 625 | 0.57460 | 0.78000 | 0.60526 | 0.63158 | 0.58957 | 0.62957 | 1.76943 | 2.04114 |
| 311 | 0.48444 | 0.80254 | 0.56842 | 0.56316 | 0.71652 | 0.76000 | 1.76939 | 2.12570 |
| 260 | 0.58254 | 0.80889 | 0.43684 | 1.00000 | 0.74957 | 0.78957 | 1.76895 | 2.59845 |
| 558 | 0.59016 | 0.87397 | 0.60526 | 0.66842 | 0.56696 | 0.66957 | 1.76238 | 2.21195 |
| 217 | 0.54730 | 0.83905 | 0.54737 | 1.00000 | 0.66522 | 0.80522 | 1.75989 | 2.64427 |
| 31 | 0.61556 | 0.71365 | 0.57368 | 0.56842 | 0.56870 | 0.60348 | 1.75794 | 1.88555 |
| 304 | 0.53048 | 0.84286 | 0.48421 | 0.50526 | 0.73739 | 0.72174 | 1.75208 | 2.06986 |
| 275 | 0.60444 | 0.85079 | 0.52105 | 1.00000 | 0.62087 | 0.85739 | 1.74637 | 2.70818 |
| 661 | 0.52159 | 0.90413 | 0.67368 | 0.75789 | 0.54783 | 0.96000 | 1.74310 | 2.62202 |
| 547 | 0.53587 | 0.86762 | 0.51579 | 0.53158 | 0.69043 | 0.73043 | 1.74210 | 2.12963 |
| 415 | 0.56413 | 0.66984 | 0.64211 | 0.58947 | 0.53565 | 0.56000 | 1.74188 | 1.81931 |
| 144 | 0.54698 | 0.83333 | 0.53158 | 0.57368 | 0.66087 | 0.66783 | 1.73943 | 2.07484 |
| 364 | 0.62063 | 0.93333 | 0.60000 | 0.92632 | 0.51826 | 0.97565 | 1.73890 | 2.83530 |
| 622 | 0.59270 | 0.86413 | 0.57368 | 0.68421 | 0.57043 | 0.77565 | 1.73682 | 2.32399 |
| 32 | 0.61270 | 0.68476 | 0.59474 | 0.49474 | 0.52870 | 0.54783 | 1.73613 | 1.72732 |
| 700 | 0.59143 | 0.93079 | 0.60526 | 0.59474 | 0.53739 | 0.92522 | 1.73408 | 2.45075 |
| 91 | 0.60794 | 0.93016 | 0.60000 | 0.93684 | 0.52174 | 0.97043 | 1.72968 | 2.83744 |
| 409 | 0.58381 | 0.71397 | 0.58947 | 0.56316 | 0.55478 | 0.60696 | 1.72807 | 1.88408 |
| 162 | 0.60698 | 0.68349 | 0.57368 | 0.48947 | 0.54609 | 0.56348 | 1.72676 | 1.73644 |
| 121 | 0.54508 | 0.82825 | 0.65263 | 1.00000 | 0.52870 | 0.73043 | 1.72641 | 2.55869 |
| 25 | 0.56286 | 0.85365 | 0.46316 | 0.56842 | 0.69913 | 0.66261 | 1.72515 | 2.08468 |
| 212 | 0.53937 | 0.87365 | 0.47895 | 1.00000 | 0.70609 | 0.89913 | 1.72440 | 2.77278 |
| 161 | 0.56857 | 0.85270 | 0.45263 | 0.56842 | 0.70087 | 0.69565 | 1.72207 | 2.11677 |
| 615 | 0.59206 | 0.77873 | 0.57895 | 0.59474 | 0.54957 | 0.71478 | 1.72058 | 2.08825 |
| 595 | 0.60762 | 0.86413 | 0.49474 | 0.56316 | 0.61739 | 0.72174 | 1.71975 | 2.14902 |
| 416 | 0.59365 | 0.71778 | 0.62105 | 0.63684 | 0.50435 | 0.54261 | 1.71905 | 1.89723 |
| 674 | 0.62254 | 0.92254 | 0.49474 | 0.72105 | 0.59826 | 0.88348 | 1.71554 | 2.52707 |
| 318 | 0.51619 | 0.82476 | 0.49474 | 0.51579 | 0.70087 | 0.73565 | 1.71180 | 2.07620 |
| 605 | 0.53937 | 0.81587 | 0.58421 | 0.57895 | 0.58783 | 0.61217 | 1.71140 | 2.00699 |
| 156 | 0.53937 | 0.71238 | 0.56316 | 0.51053 | 0.60522 | 0.59826 | 1.70774 | 1.82117 |
| 496 | 0.60794 | 0.89746 | 0.52105 | 0.67368 | 0.56870 | 0.95130 | 1.69768 | 2.52245 |
| 39 | 0.53333 | 0.74476 | 0.61053 | 0.55263 | 0.55304 | 0.58087 | 1.69690 | 1.87826 |
| 53 | 0.45841 | 0.81619 | 0.61579 | 0.52105 | 0.61913 | 0.69043 | 1.69333 | 2.02768 |
| 630 | 0.59143 | 0.78603 | 0.51579 | 0.57895 | 0.58609 | 0.63130 | 1.69331 | 1.99628 |
| 45 | 0.64286 | 0.72286 | 0.57895 | 0.60000 | 0.46783 | 0.53565 | 1.68963 | 1.85851 |
| 303 | 0.51619 | 0.82000 | 0.47368 | 0.47368 | 0.69913 | 0.85217 | 1.68901 | 2.14586 |
| 6 | 0.53619 | 0.71175 | 0.56842 | 0.52632 | 0.58087 | 0.61043 | 1.68548 | 1.84850 |

TABLE 10-continued

| | | | | | | | | |
|---|---|---|---|---|---|---|---|---|
| 532 | 0.53556 | 0.86857 | 0.51579 | 0.51053 | 0.63130 | 0.69391 | 1.68265 | 2.07301 |
| 581 | 0.50381 | 0.74825 | 0.67368 | 0.51053 | 0.50435 | 0.66609 | 1.68184 | 1.92487 |
| 462 | 0.44508 | 0.88381 | 0.50526 | 0.67368 | 0.72870 | 0.90609 | 1.67904 | 2.46358 |
| 265 | 0.57778 | 0.82889 | 0.54737 | 0.98947 | 0.54783 | 0.82609 | 1.67297 | 2.64445 |
| 685 | 0.50222 | 0.78000 | 0.50526 | 0.53684 | 0.66261 | 0.67826 | 1.67009 | 1.99510 |
| 621 | 0.54095 | 0.83778 | 0.51053 | 0.47895 | 0.61565 | 0.85913 | 1.66713 | 2.17586 |
| 669 | 0.54571 | 0.78540 | 0.53158 | 0.47895 | 0.58957 | 0.75652 | 1.66686 | 2.02087 |
| 24 | 0.49143 | 0.83905 | 0.55789 | 0.53158 | 0.61217 | 0.77391 | 1.66150 | 2.14454 |
| 426 | 0.53016 | 0.75746 | 0.68421 | 0.54211 | 0.44348 | 0.58957 | 1.65785 | 1.88913 |
| 565 | 0.53651 | 0.76159 | 0.55263 | 0.47368 | 0.56870 | 0.58087 | 1.65784 | 1.81614 |
| 580 | 0.53365 | 0.76032 | 0.55263 | 0.47895 | 0.56522 | 0.59304 | 1.65150 | 1.83231 |
| 546 | 0.51619 | 0.84698 | 0.54211 | 0.52632 | 0.58783 | 0.69913 | 1.64612 | 2.07243 |
| 190 | 0.52190 | 0.76317 | 0.46842 | 0.43684 | 0.65217 | 0.65391 | 1.64250 | 1.85393 |
| 570 | 0.54825 | 0.75619 | 0.52632 | 0.60526 | 0.56696 | 0.59304 | 1.64153 | 1.95450 |
| 222 | 0.53238 | 0.87746 | 0.51579 | 1.00000 | 0.59130 | 0.86783 | 1.63947 | 2.74529 |
| 599 | 0.53683 | 0.79111 | 0.50000 | 0.50000 | 0.60000 | 0.61739 | 1.63683 | 1.90850 |
| 48 | 0.53937 | 0.73111 | 0.51579 | 0.55789 | 0.58087 | 0.59304 | 1.63602 | 1.88205 |
| 163 | 0.51365 | 0.71937 | 0.63158 | 0.45263 | 0.49043 | 0.56174 | 1.63566 | 1.73374 |
| 157 | 0.52222 | 0.67968 | 0.56842 | 0.51053 | 0.54435 | 0.56348 | 1.63499 | 1.75369 |
| 139 | 0.52762 | 0.70825 | 0.53158 | 0.53158 | 0.57565 | 0.61043 | 1.63485 | 1.85027 |
| 670 | 0.50667 | 0.77492 | 0.51053 | 0.52105 | 0.61739 | 0.64522 | 1.63458 | 1.94119 |
| 531 | 0.50984 | 0.83937 | 0.49474 | 0.51579 | 0.62783 | 0.80000 | 1.63240 | 2.15515 |
| 171 | 0.53746 | 0.67714 | 0.46842 | 0.51053 | 0.62435 | 0.59130 | 1.63023 | 1.77897 |
| 614 | 0.53714 | 0.79333 | 0.49474 | 0.50000 | 0.59652 | 0.62261 | 1.62840 | 1.91594 |
| 538 | 0.56095 | 0.91587 | 0.43684 | 0.63684 | 0.62783 | 0.68696 | 1.62562 | 2.23967 |
| 603 | 0.50984 | 0.86000 | 0.57368 | 0.60526 | 0.54087 | 0.75826 | 1.62440 | 2.22352 |
| 441 | 0.58762 | 0.90095 | 0.48947 | 0.72632 | 0.54609 | 0.94435 | 1.62318 | 2.57162 |
| 684 | 0.51619 | 0.75937 | 0.53158 | 0.52632 | 0.57391 | 0.67478 | 1.62168 | 1.96046 |
| 40 | 0.49556 | 0.72159 | 0.60526 | 0.46316 | 0.52000 | 0.54435 | 1.62082 | 1.72909 |
| 525 | 0.52762 | 0.87238 | 0.65263 | 1.00000 | 0.44000 | 0.92000 | 1.62025 | 2.79238 |
| 417 | 0.52286 | 0.70254 | 0.55263 | 0.62632 | 0.54435 | 0.44348 | 1.61984 | 1.77233 |
| 127 | 0.56190 | 0.81365 | 0.45263 | 1.00000 | 0.60000 | 0.78087 | 1.61454 | 2.59452 |
| 140 | 0.53143 | 0.67841 | 0.50000 | 0.52105 | 0.57913 | 0.58261 | 1.61056 | 1.78207 |
| 471 | 0.50571 | 0.90381 | 0.63158 | 0.78947 | 0.47304 | 0.94087 | 1.61034 | 2.63415 |
| 564 | 0.57683 | 0.74413 | 0.52632 | 0.43158 | 0.50435 | 0.64696 | 1.60749 | 1.82266 |
| 146 | 0.49302 | 0.71619 | 0.58421 | 0.53684 | 0.52696 | 0.56174 | 1.60418 | 1.81477 |
| 591 | 0.51905 | 0.74159 | 0.54737 | 0.64737 | 0.53565 | 0.58087 | 1.60207 | 1.96983 |
| 702 | 0.56762 | 0.83460 | 0.50526 | 0.55789 | 0.52522 | 0.76870 | 1.59810 | 2.16119 |
| 579 | 0.53365 | 0.74635 | 0.53158 | 0.50526 | 0.53043 | 0.59826 | 1.59566 | 1.84987 |
| 147 | 0.52095 | 0.70825 | 0.53158 | 0.51579 | 0.54261 | 0.57739 | 1.59514 | 1.80143 |
| 16 | 0.54413 | 0.82317 | 0.48421 | 0.99474 | 0.55304 | 0.71826 | 1.58138 | 2.53617 |
| 696 | 0.45460 | 0.76508 | 0.71579 | 0.58421 | 0.40870 | 0.65739 | 1.57909 | 2.00668 |
| 175 | 0.52571 | 0.76413 | 0.48421 | 0.45789 | 0.56870 | 0.61565 | 1.57862 | 1.83767 |
| 211 | 0.52381 | 0.84254 | 0.58421 | 1.00000 | 0.46783 | 0.78087 | 1.57585 | 2.62341 |
| 55 | 0.48190 | 0.73937 | 0.55263 | 0.65263 | 0.54087 | 0.52870 | 1.57541 | 1.92069 |
| 613 | 0.52476 | 0.77968 | 0.48421 | 0.51053 | 0.56348 | 0.63478 | 1.57245 | 1.92499 |
| 572 | 0.48635 | 0.72603 | 0.55263 | 0.59474 | 0.53043 | 0.57565 | 1.56942 | 1.89642 |
| 182 | 0.53619 | 0.74952 | 0.58421 | 0.48421 | 0.43304 | 0.63130 | 1.55344 | 1.86504 |
| 164 | 0.49905 | 0.70857 | 0.53684 | 0.53684 | 0.51304 | 0.43304 | 1.54893 | 1.67846 |
| 598 | 0.50635 | 0.77905 | 0.54211 | 0.50526 | 0.49913 | 0.66087 | 1.54758 | 1.94518 |
| 227 | 0.56159 | 0.84762 | 0.49474 | 1.00000 | 0.48522 | 0.85391 | 1.54154 | 2.70153 |
| 189 | 0.53397 | 0.75333 | 0.52632 | 0.56316 | 0.47304 | 0.62957 | 1.53333 | 1.94606 |
| 54 | 0.55238 | 0.69841 | 0.48421 | 0.59474 | 0.49565 | 0.58087 | 1.53224 | 1.87402 |
| 49 | 0.49746 | 0.71143 | 0.53158 | 0.52632 | 0.50087 | 0.44522 | 1.52991 | 1.68296 |
| 606 | 0.47111 | 0.76000 | 0.46316 | 0.54737 | 0.58783 | 0.63478 | 1.52210 | 1.94215 |
| 174 | 0.56286 | 0.75460 | 0.42632 | 0.47368 | 0.53217 | 0.70957 | 1.52135 | 1.93785 |
| 571 | 0.55937 | 0.81397 | 0.47895 | 0.40526 | 0.46957 | 0.45391 | 1.50788 | 1.67314 |
| 629 | 0.46540 | 0.85238 | 0.51579 | 0.49474 | 0.50609 | 0.77739 | 1.48727 | 2.12451 |
| 677 | 0.50000 | 0.76063 | 0.56842 | 0.49474 | 0.38261 | 0.68348 | 1.45103 | 1.93885 |
| 539 | 0.47365 | 0.82095 | 0.45789 | 0.61579 | 0.36696 | 0.69217 | 1.29850 | 2.12892 |

* Expression level of transcript in subject with definite bacterial infection. Up = gene expression is up-regulated in subject with bacterial infection, Down = gene expression level is down-regulated in subject with bacterial infection.
^opposite = one gene in signature is up-regulated whilst other gene in signature is down-regulated in subject with bacterial infection.
#same = both genes in signature are up-regulated or both genes in signature are down-regulated in subject with bacterial infection.

REFERENCES

1. Iroh Tam P Y, Bernstein E, Ma X, Ferrieri P. Blood culture in evaluation of pediatric community-acquired Pneumonia: a systematic review and meta-analysis. Hosp Pediatr. 2015; 5(6):324-336.
2. Martin N G, Sadarangani M, Pollard A J, Goldacre M J. Hospital admission rates for meningitis and septicaemia caused by *Haemophilus influenzae, Neisseria meningitidis*, and *Streptococcus pneumoniae* in children in England over five decades: a population-based observational study. The Lancet Infectious diseases. 2014; 14(5):397-405.
3. Colvin J M, Muenzer J T, Jaffe D M, et al. Detection of viruses in young children with fever without an apparent source. Pediatrics. 2012; 130(6):e1455-1462.
4. Craig J C, Williams G J, Jones M, et al. The accuracy of clinical symptoms and signs for the diagnosis of serious bacterial infection in young febrile children: prospective cohort study of 15 781 febrile illnesses. BMJ (Clinical research ed.). 2010; 340:c1594.
5. Nijman R G, Vergouwe Y, Thompson M, et al. Clinical prediction model to aid emergency doctors managing febrile children at risk of serious bacterial infections: diagnostic study. BMJ. 2013; 346:f1706.

6. Sadarangani M, Willis L, Kadambari S, et al. Childhood meningitis in the conjugate vaccine era: a prospective cohort study. Archives of disease in childhood. 2015; 100(3):292-294.
7. Le Doare K, Nichols A L, Payne H, et al. Very low rates of culture-confirmed invasive bacterial infections in a prospective 3-year population-based surveillance in Southwest London. Archives of disease in childhood. 2014; 99(6):526-531.
8. Warhurst G, Dunn G, Chadwick P, et al. Rapid detection of health-care-associated bloodstream infection in critical care using multipathogen real-time polymerase chain reaction technology: a diagnostic accuracy study and systematic review. Health technology assessment (Winchester, England). 2015; 19(35):1-142.
9. Cebey Lopez M, Herberg J, Pardo-Seco J, et al. Viral Co-Infections in Pediatric Patients Hospitalized with Lower Tract Acute Respiratory Infections. PloS one. 2015; 10(9):e0136526.
10. Berkley J A, Munywoki P, Ngama M, et al. Viral etiology of severe pneumonia among Kenyan infants and children. Jama. 2010; 303(20):2051-2057.
11. Anderson S T, Kaforou M, Brent A J, et al. Diagnosis of childhood tuberculosis and host RNA expression in Africa. N Engl J Med. 2014; 370(18):1712-1723.
12. Hu X, Yu J, Crosby S D, Storch G A. Gene expression profiles in febrile children with defined viral and bacterial infection. Proceedings of the National Academy of Sciences of the United States of America. 2013; 110(31): 12792-12797.
13. Herberg J A, Kaforou M, Gormley S, et al. Transcriptomic profiling in childhood H1N1/09 influenza reveals reduced expression of protein synthesis genes. The Journal of infectious diseases. 2013; 208(10):1664-1668.
14. Mejias A, Dimo B, Suarez N M, et al. Whole blood gene expression profiles to assess pathogenesis and disease severity in infants with respiratory syncytial virus infection. PLoS medicine. 2013; 10(11):e1001549.
15. Ramilo O, Allman W, Chung W, et al. Gene expression patterns in blood leukocytes discriminate patients with acute infections. Blood. 2007; 109(5):2066-2077.
16. Pathan N, Hemingway C A, Alizadeh A A, et al. Role of interleukin 6 in myocardial dysfunction of meningococcal septic shock. Lancet, The. 2004; 363(9404):203-209.
17. Suarez N M, Bunsow E, Falsey A R, Walsh E E, Mejias A, Ramilo O. Superiority of transcriptional profiling over procalcitonin for distinguishing bacterial from viral lower respiratory tract infections in hospitalized adults. The Journal of infectious diseases. 2015; 212(2):213-222.
18. Berry M P, Graham C M, McNab F W, et al. An interferon-inducible neutrophil-driven blood transcriptional signature in human tuberculosis. Nature. 2010; 466(7309):973-977.
19. Zou H, Hastie T. Regularization and variable selection via the elastic net J. R. Statist Soc. B. 2005; 67:301-320.
20. Kaforou M, Wright V J, Oni T, et al. Detection of tuberculosis in HIV-infected and -uninfected African adults using whole blood RNA expression signatures: a case-control study. PLoS medicine. 2013; 10(10): e1001538.
21. Zaas A K, Burke T, Chen M, et al. A host-based R T-PCR gene expression signature to identify acute respiratory viral infection. Science translational medicine. 2013; 5(203):203ra126.
22. Schoggins J W, Wilson S J, Panis M, et al. A diverse range of gene products are effectors of the type I interferon antiviral response. Nature. 2011; 472(7344):481-485.
23. Wong H R, Cvijanovich N, Lin R, et al. Identification of pediatric septic shock subclasses based on genome-wide expression profiling. BMC medicine. 2009; 7:34.
24. Gurion R, Lehman T J, Moorthy L N. Systemic arthritis in children: a review of clinical presentation and treatment International journal of inflammation. 2012; 2012: 271569.
25. Rabizadeh S, Dubinsky M. Update in pediatric inflammatory bowel disease. Rheumatic diseases clinics of North America. 2013; 39(4):789-799.
26. Thierry S, Fautrel B, Lemelle I, Guillemin F. Prevalence and incidence of juvenile idiopathic arthritis: a systematic review. Joint, bone, spine: revue du rhumatisme. 2014; 81(2):112-117.
27. Gardner-Medwin J M, Dolezalova P, Cummins C, Southwood T R. Incidence of Henoch-Schonlein purpura, Kawasaki disease, and rare vasculitides in children of different ethnic origins. Lancet (London, England). 2002; 360(9341):1197-1202.
28. van den Kieboom C H, Ferwerda G, de Baere I, et al. Assessment of a molecular diagnostic platform for integrated isolation and quantification of mRNA in whole blood. European journal of clinical microbiology & infectious diseases: official publication of the European Society of Clinical Microbiology. 2015; 34(11):2209-2212.
29. Pathan, N., et al., Role of interleukin 6 in myocardial dysfunction of meningococcal septic shock. Lancet, The, 2004. 363(9404): p. 203-9.
30. Petty, R. E., et al., International League of Associations for Rheumatology classification of juvenile idiopathic arthritis: second revision, Edmonton, 2001. J Rheumatol, 2004. 31(2): p. 390-2.
31. R core development team, R: a language and environment for statistical computing. 2011.
32. Schmid, R., et al., Comparison of normalization methods for Illumina BeadChip HumanHT-12 v3. BMC Genomics, 2010. 11: p. 349.
33. Jolliffe, I. T., Principal Component Analysis. 1986: Springer-Verlag.
34. Friedman, J., T. Hastie, and R. Tibshirani, Regularization Paths for Generalized Linear Models via Coordinate Descent. J Stat Softw, 2010. 33(1): p. 1-22.
35. Robin, X., et al., pROC: an open-source package for R and S+ to analyze and compare ROC curves. BMC Bioinformatics, 2011. 12: p. 77.
36. Youden, W. J., Index for rating diagnostic tests. Cancer, 1950. 3(1): p. 32-5.
37. Leek, J. T., et al., The sva package for removing batch effects and other unwanted variation in high-throughput experiments. Bioinformatics, 2012. 28(6): p. 882-3.
38. Benjamini, Y. and Y. Hochberg, *Controlling the False Discovery Rate—a Practical and Powerful Approach to Multiple Testing*. Journal of the Royal Statistical Society Series B-Methodological, 1995. 57(1): p. 289-300.
39. Smyth, G. K., *Linear models and empirical bayes methods for assessing differential expression in microarray experiments*. Stat Appl Genet Mol Biol, 2004. 3: p. Article 3.
40. http://geneontology.org/.
41. Thomas, P. D., et al., PANTHER: a library of protein families and subfamilies indexed by function. Genome Res, 2003. 13(9): p. 2129-41.

42. Reinhart K, Bauer M, Riedemann N C, Hartog C S. New approaches to sepsis: molecular diagnostics and biomarkers. Clinical microbiology reviews. 2012; 25: 609-34.

43. Smith A M, McCullers J A. Secondary bacterial infections in influenza virus infection pathogenesis. Current topics in microbiology and immunology. 2014; 385: 327-56.

44. De S, Williams G J, Hayen A, et al. Accuracy of the "traffic light" clinical decision rule for serious bacterial infections in young children with fever: a retrospective cohort study. BMJ (Clinical research ed). 2013; 346: f866.

45. Brent A J, Lakhanpaul M, Thompson M, et al. Risk score to stratify children with suspected serious bacterial infection: observational cohort study. Archives of disease in childhood. 2011; 96: 361-7.

46. Van den Bruel A, Haj-Hassan T, Thompson M, Buntinx F, Mant D. Diagnostic value of clinical features at presentation to identify serious infection in children in developed countries: a systematic review. Lancet (London, England). 2010; 375: 834-45.

47. Banchereau R, Jordan-Villegas A, Ardura M, et al. Host immune transcriptional profiles reflect the variability in clinical disease manifestations in patients with *Staphylococcus aureus* infections. PloS one. 2012; 7: e34390.

48. Ioannidis I, McNally B, Willette M, et al. Plasticity and virus specificity of the airway epithelial cell immune response during respiratory virus infection. Journal of virology. 2012; 86: 5422-36.

49. Herberg J A, Kaforou M, Wright V J et al. Diagnostic test accuracy of a 2-transcript host RNA signature for discriminating bacterial vs viral infection in febrile children. JAMA 2016; 316(8): 835-845.

50. Mahajan P. Kuppermann N, Mejias A, et al. Association of RNA biosignatures with bacterial infections in febrile infants aged 60 days or younger. *JAMA* 2016; 316(8): 846-857.

51. Edgar R, Domrachev M, Lash A E, Gene expression omnibus. *Nucleic Acid Res.* 2002; 30(1): 207-210.

The invention claimed is:

1. A method of treating a subject identified as having a bacterial infection, the method comprising:

detecting a level of expression of IFI44L and FAM89A mRNA in a blood sample from the subject;

comparing the detected level of IFI44L and FAM89A mRNA to a control level of each mRNA, the control level being the level of each mRNA in a blood sample from a subject that does not have a bacterial infection, and wherein no other mRNA expression levels are compared with their corresponding control levels;

detecting that the expression level of IFI44L is decreased in the sample from the subject as compared to the control level, and the expression level of FAM89A is increased in the sample from the subject as compared to the control level, thereby identifying the subject as having a bacterial infection;

and administering an anti-bacterial agent to the subject.

2. The method according to claim 1, wherein the gene expression level of IFI44L shows a log 2 fold change of <−0.5 in the subject having a bacterial infection compared to the control level of IFI44L; and the gene expression level of FAM89A shows a log 2 fold change of >0.5 in the subject having a bacterial infection compared to the control level of FAM89A.

3. The method according to claim 1, wherein the gene expression level of IFIT3 is also detected in the blood sample from the subject.

4. The method according to claim 1, wherein the method incorporates detecting the gene expression levels of one or more housekeeping genes.

5. The method according to claim 4, wherein the one or more housekeeping genes are selected from the group consisting of: actin, GAPDH, ubiquitin, 18s rRNA, RPII (POLR2A), TBP, PPIA, GUSB, HSPCB, YWHAZ, SDHA, RPS13, HPRT1 and B4GALT6.

6. The method according to claim 1, wherein the bacterial infection is selected from the group consisting of: *Chlamydia pneumoniae, Chlamydia trachomatis, Chlamydophila psittaci, Mycoplasma pneumonia, Corynebacterium diphtheriae, Clostridium botulinum, Clostridium difficile, Clostridium perfringens, Clostridium tetani, Enterococcus faecalis, Enterococcus faecium, Listeria monocytogenes, Staphylococcus aureus, Staphylococcus epidermidis, Staphylococcus saprophyticus*, Group B *streptococcus, Streptococcus agalactiae, Streptococcus pneumoniae, Streptococcus pyogenes*, or acid fast bacteria such as *Mycobacterium leprae, Mycobaterium tuberculosis, Mycobacterium ulcerans, Mycobacterium avium* intercellularae, *Bordetella pertussis, Borrelia burgdorferi, Brucella abortus, Brucella canis, Brucella melitensis, Brucella suis, Campylobacter jejuni, Escherichia coli, Francisella tularensis, Haemophilus influenzae, Helicobacter pylori, Legionella pneumophila, Leptospira interrogans, Neisseria gonorrhoeae, Neisseria meningitidis, Pseudomonas aeruginosa, Pseudomonas* spp, *Rickettsia rickettsii, Salmonella typhi, Salmonella typh-*

*imurium, Shigella sonnei, Treponema pallidum, Vibrio cholerae, Yersinia pestis, Kingella kingae, Stenotrophomonas* and *Klebsiella*.

7. The method according to claim 1, wherein the subject with a bacterial infection also has a viral infection and/or an inflammatory disease.

8. The method according to claim 1, wherein the subject is a child, for example where the child is in the age range 2 to 59 months.

9. The method according to claim 1, wherein the subject is an infant in the age range 0 to 59 days.

10. The method according to claim 1, wherein the subject has a fever.

11. The method according to claim 1, wherein the anti-bacterial agent is selected from the group consisting of: erythromycin, clindamucin, gentamicin, tetracycline, meclocycline, sulfacetamide, benzoyl peroxide, azelaic acid, ceftobiprole, ceftaroline, dalbavancin, daptomycin, linezolid, mupirocin, oritavancin, tedizolid, telavancin, tigecycline, vancomycin, aminoglycosides, carbapenems, ceftazidime, cefepime, ceftobiprole, fluorquinolones, piperacillin/tazobactam, ticarcillin/clavulanic acid, linezolid, streptogramins, daptomycin, amikacin, kanamycin, neomycin, netilmicin, tobramycin, paromomycin, streptomycin, spectinomycin, geldanamycin, herbimycin, rifaximin, loracarbef, ertapenem, doripenem, imipenem/cilastatin, meropenem, cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, telavancin, dalbavancin, oritavancin, clindamycin, lincomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin, penicillin, G, penicillin V, piperacillin, temocillin, ticarcillin, amoxicillin/clavulanate, ampicillin/sulbactam, pieracillin/tazobactam, ticarcillin/clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofoxacin, trovafloxacin, grepafloxacin, sparfloxacin, temafloxacin, mafenide, sulfacetamide, sulfadiazine, silversulfadiazine, sulfadimethoxine, sulfamethizole, sulfamethoxazole, sulfanilimide, sulfasalazine, sulfisoxazole, trimethoprim-sulfamethoxazole, sulfonamidochrysoidine, demeclocycline, doxycycline, minocycline, oxytetracycline, tetracycline, clofazimine, dapsone, capreomycin, cycloserine, ethambutol, ethionamide, isoniazid, pyrazinamide, rifampicin, rifabutin, rifapentine, arsphenamine, chloramphenicol, fosfomycin, fusidic acid, metronidazole, mupirocin, platensimycin, quinupristin/dalfopristin, thiamphenicol, tinidazole and trimethoprim.

12. A method of treating a subject identified as having a bacterial infection, the method comprising:

detecting a level of expression of IFI44L and EMR1 mRNA in a blood sample from the subject;

comparing the detected level of IFI44L and EMR1 mRNA to a control level of each mRNA, the control level being the level of each mRNA in a blood sample from a subject that does not have a bacterial infection, and wherein no other mRNA expression levels are compared with their corresponding control levels;

detecting that the expression level of IFI44L is decreased in the sample from the subject as compared to the control level, and the expression level of EMR1 is increased in the sample from the subject as compared to the control level, thereby identifying the subject as having a bacterial infection;

and administering an anti-bacterial agent to the subject.

* * * * *